Figure 7:
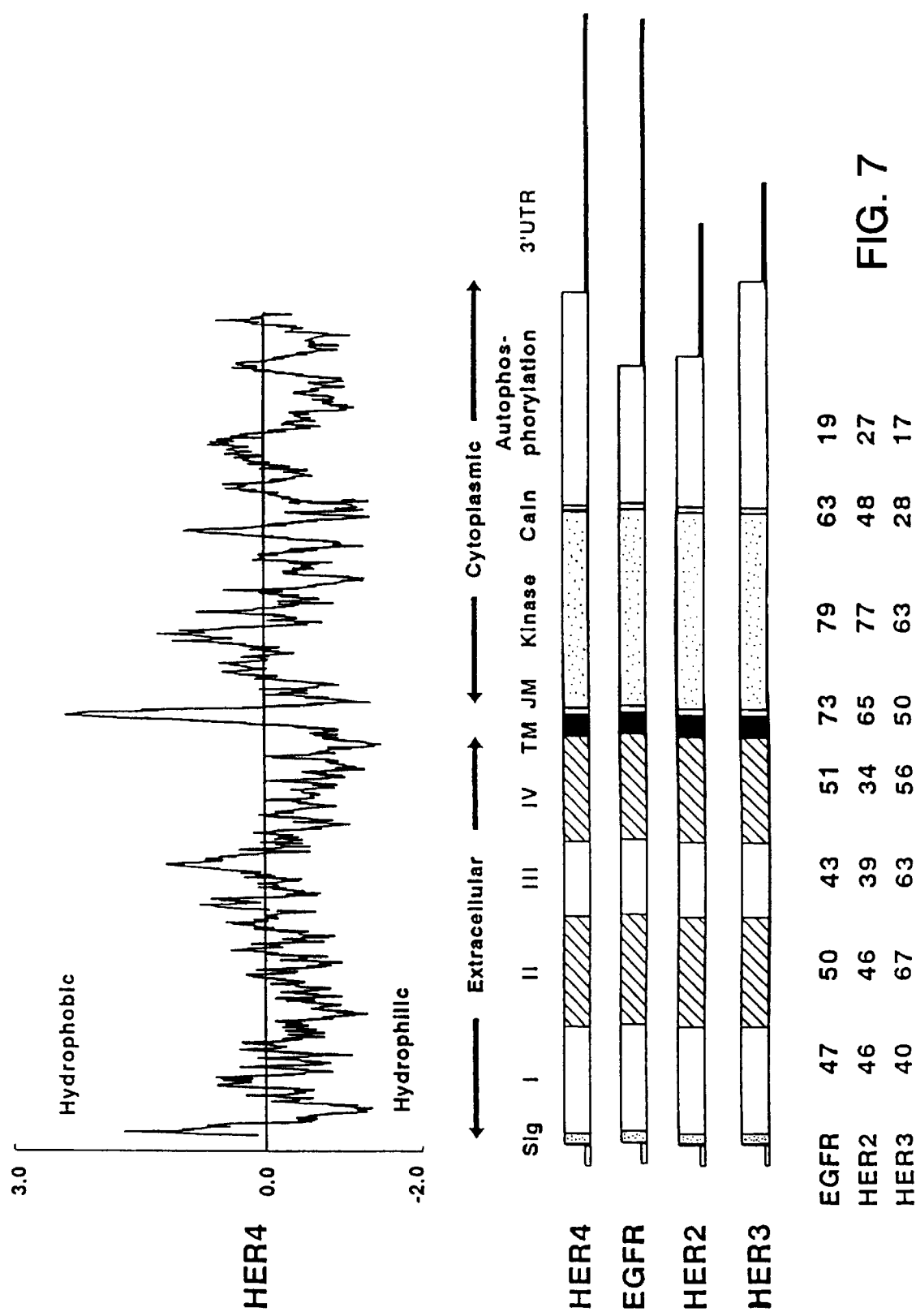

United States Patent [19]
Plowman et al.

[11] Patent Number: 5,811,098
[45] Date of Patent: Sep. 22, 1998

[54] ANTIBODIES TO HER4, HUMAN RECEPTOR TYROSINE KINASE

[75] Inventors: Gregory D. Plowman, San Carlos, Calif.; Jean-Michel Culouscou, Seattle, Wash.; Mohammed Shoyab, Seattle, Wash.; Clay B. Siegall, Seattle, Wash.; Ingegerd Hellström, Seattle, Wash.; Karl E. Hellström, Seattle, Wash.

[73] Assignee: Bristol-Myers Squibb Company, New York, N.Y.

[21] Appl. No.: 484,438

[22] Filed: Jun. 7, 1995

Related U.S. Application Data

[60] Division of Ser. No. 323,442, Oct. 14, 1994, which is a continuation-in-part of Ser. No. 150,704, Nov. 10, 1993, abandoned, which is a continuation-in-part of Ser. No. 981,165, Nov. 24, 1992, abandoned.

[51] Int. Cl.$^6$ .................................................. A61K 39/00
[52] U.S. Cl. ..................................... 424/178.1; 530/387.3; 530/387.7; 530/389.9; 530/388.85; 530/389.1; 530/391.7; 530/388.22; 530/391.3; 435/330; 424/149
[58] Field of Search ............................. 530/387.3, 387.1, 530/388.1, 388.22, 388.8, 289.1, 391.1, 391.3, 391.7; 424/178.1, 1.49

[56] References Cited

U.S. PATENT DOCUMENTS 5,367,060  11/1994  Vandleu et al. .

FOREIGN PATENT DOCUMENTS 0599274  6/1994  European Pat. Off. .
9108214  6/1991  WIPO .

OTHER PUBLICATIONS

Plowman et al *PNAS* (1993):90 pp. 1746–1750.
Plowman et al PNAS (1990):87 pp. 4905–4909.
Prigent et al Oncogene (1992):7 pp. 1273–1278.

*Primary Examiner*—Paula K. Hutzell
*Assistant Examiner*—Heather A. Bakalyar
*Attorney, Agent, or Firm*—Brian Poor; Thomas R. Savitsky

[57] ABSTRACT

The molecular cloning, expression, and biological characteristics of a novel receptor tyrosine kinase related to the epidermal growth factor receptor, termed HER4/p180$^{erbB4}$, are described. Antibodies to HER4 are disclosed. A HER4 ligand capable of inducing cellular differentiation of breast cancer cells is also disclosed. In view of the expression of HER4 in several human cancers and in certain tissues of neuronal and muscular origin, various diagnostic and therapeutic uses of HER4-derived and HER4-related biological compositions are provided.

17 Claims, 39 Drawing Sheets

FIG. 1A

HER4 cDNA

```
                                                        MetLysProAlaThrGlyLeuTrpValTrp  ValSerLeuLeuValAlaAlaGlyThr
  1   AATTGTCAGCACGGGATCTGAGACTTCCAAAAA                 ATGAAGCCGGCGACAGAGACTTGGGTCTGG  GTGAGCCTTCTCGTGGCGGCGGGGACC
  1

20   Val  GlnProSerAspGlnSerValCysAla  GlyThrGluAsnLysLeuSerSerLeuSer  AspLeuGluGlnTyrArgAlaLeu
 91   GTC  CAGCCCAGCGATTCTCAGTCAGTGTGCA  GGAACGGAGAATAAACTGAGCTCTCTCT    GACCTGGAACAGTACCGAGCCTTG

50   Arg  LysTyrTyrGluAsnCysGluValValMet  GlyAsnLeuGluIleThrSerIleGluHis  AsnArgAspLeuSerPheLeuArgSer
181   CGC  AAGTACTATGAAAACTGTGAGGTGTCATG  GGCAACCTGGAGATAACCAGCATTGAGCAC    AACCGGGACCTCTCCTTCCTGCGGTCT

80   Val  ArgGluValThrGlyTyrValLeuValAla  LeuAsnGlnPheArgTyrLeuProLeuGlu  AsnLeuArgIleIleArgGlyThrLys
271   GTT  CGAGAAGTCACAGGCTACGTGTTAGTGGCT  CTTAATCAGTTTCGTTACCTGCCTCTGGAG    AATTTACGCATTATTCGTGGGACAAAA

110   Leu  TyrGluAspArgTyrAlaLeuAlaIlePhe  LeuAsnLysPheLeuCysTyrAlaAspThr  LeuGlnLeuLeuLeuLysAsnLeu
361   CTT  TATGAGGATCGATATGCCTTGGCAATATTT  TTAAACAAATTCCTTTGTTATGCAGACAC    CTTCAAGAACTTGGATTAAAGAACTTG

140   Thr  GluIleLeuAsnGlyValGlyValTyrValAsp  GlnAsnLysPheLeuCysTyrAlaAspThr  IleHisTrpGlnAsnIleValArgAsn
451   ACA  GAAATCCTAAATGGTGGAGTCGTATGTAGAC  CAGAACAAATTCCTTTGTTATGCAGACAC    ATTCATTGGCAAGATATTGTCGAAAC

170   Pro  TrpProSerAsnLeuThrLeuValSerThr  AsnGlySerSerGlyCysGlyArgCysHis  LysSerCysThrGlyArgCysTrpGly
541   CCA  TGGCCTTCCAACTTGACTCTTGTGTCAACA  AATGGTAGTTCAGGATGTGGACGTTGCCAT    AAGTCCTGTACTGGCCGTTGCTGGGGA

200   Pro  ThrGluAsnHisCysGlnIleThrLeuThrArg  ThrValCysAlaGluGlnCysAspGlyArg  CysTyrGlyProTyrValSerAspCys
631   CCC  ACAGAAAATCATTGCCAGATTTGACAAGG  ACGGTGTGTGCAGAACAATGTGACGGCAGA    TGCTACGGACCTTACGTCAGTGACTGC

230   Cys  HisArgGluCysAlaGlyGlyCysSerGly  ProLysAspThrAspCysPheAlaCysMet  AsnPheAsnAspSerGlyAlaCysVal
721   TGC  CATCGAGAATGTGCTGGAGGCTGCTCAGGA  CCTAAGGACACAGACTGCTTTGCCTGCATG    AATTTCAATGACAGTGGAGCATGTGTT

260   Thr  GlnCysProGlnThrPheValTyrAsnPro  ThrThrPheGlnLeuGluHisAsnPheAsn  AlaLysTyrThrTyrGlyAlaPheCys
811   ACT  CAGTGTCCCCAAACCTTTGTCTACAATCCA  ACCACCTTCCAACTGGAGCACAATTTCAAT    GCAAAGTACACATATGGAGCATTCTGT

290   Val  LysLysCysProHisAsnPheValValAsp  SerSerSerCysValArgAlaCysProSer  SerLysMetGluValGluGluAsnGly
901   GTC  AAGAAATGTCCACATAACTTTGTGGTAGAT  TCCAGTTCTTGTGTGCGTGCCTGCCCTAGT    TCCAAGATGGAAGTAGAAGAAAATGGG

320   Ile  LysMetCysLysProCysThrAspIleCys  ProLysAlaCysAspGlyIleGlyThrGly  SerLeuMetSerAlaGlnThrValAsp
991   ATT  AAAATGTGTAAACCTTGCACTGACATTTGC  CCAAAAGCTTGTGATGGCATTGGCACAGGA    TCATTGATGTCAGCTCAGACTGTGGAT
```

FIG. 1B

| | | | | |
|---|---|---|---|---|
| 350 1081 | Ser TCC | SerAsnIleAspLysPheIleAsnCysThr AGTAACATTGACAAATTCATAAACTGTACC | LysIleAsnGlyAsnLeuIlePheLeuVal AAGATCAATGGAAATTGATCTTTCTAGTC | ThrGlyIleHisGlyAspProTyrAsn ACTGGTATTCATGGGACCCTTACAAT |
| 380 1171 | Ala GCA | IleGluAlaIleAspProGluLysLeuAsn ATTGAAGCCATAGACCCAGAGAAACTGAAC | ValPheArgThrValArgGluIleThrGly GTCTTTCGGACAGTCAGAGAGATAACAGGT | PheLeuAsnIleGlnSerTrpProPro TTCCTGAACATACAGTCATGGCCACCA |
| 410 1261 | Asn AAC | MetThrAspPheSerValPheSerAsnLeu ATGACTGACTTCAGTGTTTTTTCTAACCTG | ValThrIleGlyGlyArgValLeuTyrSer GTGACCATTGGTGGAAGAGTACTCTATAGT | GlyLeuSerLeuLeuIleLeuLysGln GGCCTGTCCCTGCTTATCCTCAAGCAA |
| 440 1351 | Gln CAG | GlyIleThrSerLeuGlnPheGlnSerLeu GGCATCACCTCTCTACAGTTCCAGTCCCTG | LysGluIleSerAlaGlyAsnIleTyrIle AAGGAAATCAGCGCAGGAAACATCTATATT | ThrAspAsnSerAsnLeuCysTyrTyr ACTGACAACAGCAACCTGTGTTATTAT |
| 470 1441 | His CAT | ThrIleAsnTrpThrThrLeuPheSerThr ACCATTAACTGGACAACACTCTTCAGCACA | IleAsnGlnArgIleValIleArgAspAsn ATCAACCAGAGAATAGTAATCCGGGACAAC | ArgLysAlaGluAsnCysThrAlaGlu AGAAAAGCTGAAAATTGTACTGCTGAA |
| 500 1531 | Gly GGA | MetValCysAsnHisLeuCysSerSerAsp ATGGTGTGCAACCATCTGTGTTCCAGTGAT | GlyCysTrpGlyProGlyProAspGlnCys GGCTGTTGGGGACCTGGGCCAGACCAATGT | LeuSerCysArgArgPheSerArgGly CTGTCGTGTCGCCGCTTCAGTAGAGGA |
| 530 1621 | Arg AGG | IleCysIleGluSerCysAsnLeuTyrAsp ATCTGCATAGAGTCTTGTAACCTCTATGAT | GlyGluPheArgGluPheGluAsnGlySer GGTGAATTCGGGAGTTTGAGAATGGCTCC | IleCysValGluCysAspProGlnCys ATCTGTGTGGAGTGTGACCCCCAGTGT |
| 560 1711 | Glu GAG | LysMetGluAspGlyLeuLeuThrCysHis AAGATGGAAGATGGCCTCCTCACATGCCAT | GlyProGlyProAspAsnCysThrLysCys GGACCGGGTCCTGACAACTGTACAAAGTGC | SerHisPheLysAspGlyProAsnCys TCTCATTTTAAAGATGGCCCAAACTGT |
| 590 1801 | Val GTG | GluLysCysProAspGlyLeuGlnGlyAla GAAAAATGTCCAGATGGCTTACAGGGGGCA | AsnSerPheIlePheLysTyrAlaAspPro AACAGTTTCATTTTCAAGTATGCTGATCCA | AspArgGluCysHisProCysHisPro GATCGGGAGTGCCACCCATGCCATCCA |
| 620 1891 | Asn AAC | CysThrGlnGlyCysAsnGlyProThrSer TGCACCCAAGGGTGTAACGGTCCCACTAGT | HisAspCysIleTyrTyrProTrpThrGly CATGACTGCATTTACTACCCATGGACGGGC | HisSerThrLeuProGlnHisAlaArg CATTCCACTTTACCACAACATGCTAGA |
| 650 1981 | Thr ACT | ProLeuIleAlaAlaGlyValIleGlyGly CCCCTGATTGCAGCTGGAGTAATTGGTGGG | LeuPheIleLeuValIleValGlyLeuThr CTCTTCATTCTGGTCATTGTGGGTCTGACA | PheAlaValTyrValArgArgLysSer TTTGCTGTTTATGTTAGAAGGAAGAGC |
| 680 2071 | Ile ATC | LysLysLysArgAlaLeuArgArgPheLeu AAAAAGAAAAGAGCCTTGAGAAGATTCTTG | GluThrGluLeuValGluProLeuThrPro GAAACAGAGTTGGTGGAACCATTAACTCCC | SerGlyThrAlaProAsnGlnAlaGln AGTGGCACAGCACCCAATCAAGCTCAA |

```
 710        Leu  ArgIleLeuTyrGluThrGluLeuLysArg  ValLysValLeuGlyLysGlyAlaPheGly  ThrValTyrLysGlyIleTrpValPro
2161        CTT  CGTATTTGAAAGAACTGAGCTGAAGAGG    GTAAAGTCCTTGGCTCAGGTGCTTTTGGA   ACGGTTTATAAAGGTATTTGGGTACCT

740        Gly  GlyGluThrValLysIleProValAlaIle  LysIleLeuAsnGluThrThrGlyProLys  AlaAsnValGluPheMetAspGluAla
2251        GGA  GGAGAAACTGTGAAGATTCCTGTGGCTATT  AAGATTCTTAATGAGACAACTGGTCCCAAG  GCAAATGTGGAGTTCATGGATGAAGCT

770        Leu  IleMetAlaSerMetAspHisProHisLeu  ValArgLeuLeuGlyValCysLeuSerPro  ThrIleGlnLeuValThrGlnLeuMet
2341        CTG  ATCATGGCAAGTATGGATCATCCACACCTA  GTCCGGTTGCTGGGTGTGTGTCTGAGCCCA  ACCATCCAGCTGGTTACTCAACTTATG

800        Pro  HisGlyCysLeuLeuGluTyrValHisGlu  HisLysAspAsnIleGlySerGlnLeuLeu  LeuAsnTrpCysValGlnIleAlaLys
2431        CCC  CATGGCTGCCTGTTGGAGTATGTCCACGAG  CACAAGGATAACATTGGATCACAACTGCTG  CTTAACTGGTGTGTCCAGATAGCTAAG

830        Gly  MetMetTyrLeuGluGluArgArgLeuVal  HisArgAspLeuAlaAlaAlaArgAsnValLeu  ValLysSerProAsnHisValLysIle
2521        GGA  ATGATGTACCTGGAAGAACGACGTCGTT   CATCGGGATTTGGCAGCCGCCCGTAATGTCTTA  GTGAAATCTCCAAACATGTGAAAATC

860        Thr  AspPheGlyLeuAlaArgLeuLeuGluGly  AspGluLysGlyTyrAsnAlaAspGlyGly  LysMetProIleLysTrpMetAlaLeu
2611        ACA  GATTTTGGGCTAGCCAGACTCTTGGAAGGA  GATGAAAAGAGTACAATGCTGATGGAGGA   AAGATGCCAATTAAATGGATGGCTCTG

890        Glu  CysIleHisTyrArgLysPheThrHisGln  SerAspValTrpSerTyrGlyValThrIle  TrpGluLeuMetThrPheGlyLeuLys
2701        GAG  TGTATACATTACAGAGAATTCACCCATCAG  AGTGACGTTTGGAGCTATGGAGTTACTATA  TGGGAACTGATGACCTTTGGAGAAAA

920        Pro  TyrAspGlyIleProThrArgGluIlePro  GlnProProIleCysThrIleAspVal
2791        CCC  TATGATGGAATTCCAACGCGAGAAATCCCT  CAGCCTCCCATCTGCACTATTGACGTT

950        Tyr  MetValMetValLysCysTrpMetIleAsp  AlaAspSerArgProLysPheLysGluLeu  AlaAlaGluPheSerArgMetAlaArg
2881        TAC  ATGGTCATGGTCAAATGTTGGATGATTGAT  GCTGACAGTAGACCTAAATTTAAGGAACTG  GCTGCTGAGTTTTCAAGGATGGCTCGA

980        Asp  ProGlnArgTyrLeuValIleGlnGlyAsp  AspArgMetLysLeuProSerProAsnAsp  SerLysPhePheGlnAsnLeuLeuAsp
2971        GAC  CCTCAAAGATACCTAGTTATTCAGGGTGAT  GATCGTATGAAGCTTCCCAGTCCAAATGAC  AGCAAGTTCTTTCAGAATCTCTTGGAT

1010        Glu  GluAspLeuGluAspMetMetAspAlaGlu  GluTyrLeuValProGlnAlaPheAsnIle  ProProProIleTyrThrSerArgAla
3061        GAA  GAGGATTTGGAAGATATGATGGATGCTGAG  GAGTACTTGGTCCCTCAGGCTTTCAACATC  CCACCTCCCATCTATACTTCCAGAGCA

1040        Arg  IleAspSerAsnArgGluIleGlyHis     SerProProProAlaTyrThrProMetSer  GlyAsnGlnPheValTyrArgAspGly
3151        AGA  ATTGACTCGAACAGAGAAATTGGACAC     AGCCCTCCTCCTGCTACACCCCATGTCA   GGAAACCAGTTGTATACCGAGATGGA

1070        Gly  PheAlaAlaGluGluGlyValSerValPro  TyrArgAlaProThrSerThrIleProGlu  AlaProValAlaGlnGlyAlaThrAla
3241        GGT  TTTGCTGCTGAACAAGGAGTGTCTGTGCCC  TACAGAGCCCCAACTAGCACACAATTCCAGAA  GCTCCTGTGGCACAGGGTGCTACTGCT

1100        Glu  IlePheAspSerCysCysAsnGlyThr     LeuArgLysProValAlaProHisValGln  GluAspSerSerThrGlnArgTyrSer
3331        GAG  ATTTTTGATGACTCCTGCTGTAATGGCACC  CTACGCAAGCCAGTGGCACCCCATGTCCAA  GAGGACAGTAGCACCCAGAGGTACAGT
```

FIG. 1C

```
1130  Ala  AspProThrValPheAlaProGluArgSer  ProArgGlyGluLeuAspGluGluGlyTyr  MetThrProMetArgAspLysProLys
3421  GCT  GACCCCACCGTGTTGCCCCAGAACGAGC    CCACGAGGAGAGCTGGATGAGGAAGGTTAC  ATGACTCCTATGCGAGACAAACCCAAA

1160  Gln  GluTyrLeuAsnProValGluGluAsnPro  PheValSerArgArgLysAsnGlyAspLeu  GlnAlaLeuAspAsnProGluTyrHis
3511  CAA  GAATACCTGAATCCAGTGGAGGAGAACCCT  TTTGTTTCTCGGAGAAAAATGGAGACCTT  CAAGCATTGGATAATCCCGAATATCAC

1190  Asn  AlaSerAsnGlyProProLysAlaGluAsp  GluTyrValAsnGluProLeuTyrLeuAsn  ThrPheAlaAsnThrLeuGlyLysAla
3601  AAT  GCATCCAATGGTCCACCCAAGGCCGAGGAT  GAGTATGTAAATGAGCCACTGTACCTCAAC  ACCTTTGCCAACACCTTGGGAAAGCT

1220  Glu  TyrLeuLysAsnAsnIleLeuSerMetPro  GluLysAlaLysLysAlaPheAspAsnPro  AspTyrTrpAsnHisSerLeuProPro
3691  GAG  TACCTGAAGAACAACATACTGTCAATGCCA  GAGAAGGCCAAGAAGGCTTTGACAACCCT  GACTACTGGAACCACAGCCTGCCACCT

1250  Arg  SerThrLeuGlnHisProAspTyrLeuGln  GluTyrSerThrLysTyrPheTyrLysGln  AsnGlyArgIleArgProIleValAla
3781  CGG  AGCACCCTTCAGCACCCAGACTACCTGCAG  GAGTACAGCACCAAATATTTTTATAAACAG  AATGGGCGGATCCGGCCTATTGTGGCA

1280  Glu  AsnProGluTyrLeuSerGluPheSerLeu  LysProGlyThrValLeuProProProPro  TyrArgHisArgAsnThrValVal***
3871  GAG  AATCCTGAATACCTCTCTGAGTTCTCCCTG  AAGCCAGGCACTGTGCTGCCGCCTCCACCT  TACAGACACCGGAATACCGTGGTGTAA

3961  GCTCAGTGTGTGTTTTTAGGTGGAGAGACACACCTGCTCCCAATTCCCACCCCCTCTCTTCTCTGGTCTTCCTTCTCTACCCAGGC
4054  CAGTAGTTTGACACTTCCCAGTGGAAGATACAGAGATGTATGTGCTTACCTAACTTGAACATTGAACATTAGAGGGAAAGACTGAAAGA
4147  GAAAGATAGGAGGAGAACCACAGTGTTTCTTCATTCTCTGCATGGGTTGGTCAGAGAATGAAACAGCTAGAACAGAGAAATGTAAGGC
4240  AATGCTGCCTACTATCAAACTACCCATGCTGTCTATGCTACTTAGCATCCCTGAGTGTGAGAATTAGTTGCATATTAGCATCCTGAAATCATAATAAGTTTA
4333  AAGCAGATAGTTGAAACAAAGAATAACATTTCTATAACATTTTTCATTAAAATCTCAGTTCTCTTCCCCAGCAGTTTCTGTCCTAGCAA
4426  CATTAGAACAAAGATAACTCAACTTGTCTATAACATTTTCATAATTTAAAATCTCAGTTCTCTTCCCCAGCAGTTTCTGTCCTAGCAA
4519  GTAAGAATGGCCAACTCAACTTGTCTGACCGATTCCTTTATATTTATTGCTTAAGTATACAAATCTTAAATGACACTACTTGAAGTTTACATCAAAGCTTCTTCAC
4612  TTTGTTTGCTCTGACCGATTCCTTTATATTTATTGCTTAAGTATACAAATCTTAAATGACACTACTTGAAGTTTACATCAAAGCTTCTTCAC
4705  AGAATTAAGCAAGAAATTATTTCACCCTTTACACATTTTCCTCCTCTGTGTTCAGGAGAAAACTACTTTTCAGGGGTGGCCAATGAGGGGAATCCATTGAACT
4798  TGCTATCAAATTATCTCACCCTTTACACATTTTCAACATTTTCCTCCTCTGTGTTCAGGAGAAAACTACTTTTCAGGGGTGGCCAATGAGGGGAATCCATTGAACT
4891  AAGAGTAGAAGGAAACTAAGACACAGTTCTGTTCAGCAGATGTCTACCTGGCAGAAGCACTTGCACTTAAGCTGTAATTAGTACATTTTAAAAAGAGCTAAGATAAAGAC
4984  GAAGAAAACACACTGGATTGGGTATGTCTACCTGGCAGAAGCACTTGCACTTAAGCTGTAATTAGTACATTTTAAAAAGAGCTAAGATAAAGAC
5077  ACTCCATTTGGATTTGAATCAAGCAATAGGAAGCAACCAGCACATTTAAGTACATTTTAAAAAGAGCTAAGATAAAGAC
5170  TGTGAAATGCCAAGCAAATTGTTCAGTTGCTTATACTCGTAAGAATGGCTTGAATTCCATGCTTGAATTCCATGAATTCTCATATGAGA
5263  TGCTACGCAAGGAAATTGTTCAGTTGCTTATACTCGTACATAAATTGTATAATAAAAGAAAAACAAACATTCAAAGCTTAGGGATAAGTTCTAGTATGAGA
5356  CTATTATATGAAGTTGTAAATAATGTGAAACATCTTCAAAAATGAACATCTTCAAAAATGAAACATCTTCAAAGCTTAGGGATAAGTCCTTG
5449  GGTCAAAGTTGTAAATAATGTGAAACATCTTCAAAAATGAACATCTTCAAAGCTTAGGGATAAGTCCTTG
```

FIG. 1D

FIG. 2A

HER4 with alternate 3'-end without AP domain

```
                    MetLysProAlaThrGlyLeuTrpValTrp ValSerLeuLeuValAlaAlaGlyThr
  1                 ATGAAGCCGGGCGACAGAGACTTCCAAAAA GTGAGCCTTCTCGTGGCGGCGGGACC
  1  AATTGTCAGCACGGGATCTGAGACTTCCAAAAA

20  Val GlnProSerAspSerGlnSerValCysAla GlyThrAsnLysLeuSerSerLeuSer AspLeuGluGlnGlnTyrArgAlaLeu
 91  GTC CAGCCCAGCGATTCCCAGTCAGTGTGCA GGAACGGAGAATAAACTGAGCTCTCTCT GACCTGGAACAGCAGTACCGAGCCTTG

50  Arg LysTyrTyrGluAsnCysGluValValMet GlyAsnLeuGluIleThrSerIleGluHis AsnArgAspLeuSerPheLeuArgSer
181  CGC AAGTACTATGAAAACTGTGAGGTTGTCATG GGCAACCTGGAGATAACCAGCATTGAGCAC AACCGGGACCTCTCTTTCCTGCGGTCT

80  Val ArgGluValThrGlyTyrValLeuValAla LeuAsnGlnPheArgTyrLeuProLeuGlu AsnLeuArgIleIleArgGlyThrLys
271  GTT CGAGAAGTCACAGGCTACGTGTTAGTGGCT CTTAATCAGTTTCGTTACCTGCCTCTGGAG AATTTACGCATTATTCGTGGGACAAAA

110  Leu TyrGluAspArgTyrAlaLeuAlaIlePhe LeuAsnTyrArgLysAspGlyAsnPheGly LeuGlnGluLeuLeuGlyLeuLysAsnLeu
361  CTT TATGAGGATCGATATGCCTTGGCAATATTT TTAAACTACAGAAAAGATGGAAACTTTGGA CTTCAAGAACTTGGATTAAAGAACTTG

140  Thr GluIleLeuAsnGlyGlyValTyrValAsp GlnAsnLysPheLeuCysTyrAlaAspThr IleHisTrpGlnAspIleValArgAsn
451  ACA GAAATCCTAAATGGTGGAGTCTATGTAGAC CAGAACAAATTCCTTTGTTATGCAGACACC ATTCATTGGCAAGATATTGTTCGGAAC

170  Pro TrpProSerAsnLeuThrLeuValSerThr AsnGlySerSerGlyCysGlyArgCysHis LysSerCysThrGlyArgCysTrpGly
541  CCA TGGCCTTCCAACTTGACTCTTGTCAGCACA AATGGTAGTTCAGGATGTGGACGTTGCCAT AAGTCCTGTACTGGCCGTTGCTGGGGA

200  Pro ThrGluAsnHisCysGlnThrLeuThrArg ThrValCysAlaGluGlnCysAspGlyArg CysTyrGlyProTyrValSerAspCys
631  CCC ACAGAAAATCATTGCCAGACTTTGACAAGG ACGGTGTGCAGAACAATGTGACGGCCAGA TGCTACGGACCTTACGTCAGTGACTGC

230  Cys HisArgGluCysAlaGlyGlyCysSerGly ProLysAspThrAspCysPheAlaCysMet AsnPheAsnAspSerGlyAlaCysValVal
721  TGC CATCGAGAATGTGCTGGAGGCTGCTCAGGA CCTAAGGACACAGACTGCTTTGCCTGCATG AATTTCAATGACAGTGGAGCATGTGTT

260  Thr GlnCysProGlnThrPheGlnLeuHisAsnPro ThrThrPheGlnLeuGluHisAsnPheAsn AlaLysTyrThrTyrGlyAlaPheCys
811  ACT CAGTGTCCCCAAACCTTTCAACTGCACAATCCA ACCACCTTTCAACTGGAGCACAATTTCAAT GCAAAGTACACATATGGAGCATTCTGT

290  Val LysLysProHisAsnPheValTyrAspAsp SerSerCysValArgAlaCysProSer SerLysMetGluValGluAsnGly
901  GTC AAGAAATGTCCACATAACTTTGTGTAGAT TCCAGTTCTTGTGTGCGTGCCTGCCCTAGT TCCAAGATGGAAGTAGAGAAAATGGG

320  Ile LysMetCysLysProCysThrAspIleCys ProLysAlaCysLysGlyIleGlyThrGly SerLeuMetSerAlaGlnThrValAsp
991  ATT AAAATGTGTAAACCTTGCACTGACATTGC CCAAAGCTTGTGATTGGCATTGGCACAGGA TCATTGATGTCAGCTCAGACTGTGGAT
```

```
350   Ser SerAsnIleAspLysPheIleAsnCysThr   LysIleAsnGlyAsnLeuIlePheLeuVal   ThrGlyIleHisGlyAspProTyrAsn
1081      TCC AGTAACATTGACAAATTCATAAACTGTACC   AAGATCAATGGAAATTGATCTTTCTAGTC    ACTGGTATTCATGGGGACCCTTACAAT

380   Ala IleGluAlaIleAspProGluLysLeuAsn   ValPheArgThrValArgGluIleThrGly   PheLeuAsnIleGlnSerTrpProPro
1171      GCA ATTGAAGCCATAGACCCAGAGAAACTGAAC   GTCTTTCGGACAGTCAGAGAGATAACAGT    TTCCTGAACATACAGTCATGGCCACCA

410   Asn MetThrAspPheSerValPheSerAsnLeu   ValThrIleGlyGlyArgValLeuTyrSer   GlyLeuSerLeuLeuIleLeuLysGln
1261      AAC ATGACTGACTTCAGTGTTTTTTCTAACCTG   GTGACCATTGGTGGAAGAGTACTCTATAGT   GGCCTGTCCTTGCTTATCCTCAAGCAA

440   Gln GlyIleThrSerLeuGlnPheGlnSerLeu   LysGluIleSerAlaGlyAsnIleTyrIle   ThrAspAsnSerAsnLeuCysTyrTyr
1351      CAG GGCATCACCTCTCTACAGTTCCAGTCCCTG   AAGGAAATCAGCGCAGGAAACATCTATAT    ACTGACAACAGCAACCTGTGTTATTAT

470   His ThrIleAsnTrpThrThrLeuPheSerThr   IleAsnGlnArgIleValIleArgAspAsn   ArgLysAlaGluAsnCysThrAlaGlu
1441      CAT ACCATAAACTGGACAACACACTCTTCAGCAC   ATCAACCAGAGAATAGTAATCCGGGACAAC   AGAAAAGCTGAAAATTGTACTGCTGAA

500   Gly MetValCysAsnHisLeuCysSerSerAsp   GlyCysTrpGlyProGlyProAspGlnCys   LeuSerCysArgArgPheSerArgGly
1531      GGA ATGGTGTGCAACCATCTGTGTTCCAGTGAT   GGCTGTTGGGGACCTGGGCCAGACCAATGT   CTGTCGTGCCGCCTTCAGTAGAGGA

530   Arg IleCysIleGluSerCysAsnLeuTyrAsp   GlyGluPheArgGluPheGlnAsnGlySer   IleCysValGluCysAspProGlnCys
1621      AGG ATCTGCATAGAGTCTTGTAACCTCTATGAT   GGTGAATTCGGGAGTTTGAGAATGGCTCC    ATCTGTGTGGAGTGTGACCCCCAGTGT

560   Glu LysMetGluAspGlyLeuLeuThrCysHis   GlyProGlyProAspAsnCysThrLysCys   SerHisPheLysAspGlyProAsnCys
1711      GAG AAGATGGAAGATGGCCTCCTCACATGCCAT   GGACCGGGTCCTGACAACTGTACAAAGTGC   TCTCATTTAAAGATGGCCCAAACTGT

590   Val GluLysCysProAspGlyLeuGlnGlyAla   AsnSerPheIlePheLysTyrAlaAspPro   AspArgGluCysHisProCysHisPro
1801      GTG GAAAAATGTCCAGATGGCTTACAGGGGGCA   AACAGTTTCATTTTCAAGTATGCTGATCCA   GATCGGGAGTGCCACCCATGCCATCCA

620   Asn CysThrGlnGlyCysAsnGlyProThrSer   HisAspCysIleTyrTyrProTrpThrGly   HisSerThrLeuProGlnHisAlaArg
1891      AAC TGCACCCAAGGGTGTAACGGTCCCACTAGT   CATGACTGCATTTACTACCCATGGACGGGC   CATTCCACTTACCACAACATGCTAGA

650   Thr ProLeuIleAlaAlaGlyValIleIleGlyGly   LeuPheIleLeuValIleValGlyLeuThr   PheAlaValTyrValArgArgLysSer
1981      ACT CCCCTGATTGCTGCAGGTGAGTAATTGGTGGG   CTCTTCATTCTGGTCATTGTGGGTCTGACA   TTTGCTGTTTATGTTAGAGGAAGAGC
```

FIG. 2B

```
 680  Ile LysLysLysArgAlaLeuArgArgPheLeu GluThrGluLeuValGluProLeuThrPro SerGlyThrAlaProAsnGlnAlaGln
2071  ATC AAAAAGAAAAGAGCCTTGAGAAGATTCTTG GAAACAGAGTTGGTGAACCATTAACTCCC AGTGGCACAGCACCAATCAAGCTCAA

710  Leu ArgIleLeuLysGluThrGluLeuLysArg ValLysValLeuGlySerGlyAlaPheGly ThrValTyrLysGlyIleTrpValPro
2161  CTT CGTATTTGAGAAAGAACTTGAGCTGAAGAGG GTAAAGTCCTTGGCTCAGTGCTTTTGA ACGGTTATAAAGTATTTGGGTACCT

740  Glu GlyGluThrValLysIleProValAlaIle LysIleLeuAsnGluThrThrGlyProLys AlaAsnValGluPheMetAspGluAla
2251  GAA GGAGAAACTGTGAAGATTCCTGTGGCTATT AAGATTCTTAATGAGACAACTGGTCCAAG GCAAATGTGGAGTTCATGGATGAAGCT

770  Leu IleMetAlaSerMetAspHisProHisLeu ValArgLeuLeuGlyValCysLeuSerPro ThrIleGlnLeuValThrGlnLeuMet
2341  CTG ATCATGGCAAGTATGGATCATCCACACCTA GTCCGGTTGCTGGGTGTGTGTCTGAGCCCA ACCATCCAGCTGGTTACTCAACTTATG

800  Pro HisGlyCysLeuLeuGluTyrValHisGlu HisLysAspAsnIleGlySerGlnLeuLeu LeuAsnTrpCysValGlnIleAlaLys
2431  CCC CATGGCTGCCTGTTGGAGTATGTCCACGAG CACAAGGATAACATTGGATCACAACTGCTG CTTAACTGGTGTGTCCAGATAGCTAAG

830  Gly MetMetTyrLeuGluArgLeuArgLeuVal HisArgAspLeuAlaAlaArgAsnValLeu ValLysSerProAsnHisValLysIle
2521  GGA ATGATGTACCTGGAGAGACTGAGACTCGTT CATCGGGATTTGGCAGCCCGTAATGTCTTA GTGAAATCCCAAACCATGTGAAATC

860  Thr AspPheGlyLeuAlaArgLeuLeuGluGly AspGluLysGluTyrAsnAlaAspGlyGly LysMetProIleLysTrpMetAlaLeu
2611  ACA GATTTTGGGCTAGCCAGACTCTTGGAAGGA GATGAAAAGAGTACAATGCTGATGGAGGA AAGATGCCAATTAAATGATGGCTCTG

890  Glu CysIleHisTyrArgLysPheThrHisGln SerAspValTrpSerTyrGlyValThrIle TrpGluLeuMetThrPheGlyGlyLys
2701  GAG TGTATACATTACAGAGAAATTCACCCATCAG AGTGACGTTTGGAGCTATGGAGTTACTATA TGGGAACTGATGACCTTTGGAGGAAAA

920  Pro TyrAspGlyIleProThrArgGluIlePro AspLeuLeuLysGlyGluArgLeuPro GlnProProIleCysThrIleAspVal
2791  CCC TATGATGGAATTCCAACGCGAGAAATCCCT GATTTATTAGAAGGAGAACGTTGCCT CAGCCTCCCATCTGCACTATTGACGTT

950  Tyr MetValMetValCysTrpMetIleAspGlu AlaAspSerArgProLysPheLysGluLeu AlaAlaGluPheSerArgMetAlaArg
2881  TAC ATGGTCATGTCAAATGTGGATATTGATGAT GCTGACAGTAGACCTAAATTAAGGAACTG GCTGCTGAGTTTTCAAGGATGGCTCGA

980  Asp ProGlnArgTyrLeuValIleGlnGlyAsp AspArgMetLysLeuProSerProAsnAsp SerLysPhePheGlnAsnLeuLeuAsp
2971  GAC CCTCAAAGATACCTAGTTATTCAGGGTGAT GATCGTATGAAGCTTCCCAGTCCAAATGAC AGCAAGTTCTTTCAGAATCTCTTGGAT

1010  Glu GluAspLeuGluAspMetMetAspAlaGlu GluTyrLeuValProGlnAlaPheAsnIle ProProIleTyrThrSerArgAla
3061  GAA GAGGATTTGGAAGATATGATGGATGCTGAG GAGTACTTGGTCCCTCAGGCTTTCAACATC CCACCTCCCATCTATACTTCCAGAGCA
```

FIG. 2C

```
1040  Arg IleAspSerAsnArgSerValArgAsnAsn TyrIleHisIleSerTyrSerPhe***
3151  AGA ATTGACTCGAATAGGAGTGTAAGAAATAAT TATATACACATATCATATTCTTTCTGA
3211  GATATAAATCATGTAATAGTTACATAAGCACTAACATTCAAATAATAATTATAGCTCAAATCAATGTGATGCCTAGATTAAAATATAC
3301  CATACCCACAAAAGATGTGCCAATCTTGCTATATGTAGTAGTTAATTTGGAAGACAAGCATGACAATGTACTCTGAAATACCTT
3391  CAAGATTCAGAAGCAAACATTTCCTACCATCTAATTATTTAAACAAATCTTAAAACATTTAAAAAACATATAAAACCATT
3481  ATGTGTATATAAATGAAAATTCCTACCAAGTAGGCTTTCTACTTTCTTCTTTCTAAAAGATATATGATATATTAGTCAAGAAGTA
3571  ATACAAGTATAAATCTTTCACTTATTAAGAAAATAAATATTTCTGTCAAGTGAAGTAGAACACAGAAACACCGTGCAGTCCTT
3661  TGAACCTAATCACATCGAAAAGCTGCTGAGAAGTAGATTTTGTTTTAAGAAGTAGATTTAAGTTTGAAGGAGTTTCTGAAACAC
3751  TTTACATTTAAATGTAAACATATATTGAATTCCATTCTTTCTTTGAAAGCTGTCAAATCCATGCATTTATTTTTATAAATCAT
3841  TCCTCATACATTCAACATATTGAGTACCACTGTATGTGAAGCATTAGTAGTACATTAAGACTCAAAGAATTTGATACAACTTCTGCT
3931  TTCAAGAAGTGAAAACCTTAATCAAAGAATCATCAGATAGAGGGACTGCATAGTAAGTGCTGTAATCCAGTATTCACTGACCAGTACGG
4021  AGCATGAAGAAGTAGTAAATTGTGTCTGTAATCAGTTTCTTCCATTGATAATAAACATGATGCTTAATTTTTCTAGAAGATAAT
4111  TCTTTCTCTTAATCTAACAACAACATAATTTTCTTTATTTCATAGAGTTCTAGTAGAACCGACAGCATCCGATTTCTCTTGACCATAGCCATAGAAGTTTACTATTCAAC
4201  TTGCTGCTCATTATCTAACAACATAATTCCTTAAACAACAGCAGCTAGTGATGGCAATAATTACACTCTGAGTTCTATTATTCATCCCCCTTCAAGGAAGAAACTGCCACAGA
4291  TATATGTTAACCTCCTTAATCAACAGCTAGTGATATGCAGTTATTCAGCAGTCCTGTCACACAGCTTATTCAGTTATTCCTTAAACAACAGCTAGTTATTCATCCCCCTTCTAGATATCTGCCTACTACACTGTAGTTT
4381  GAAGTCAGGTGATATGACTTACTGAAGYCATGTTATTCAGCTTATTCCAACACTGACCCTGGGACTTGTCGTCTGTTGTTGATGGGAATACATATGGGAATAGATAACTAAAAGTTAAAAT
4471  GCTTCAAAGTTACTGAAGYCATGTTATTCCATGATGTGATTACTACTCCTCCATTGAAGATCTGATATGGAAAGACAAAGATGGAGACCT
4561  ATAAAATGCATCTCAAATCTGCTCTACACCTTTTCTGTAAAAATATATAGTACAACTGAAACTTATCACACATGCGAAACAATTAAAGTTTAAAAT
4651  CAATTATTTTCTTTCTGTAAAATGAATAATCNTTCCTTTGCTTGGAGAGGGAAGAAAGCGTTAAGTGGTTAAGTACTTCTGGTTACAACAGTGAAATTA
4741  TAGATCAATGGATAGTAAATGATCAAATTATATACCCTTGTATTATAATTTTTCTTTATAAATCTTTTATAAGCTAGTAACATGTTGAGCTAGCTAGAATTATGAGATGGAATTATTGAGACTAGCTAGAATTATG
4831  GTACACTTGCAAAATGATCAAATTATATACCCTTGTATTATAATTTTTCTTTATAAATCTTTTATAAGCTAGTAACATGTTGAGCTAGCTAGAATTATG
4921  AAAAAAATAGTTTTCTTTCTTCAGTGCAAGAAATTCTTAATTCCACATTAATAAAGTTTGAGCTAGCTAGAATTATGAGATGGAATTATTGAGACTAGCTAGAATTATG
5011  AATTATATATTCTCAGTGCAAGAAATTCTTAATTCCACATTAATAAAAACAATGTTACCTGTAGATTTCTTTTTACTTTTCAGTCCTGGAAAAG
5101  TTATTGACCTTAGCCATCATTCATTATATCTTAATTCCACATTAATAAAAACAATGTTACCTGTAGATTTCTTTTTACTTTTCAGTCCTGGAAAAG
5191  AAATGTGATTAAATATCATTATTACGGAAATTCTAACATGTCAACATGTACAAATGCCATGTTCCTCCTTTCATCTATATGTCCTAAATGTCCTAATAGTTTCAGTC
5281  TGGCTTTACGTAACTTTTTACGTAACTTTTTAAGTTTGGCTAAATTTAAGAAATGCCATGTTCCTCCTTTCATCTATATGTCCTAAATGTCCTAATAGTTTCAGTC
5371  TACTTCCATTTAAGTTTGATCAAATATTTCTTAAGCATAACGTGTAAGGGAACATCTTAA
5461  AAAGTGAATTTGATCAAATATTTCTTAAGCATGATAGACTTTGAAACCAAAAAAAAAAAAAAAAAAAAAA
5551  AAAAA
```

FIG. 2D

FIG. 3A

HER4 N-terminal truncated with AP domain

```
         CATTAGCTGCAATTGATCAAGTGACTGAGAGAAGGCAACATTCATGCAACAGTATAGTGGTATGGAAAGCCCTGATGTTGA
    1    AATCTAGCTTCAAAAGCCTGTCTGAAAATGTAGTTAATTGGATGAAGTGAGAAGAGATAAAACCAGAGAG GAAGCTCTGATC
   85

MetAlaSerMetAspHisLeuVal ArgLeuLeuGlyLysValCysLeuSerProThr IleGlnLeuValThrGlnLeuMetProHis
    1    ATGGCAAGTATGGATCATCCACACCTAGTC CGGTTGCTGGGTGTGTGTCTGAGCCCAACC ATCCAGCTGTTACTCAACTTATGCCCCAT
  168

GlyCysLeuLeuGluTyrValHisGluHis LysAspAsnIleGlySerGlnLeuLeuLeu AsnTrpCysValGlnIleAlaLysGlyMet
   31    GGCTGCCTGTTGGAGTATGTCGAGCAC AAGGATAACATTGGATCACAACTGCTCTT AACTGGTGTCCAGATAGCTAAGGAATG
  258

MetTyrLeuGluGluArgArgLeuValHis ArgAspLeuAlaAlaArgAsnValLeuVal LysSerProAsnHisValLysIleThrAsp
   61    ATGTACCTGGAAGAAAGACGACTCGTTCAT CGGGATTTGGCAGCCCGTAATGTCTTAGTG AAATCCCAAACCATGTGAAAATCACAGAT
  348

PheGlyLeuAlaArgLeuLeuGluGlyAsp GluLysGluTyrAsnAlaAspGlyGlyLys MetProIleLysTrpMetAlaLeuGluCys
   91    TTTGGGCTAGCCAGACTCTTGGAAGAGAT GAAAAAGAGTACAATGCTGATGGAGAAAG ATGCCAATTAAATGGATGGCTCTGGAGTGT
  438

IleHisTyrArgLysPheThrHisGlnSer AspValTrpSerTyrGlyValThrIleTrp GluLeuMetThrPheGlyLysProTyr
  121    ATACATTACAGGAAATTCACCCATCAGAGT GACGTTTGGAGCTATGGAGTTACTATATGG GAACTGATGACCTTTGGAGAAAACCCTAT
  528

AspGlyIleProThrArgGluIleProAsp LeuLeuGluLysGlyGluArgLeuProGln ProProIleCysThrIleAspValTyrMet
  151    GATGGAATTCCAACGCGAGAAATCCCTGAT TTATTAGAGAAAGGAGAGACGTTGCCTCAG CCTCCCATCTGCACTATTGACGTTTACATG
  618

ValMetValLysCysTrpMetIleAspAla AspSerArgProLysPheLysGluLeuAla AlaGluPheSerArgMetAlaArgAspPro
  181    GTCATGGTCAAATGTTGGATGATTGATGCT GACAGTAGACCTAAATTTAAGGAACTGGCT GCTGAGTTTCAAGGATGGCTCGAGACCCT
  708

GlnArgTyrLeuValIleGlnGlyAspAsp ArgMetLysLeuProSerProAsnAspSer LysPhePheGlnAsnLeuLeuAspGluGlu
  211    CAAAGATACCTAGTTATTCAGGGTGATGAT CGTATGAAGCTTCCAGTCCAAATGACAGC AAGTTCTTCAGAATCTTCTTGATGAAGAG
  798

AspLeuGluAspMetMetAspAlaGluGlu TyrLeuValProGlnAlaPheAsnIlePro ProProIleTyrThrSerArgAlaArgIle
  241    GATTTGGAAGATATGATGGATGCTGAGGAG TACTTGGTCCCTCAGGCTTTCAACATCCA CCTCCCATCTACATCTTCCAGAGCAAGAATT
  888

AspSerAsnArgSerGluIleGlyHisSer ProProProAlaTyrThrProMetSerGly AsnGlnPheValTyrArgAspGlyGlyPhe
  271    GACTCGAATAGGAGTGAAATTGGACACAGC CCTCCTCCTGCCTACACCCCATGTCAGGA AACCAGTTTGTATACCGAGATGGAGGTTTT
  978

AlaAlaGluGlnGlyValSerValProTyr ArgAlaProThrSerThrIleProGluAla ProValAlaGlnGlyAlaThrAlaGluIle
  301    GCTGCTGAACAAGGAGTGTCTGTGCCCTAC AGAGCCCCAACTAGCACAATTCCAGAAGCT CCTGTGGCACAGGGTGCTACTGCTGAGATT
 1068
```

FIG. 3B

HER4
HER4 with alternate 3'-end without Autophosphorylation domain

```
MKPATGLWVWVSLLVAAGTVQPSDSQSVCAGTENKLSSLSDLEQQYRALRKYYENCEVVM    60
::::::::::::::::::::::::::::::::::::::::::::::::::::::::::::
MKPATGLWVWVSLLVAAGTVQPSDSQSVCAGTENKLSSLSDLEQQYRALRKYYENCEVVM    60

GNLEITSIEHNRDLSFLRSVREVTGYVLVALNQFRYLPLENLRIIRGTKLYEDRYALAIF   120
::::::::::::::::::::::::::::::::::::::::::::::::::::::::::::
GNLEITSIEHNRDLSFLRSVREVTGYVLVALNQFRYLPLENLRIIRGTKLYEDRYALAIF   120

LNYRKDGNFGLQELGLKNLTEILNGGVYVDQNKFLCYADTIHWQDIVRNPWPSNLTLVST   180
::::::::::::::::::::::::::::::::::::::::::::::::::::::::::::
LNYRKDGNFGLQELGLKNLTEILNGGVYVDQNKFLCYADTIHWQDIVRNPWPSNLTLVST   180

NGSSGCGRCHKSCTGRCWGPTENHCQTLTRTVCAEQCDGRCYGPYVSDCCHRECAGGCSG   240
::::::::::::::::::::::::::::::::::::::::::::::::::::::::::::
NGSSGCGRCHKSCTGRCWGPTENHCQTLTRTVCAEQCDGRCYGPYVSDCCHRECAGGCSG   240

PKDTDCFACMNFNDSGACVTQCPQTFVYNPTTFQLEHNFNAKYTYGAFCVKKCPHNFVVD   300
::::::::::::::::::::::::::::::::::::::::::::::::::::::::::::
PKDTDCFACMNFNDSGACVTQCPQTFVYNPTTFQLEHNFNAKYTYGAFCVKKCPHNFVVD   300

SSSCVRACPSSKMEVEENGIKMCKPCTDICPKACDGIGTGSLMSAQTVDSSNIDKFINCT   360
::::::::::::::::::::::::::::::::::::::::::::::::::::::::::::
SSSCVRACPSSKMEVEENGIKMCKPCTDICPKACDGIGTGSLMSAQTVDSSNIDKFINCT   360

KINGNLIFLVTGIHGDPYNAIEAIDPEKLNVFRTVREITGFLNIQSWPPNMTDFSVFSNL   420
::::::::::::::::::::::::::::::::::::::::::::::::::::::::::::
KINGNLIFLVTGIHGDPYNAIEAIDPEKLNVFRTVREITGFLNIQSWPPNMTDFSVFSNL   420

VTIGGRVLYSGLSLLILKQQGITSLQFQSLKEISAGNIYITDNSNLCYYHTINWTTLFST   480
::::::::::::::::::::::::::::::::::::::::::::::::::::::::::::
VTIGGRVLYSGLSLLILKQQGITSLQFQSLKEISAGNIYITDNSNLCYYHTINWTTLFST   480

INQRIVIRDNRKAENCTAEGMVCNHLCSSDGCWGPGPDQCLSCRRFSRGRICIESCNLYD   540
::::::::::::::::::::::::::::::::::::::::::::::::::::::::::::
INQRIVIRDNRKAENCTAEGMVCNHLCSSDGCWGPGPDQCLSCRRFSRGRICIESCNLYD   540

GEFREFENGSICVECDPQCEKMEDGLLTCHGPGPDNCTKCSHFKDGPNCVEKCPDGLQGA   600
::::::::::::::::::::::::::::::::::::::::::::::::::::::::::::
GEFREFENGSICVECDPQCEKMEDGLLTCHGPGPDNCTKCSHFKDGPNCVEKCPDGLQGA   600
```

FIG. 4A

```
NSFIFKYADPDRECHPCHPNCTQGCNGPTSHDCIYYPWTGHSTLPQHARTPLIAAGVIGG          660
::::::::::::::::::::::::::::::::::::::::::::::::::::::::::::
NSFIFKYADPDRECHPCHPNCTQGCNGPTSHDCIYYPWTGHSTLPQHARTPLIAAGVIGG          660

LFILVIVGLTFAVYVRRKSIKKKRALRRFLETELVEPLTPSGTAPNQAQLRILKETELKR          720
::::::::::::::::::::::::::::::::::::::::::::::::::::::::::::
LFILVIVGLTFAVYVRRKSIKKKRALRRFLETELVEPLTPSGTAPNQAQLRILKETELKR          720

VKVLGSGAFGTVYKGIWVPEGETVKIPVAIKILNETTGPKANVEFMDEALIMASMDHPHL          780
::::::::::::::::::::::::::::::::::::::::::::::::::::::::::::
VKVLGSGAFGTVYKGIWVPEGETVKIPVAIKILNETTGPKANVEFMDEALIMASMDHPHL          780

VRLLGVCLSPTIQLVTQLMPHGCLLEYVHEHKDNIGSQLLLNWCVQIAKGMMYLEERRLV          840
::::::::::::::::::::::::::::::::::::::::::::::::::::::::::::
VRLLGVCLSPTIQLVTQLMPHGCLLEYVHEHKDNIGSQLLLNWCVQIAKGMMYLEERRLV          840

HRDLAARNVLVKSPNHVKITDFGLARLLEGDEKEYNADGGKMPIKWMALECIHYRKFTHQ          900
::::::::::::::::::::::::::::::::::::::::::::::::::::::::::::
HRDLAARNVLVKSPNHVKITDFGLARLLEGDEKEYNADGGKMPIKWMALECIHYRKFTHQ          900

SDVWSYGVTIWELMTFGGKPYDGIPTREIPDLLEKGERLPQPPICTIDVYMVMVKCWMID          960
::::::::::::::::::::::::::::::::::::::::::::::::::::::::::::
SDVWSYGVTIWELMTFGGKPYDGIPTREIPDLLEKGERLPQPPICTIDVYMVMVKCWMID          960

ADSRPKFKELAAEFSRMARDPQRYLVIQGDDRMKLPSPNDSKFFQNLLDEEDLEDMMDAE         1020
::::::::::::::::::::::::::::::::::::::::::::::::::::::::::::
ADSRPKFKELAAEFSRMARDPQRYLVIQGDDRMKLPSPNDSKFFQNLLDEEDLEDMMDAE         1020

EYLVPQAFNIPPPIYTSRARIDSNRSEIGHSPPPAYTPMSGNQFVYRDGGFAAEQGVSVP         1080
:::::::::::::::::::::::::::::           :.
EYLVPQAFNIPPPIYTSRARIDSNRVRNNYIHIS-YSF                               1057

YRAPTSTIPEAPVAQGATAEIFDDSCCNGTLRKPVAPHVQEDSSTQRYSADPTVFAPERS         1140
PRGELDEEGYMTPMRDKPKQEYLNPVEENPFVSRRKNGDLQALDNPEYHNASNGPPKAED         1200
EYVNEPLYLNTFANTLGKAEYLKNNILSMPEKAKKAFDNPDYWNHSLPPRSTLQHPDYLQ         1260
EYSTKYFYKQNGRIRPIVAENPEYLSEFSLKPGTVLPPPPYRHRNTVV                     1308
```

Aligned 1058, Matches 1046, Mismatches 12, Score 132, Homology 98%

FIG. 4B

HER4
HER4 N-terminal truncated with autophosphorylation domain

```
MKPATGLWVWVSLLVAAGTVQPSDSQSVCAGTENKLSSLSDLEQQYRALRKYYENCEVVM        60
GNLEITSIEHNRDLSFLRSVREVTGYVLVALNQFRYLPLENLRIIRGTKLYEDRYALAIF       120
LNYRKDGNFGLQELGLKNLTEILNGGVYVDQNKFLCYADTIHWQDIVRNPWPSNLTLVST       180
NGSSGCGRCHKSCTGRCWGPTENHCQTLTRTVCAEQCDGRCYGPYVSDCCHRECAGGCSG       240
PKDTDCFACMNFNDSGACVTQCPQTFVYNPTTFQLEHNFNAKYTYGAFCVKKCPHNFVVD       300
SSSCVRACPSSKMEVEENGIKMCKPCTDICPKACDGIGTGSLMSAQTVDSSNIDKFINCT       360
KINGNLIFLVTGIHGDPYNAIEAIDPEKLNVFRTVREITGFLNIQSWPPNMTDFSVFSNL       420
VTIGGRVLYSGLSLLILKQQGITSLQFQSLKEISAGNIYITDNSNLCYYHTINWTTLFST       480
INQRIVIRDNRKAENCTAEGMVCNHLCSSDGCWGPGPDQCLSCRRFSRGRICIESCNLYD       540
GEFREFENGSICVECDPQCEKMEDGLLTCHGPGPDNCTKCSHFKDGPNCVEKCPDGLQGA       600
NSFIFKYADPDRECHPCHPNCTQGCNGPTSHDCIYYPWTGHSTLPQHARTPLIAAGVIGG       660

VKVLGSGAFGTVYKGIWVPEGETVKIPVAIKILNETTGPKANVEFMDEALIMASMDHPHL       780
                                        ::::::::::::
                                        EALIMASMDHPHL        13

VRLLGVCLSPTIQLVTQLMPHGCLLEYVHEHKDNIGSQLLLNWCVQIAKGMMYLEERRLV       840
::::::::::::::::::::::::::::::::::::::::::::::::::::::::::::
VRLLGVCLSPTIQLVTQLMPHGCLLEYVHEHKDNIGSQLLLNWCVQIAKGMMYLEERRLV        73

HRDLAARNVLVKSPNHVKITDFGLARLLEGDEKEYNADGGKMPIKWMALECIHYRKFTHQ       900
::::::::::::::::::::::::::::::::::::::::::::::::::::::::::::
HRDLAARNVLVKSPNHVKITDFGLARLLEGDEKEYNADGGKMPIKWMALECIHYRKFTHQ       133

SDVWSYGVTIWELMTFGGKPYDGIPTREIPDLLEKGERLPQPPICTIDVYMVMVKCWMID       960
::::::::::::::::::::::::::::::::::::::::::::::::::::::::::::
SDVWSYGVTIWELMTFGGKPYDGIPTREIPDLLEKGERLPQPPICTIDVYMVMVKCWMID       193

ADSRPKFKELAAEFSRMARDPQRYLVIQGDDRMKLPSPNDSKFFQNLLDEEDLEDMMDAE      1020
::::::::::::::::::::::::::::::::::::::::::::::::::::::::::::
ADSRPKFKELAAEFSRMARDPQRYLVIQGDDRMKLPSPNDSKFFQNLLDEEDLEDMMDAE       253

EYLVPQAFNIPPPIYTSRARIDSNRSEIGHSPPPAYTPMSGNQFVYRDGGFAAEQGVSVP      1080
::::::::::::::::::::::::::::::::::::::::::::::::::::::::::::
EYLVPQAFNIPPPIYTSRARIDSNRSEIGHSPPPAYTPMSGNQFVYRDGGFAAEQGVSVP       313

YRAPTSTIPEAPVAQGATAEIFDDSCCNGTLRKPVAPHVQEDSSTQRYSADPTVFAPERS      1140
::::::::::::::::::::::::::::::::::::::::::::::::::::::::::::
YRAPTSTIPEAPVAQGATAEIFDDSCCNGTLRKPVAPHVQEDSSTQRYSADPTVFAPERS       373

PRGELDEEGYMTPMRDKPKQEYLNPVEENPFVSRRKNGDLQALDNPEYHNASNGPPKAED      1200
::::::::::::::::::::::::::::::::::::::::::::::::::::::::::::
PRGELDEEGYMTPMRDKPKQEYLNPVEENPFVSRRKNGDLQALDNPEYHNASNGPPKAED       433

EYVNEPLYLNTFANTLGKAEYLKNNILSMPEKAKKAFDNPDYWNHSLPPRSTLQHPDYLQ      1260
::::::::::::::::::::::::::::::::::::::::::::::::::::::::::::
EYVNEPLYLNTFANTLGKAEYLKNNILSMPEKAKKAFDNPDYWNHSLPPRSTLQHPDYLQ       493

EYSTKYFYKQNGRIRPIVAENPEYLSEFSLKPGTVLPPPPYRHRNTVV                  1308
:::::::::::::::::::::::::::::::::::::::::::::::
EYSTKYFYKQNGRIRPIVAENPEYLSEFSLKPGTVLPPPPYRHRNTVV                   541
```

Aligned 541, Matches 541, Mismatches 0, Score 130, Homology 100%

FIG. 5

```
                                                                                                                                         I
HER4    1   MKPA----TGLWVWVSLLVAAGTVQPSDSQSVCAGTENKLSSLSDLEQQYRALRKYYENCEVVMGNLEITSIEHNRDLSFLRSVREVTGYVLVALNQFRY
EGFR  -24   MR.SGTAGAA.LALLAA.CP.S--RALEEKK..Q..S...TQ.GTF.DHFLS.QRMFN.....L.....YVQR.Y.....KTIQ.A....I..TVER
HER2    1   M---ELAALCR.GLLLA.LPP.AA----.TQ..T..DM.RLPASP.THLDM..HL.QG.Q..Q...L.YLPT.AS....QDIQ..Q....I.K..V.Q
HER3  -19   MRAND-ALQVLGLLFS.ARGSE.--GN..A..P..L.G..VTG.A.N..QT.Y.L..R.............VLTG..A......QWI........M.E.ST

II
HER4   97   LPLENLRIIRGTKLYEDRYALAIFLN------YRKDGNFGLQELGLKNLTEILNGGVYVDQNKFLCYADTIHWQDIVRNPWPSNLTIVSTNGSSGCG
EGFR   75   I....Q....NMY..NS....VLS.------.DANKT-..K..PMR..Q...H.A.RFSN.PA..NVES.Q.R...SSDFL..MSMDFQ.HLGS.Q
HER2   94   V..QR...V...Q.F.N...VLD.GDPLNNTTPVTGASPG..R..Q.RS......K...LIQR.PQ...Q...L.K..FHKNNQLA..ID..R.RA.H
HER3   78   ...P....VV...QV.DGKF.IFVM..------.NTNSSHA.RQ.RL.TQ......S....IEK.DK..HM...D.R....DR---DAEI.VKDNGRS.P

III
HER4  188   RCHKSCT-GRCWGPTENHCQTLTRTVCAEQCDGRCYGPYVSDCCHRECAGGCSGPKDTCFACMNFNDSGACVTQCPQTFVYNPTTFQLEHNFNAKYTG
EGFR  165   K.DP..PN.S...AG.EN..K.KII..Q.S...R.KSP....NQ..A..T...RES..LV.RK.R.EAT.KDT..PLML.....Y.MDV.PEG..SF.
HER2  194   P.SPM.KGS...ESSED..S......GG.A-..K..LPT....EQ..A..T....HS..L..LH..H..I.ELH..ALVT..TD..ESMP.PEGR..F.
HER3  166   P..EV.K-.......GSED.........K.I..P..N.H.F..NPNQ....D.......Q........RH......PR....PL...KL....P.PHT..Q..

IV
HER4  287   AFCVKKCPHNFVV-DSSSCVRACPSSKMEVE-ENGIKMCKPCTDICPKADGIGTGSLMSAQTVDSSNIDKFINCTKINGNLIFLVTGIHGDPYNAIEAI
EGFR  265   .T......R.Y..T.HG.....GADSY.M..-.D.VRK..K.EGP.R.V.N...I.EFKDSLSINAT..KH.K...S.S.D.HILPVAFR..SETHTPPL
HER2  293   .S..TA..Y.YLST.VG..TLV..LHNQ.VTA.D.TQR.EK.SKP.ARV.Y..L.MEH.REVRA.T.A..QE.AG.KK.F.S.A..PESFD..ASNTAPL
HER3  265   GV..AS.......QT.......PD.-D-K..L..E..GGL.....E.T.S.--RE......G.V......L...D.I..LN...WHK.P.L

HER4  385   DPEKLNVFRTVREITGFLNIQSWPPNMTDFSVFSNLVTIGGRVLYSGLSLL-ILKQQGITSLQFQSLKEISAGNIYITDNSNLCYHTINWTTLFSTI-N
EGFR  364   ..QE.DILK..K......L..A..E.R..LHA.E..EI.R..TKQH.QFS.-AVVSLN...GLR.......D.DVI.SG.K....AN....KK..G.S-G
HER2  393   Q..Q.Q..E.LE......Y.Y..SA..DSLP.L...Q..QV.R..I.HN.AYS.-T.QGL..SW.GLR...R.LGS.LAL.HH..TH..FV..VP.DQ..RNP-H
HER3  361   ................T......S..NRGFS.L.M.NLNV...G.R.........R...SA.RQ....HHSL......KVLRGPTE

TM
HER4  483   QRIVIRDNRKAENCTAEGMVCNHLCSSDGCWGPGPDQCLSCRRFESRGRICIESCNLYDGEFREFENGSICVECDPQCEKMEDGL-LTCHGPDNCTKCS
EGFR  462   .KTK.IS..GENS.K.T.Q..HA...PE.....E.RD.V...NVS.....E.VDK.K.LE..P...VEN..E.IQ.H.E.--LPQAMNI..T.R....IQ.A
HER2  491   .ALLHTA..PEDE..VG..LA.HQ..ARRALL.S....T..VN.SQ.L..QE.V.E.RVLQ..LP...YV.ARH.LP.H.E.Q--PQNGSV..F..EA.Q.VA.A
HER3  461   E.LD.KH..PRRC..V..K..DP....G.......G.......NY....GV.VTH...FLN...P....AHEAE..FS.H.E..QP.--GTA..N.S.T.AQ.A

HER4  582   HFKDGPNCVEKCPDGLQGANS-F-IFKYADPDRECHPCHNCTQGCNGPTSHDCIYYPWTGHSTLPQHARTPLIAAGVIGGLFILVIVGLTFAVYVRRKS
EGFR  560   .YI..H..KT..A.VM.E.NTL-VW...AGHV..L.....Y..T..GLEG.P------TNGPKI.S..T.MV.A.LL.LV.A.GIGLEM..RH
HER2  589   .Y..P.F..AR..S.VKPDL.YMP.WKFP.EEGA.Q..PI...HS.VDLDDKG.P--------AEQRASPLTS.VSA.V.-ILLV.VL.VV.GILIK.RQ
HER3  559   ..R...H..SS..H.VL..KG--P.Y..P.VQN..R....E......K..ELQ.L-----.QTLVLIGKTHLTM..LT..A..VVIFMM--GGTELYW.GR
```

FIG. 6A

FIG. 6B

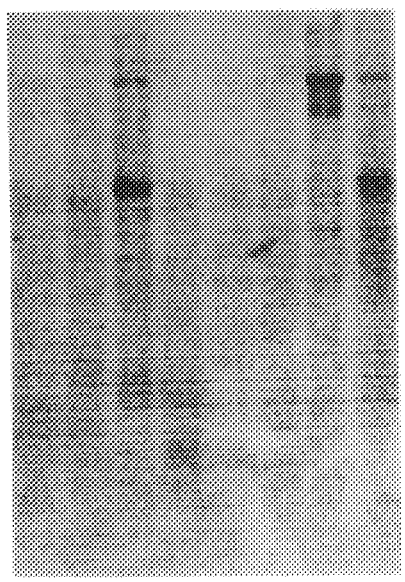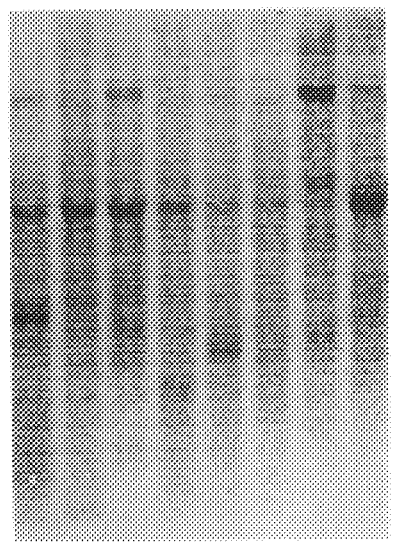
FIG. 8

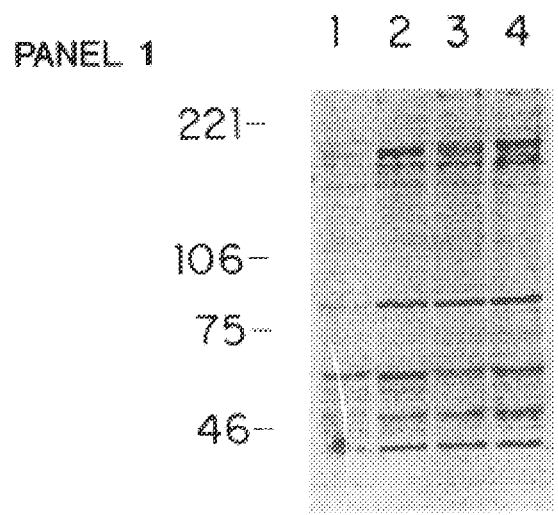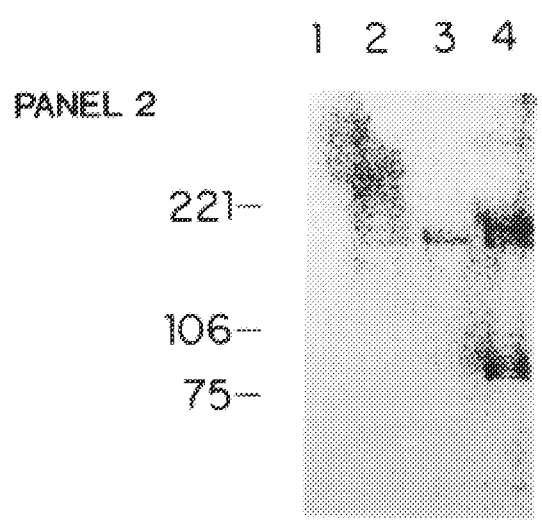
FIG. 9

PANEL 1   1  2  3  4

← HER4

PANEL 2   1  2

HER4-Ig
HER4 extracellular domain-human Ig fusion construct

MKPATGLWVWVSLLVAAGTVQPSDSQSVCAGTENKLSSLSDLEQQYRALRKYYENCEVVM
GNLEITSIEHNRDLSFLRSVREVTGYVLVALNQFRYLPLENLRIIRGTKLYEDRYALAIF
LNYRKDGNFGLQELGLKNLTEILNGGVYVDQNKFLCYADTIHWQDIVRNPWPSNLTLVST
NGSSGGCGRCHKSCTGRCWGPTENHCQTLTRTVCAEQCDGRCYGPYVSDCCHRECAGGCSG
PKDTDCFACMNFNDSGACVTQCPQTFVYNPTTFQLEHNFNAKYTYGAFCVKKCPHNFVVD
SSSCVRACPSSKMEVEENGIKMCKPCTDICPKACDGIGTGSLMSAQTVDSSNIDKFINCT
KINGNLIFLVTGIHGDPYNAIEAIDPEKLNVFRTVREITGFLNIQSWPPNMTDFSVFSNL
VTIGGRVLYSGLSLLILKQQGITSLQFQSLKEISAGNIYITDNSNLCYHTINWTTLFST
INQRIVIRDNRKAENCTAEGMVCNHLCSSDGCWGPGPDQCLSCRRFSRGRICIESCNLYD
GEFREFENGSICVECDPQCEKMEDGLLTCHGPGPDNCTKCSHFKDGPNCVEKCPDGLQGA
NSFIFKYADPDRECHPCHPNCTQGCNGPTSHDCIYYPWTGHSTLPQDPVKVKALEGFPRL
VGPDFFGCAEPANTFLDPEEPKSCDKTHTCPPCPAPELLGGPSVFLFPPKPKDTLMISRT
PEVTCVVVDVSHEDPEVKFNWYVDGVEVHVAKTKPREEQYNSTYRVVSVLTVLHQDWLNG
KEYKCKVSNKALPAPIEKTISKAKGQPREPQVYTLPPSRDELTKNQVSLTCLVKGFYPSD
IAVEWESNGQPENNYKTTPPVLDSDGSFFLYSKLTVDKSRWQQGNVFSCSVMHEALHNHY
TQKSLSLSPGK

Bold = Signal Sequence
 = Immunoglobin domain

Lower case = HER4 ECD

FIG. 14

Unlabeled p45:   —  +  —  +  —  +

PANEL 1

PANEL 2

AR leader MVVKPPQNKTESENTSDKPKRKKKGGKNGKNRRNR-

HRGβ2 SHLIKCAEKEKTFCVNGGECFTVKDLSNPSRYLCKC

PNEFTGDRCQNYVMASFYKAEELY

```
ATG GTA GTT AAG CCC CCC CAA AAC AAG ACG GAA AGT GAA AAT ACT TCA    48
Met Val Val Lys Pro Pro Gln Asn Lys Thr Glu Ser Glu Asn Thr Ser
1                5                 10                  15

GAT AAA CCC AAA AGA AAG AAA AAG GGA GGC AAA AAT GGA AAA AAT AGA    96
Asp Lys Pro Lys Arg Lys Lys Lys Gly Gly Lys Asn Gly Lys Asn Arg
            20                  25                  30

AGA AAC AGA AGC CAT CTC ATA AAG TGT GCG GAG AAG GAG AAA ACT TTC   144
Arg Asn Arg Ser His Leu Ile Lys Cys Ala Glu Lys Glu Lys Thr Phe
        35                  40                  45

TGT GTG AAT GGG GGC GAG TGC TTC ACG GTG AAG GAC CTG TCA AAC CCG   192
Cys Val Asn Gly Gly Glu Cys Phe Thr Val Lys Asp Leu Ser Asn Pro
    50                  55                  60

TCA AGA TAC TTG TGC AAG TGC CCG AAC GAA TTT ACT GGC GAC CGT TGC   240
Ser Arg Tyr Leu Cys Lys Cys Pro Asn Glu Phe Thr Gly Asp Arg Cys
65                  70                  75                  80

CAG AAC TAT GTT ATG GCA TCT TTT TAC AAA GCG GAG GAA CTC TAC AAG   288
Gln Asn Tyr Val Met Ala Ser Phe Tyr Lys Ala Glu Glu Leu Tyr Lys
                85                  90                  95

CTT ATG GCC GAG GAA GGC GGC AGC CTG GCC GCG CTG ACC GCG CAC CAG   336
Leu Met Ala Glu Glu Gly Gly Ser Leu Ala Ala Leu Thr Ala His Gln
            100                 105                 110

GCT TGC CAC CTG CCG CTG GAG ACT TTC ACC CGT CAT CGC CAG CCG CGC   384
Ala Cys His Leu Pro Leu Glu Thr Phe Thr Arg His Arg Gln Pro Arg
        115                 120                 125

GGC TGG GAA CAA CTG GAG CAG TGC GGC TAT CCG GTG CAG CGG CTG GTC   432
Gly Trp Glu Gln Leu Glu Gln Cys Gly Tyr Pro Val Gln Arg Leu Val
    130                 135                 140

GCC CTC TAC CTG GCG GCG CGG CTG TCG TGG AAC CAG GTC GAC CAG GTG   480
Ala Leu Tyr Leu Ala Ala Arg Leu Ser Trp Asn Gln Val Asp Gln Val
145                 150                 155                 160

ATC CGC AAC GCC CTG GCC AGC CCC GGC AGC GGC GGC GAC CTG GGC GAA   528
Ile Arg Asn Ala Leu Ala Ser Pro Gly Ser Gly Gly Asp Leu Gly Glu
                165                 170                 175

GCG ATC CGC GAG CAG CCG GAG CAG GCC CGT CTG GCC CTG ACC CTG GCC   576
Ala Ile Arg Glu Gln Pro Glu Gln Ala Arg Leu Ala Leu Thr Leu Ala
            180                 185                 190

GCC GCC GAG AGC GAG CGC TTC GTC CGG CAG GGC ACC GGC AAC GAC GAG   624
Ala Ala Glu Ser Glu Arg Phe Val Arg Gln Gly Thr Gly Asn Asp Glu
        195                 200                 205

GCC GGC GCG GCC AAC GCC GAC GTG GTG AGC CTG ACC TGC CCG GTC GCC   672
Ala Gly Ala Ala Asn Ala Asp Val Val Ser Leu Thr Cys Pro Val Ala
    210                 215                 220

GCC GGT GAA TGC GCG GGC CCG GCG GAC AGC GGC GAC GCC CTG CTG GAG   720
Ala Gly Glu Cys Ala Gly Pro Ala Asp Ser Gly Asp Ala Leu Leu Glu
225                 230                 235                 240
```

FIG. 24A

```
CGC AAC TAT CCC ACT GGC GCG GAG TTC CTC GGC GAC GGC GGC GAC GTC      768
Arg Asn Tyr Pro Thr Gly Ala Glu Phe Leu Gly Asp Gly Gly Asp Val
            245             250             255

AGC TTC AGC ACC CGC GGC ACG CAG AAC TGG ACG GTG GAG CGG CTG CTC      816
Ser Phe Ser Thr Arg Gly Thr Gln Asn Trp Thr Val Glu Arg Leu Leu
            260             265             270

CAG GCG CAC CGC CAA CTG GAG GAG CGC GGC TAT GTG TTC GTC GGC TAC      864
Gln Ala His Arg Gln Leu Glu Glu Arg Gly Tyr Val Phe Val Gly Tyr
            275             280             285

CAC GGC ACC TTC CTC GAA GCG GCG CAA AGC ATC GTC TTC GGC GGG GTG      912
His Gly Thr Phe Leu Glu Ala Ala Gln Ser Ile Val Phe Gly Gly Val
            290             295             300

CGC GCG CGC AGC CAG GAC CTC GAC GCG ATC TGG CGC GGT TTC TAT ATC      960
Arg Ala Arg Ser Gln Asp Leu Asp Ala Ile Trp Arg Gly Phe Tyr Ile
305             310             315             320

GCC GGC GAT CCG GCG CTG GCC TAC GGC TAC GCC CAG GAC CAG GAA CCC     1008
Ala Gly Asp Pro Ala Leu Ala Tyr Gly Tyr Ala Gln Asp Gln Glu Pro
            325             330             335

GAC GCA CGC GGC CGG ATC CGC AAC GGT GCC CTG CTG CGG GTC TAT GTG     1056
Asp Ala Arg Gly Arg Ile Arg Asn Gly Ala Leu Leu Arg Val Tyr Val
            340             345             350

CCG CGC TCG AGC CTG CCG GGC TTC TAC CGC ACC AGC CTG ACC CTG GCC     1104
Pro Arg Ser Ser Leu Pro Gly Phe Tyr Arg Thr Ser Leu Thr Leu Ala
            355             360             365

GGC GGC GAG GCG GCG GGC GAG GTC GAA CGG CTG ATC GGC CAT CCG CTG     1152
Gly Gly Glu Ala Ala Gly Glu Val Glu Arg Leu Ile Gly His Pro Leu
            370             375             380

CCG CTG CGC CTG GAC GCC ATC ACC GGC CCC GAG GAG GAA GGC GGG CGC     1200
Pro Leu Arg Leu Asp Ala Ile Thr Gly Pro Glu Glu Glu Gly Gly Arg
385             390             395             400

CTG GAG ACC ATT CTC GGC TGG CCG CTG GCC GAG CGC ACC GTG GTG ATT     1248
Leu Glu Thr Ile Leu Gly Trp Pro Leu Ala Glu Arg Thr Val Val Ile
            405             410             415

CCC TCG GCG ATC CCC ACC GAC CCG CGC AAC GTC GGC GGC GAC CTC GAC     1296
Pro Ser Ala Ile Pro Thr Asp Pro Arg Asn Val Gly Gly Asp Leu Asp
            420             425             430

CCG TCC AGC ATC CCC GAC AAG GAA CAG GCG ATC AGC GCC CTG CCG GAC     1344
Pro Ser Ser Ile Pro Asp Lys Glu Gln Ala Ile Ser Ala Leu Pro Asp
            435             440             445

TAC GCC AGC CAG CCC GGC AAA CCG CCG CGC GAG GAC CTG AAG              1386
Tyr Ala Ser Gln Pro Gly Lys Pro Pro Arg Glu Asp Leu Lys
450             455             460

TAA
```

FIG. 24B

PANEL 1
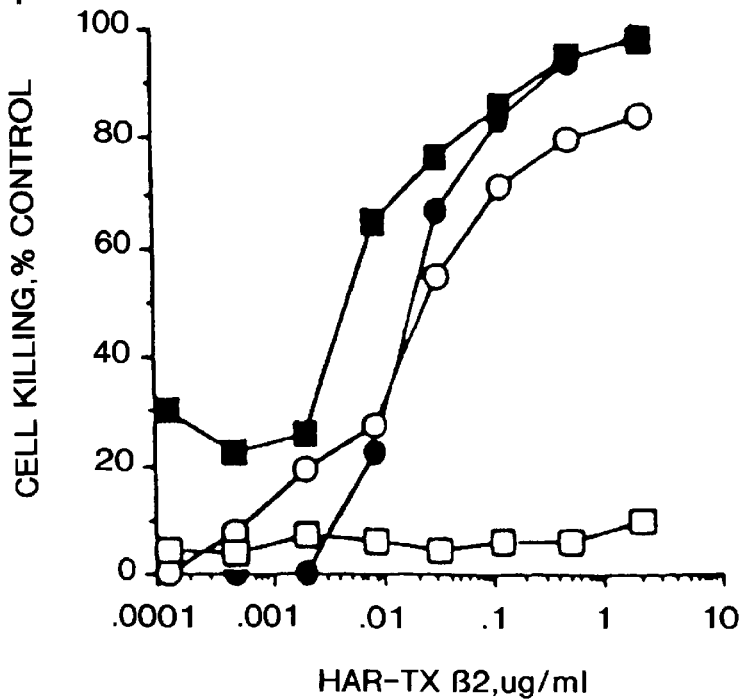
PANEL 2
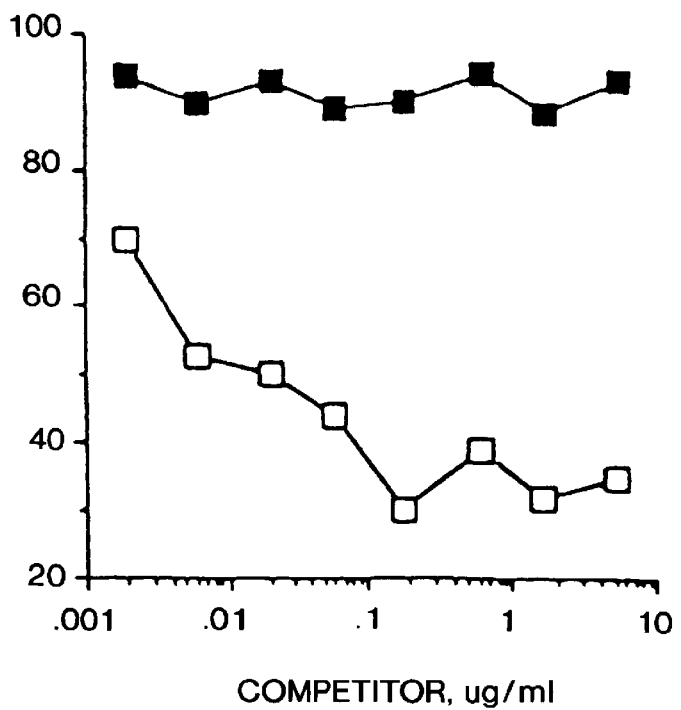
FIG. 28

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 5501 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 34..3961

( x i ) SEQUENCE DESCRIPTION: SEQ ID NO:1:

```
AATTGTCAGC ACGGGATCTG AGACTTCCAA AAA ATG AAG CCG GCG ACA GGA CTT         54
                                    Met Lys Pro Ala Thr Gly Leu
                                     1               5

TGG GTC TGG GTG AGC CTT CTC GTG GCG GCG GGG ACC GTC CAG CCC AGC        102
Trp Val Trp Val Ser Leu Leu Val Ala Ala Gly Thr Val Gln Pro Ser
         10              15                  20

GAT TCT CAG TCA GTG TGT GCA GGA ACG GAG AAT AAA CTG AGC TCT CTC        150
Asp Ser Gln Ser Val Cys Ala Gly Thr Glu Asn Lys Leu Ser Ser Leu
     25                  30                  35

TCT GAC CTG GAA CAG CAG TAC CGA GCC TTG CGC AAG TAC TAT GAA AAC        198
Ser Asp Leu Glu Gln Gln Tyr Arg Ala Leu Arg Lys Tyr Tyr Glu Asn
 40              45                  50                      55

TGT GAG GTT GTC ATG GGC AAC CTG GAG ATA ACC AGC ATT GAG CAC AAC        246
Cys Glu Val Val Met Gly Asn Leu Glu Ile Thr Ser Ile Glu His Asn
                 60                  65                  70

CGG GAC CTC TCC TTC CTG CGG TCT GTT CGA GAA GTC ACA GGC TAC GTG        294
Arg Asp Leu Ser Phe Leu Arg Ser Val Arg Glu Val Thr Gly Tyr Val
             75                  80                  85

TTA GTG GCT CTT AAT CAG TTT CGT TAC CTG CCT CTG GAG AAT TTA CGC        342
Leu Val Ala Leu Asn Gln Phe Arg Tyr Leu Pro Leu Glu Asn Leu Arg
             90                  95                 100

ATT ATT CGT GGG ACA AAA CTT TAT GAG GAT CGA TAT GCC TTG GCA ATA        390
Ile Ile Arg Gly Thr Lys Leu Tyr Glu Asp Arg Tyr Ala Leu Ala Ile
     105                 110                 115

TTT TTA AAC TAC AGA AAA GAT GGA AAC TTT GGA CTT CAA GAA CTT GGA        438
Phe Leu Asn Tyr Arg Lys Asp Gly Asn Phe Gly Leu Gln Glu Leu Gly
120              125                 130                     135

TTA AAG AAC TTG ACA GAA ATC CTA AAT GGT GGA GTC TAT GTA GAC CAG        486
Leu Lys Asn Leu Thr Glu Ile Leu Asn Gly Gly Val Tyr Val Asp Gln
                 140                 145                 150

AAC AAA TTC CTT TGT TAT GCA GAC ACC ATT CAT TGG CAA GAT ATT GTT        534
Asn Lys Phe Leu Cys Tyr Ala Asp Thr Ile His Trp Gln Asp Ile Val
                     155                 160                 165

CGG AAC CCA TGG CCT TCC AAC TTG ACT CTT GTG TCA ACA AAT GGT AGT        582
Arg Asn Pro Trp Pro Ser Asn Leu Thr Leu Val Ser Thr Asn Gly Ser
             170                 175                 180

TCA GGA TGT GGA CGT TGC CAT AAG TCC TGT ACT GGC CGT TGC TGG GGA        630
Ser Gly Cys Gly Arg Cys His Lys Ser Cys Thr Gly Arg Cys Trp Gly
 185                 190                 195
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| CCC | ACA | GAA | AAT | CAT | TGC | CAG | ACT | TTG | ACA | AGG | ACG | GTG | TGT | GCA | GAA | 678  |
| Pro | Thr | Glu | Asn | His | Cys | Gln | Thr | Leu | Thr | Arg | Thr | Val | Cys | Ala | Glu |      |
| 200 |     |     |     |     | 205 |     |     |     |     | 210 |     |     |     |     | 215 |      |
| CAA | TGT | GAC | GGC | AGA | TGC | TAC | GGA | CCT | TAC | GTC | AGT | GAC | TGC | TGC | CAT | 726  |
| Gln | Cys | Asp | Gly | Arg | Cys | Tyr | Gly | Pro | Tyr | Val | Ser | Asp | Cys | Cys | His |      |
|     |     |     |     | 220 |     |     |     |     | 225 |     |     |     |     |     | 230 |      |
| CGA | GAA | TGT | GCT | GGA | GGC | TGC | TCA | GGA | CCT | AAG | GAC | ACA | GAC | TGC | TTT | 774  |
| Arg | Glu | Cys | Ala | Gly | Gly | Cys | Ser | Gly | Pro | Lys | Asp | Thr | Asp | Cys | Phe |      |
|     |     |     | 235 |     |     |     |     | 240 |     |     |     |     | 245 |     |     |      |
| GCC | TGC | ATG | AAT | TTC | AAT | GAC | AGT | GGA | GCA | TGT | GTT | ACT | CAG | TGT | CCC | 822  |
| Ala | Cys | Met | Asn | Phe | Asn | Asp | Ser | Gly | Ala | Cys | Val | Thr | Gln | Cys | Pro |      |
|     | 250 |     |     |     |     | 255 |     |     |     |     | 260 |     |     |     |     |      |
| CAA | ACC | TTT | GTC | TAC | AAT | CCA | ACC | ACC | TTT | CAA | CTG | GAG | CAC | AAT | TTC | 870  |
| Gln | Thr | Phe | Val | Tyr | Asn | Pro | Thr | Thr | Phe | Gln | Leu | Glu | His | Asn | Phe |      |
| 265 |     |     |     |     |     | 270 |     |     |     |     | 275 |     |     |     |     |      |
| AAT | GCA | AAG | TAC | ACA | TAT | GGA | GCA | TTC | TGT | GTC | AAG | AAA | TGT | CCA | CAT | 918  |
| Asn | Ala | Lys | Tyr | Thr | Tyr | Gly | Ala | Phe | Cys | Val | Lys | Lys | Cys | Pro | His |      |
| 280 |     |     |     |     | 285 |     |     |     |     | 290 |     |     |     |     | 295 |      |
| AAC | TTT | GTG | GTA | GAT | TCC | AGT | TCT | TGT | GTG | CGT | GCC | TGC | CCT | AGT | TCC | 966  |
| Asn | Phe | Val | Val | Asp | Ser | Ser | Ser | Cys | Val | Arg | Ala | Cys | Pro | Ser | Ser |      |
|     |     |     |     | 300 |     |     |     |     | 305 |     |     |     |     | 310 |     |      |
| AAG | ATG | GAA | GTA | GAA | GAA | AAT | GGG | ATT | AAA | ATG | TGT | AAA | CCT | TGC | ACT | 1014 |
| Lys | Met | Glu | Val | Glu | Glu | Asn | Gly | Ile | Lys | Met | Cys | Lys | Pro | Cys | Thr |      |
|     |     |     | 315 |     |     |     |     | 320 |     |     |     |     | 325 |     |     |      |
| GAC | ATT | TGC | CCA | AAA | GCT | TGT | GAT | GGC | ATT | GGC | ACA | GGA | TCA | TTG | ATG | 1062 |
| Asp | Ile | Cys | Pro | Lys | Ala | Cys | Asp | Gly | Ile | Gly | Thr | Gly | Ser | Leu | Met |      |
|     |     | 330 |     |     |     |     | 335 |     |     |     |     | 340 |     |     |     |      |
| TCA | GCT | CAG | ACT | GTG | GAT | TCC | AGT | AAC | ATT | GAC | AAA | TTC | ATA | AAC | TGT | 1110 |
| Ser | Ala | Gln | Thr | Val | Asp | Ser | Ser | Asn | Ile | Asp | Lys | Phe | Ile | Asn | Cys |      |
| 345 |     |     |     |     |     | 350 |     |     |     |     | 355 |     |     |     |     |      |
| ACC | AAG | ATC | AAT | GGG | AAT | TTG | ATC | TTT | CTA | GTC | ACT | GGT | ATT | CAT | GGG | 1158 |
| Thr | Lys | Ile | Asn | Gly | Asn | Leu | Ile | Phe | Leu | Val | Thr | Gly | Ile | His | Gly |      |
| 360 |     |     |     |     | 365 |     |     |     |     | 370 |     |     |     |     | 375 |      |
| GAC | CCT | TAC | AAT | GCA | ATT | GAA | GCC | ATA | GAC | CCA | GAG | AAA | CTG | AAC | GTC | 1206 |
| Asp | Pro | Tyr | Asn | Ala | Ile | Glu | Ala | Ile | Asp | Pro | Glu | Lys | Leu | Asn | Val |      |
|     |     |     |     | 380 |     |     |     |     | 385 |     |     |     |     | 390 |     |      |
| TTT | CGG | ACA | GTC | AGA | GAG | ATA | ACA | GGT | TTC | CTG | AAC | ATA | CAG | TCA | TGG | 1254 |
| Phe | Arg | Thr | Val | Arg | Glu | Ile | Thr | Gly | Phe | Leu | Asn | Ile | Gln | Ser | Trp |      |
|     |     |     | 395 |     |     |     |     | 400 |     |     |     |     | 405 |     |     |      |
| CCA | CCA | AAC | ATG | ACT | GAC | TTC | AGT | GTT | TTT | TCT | AAC | CTG | GTG | ACC | ATT | 1302 |
| Pro | Pro | Asn | Met | Thr | Asp | Phe | Ser | Val | Phe | Ser | Asn | Leu | Val | Thr | Ile |      |
|     |     | 410 |     |     |     |     | 415 |     |     |     |     | 420 |     |     |     |      |
| GGT | GGA | AGA | GTA | CTC | TAT | AGT | GGC | CTG | TCC | TTG | CTT | ATC | CTC | AAG | CAA | 1350 |
| Gly | Gly | Arg | Val | Leu | Tyr | Ser | Gly | Leu | Ser | Leu | Leu | Ile | Leu | Lys | Gln |      |
| 425 |     |     |     |     |     | 430 |     |     |     |     | 435 |     |     |     |     |      |
| CAG | GGC | ATC | ACC | TCT | CTA | CAG | TTC | CAG | TCC | CTG | AAG | GAA | ATC | AGC | GCA | 1398 |
| Gln | Gly | Ile | Thr | Ser | Leu | Gln | Phe | Gln | Ser | Leu | Lys | Glu | Ile | Ser | Ala |      |
| 440 |     |     |     |     | 445 |     |     |     |     | 450 |     |     |     |     | 455 |      |
| GGA | AAC | ATC | TAT | ATT | ACT | GAC | AAC | AGC | AAC | CTG | TGT | TAT | TAT | CAT | ACC | 1446 |
| Gly | Asn | Ile | Tyr | Ile | Thr | Asp | Asn | Ser | Asn | Leu | Cys | Tyr | Tyr | His | Thr |      |
|     |     |     |     | 460 |     |     |     |     | 465 |     |     |     |     | 470 |     |      |
| ATT | AAC | TGG | ACA | ACA | CTC | TTC | AGC | ACA | ATC | AAC | CAG | AGA | ATA | GTA | ATC | 1494 |
| Ile | Asn | Trp | Thr | Thr | Leu | Phe | Ser | Thr | Ile | Asn | Gln | Arg | Ile | Val | Ile |      |
|     |     |     | 475 |     |     |     |     | 480 |     |     |     |     | 485 |     |     |      |
| CGG | GAC | AAC | AGA | AAA | GCT | GAA | AAT | TGT | ACT | GCT | GAA | GGA | ATG | GTG | TGC | 1542 |
| Arg | Asp | Asn | Arg | Lys | Ala | Glu | Asn | Cys | Thr | Ala | Glu | Gly | Met | Val | Cys |      |
|     |     | 490 |     |     |     |     | 495 |     |     |     |     | 500 |     |     |     |      |
| AAC | CAT | CTG | TGT | TCC | AGT | GAT | GGC | TGT | TGG | GGA | CCT | GGG | CCA | GAC | CAA | 1590 |
| Asn | His | Leu | Cys | Ser | Ser | Asp | Gly | Cys | Trp | Gly | Pro | Gly | Pro | Asp | Gln |      |
| 505 |     |     |     |     |     | 510 |     |     |     |     | 515 |     |     |     |     |      |

| | | | | | | | | | | | | | | | | |
|---|---|---|---|---|---|---|---|---|---|---|---|---|---|---|---|---|
| TGT | CTG | TCG | TGT | CGC | CGC | TTC | AGT | AGA | GGA | AGG | ATC | TGC | ATA | GAG | TCT | 1638 |
| Cys | Leu | Ser | Cys | Arg | Arg | Phe | Ser | Arg | Gly | Arg | Ile | Cys | Ile | Glu | Ser | |
| 520 | | | | | 525 | | | | | 530 | | | | | 535 | |
| TGT | AAC | CTC | TAT | GAT | GGT | GAA | TTT | CGG | GAG | TTT | GAG | AAT | GGC | TCC | ATC | 1686 |
| Cys | Asn | Leu | Tyr | Asp | Gly | Glu | Phe | Arg | Glu | Phe | Glu | Asn | Gly | Ser | Ile | |
| | | | | 540 | | | | | 545 | | | | | 550 | | |
| TGT | GTG | GAG | TGT | GAC | CCC | CAG | TGT | GAG | AAG | ATG | GAA | GAT | GGC | CTC | CTC | 1734 |
| Cys | Val | Glu | Cys | Asp | Pro | Gln | Cys | Glu | Lys | Met | Glu | Asp | Gly | Leu | Leu | |
| | | | | 555 | | | | | 560 | | | | | 565 | | |
| ACA | TGC | CAT | GGA | CCG | GGT | CCT | GAC | AAC | TGT | ACA | AAG | TGC | TCT | CAT | TTT | 1782 |
| Thr | Cys | His | Gly | Pro | Gly | Pro | Asp | Asn | Cys | Thr | Lys | Cys | Ser | His | Phe | |
| | | 570 | | | | | 575 | | | | | 580 | | | | |
| AAA | GAT | GGC | CCA | AAC | TGT | GTG | GAA | AAA | TGT | CCA | GAT | GGC | TTA | CAG | GGG | 1830 |
| Lys | Asp | Gly | Pro | Asn | Cys | Val | Glu | Lys | Cys | Pro | Asp | Gly | Leu | Gln | Gly | |
| | 585 | | | | | 590 | | | | | 595 | | | | | |
| GCA | AAC | AGT | TTC | ATT | TTC | AAG | TAT | GCT | GAT | CCA | GAT | CGG | GAG | TGC | CAC | 1878 |
| Ala | Asn | Ser | Phe | Ile | Phe | Lys | Tyr | Ala | Asp | Pro | Asp | Arg | Glu | Cys | His | |
| 600 | | | | | 605 | | | | | 610 | | | | | 615 | |
| CCA | TGC | CAT | CCA | AAC | TGC | ACC | CAA | GGG | TGT | AAC | GGT | CCC | ACT | AGT | CAT | 1926 |
| Pro | Cys | His | Pro | Asn | Cys | Thr | Gln | Gly | Cys | Asn | Gly | Pro | Thr | Ser | His | |
| | | | | 620 | | | | | 625 | | | | | 630 | | |
| GAC | TGC | ATT | TAC | TAC | CCA | TGG | ACG | GGC | CAT | TCC | ACT | TTA | CCA | CAA | CAT | 1974 |
| Asp | Cys | Ile | Tyr | Tyr | Pro | Trp | Thr | Gly | His | Ser | Thr | Leu | Pro | Gln | His | |
| | | | 635 | | | | | 640 | | | | | 645 | | | |
| GCT | AGA | ACT | CCC | CTG | ATT | GCA | GCT | GGA | GTA | ATT | GGT | GGG | CTC | TTC | ATT | 2022 |
| Ala | Arg | Thr | Pro | Leu | Ile | Ala | Ala | Gly | Val | Ile | Gly | Gly | Leu | Phe | Ile | |
| | | 650 | | | | | 655 | | | | | 660 | | | | |
| CTG | GTC | ATT | GTG | GGT | CTG | ACA | TTT | GCT | GTT | TAT | GTT | AGA | AGG | AAG | AGC | 2070 |
| Leu | Val | Ile | Val | Gly | Leu | Thr | Phe | Ala | Val | Tyr | Val | Arg | Arg | Lys | Ser | |
| | 665 | | | | | 670 | | | | | 675 | | | | | |
| ATC | AAA | AAG | AAA | AGA | GCC | TTG | AGA | AGA | TTC | TTG | GAA | ACA | GAG | TTG | GTG | 2118 |
| Ile | Lys | Lys | Lys | Arg | Ala | Leu | Arg | Arg | Phe | Leu | Glu | Thr | Glu | Leu | Val | |
| 680 | | | | | 685 | | | | | 690 | | | | | 695 | |
| GAA | CCA | TTA | ACT | CCC | AGT | GGC | ACA | GCA | CCC | AAT | CAA | GCT | CAA | CTT | CGT | 2166 |
| Glu | Pro | Leu | Thr | Pro | Ser | Gly | Thr | Ala | Pro | Asn | Gln | Ala | Gln | Leu | Arg | |
| | | | | 700 | | | | | 705 | | | | | 710 | | |
| ATT | TTG | AAA | GAA | ACT | GAG | CTG | AAG | AGG | GTA | AAA | GTC | CTT | GGC | TCA | GGT | 2214 |
| Ile | Leu | Lys | Glu | Thr | Glu | Leu | Lys | Arg | Val | Lys | Val | Leu | Gly | Ser | Gly | |
| | | | | 715 | | | | | 720 | | | | | 725 | | |
| GCT | TTT | GGA | ACG | GTT | TAT | AAA | GGT | ATT | TGG | GTA | CCT | GAA | GGA | GAA | ACT | 2262 |
| Ala | Phe | Gly | Thr | Val | Tyr | Lys | Gly | Ile | Trp | Val | Pro | Glu | Gly | Glu | Thr | |
| | | 730 | | | | | 735 | | | | | 740 | | | | |
| GTG | AAG | ATT | CCT | GTG | GCT | ATT | AAG | ATT | CTT | AAT | GAG | ACA | ACT | GGT | CCC | 2310 |
| Val | Lys | Ile | Pro | Val | Ala | Ile | Lys | Ile | Leu | Asn | Glu | Thr | Thr | Gly | Pro | |
| | 745 | | | | | 750 | | | | | 755 | | | | | |
| AAG | GCA | AAT | GTG | GAG | TTC | ATG | GAT | GAA | GCT | CTG | ATC | ATG | GCA | AGT | ATG | 2358 |
| Lys | Ala | Asn | Val | Glu | Phe | Met | Asp | Glu | Ala | Leu | Ile | Met | Ala | Ser | Met | |
| 760 | | | | | 765 | | | | | 770 | | | | | 775 | |
| GAT | CAT | CCA | CAC | CTA | GTC | CGG | TTG | CTG | GGT | GTG | TGT | CTG | AGC | CCA | ACC | 2406 |
| Asp | His | Pro | His | Leu | Val | Arg | Leu | Leu | Gly | Val | Cys | Leu | Ser | Pro | Thr | |
| | | | | 780 | | | | | 785 | | | | | 790 | | |
| ATC | CAG | CTG | GTT | ACT | CAA | CTT | ATG | CCC | CAT | GGC | TGC | CTG | TTG | GAG | TAT | 2454 |
| Ile | Gln | Leu | Val | Thr | Gln | Leu | Met | Pro | His | Gly | Cys | Leu | Leu | Glu | Tyr | |
| | | | 795 | | | | | 800 | | | | | 805 | | | |
| GTC | CAC | GAG | CAC | AAG | GAT | AAC | ATT | GGA | TCA | CAA | CTG | CTG | CTT | AAC | TGG | 2502 |
| Val | His | Glu | His | Lys | Asp | Asn | Ile | Gly | Ser | Gln | Leu | Leu | Leu | Asn | Trp | |
| | | 810 | | | | | 815 | | | | | 820 | | | | |
| TGT | GTC | CAG | ATA | GCT | AAG | GGA | ATG | ATG | TAC | CTG | GAA | GAA | AGA | CGA | CTC | 2550 |
| Cys | Val | Gln | Ile | Ala | Lys | Gly | Met | Met | Tyr | Leu | Glu | Glu | Arg | Arg | Leu | |
| | 825 | | | | | 830 | | | | | 835 | | | | | |

```
GTT CAT CGG GAT TTG GCA GCC CGT AAT GTC TTA GTG AAA TCT CCA AAC      2598
Val His Arg Asp Leu Ala Ala Arg Asn Val Leu Val Lys Ser Pro Asn
840             845             850             855

CAT GTG AAA ATC ACA GAT TTT GGG CTA GCC AGA CTC TTG GAA GGA GAT      2646
His Val Lys Ile Thr Asp Phe Gly Leu Ala Arg Leu Leu Glu Gly Asp
        860             865             870

GAA AAA GAG TAC AAT GCT GAT GGA GGA AAG ATG CCA ATT AAA TGG ATG      2694
Glu Lys Glu Tyr Asn Ala Asp Gly Gly Lys Met Pro Ile Lys Trp Met
        875             880             885

GCT CTG GAG TGT ATA CAT TAC AGG AAA TTC ACC CAT CAG AGT GAC GTT      2742
Ala Leu Glu Cys Ile His Tyr Arg Lys Phe Thr His Gln Ser Asp Val
        890             895             900

TGG AGC TAT GGA GTT ACT ATA TGG GAA CTG ATG ACC TTT GGA GGA AAA      2790
Trp Ser Tyr Gly Val Thr Ile Trp Glu Leu Met Thr Phe Gly Gly Lys
        905             910             915

CCC TAT GAT GGA ATT CCA ACG CGA GAA ATC CCT GAT TTA TTA GAG AAA      2838
Pro Tyr Asp Gly Ile Pro Thr Arg Glu Ile Pro Asp Leu Leu Glu Lys
920             925             930             935

GGA GAA CGT TTG CCT CAG CCT CCC ATC TGC ACT ATT GAC GTT TAC ATG      2886
Gly Glu Arg Leu Pro Gln Pro Pro Ile Cys Thr Ile Asp Val Tyr Met
        940             945             950

GTC ATG GTC AAA TGT TGG ATG ATT GAT GCT GAC AGT AGA CCT AAA TTT      2934
Val Met Val Lys Cys Trp Met Ile Asp Ala Asp Ser Arg Pro Lys Phe
        955             960             965

AAG GAA CTG GCT GCT GAG TTT TCA AGG ATG GCT CGA GAC CCT CAA AGA      2982
Lys Glu Leu Ala Ala Glu Phe Ser Arg Met Ala Arg Asp Pro Gln Arg
        970             975             980

TAC CTA GTT ATT CAG GGT GAT GAT CGT ATG AAG CTT CCC AGT CCA AAT      3030
Tyr Leu Val Ile Gln Gly Asp Asp Arg Met Lys Leu Pro Ser Pro Asn
985             990             995

GAC AGC AAG TTC TTT CAG AAT CTC TTG GAT GAA GAG GAT TTG GAA GAT      3078
Asp Ser Lys Phe Phe Gln Asn Leu Leu Asp Glu Glu Asp Leu Glu Asp
1000            1005            1010            1015

ATG ATG GAT GCT GAG GAG TAC TTG GTC CCT CAG GCT TTC AAC ATC CCA      3126
Met Met Asp Ala Glu Glu Tyr Leu Val Pro Gln Ala Phe Asn Ile Pro
                1020            1025            1030

CCT CCC ATC TAT ACT TCC AGA GCA AGA ATT GAC TCG AAT AGG AGT GAA      3174
Pro Pro Ile Tyr Thr Ser Arg Ala Arg Ile Asp Ser Asn Arg Ser Glu
                1035            1040            1045

ATT GGA CAC AGC CCT CCT CCT GCC TAC ACC CCC ATG TCA GGA AAC CAG      3222
Ile Gly His Ser Pro Pro Pro Ala Tyr Thr Pro Met Ser Gly Asn Gln
        1050            1055            1060

TTT GTA TAC CGA GAT GGA GGT TTT GCT GCT GAA CAA GGA GTG TCT GTG      3270
Phe Val Tyr Arg Asp Gly Gly Phe Ala Ala Glu Gln Gly Val Ser Val
        1065            1070            1075

CCC TAC AGA GCC CCA ACT AGC ACA ATT CCA GAA GCT CCT GTG GCA CAG      3318
Pro Tyr Arg Ala Pro Thr Ser Thr Ile Pro Glu Ala Pro Val Ala Gln
1080            1085            1090            1095

GGT GCT ACT GCT GAG ATT TTT GAT GAC TCC TGC TGT AAT GGC ACC CTA      3366
Gly Ala Thr Ala Glu Ile Phe Asp Asp Ser Cys Cys Asn Gly Thr Leu
                1100            1105            1110

CGC AAG CCA GTG GCA CCC CAT GTC CAA GAG GAC AGT AGC ACC CAG AGG      3414
Arg Lys Pro Val Ala Pro His Val Gln Glu Asp Ser Ser Thr Gln Arg
        1115            1120            1125

TAC AGT GCT GAC CCC ACC GTG TTT GCC CCA GAA CGG AGC CCA CGA GGA      3462
Tyr Ser Ala Asp Pro Thr Val Phe Ala Pro Glu Arg Ser Pro Arg Gly
        1130            1135            1140

GAG CTG GAT GAG GAA GGT TAC ATG ACT CCT ATG CGA GAC AAA CCC AAA      3510
Glu Leu Asp Glu Glu Gly Tyr Met Thr Pro Met Arg Asp Lys Pro Lys
        1145            1150            1155
```

-continued

| | | | | | | | | | | | | | | | | |
|---|---|---|---|---|---|---|---|---|---|---|---|---|---|---|---|---|
| CAA | GAA | TAC | CTG | AAT | CCA | GTG | GAG | GAG | AAC | CCT | TTT | GTT | TCT | CGG | AGA | 3558 |
| Gln | Glu | Tyr | Leu | Asn | Pro | Val | Glu | Glu | Asn | Pro | Phe | Val | Ser | Arg | Arg | |
| 1160 | | | | | 1165 | | | | | 1170 | | | | | 1175 | |
| AAA | AAT | GGA | GAC | CTT | CAA | GCA | TTG | GAT | AAT | CCC | GAA | TAT | CAC | AAT | GCA | 3606 |
| Lys | Asn | Gly | Asp | Leu | Gln | Ala | Leu | Asp | Asn | Pro | Glu | Tyr | His | Asn | Ala | |
| | | | | 1180 | | | | | 1185 | | | | | 1190 | | |
| TCC | AAT | GGT | CCA | CCC | AAG | GCC | GAG | GAT | GAG | TAT | GTG | AAT | GAG | CCA | CTG | 3654 |
| Ser | Asn | Gly | Pro | Pro | Lys | Ala | Glu | Asp | Glu | Tyr | Val | Asn | Glu | Pro | Leu | |
| | | | 1195 | | | | | 1200 | | | | | 1205 | | | |
| TAC | CTC | AAC | ACC | TTT | GCC | AAC | ACC | TTG | GGA | AAA | GCT | GAG | TAC | CTG | AAG | 3702 |
| Tyr | Leu | Asn | Thr | Phe | Ala | Asn | Thr | Leu | Gly | Lys | Ala | Glu | Tyr | Leu | Lys | |
| | | 1210 | | | | | 1215 | | | | | 1220 | | | | |
| AAC | AAC | ATA | CTG | TCA | ATG | CCA | GAG | AAG | GCC | AAG | AAA | GCG | TTT | GAC | AAC | 3750 |
| Asn | Asn | Ile | Leu | Ser | Met | Pro | Glu | Lys | Ala | Lys | Lys | Ala | Phe | Asp | Asn | |
| | | 1225 | | | | | 1230 | | | | | 1235 | | | | |
| CCT | GAC | TAC | TGG | AAC | CAC | AGC | CTG | CCA | CCT | CGG | AGC | ACC | CTT | CAG | CAC | 3798 |
| Pro | Asp | Tyr | Trp | Asn | His | Ser | Leu | Pro | Pro | Arg | Ser | Thr | Leu | Gln | His | |
| 1240 | | | | | 1245 | | | | | 1250 | | | | | 1255 | |
| CCA | GAC | TAC | CTG | CAG | GAG | TAC | AGC | ACA | AAA | TAT | TTT | TAT | AAA | CAG | AAT | 3846 |
| Pro | Asp | Tyr | Leu | Gln | Glu | Tyr | Ser | Thr | Lys | Tyr | Phe | Tyr | Lys | Gln | Asn | |
| | | | | 1260 | | | | | 1265 | | | | | 1270 | | |
| GGG | CGG | ATC | CGG | CCT | ATT | GTG | GCA | GAG | AAT | CCT | GAA | TAC | CTC | TCT | GAG | 3894 |
| Gly | Arg | Ile | Arg | Pro | Ile | Val | Ala | Glu | Asn | Pro | Glu | Tyr | Leu | Ser | Glu | |
| | | | 1275 | | | | | 1280 | | | | | 1285 | | | |
| TTC | TCC | CTG | AAG | CCA | GGC | ACT | GTG | CTG | CCG | CCT | CCA | CCT | TAC | AGA | CAC | 3942 |
| Phe | Ser | Leu | Lys | Pro | Gly | Thr | Val | Leu | Pro | Pro | Pro | Pro | Tyr | Arg | His | |
| | | 1290 | | | | | 1295 | | | | | 1300 | | | | |
| CGG | AAT | ACT | GTG | GTG | TAAGCTCAGT | | TGTGGTTTTT | | TAGGTGGAGA | | GACACACCTG | | | | | 3997 |
| Arg | Asn | Thr | Val | Val | | | | | | | | | | | | |
| | | 1305 | | | | | | | | | | | | | | |

```
CTCCAATTTC  CCCACCCCCC  TCTCTTTCTC  TGGTGGTCTT  CCTTCTACCC  CAAGGCCAGT   4057
AGTTTTGACA  CTTCCCAGTG  GAAGATACAG  AGATGCAATG  ATAGTTATGT  GCTTACCTAA   4117
CTTGAACATT  AGAGGGAAAG  ACTGAAAGAG  AAAGATAGGA  GGAACCACAA  TGTTTCTTCA   4177
TTTCTCTGCA  TGGGTTGGTC  AGGAGAATGA  AACAGCTAGA  GAAGGACCAG  AAAATGTAAG   4237
GCAATGCTGC  CTACTATCAA  ACTAGCTGTC  ACTTTTTTTC  TTTTTCTTTT  TCTTTCTTTG   4297
TTTCTTTCTT  CCTCTTCTTT  TTTTTTTTTT  TTTTAAAGCA  GATGGTTGAA  ACACCCATGC   4357
TATCTGTTCC  TATCTGCAGG  AACTGATGTG  TGCATATTTA  GCATCCCTGG  AAATCATAAT   4417
AAAGTTTCCA  TTAGAACAAA  AGAATAACAT  TTTCTATAAC  ATATGATAGT  GTCTGAAATT   4477
GAGAATCCAG  TTTCTTTCCC  CAGCAGTTTC  TGTCCTAGCA  AGTAAGAATG  CCAACTCAA    4537
CTTTCATAAT  TTAAAAATCT  CCATTAAAGT  TATAACTAGT  AATTATGTTT  TCAACACTTT   4597
TTGGTTTTTT  TCATTTTGTT  TTGCTCTGAC  CGATTCCTTT  ATATTTGCTC  CCCTATTTTT   4657
GGCTTTAATT  TCTAATTGCA  AAGATGTTTA  CATCAAAGCT  TCTTCACAGA  ATTTAAGCAA   4717
GAAATATTTT  AATATAGTGA  AATGGCCACT  ACTTTAAGTA  TACAATCTTT  AAAATAAGAA   4777
AGGGAGGCTA  ATATTTTTCA  TGCTATCAAA  TTATCTTCAC  CCTCATCCTT  TACATTTTTC   4837
AACATTTTTT  TTTCTCCATA  AATGACACTA  CTTGATAGGC  CGTTGGTTGT  CTGAAGAGTA   4897
GAAGGGAAAC  TAAGAGACAG  TTCTCTGTGG  TTCAGGAAAA  CTACTGATAC  TTTCAGGGGT   4957
GGCCCAATGA  GGGAATCCAT  TGAACTGGAA  GAAACACACT  GGATTGGGTA  TGTCTACCTG   5017
GCAGATACTC  AGAAATGTAG  TTTGCACTTA  AGCTGTAATT  TTATTTGTTC  TTTTTCTGAA   5077
CTCCATTTTG  GATTTTGAAT  CAAGCAATAT  GGAAGCAACC  AGCAAATTAA  CTAATTTAAG   5137
TACATTTTTA  AAAAAAGAGC  TAAGATAAAG  ACTGTGGAAA  TGCCAAACCA  AGCAAATTAG   5197
```

-continued

```
GAACCTTGCA  ACGGTATCCA  GGGACTATGA  TGAGAGGCCA  GCACATTATC  TTCATATGTC    5257

ACCTTTGCTA  CGCAAGGAAA  TTTGTTCAGT  TCGTATACTT  CGTAAGAAGG  AATGCGAGTA    5317

AGGATTGGCT  TGAATTCCAT  GGAATTTCTA  GTATGAGACT  ATTTATATGA  AGTAGAAGGT    5377

AACTCTTTGC  ACATAAATTG  GTATAATAAA  AGAAAAACA   CAAACATTCA  AAGCTTAGGG    5437

ATAGGTCCTT  GGGTCAAAAG  TTGTAAATAA  ATGTGAAACA  TCTTCTCAAA  AAAAAAAAA    5497

AAAA                                                                      5501
```

(2) INFORMATION FOR SEQ ID NO:2:

(i) SEQUENCE CHARACTERISTICS:
        (A) LENGTH: 1308 amino acids
        (B) TYPE: amino acid
        (D) TOPOLOGY: linear (ii) MOLECULE TYPE: protein (xi) SEQUENCE DESCRIPTION: SEQ ID NO:2:

```
Met Lys Pro Ala Thr Gly Leu Trp Val Trp Val Ser Leu Leu Val Ala
  1               5                  10                  15

Ala Gly Thr Val Gln Pro Ser Asp Ser Gln Ser Val Cys Ala Gly Thr
             20                  25                  30

Glu Asn Lys Leu Ser Ser Leu Ser Asp Leu Glu Gln Gln Tyr Arg Ala
         35                  40                  45

Leu Arg Lys Tyr Tyr Glu Asn Cys Glu Val Val Met Gly Asn Leu Glu
     50                  55                  60

Ile Thr Ser Ile Glu His Asn Arg Asp Leu Ser Phe Leu Arg Ser Val
 65                  70                  75                  80

Arg Glu Val Thr Gly Tyr Val Leu Val Ala Leu Asn Gln Phe Arg Tyr
                 85                  90                  95

Leu Pro Leu Glu Asn Leu Arg Ile Ile Arg Gly Thr Lys Leu Tyr Glu
                100                 105                 110

Asp Arg Tyr Ala Leu Ala Ile Phe Leu Asn Tyr Arg Lys Asp Gly Asn
            115                 120                 125

Phe Gly Leu Gln Glu Leu Gly Leu Lys Asn Leu Thr Glu Ile Leu Asn
    130                 135                 140

Gly Gly Val Tyr Val Asp Gln Asn Lys Phe Leu Cys Tyr Ala Asp Thr
145                 150                 155                 160

Ile His Trp Gln Asp Ile Val Arg Asn Pro Trp Pro Ser Asn Leu Thr
                165                 170                 175

Leu Val Ser Thr Asn Gly Ser Ser Gly Cys Gly Arg Cys His Lys Ser
            180                 185                 190

Cys Thr Gly Arg Cys Trp Gly Pro Thr Glu Asn His Cys Gln Thr Leu
        195                 200                 205

Thr Arg Thr Val Cys Ala Glu Gln Cys Asp Gly Arg Cys Tyr Gly Pro
    210                 215                 220

Tyr Val Ser Asp Cys Cys His Arg Glu Cys Ala Gly Gly Cys Ser Gly
225                 230                 235                 240

Pro Lys Asp Thr Asp Cys Phe Ala Cys Met Asn Phe Asn Asp Ser Gly
                245                 250                 255

Ala Cys Val Thr Gln Cys Pro Gln Thr Phe Val Tyr Asn Pro Thr Thr
            260                 265                 270

Phe Gln Leu Glu His Asn Phe Asn Ala Lys Tyr Thr Tyr Gly Ala Phe
        275                 280                 285

Cys Val Lys Lys Cys Pro His Asn Phe Val Val Asp Ser Ser Ser Cys
```

-continued

|     |     |     | 290 |     |     |     |     | 295 |     |     |     |     | 300 |     |     |
| --- | --- | --- | --- | --- | --- | --- | --- | --- | --- | --- | --- | --- | --- | --- | --- |

Val Arg Ala Cys Pro Ser Ser Lys Met Glu Val Glu Glu Asn Gly Ile
305                 310                 315                 320

Lys Met Cys Lys Pro Cys Thr Asp Ile Cys Pro Lys Ala Cys Asp Gly
                325                 330                 335

Ile Gly Thr Gly Ser Leu Met Ser Ala Gln Thr Val Asp Ser Ser Asn
                340                 345                 350

Ile Asp Lys Phe Ile Asn Cys Thr Lys Ile Asn Gly Asn Leu Ile Phe
            355                 360                 365

Leu Val Thr Gly Ile His Gly Asp Pro Tyr Asn Ala Ile Glu Ala Ile
    370                 375                 380

Asp Pro Glu Lys Leu Asn Val Phe Arg Thr Val Arg Glu Ile Thr Gly
385                 390                 395                 400

Phe Leu Asn Ile Gln Ser Trp Pro Pro Asn Met Thr Asp Phe Ser Val
                405                 410                 415

Phe Ser Asn Leu Val Thr Ile Gly Gly Arg Val Leu Tyr Ser Gly Leu
            420                 425                 430

Ser Leu Leu Ile Leu Lys Gln Gln Gly Ile Thr Ser Leu Gln Phe Gln
        435                 440                 445

Ser Leu Lys Glu Ile Ser Ala Gly Asn Ile Tyr Ile Thr Asp Asn Ser
    450                 455                 460

Asn Leu Cys Tyr Tyr His Thr Ile Asn Trp Thr Thr Leu Phe Ser Thr
465                 470                 475                 480

Ile Asn Gln Arg Ile Val Ile Arg Asp Asn Arg Lys Ala Glu Asn Cys
                485                 490                 495

Thr Ala Glu Gly Met Val Cys Asn His Leu Cys Ser Ser Asp Gly Cys
                500                 505                 510

Trp Gly Pro Gly Pro Asp Gln Cys Leu Ser Cys Arg Arg Phe Ser Arg
            515                 520                 525

Gly Arg Ile Cys Ile Glu Ser Cys Asn Leu Tyr Asp Gly Glu Phe Arg
    530                 535                 540

Glu Phe Glu Asn Gly Ser Ile Cys Val Glu Cys Asp Pro Gln Cys Glu
545                 550                 555                 560

Lys Met Glu Asp Gly Leu Leu Thr Cys His Gly Pro Gly Pro Asp Asn
                565                 570                 575

Cys Thr Lys Cys Ser His Phe Lys Asp Gly Pro Asn Cys Val Glu Lys
            580                 585                 590

Cys Pro Asp Gly Leu Gln Gly Ala Asn Ser Phe Ile Phe Lys Tyr Ala
        595                 600                 605

Asp Pro Asp Arg Glu Cys His Pro Cys His Pro Asn Cys Thr Gln Gly
610                 615                 620

Cys Asn Gly Pro Thr Ser His Asp Cys Ile Tyr Tyr Pro Trp Thr Gly
625                 630                 635                 640

His Ser Thr Leu Pro Gln His Ala Arg Thr Pro Leu Ile Ala Ala Gly
                645                 650                 655

Val Ile Gly Gly Leu Phe Ile Leu Val Ile Val Gly Leu Thr Phe Ala
            660                 665                 670

Val Tyr Val Arg Arg Lys Ser Ile Lys Lys Lys Arg Ala Leu Arg Arg
        675                 680                 685

Phe Leu Glu Thr Glu Leu Val Glu Pro Leu Thr Pro Ser Gly Thr Ala
    690                 695                 700

Pro Asn Gln Ala Gln Leu Arg Ile Leu Lys Glu Thr Glu Leu Lys Arg
705                 710                 715                 720

-continued

```
Val Lys Val Leu Gly Ser Gly Ala Phe Gly Thr Val Tyr Lys Gly Ile
            725             730             735

Trp Val Pro Glu Gly Glu Thr Val Lys Ile Pro Val Ala Ile Lys Ile
            740             745             750

Leu Asn Glu Thr Thr Gly Pro Lys Ala Asn Val Glu Phe Met Asp Glu
            755             760             765

Ala Leu Ile Met Ala Ser Met Asp His Pro His Leu Val Arg Leu Leu
770             775             780

Gly Val Cys Leu Ser Pro Thr Ile Gln Leu Val Thr Gln Leu Met Pro
785             790             795             800

His Gly Cys Leu Leu Glu Tyr Val His Glu His Lys Asp Asn Ile Gly
            805             810             815

Ser Gln Leu Leu Leu Asn Trp Cys Val Gln Ile Ala Lys Gly Met Met
            820             825             830

Tyr Leu Glu Glu Arg Arg Leu Val His Arg Asp Leu Ala Ala Arg Asn
            835             840             845

Val Leu Val Lys Ser Pro Asn His Val Lys Ile Thr Asp Phe Gly Leu
            850             855             860

Ala Arg Leu Leu Glu Gly Asp Glu Lys Glu Tyr Asn Ala Asp Gly Gly
865             870             875             880

Lys Met Pro Ile Lys Trp Met Ala Leu Glu Cys Ile His Tyr Arg Lys
            885             890             895

Phe Thr His Gln Ser Asp Val Trp Ser Tyr Gly Val Thr Ile Trp Glu
            900             905             910

Leu Met Thr Phe Gly Gly Lys Pro Tyr Asp Gly Ile Pro Thr Arg Glu
            915             920             925

Ile Pro Asp Leu Leu Glu Lys Gly Glu Arg Leu Pro Gln Pro Pro Ile
            930             935             940

Cys Thr Ile Asp Val Tyr Met Val Met Val Lys Cys Trp Met Ile Asp
945             950             955             960

Ala Asp Ser Arg Pro Lys Phe Lys Glu Leu Ala Ala Glu Phe Ser Arg
            965             970             975

Met Ala Arg Asp Pro Gln Arg Tyr Leu Val Ile Gln Gly Asp Asp Arg
            980             985             990

Met Lys Leu Pro Ser Pro Asn Asp Ser Lys Phe Phe Gln Asn Leu Leu
            995             1000            1005

Asp Glu Glu Asp Leu Glu Asp Met Met Asp Ala Glu Glu Tyr Leu Val
            1010            1015            1020

Pro Gln Ala Phe Asn Ile Pro Pro Pro Ile Tyr Thr Ser Arg Ala Arg
1025            1030            1035            1040

Ile Asp Ser Asn Arg Ser Glu Ile Gly His Ser Pro Pro Pro Ala Tyr
            1045            1050            1055

Thr Pro Met Ser Gly Asn Gln Phe Val Tyr Arg Asp Gly Gly Phe Ala
            1060            1065            1070

Ala Glu Gln Gly Val Ser Val Pro Tyr Arg Ala Pro Thr Ser Thr Ile
            1075            1080            1085

Pro Glu Ala Pro Val Ala Gln Gly Ala Thr Ala Glu Ile Phe Asp Asp
            1090            1095            1100

Ser Cys Cys Asn Gly Thr Leu Arg Lys Pro Val Ala Pro His Val Gln
1105            1110            1115            1120

Glu Asp Ser Ser Thr Gln Arg Tyr Ser Ala Asp Pro Thr Val Phe Ala
            1125            1130            1135

Pro Glu Arg Ser Pro Arg Gly Glu Leu Asp Glu Glu Gly Tyr Met Thr
            1140            1145            1150
```

| | | | | | | | | | | | | | | |
|---|---|---|---|---|---|---|---|---|---|---|---|---|---|---|
| Pro | Met | Arg | Asp | Lys | Pro | Lys | Gln | Glu | Tyr | Leu | Asn | Pro | Val | Glu | Glu |
| | | | 1155 | | | | 1160 | | | | | 1165 | | | |
| Asn | Pro | Phe | Val | Ser | Arg | Arg | Lys | Asn | Gly | Asp | Leu | Gln | Ala | Leu | Asp |
| | 1170 | | | | | 1175 | | | | | 1180 | | | | |
| Asn | Pro | Glu | Tyr | His | Asn | Ala | Ser | Asn | Gly | Pro | Pro | Lys | Ala | Glu | Asp |
| 1185 | | | | | 1190 | | | | | 1195 | | | | | 1200 |
| Glu | Tyr | Val | Asn | Glu | Pro | Leu | Tyr | Leu | Asn | Thr | Phe | Ala | Asn | Thr | Leu |
| | | | | 1205 | | | | | 1210 | | | | | 1215 | |
| Gly | Lys | Ala | Glu | Tyr | Leu | Lys | Asn | Asn | Ile | Leu | Ser | Met | Pro | Glu | Lys |
| | | | | 1220 | | | | | 1225 | | | | 1230 | | |
| Ala | Lys | Lys | Ala | Phe | Asp | Asn | Pro | Asp | Tyr | Trp | Asn | His | Ser | Leu | Pro |
| | | | 1235 | | | | | 1240 | | | | | 1245 | | |
| Pro | Arg | Ser | Thr | Leu | Gln | His | Pro | Asp | Tyr | Leu | Gln | Glu | Tyr | Ser | Thr |
| | | 1250 | | | | | 1255 | | | | | 1260 | | | |
| Lys | Tyr | Phe | Tyr | Lys | Gln | Asn | Gly | Arg | Ile | Arg | Pro | Ile | Val | Ala | Glu |
| 1265 | | | | | | 1270 | | | | | 1275 | | | | 1280 |
| Asn | Pro | Glu | Tyr | Leu | Ser | Glu | Phe | Ser | Leu | Lys | Pro | Gly | Thr | Val | Leu |
| | | | | | 1285 | | | | | 1290 | | | | | 1295 |
| Pro | Pro | Pro | Pro | Tyr | Arg | His | Arg | Asn | Thr | Val | Val | | | | |
| | | | 1300 | | | | | 1305 | | | | | | | |

( 2 ) INFORMATION FOR SEQ ID NO:3:

( i ) SEQUENCE CHARACTERISTICS:
        ( A ) LENGTH: 5555 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 34..3210

( x i ) SEQUENCE DESCRIPTION: SEQ ID NO:3:

| | | | | | | | | | | | | | | | | |
|---|---|---|---|---|---|---|---|---|---|---|---|---|---|---|---|---|
| AATTGTCAGC | ACGGGATCTG | AGACTTCCAA | AAA | ATG | AAG | CCG | GCG | ACA | GGA | CTT | | | | | | 54 |
| | | | | Met | Lys | Pro | Ala | Thr | Gly | Leu | | | | | | |
| | | | | 1 | | | | 5 | | | | | | | | |
| TGG | GTC | TGG | GTG | AGC | CTT | CTC | GTG | GCG | GCG | GGG | ACC | GTC | CAG | CCC | AGC | 102 |
| Trp | Val | Trp | Val | Ser | Leu | Leu | Val | Ala | Ala | Gly | Thr | Val | Gln | Pro | Ser | |
| | | 10 | | | | | 15 | | | | | 20 | | | | |
| GAT | TCT | CAG | TCA | GTG | TGT | GCA | GGA | ACG | GAG | AAT | AAA | CTG | AGC | TCT | CTC | 150 |
| Asp | Ser | Gln | Ser | Val | Cys | Ala | Gly | Thr | Glu | Asn | Lys | Leu | Ser | Ser | Leu | |
| | 25 | | | | 30 | | | | | 35 | | | | | | |
| TCT | GAC | CTG | GAA | CAG | CAG | TAC | CGA | GCC | TTG | CGC | AAG | TAC | TAT | GAA | AAC | 198 |
| Ser | Asp | Leu | Glu | Gln | Gln | Tyr | Arg | Ala | Leu | Arg | Lys | Tyr | Tyr | Glu | Asn | |
| 40 | | | | | 45 | | | | | 50 | | | | | 55 | |
| TGT | GAG | GTT | GTC | ATG | GGC | AAC | CTG | GAG | ATA | ACC | AGC | ATT | GAG | CAC | AAC | 246 |
| Cys | Glu | Val | Val | Met | Gly | Asn | Leu | Glu | Ile | Thr | Ser | Ile | Glu | His | Asn | |
| | | | | 60 | | | | | 65 | | | | | 70 | | |
| CGG | GAC | CTC | TCC | TTC | CTG | CGG | TCT | GTT | CGA | GAA | GTC | ACA | GGC | TAC | GTG | 294 |
| Arg | Asp | Leu | Ser | Phe | Leu | Arg | Ser | Val | Arg | Glu | Val | Thr | Gly | Tyr | Val | |
| | | | 75 | | | | | 80 | | | | | 85 | | | |
| TTA | GTG | GCT | CTT | AAT | CAG | TTT | CGT | TAC | CTG | CCT | CTG | GAG | AAT | TTA | CGC | 342 |
| Leu | Val | Ala | Leu | Asn | Gln | Phe | Arg | Tyr | Leu | Pro | Leu | Glu | Asn | Leu | Arg | |
| | | 90 | | | | | 95 | | | | | 100 | | | | |
| ATT | ATT | CGT | GGG | ACA | AAA | CTT | TAT | GAG | GAT | CGA | TAT | GCC | TTG | GCA | ATA | 390 |
| Ile | Ile | Arg | Gly | Thr | Lys | Leu | Tyr | Glu | Asp | Arg | Tyr | Ala | Leu | Ala | Ile | |
| | | 105 | | | | | 110 | | | | | 115 | | | | |

-continued

| | | | | | | | | | | | | | | | | |
|---|---|---|---|---|---|---|---|---|---|---|---|---|---|---|---|---|
| TTT | TTA | AAC | TAC | AGA | AAA | GAT | GGA | AAC | TTT | GGA | CTT | CAA | GAA | CTT | GGA | 438 |
| Phe | Leu | Asn | Tyr | Arg | Lys | Asp | Gly | Asn | Phe | Gly | Leu | Gln | Glu | Leu | Gly | |
| 120 | | | | 125 | | | | | 130 | | | | | | 135 | |
| TTA | AAG | AAC | TTG | ACA | GAA | ATC | CTA | AAT | GGT | GGA | GTC | TAT | GTA | GAC | CAG | 486 |
| Leu | Lys | Asn | Leu | Thr | Glu | Ile | Leu | Asn | Gly | Gly | Val | Tyr | Val | Asp | Gln | |
| | | | 140 | | | | 145 | | | | | | 150 | | | |
| AAC | AAA | TTC | CTT | TGT | TAT | GCA | GAC | ACC | ATT | CAT | TGG | CAA | GAT | ATT | GTT | 534 |
| Asn | Lys | Phe | Leu | Cys | Tyr | Ala | Asp | Thr | Ile | His | Trp | Gln | Asp | Ile | Val | |
| | | | 155 | | | | 160 | | | | | | 165 | | | |
| CGG | AAC | CCA | TGG | CCT | TCC | AAC | TTG | ACT | CTT | GTG | TCA | ACA | AAT | GGT | AGT | 582 |
| Arg | Asn | Pro | Trp | Pro | Ser | Asn | Leu | Thr | Leu | Val | Ser | Thr | Asn | Gly | Ser | |
| | | 170 | | | | | 175 | | | | | 180 | | | | |
| TCA | GGA | TGT | GGA | CGT | TGC | CAT | AAG | TCC | TGT | ACT | GGC | CGT | TGC | TGG | GGA | 630 |
| Ser | Gly | Cys | Gly | Arg | Cys | His | Lys | Ser | Cys | Thr | Gly | Arg | Cys | Trp | Gly | |
| | 185 | | | | | 190 | | | | | 195 | | | | | |
| CCC | ACA | GAA | AAT | CAT | TGC | CAG | ACT | TTG | ACA | AGG | ACG | GTG | TGT | GCA | GAA | 678 |
| Pro | Thr | Glu | Asn | His | Cys | Gln | Thr | Leu | Thr | Arg | Thr | Val | Cys | Ala | Glu | |
| 200 | | | | | 205 | | | | | 210 | | | | | 215 | |
| CAA | TGT | GAC | GGC | AGA | TGC | TAC | GGA | CCT | TAC | GTC | AGT | GAC | TGC | TGC | CAT | 726 |
| Gln | Cys | Asp | Gly | Arg | Cys | Tyr | Gly | Pro | Tyr | Val | Ser | Asp | Cys | Cys | His | |
| | | | | 220 | | | | | 225 | | | | | | 230 | |
| CGA | GAA | TGT | GCT | GGA | GGC | TGC | TCA | GGA | CCT | AAG | GAC | ACA | GAC | TGC | TTT | 774 |
| Arg | Glu | Cys | Ala | Gly | Gly | Cys | Ser | Gly | Pro | Lys | Asp | Thr | Asp | Cys | Phe | |
| | | | 235 | | | | | 240 | | | | | 245 | | | |
| GCC | TGC | ATG | AAT | TTC | AAT | GAC | AGT | GGA | GCA | TGT | GTT | ACT | CAG | TGT | CCC | 822 |
| Ala | Cys | Met | Asn | Phe | Asn | Asp | Ser | Gly | Ala | Cys | Val | Thr | Gln | Cys | Pro | |
| | | 250 | | | | | 255 | | | | | 260 | | | | |
| CAA | ACC | TTT | GTC | TAC | AAT | CCA | ACC | ACC | TTT | CAA | CTG | GAG | CAC | AAT | TTC | 870 |
| Gln | Thr | Phe | Val | Tyr | Asn | Pro | Thr | Thr | Phe | Gln | Leu | Glu | His | Asn | Phe | |
| | | 265 | | | | | 270 | | | | | 275 | | | | |
| AAT | GCA | AAG | TAC | ACA | TAT | GGA | GCA | TTC | TGT | GTC | AAG | AAA | TGT | CCA | CAT | 918 |
| Asn | Ala | Lys | Tyr | Thr | Tyr | Gly | Ala | Phe | Cys | Val | Lys | Lys | Cys | Pro | His | |
| 280 | | | | | 285 | | | | | 290 | | | | | 295 | |
| AAC | TTT | GTG | GTA | GAT | TCC | AGT | TCT | TGT | GTG | CGT | GCC | TGC | CCT | AGT | TCC | 966 |
| Asn | Phe | Val | Val | Asp | Ser | Ser | Ser | Cys | Val | Arg | Ala | Cys | Pro | Ser | Ser | |
| | | | | 300 | | | | | 305 | | | | | 310 | | |
| AAG | ATG | GAA | GTA | GAA | GAA | AAT | GGG | ATT | AAA | ATG | TGT | AAA | CCT | TGC | ACT | 1014 |
| Lys | Met | Glu | Val | Glu | Glu | Asn | Gly | Ile | Lys | Met | Cys | Lys | Pro | Cys | Thr | |
| | | | 315 | | | | 320 | | | | | 325 | | | | |
| GAC | ATT | TGC | CCA | AAA | GCT | TGT | GAT | GGC | ATT | GGC | ACA | GGA | TCA | TTG | ATG | 1062 |
| Asp | Ile | Cys | Pro | Lys | Ala | Cys | Asp | Gly | Ile | Gly | Thr | Gly | Ser | Leu | Met | |
| | | 330 | | | | | 335 | | | | | 340 | | | | |
| TCA | GCT | CAG | ACT | GTG | GAT | TCC | AGT | AAC | ATT | GAC | AAA | TTC | ATA | AAC | TGT | 1110 |
| Ser | Ala | Gln | Thr | Val | Asp | Ser | Ser | Asn | Ile | Asp | Lys | Phe | Ile | Asn | Cys | |
| | 345 | | | | | 350 | | | | | 355 | | | | | |
| ACC | AAG | ATC | AAT | GGG | AAT | TTG | ATC | TTT | CTA | GTC | ACT | GGT | ATT | CAT | GGG | 1158 |
| Thr | Lys | Ile | Asn | Gly | Asn | Leu | Ile | Phe | Leu | Val | Thr | Gly | Ile | His | Gly | |
| 360 | | | | | 365 | | | | | 370 | | | | | 375 | |
| GAC | CCT | TAC | AAT | GCA | ATT | GAA | GCC | ATA | GAC | CCA | GAG | AAA | CTG | AAC | GTC | 1206 |
| Asp | Pro | Tyr | Asn | Ala | Ile | Glu | Ala | Ile | Asp | Pro | Glu | Lys | Leu | Asn | Val | |
| | | | | 380 | | | | | 385 | | | | | | 390 | |
| TTT | CGG | ACA | GTC | AGA | GAG | ATA | ACA | GGT | TTC | CTG | AAC | ATA | CAG | TCA | TGG | 1254 |
| Phe | Arg | Thr | Val | Arg | Glu | Ile | Thr | Gly | Phe | Leu | Asn | Ile | Gln | Ser | Trp | |
| | | | 395 | | | | 400 | | | | | | 405 | | | |
| CCA | CCA | AAC | ATG | ACT | GAC | TTC | AGT | GTT | TTT | TCT | AAC | CTG | GTG | ACC | ATT | 1302 |
| Pro | Pro | Asn | Met | Thr | Asp | Phe | Ser | Val | Phe | Ser | Asn | Leu | Val | Thr | Ile | |
| | | | 410 | | | | 415 | | | | | 420 | | | | |
| GGT | GGA | AGA | GTA | CTC | TAT | AGT | GGC | CTG | TCC | TTG | CTT | ATC | CTC | AAG | CAA | 1350 |
| Gly | Gly | Arg | Val | Leu | Tyr | Ser | Gly | Leu | Ser | Leu | Leu | Ile | Leu | Lys | Gln | |
| | 425 | | | | | 430 | | | | | 435 | | | | | |

| | | | | | | | | | | | | | | | | |
|---|---|---|---|---|---|---|---|---|---|---|---|---|---|---|---|---|
| CAG | GGC | ATC | ACC | TCT | CTA | CAG | TTC | CAG | TCC | CTG | AAG | GAA | ATC | AGC | GCA | 1398 |
| Gln | Gly | Ile | Thr | Ser | Leu | Gln | Phe | Gln | Ser | Leu | Lys | Glu | Ile | Ser | Ala | |
| 440 | | | | | 445 | | | | 450 | | | | | | 455 | |
| GGA | AAC | ATC | TAT | ATT | ACT | GAC | AAC | AGC | AAC | CTG | TGT | TAT | TAT | CAT | ACC | 1446 |
| Gly | Asn | Ile | Tyr | Ile | Thr | Asp | Asn | Ser | Asn | Leu | Cys | Tyr | Tyr | His | Thr | |
| | | | | 460 | | | | | 465 | | | | | 470 | | |
| ATT | AAC | TGG | ACA | ACA | CTC | TTC | AGC | ACA | ATC | AAC | CAG | AGA | ATA | GTA | ATC | 1494 |
| Ile | Asn | Trp | Thr | Thr | Leu | Phe | Ser | Thr | Ile | Asn | Gln | Arg | Ile | Val | Ile | |
| | | | 475 | | | | | 480 | | | | | 485 | | | |
| CGG | GAC | AAC | AGA | AAA | GCT | GAA | AAT | TGT | ACT | GCT | GAA | GGA | ATG | GTG | TGC | 1542 |
| Arg | Asp | Asn | Arg | Lys | Ala | Glu | Asn | Cys | Thr | Ala | Glu | Gly | Met | Val | Cys | |
| | | 490 | | | | | 495 | | | | | 500 | | | | |
| AAC | CAT | CTG | TGT | TCC | AGT | GAT | GGC | TGT | TGG | GGA | CCT | GGG | CCA | GAC | CAA | 1590 |
| Asn | His | Leu | Cys | Ser | Ser | Asp | Gly | Cys | Trp | Gly | Pro | Gly | Pro | Asp | Gln | |
| | 505 | | | | | 510 | | | | | 515 | | | | | |
| TGT | CTG | TCG | TGT | CGC | CGC | TTC | AGT | AGA | GGA | AGG | ATC | TGC | ATA | GAG | TCT | 1638 |
| Cys | Leu | Ser | Cys | Arg | Arg | Phe | Ser | Arg | Gly | Arg | Ile | Cys | Ile | Glu | Ser | |
| 520 | | | | | 525 | | | | | 530 | | | | | 535 | |
| TGT | AAC | CTC | TAT | GAT | GGT | GAA | TTT | CGG | GAG | TTT | GAG | AAT | GGC | TCC | ATC | 1686 |
| Cys | Asn | Leu | Tyr | Asp | Gly | Glu | Phe | Arg | Glu | Phe | Glu | Asn | Gly | Ser | Ile | |
| | | | | 540 | | | | | 545 | | | | | 550 | | |
| TGT | GTG | GAG | TGT | GAC | CCC | CAG | TGT | GAG | AAG | ATG | GAA | GAT | GGC | CTC | CTC | 1734 |
| Cys | Val | Glu | Cys | Asp | Pro | Gln | Cys | Glu | Lys | Met | Glu | Asp | Gly | Leu | Leu | |
| | | | 555 | | | | | 560 | | | | | 565 | | | |
| ACA | TGC | CAT | GGA | CCG | GGT | CCT | GAC | AAC | TGT | ACA | AAG | TGC | TCT | CAT | TTT | 1782 |
| Thr | Cys | His | Gly | Pro | Gly | Pro | Asp | Asn | Cys | Thr | Lys | Cys | Ser | His | Phe | |
| | | 570 | | | | | 575 | | | | | 580 | | | | |
| AAA | GAT | GGC | CCA | AAC | TGT | GTG | GAA | AAA | TGT | CCA | GAT | GGC | TTA | CAG | GGG | 1830 |
| Lys | Asp | Gly | Pro | Asn | Cys | Val | Glu | Lys | Cys | Pro | Asp | Gly | Leu | Gln | Gly | |
| | 585 | | | | | 590 | | | | | 595 | | | | | |
| GCA | AAC | AGT | TTC | ATT | TTC | AAG | TAT | GCT | GAT | CCA | GAT | CGG | GAG | TGC | CAC | 1878 |
| Ala | Asn | Ser | Phe | Ile | Phe | Lys | Tyr | Ala | Asp | Pro | Asp | Arg | Glu | Cys | His | |
| 600 | | | | | 605 | | | | | 610 | | | | | 615 | |
| CCA | TGC | CAT | CCA | AAC | TGC | ACC | CAA | GGG | TGT | AAC | GGT | CCC | ACT | AGT | CAT | 1926 |
| Pro | Cys | His | Pro | Asn | Cys | Thr | Gln | Gly | Cys | Asn | Gly | Pro | Thr | Ser | His | |
| | | | | 620 | | | | | 625 | | | | | 630 | | |
| GAC | TGC | ATT | TAC | TAC | CCA | TGG | ACG | GGC | CAT | TCC | ACT | TTA | CCA | CAA | CAT | 1974 |
| Asp | Cys | Ile | Tyr | Tyr | Pro | Trp | Thr | Gly | His | Ser | Thr | Leu | Pro | Gln | His | |
| | | | 635 | | | | | 640 | | | | | 645 | | | |
| GCT | AGA | ACT | CCC | CTG | ATT | GCA | GCT | GGA | GTA | ATT | GGT | GGG | CTC | TTC | ATT | 2022 |
| Ala | Arg | Thr | Pro | Leu | Ile | Ala | Ala | Gly | Val | Ile | Gly | Gly | Leu | Phe | Ile | |
| | | 650 | | | | | 655 | | | | | 660 | | | | |
| CTG | GTC | ATT | GTG | GGT | CTG | ACA | TTT | GCT | GTT | TAT | GTT | AGA | AGG | AAG | AGC | 2070 |
| Leu | Val | Ile | Val | Gly | Leu | Thr | Phe | Ala | Val | Tyr | Val | Arg | Arg | Lys | Ser | |
| | | 665 | | | | | 670 | | | | | 675 | | | | |
| ATC | AAA | AAG | AAA | AGA | GCC | TTG | AGA | AGA | TTC | TTG | GAA | ACA | GAG | TTG | GTG | 2118 |
| Ile | Lys | Lys | Lys | Arg | Ala | Leu | Arg | Arg | Phe | Leu | Glu | Thr | Glu | Leu | Val | |
| 680 | | | | | 685 | | | | | 690 | | | | | 695 | |
| GAA | CCA | TTA | ACT | CCC | AGT | GGC | ACA | GCA | CCC | AAT | CAA | GCT | CAA | CTT | CGT | 2166 |
| Glu | Pro | Leu | Thr | Pro | Ser | Gly | Thr | Ala | Pro | Asn | Gln | Ala | Gln | Leu | Arg | |
| | | | | 700 | | | | | 705 | | | | | 710 | | |
| ATT | TTG | AAA | GAA | ACT | GAG | CTG | AAG | AGG | GTA | AAA | GTC | CTT | GGC | TCA | GGT | 2214 |
| Ile | Leu | Lys | Glu | Thr | Glu | Leu | Lys | Arg | Val | Lys | Val | Leu | Gly | Ser | Gly | |
| | | | 715 | | | | | 720 | | | | | 725 | | | |
| GCT | TTT | GGA | ACG | GTT | TAT | AAA | GGT | ATT | TGG | GTA | CCT | GAA | GGA | GAA | ACT | 2262 |
| Ala | Phe | Gly | Thr | Val | Tyr | Lys | Gly | Ile | Trp | Val | Pro | Glu | Gly | Glu | Thr | |
| | | 730 | | | | | 735 | | | | | 740 | | | | |
| GTG | AAG | ATT | CCT | GTG | GCT | ATT | AAG | ATT | CTT | AAT | GAG | ACA | ACT | GGT | CCC | 2310 |
| Val | Lys | Ile | Pro | Val | Ala | Ile | Lys | Ile | Leu | Asn | Glu | Thr | Thr | Gly | Pro | |
| 745 | | | | | 750 | | | | | 755 | | | | | | |

| | | | | | | | | | | | | | | | | |
|---|---|---|---|---|---|---|---|---|---|---|---|---|---|---|---|---|
| AAG | GCA | AAT | GTG | GAG | TTC | ATG | GAT | GAA | GCT | CTG | ATC | ATG | GCA | AGT | ATG | 2358 |
| Lys | Ala | Asn | Val | Glu | Phe | Met | Asp | Glu | Ala | Leu | Ile | Met | Ala | Ser | Met | |
| 760 | | | | 765 | | | | | 770 | | | | | | 775 | |
| GAT | CAT | CCA | CAC | CTA | GTC | CGG | TTG | CTG | GGT | GTG | TGT | CTG | AGC | CCA | ACC | 2406 |
| Asp | His | Pro | His | Leu | Val | Arg | Leu | Leu | Gly | Val | Cys | Leu | Ser | Pro | Thr | |
| | | | | 780 | | | | | 785 | | | | | | 790 | |
| ATC | CAG | CTG | GTT | ACT | CAA | CTT | ATG | CCC | CAT | GGC | TGC | CTG | TTG | GAG | TAT | 2454 |
| Ile | Gln | Leu | Val | Thr | Gln | Leu | Met | Pro | His | Gly | Cys | Leu | Leu | Glu | Tyr | |
| | | | | 795 | | | | | 800 | | | | | | 805 | |
| GTC | CAC | GAG | CAC | AAG | GAT | AAC | ATT | GGA | TCA | CAA | CTG | CTG | CTT | AAC | TGG | 2502 |
| Val | His | Glu | His | Lys | Asp | Asn | Ile | Gly | Ser | Gln | Leu | Leu | Leu | Asn | Trp | |
| | | | 810 | | | | | 815 | | | | | 820 | | | |
| TGT | GTC | CAG | ATA | GCT | AAG | GGA | ATG | ATG | TAC | CTG | GAA | GAA | AGA | CGA | CTC | 2550 |
| Cys | Val | Gln | Ile | Ala | Lys | Gly | Met | Met | Tyr | Leu | Glu | Glu | Arg | Arg | Leu | |
| | | 825 | | | | | 830 | | | | | 835 | | | | |
| GTT | CAT | CGG | GAT | TTG | GCA | GCC | CGT | AAT | GTC | TTA | GTG | AAA | TCT | CCA | AAC | 2598 |
| Val | His | Arg | Asp | Leu | Ala | Ala | Arg | Asn | Val | Leu | Val | Lys | Ser | Pro | Asn | |
| 840 | | | | | 845 | | | | | 850 | | | | | 855 | |
| CAT | GTG | AAA | ATC | ACA | GAT | TTT | GGG | CTA | GCC | AGA | CTC | TTG | GAA | GGA | GAT | 2646 |
| His | Val | Lys | Ile | Thr | Asp | Phe | Gly | Leu | Ala | Arg | Leu | Leu | Glu | Gly | Asp | |
| | | | | 860 | | | | | 865 | | | | | 870 | | |
| GAA | AAA | GAG | TAC | AAT | GCT | GAT | GGA | GGA | AAG | ATG | CCA | ATT | AAA | TGG | ATG | 2694 |
| Glu | Lys | Glu | Tyr | Asn | Ala | Asp | Gly | Gly | Lys | Met | Pro | Ile | Lys | Trp | Met | |
| | | | 875 | | | | | 880 | | | | | 885 | | | |
| GCT | CTG | GAG | TGT | ATA | CAT | TAC | AGG | AAA | TTC | ACC | CAT | CAG | AGT | GAC | GTT | 2742 |
| Ala | Leu | Glu | Cys | Ile | His | Tyr | Arg | Lys | Phe | Thr | His | Gln | Ser | Asp | Val | |
| | | 890 | | | | | 895 | | | | | 900 | | | | |
| TGG | AGC | TAT | GGA | GTT | ACT | ATA | TGG | GAA | CTG | ATG | ACC | TTT | GGA | GGA | AAA | 2790 |
| Trp | Ser | Tyr | Gly | Val | Thr | Ile | Trp | Glu | Leu | Met | Thr | Phe | Gly | Gly | Lys | |
| | 905 | | | | | 910 | | | | | 915 | | | | | |
| CCC | TAT | GAT | GGA | ATT | CCA | ACG | CGA | GAA | ATC | CCT | GAT | TTA | TTA | GAG | AAA | 2838 |
| Pro | Tyr | Asp | Gly | Ile | Pro | Thr | Arg | Glu | Ile | Pro | Asp | Leu | Leu | Glu | Lys | |
| 920 | | | | | 925 | | | | | 930 | | | | | 935 | |
| GGA | GAA | CGT | TTG | CCT | CAG | CCT | CCC | ATC | TGC | ACT | ATT | GAC | GTT | TAC | ATG | 2886 |
| Gly | Glu | Arg | Leu | Pro | Gln | Pro | Pro | Ile | Cys | Thr | Ile | Asp | Val | Tyr | Met | |
| | | | | 940 | | | | | 945 | | | | | 950 | | |
| GTC | ATG | GTC | AAA | TGT | TGG | ATG | ATT | GAT | GCT | GAC | AGT | AGA | CCT | AAA | TTT | 2934 |
| Val | Met | Val | Lys | Cys | Trp | Met | Ile | Asp | Ala | Asp | Ser | Arg | Pro | Lys | Phe | |
| | | | 955 | | | | | 960 | | | | | 965 | | | |
| AAG | GAA | CTG | GCT | GCT | GAG | TTT | TCA | AGG | ATG | GCT | CGA | GAC | CCT | CAA | AGA | 2982 |
| Lys | Glu | Leu | Ala | Ala | Glu | Phe | Ser | Arg | Met | Ala | Arg | Asp | Pro | Gln | Arg | |
| | | 970 | | | | | 975 | | | | | 980 | | | | |
| TAC | CTA | GTT | ATT | CAG | GGT | GAT | GAT | CGT | ATG | AAG | CTT | CCC | AGT | CCA | AAT | 3030 |
| Tyr | Leu | Val | Ile | Gln | Gly | Asp | Asp | Arg | Met | Lys | Leu | Pro | Ser | Pro | Asn | |
| | 985 | | | | | 990 | | | | | 995 | | | | | |
| GAC | AGC | AAG | TTC | TTT | CAG | AAT | CTC | TTG | GAT | GAA | GAG | GAT | TTG | GAA | GAT | 3078 |
| Asp | Ser | Lys | Phe | Phe | Gln | Asn | Leu | Leu | Asp | Glu | Glu | Asp | Leu | Glu | Asp | |
| 1000 | | | | | 1005 | | | | | 1010 | | | | | 1015 | |
| ATG | ATG | GAT | GCT | GAG | GAG | TAC | TTG | GTC | CCT | CAG | GCT | TTC | AAC | ATC | CCA | 3126 |
| Met | Met | Asp | Ala | Glu | Glu | Tyr | Leu | Val | Pro | Gln | Ala | Phe | Asn | Ile | Pro | |
| | | | | 1020 | | | | | 1025 | | | | | 1030 | | |
| CCT | CCC | ATC | TAT | ACT | TCC | AGA | GCA | AGA | ATT | GAC | TCG | AAT | AGG | AGT | GTA | 3174 |
| Pro | Pro | Ile | Tyr | Thr | Ser | Arg | Ala | Arg | Ile | Asp | Ser | Asn | Arg | Ser | Val | |
| | | | 1035 | | | | | 1040 | | | | | 1045 | | | |
| AGA | AAT | AAT | TAT | ATA | CAC | ATA | TCA | TAT | TCT | TTC | TGAGATATAA | | AATCATGTAA | | | 3227 |
| Arg | Asn | Asn | Tyr | Ile | His | Ile | Ser | Tyr | Ser | Phe | | | | | | |
| | | | 1050 | | | | | 1055 | | | | | | | | |

| | | | |
|---|---|---|---|
| TAGTTCATAA | GCACTAACAT | TTCAAAATAA | TTATATAGCT CAAATCAATG TGATGCCTAG | 3287 |
| ATTAAAAATA | TACCATACCC | ACAAAAGATG | TGCCAATCTT GCTATATGTA GTTAATTTTG | 3347 |

| | | | | | | |
|---|---|---|---|---|---|---|
| GAAGACAAGC | ATGGACAATA | CAACATGTAC | TCTGAAATAC | CTTCAAGATT | TCAGAAGCAA | 3407 |
| AACATTTTCC | TCATCTTAAT | TTATTTAAAA | CAAATCTTAA | CTTTAAAAAA | CAATTCCAAC | 3467 |
| TAATAAAACC | ATTATGTGTA | TATAAATAAA | TGAAAATTCC | TACCAAGTAG | GCTTTCTACT | 3527 |
| TTTCTTTCTT | AAAAAGATAT | TATGATATAT | TAGTCAAGAA | GTAATACAAG | TATAAATCTC | 3587 |
| TTTCACTTAT | TTAAGAAAAA | TTAAATATTT | TCTGTCAAGT | TGAAGTAGAA | ACACAGAAAA | 3647 |
| CCGTGCAGTC | CTTTGAACCT | AATCACATCG | AAAAGGCTGC | TGAGAAGTAG | ATTTTGTTT | 3707 |
| TTAAGAAGTA | GATTAAGTT | TTGAAGGAAG | TTTCTGAAAA | CACTTTACAT | TTAAATGTT | 3767 |
| AAACCTACTC | TATATGAATT | CCATTCTTTC | TTTGAAAGCT | GTCAAATCCA | TGCATTTATT | 3827 |
| TTTATAAATT | CATTCCTCAT | ACATTCAACA | TATATTGAGT | ACCACTGTAT | GTGAAGCATT | 3887 |
| AGTATACATT | TAAGACTCAA | AGAATTTTGA | TACAACTTCT | GCTTTCAAGA | AGTGAAAACC | 3947 |
| TTAATCAAAG | AATCATACAG | ATAGAGGGAC | TGCATAGTAA | GTGCTGTAAT | CCAGTATTCA | 4007 |
| CTGACCAGTA | CGGAGCATGA | AGAAGTAGTA | AATTTGTGTC | TGTAATCAGT | TTCTTCCATT | 4067 |
| GATAAGATAT | AAACATGATG | CTTAATTTTT | TCTAGAAGAT | AATTCTTTTC | TCTTAATCTA | 4127 |
| AGAACATTAT | CATAGCTAGT | AGAACCGACA | GCATCCGATT | TCTCTTGACC | ATAGCCATAA | 4187 |
| GAATATCTTC | AACTTGCTGC | TCATTATCTA | ACAAACATAA | TTTTCTTTAT | TTCATATTGA | 4247 |
| TTGTAATAAG | TAATATCCCC | CTGGAAGTTT | ACTATTCAAC | ACATATATGT | TAACCTCCTT | 4307 |
| AATTCCTTAA | ACAAACTTCA | TGAGGTTCTA | TTATTATCAT | CCCCTTCTTT | CAAAGGAAGA | 4367 |
| AACTTGCCAC | AGAGAAGTCA | GGTGATATGA | CTGGTGTCAC | ACAGCTAGTC | AGTGGAAGAG | 4427 |
| AGGAATAAGT | AATCTAGATA | TCTGCCTACT | ACACTGTAGG | TTTGCTTCAA | AGTTACTGAA | 4487 |
| GYCATGTTAT | TTCCATGATG | TGATTAGAGT | CTGGGACTTG | TCTTGTTTGG | GAAATTTCCC | 4547 |
| AGGTGGTTTT | CTTATAAAAT | GCATCTCAAA | TCTGCTCTAC | ACCTTTTACT | CATCTACCTC | 4607 |
| CATTTAGAAG | ATCTGATATG | GAAAGAGACA | AAGATGGAGA | CCTCAATTAT | TTTTTCTTTT | 4667 |
| CTGTTAAAAA | TATTATAGTA | CAACTGAAAC | TTATCACATG | CCAATGGGGA | ATAGATAACT | 4727 |
| AAAAGTTTAA | AATTAGATCA | ATGGATAGGT | AAATGAATAA | TCNTTCTTTT | GCTTGTGAGA | 4787 |
| GGGGAAGGAA | AAGCGGTTAA | GGTGGTATAA | AGGAGGCTCC | TCTGTACACT | TGCAAAATGA | 4847 |
| TCAAATTATA | TACCCTTGTA | TTTATAATTT | TAAGTGACAA | ATTCATTACT | TCTGGTTACA | 4907 |
| ACAGTGAAAT | TTAAAAAAAA | ATAGTTTTC | TTTCTTAGCT | TGCAATGCTA | TAAATCTTTT | 4967 |
| TCTTTTTATA | AGAATTCTTA | CATTTCAGCT | TTTTGTTCAT | TTTAATTTAT | AATTCTCAGT | 5027 |
| GCAAGAAATT | CTTAATAAAG | GTTTGAGCTA | GCTAGATGGA | ATTATTGAGA | CAAAGTCTAA | 5087 |
| ATCACCCGTG | GACTTATTTG | ACCTTTAGCC | ATCATTTCTT | ATTCCACATT | ATAAAACAAT | 5147 |
| GTTACCTGTA | GATTTCTTTT | TACTTTTTCA | GTCCTTGGAA | AAGAAATGGT | GATTAAATAT | 5207 |
| CATTATATCA | TTTTATGTTC | AGGCATTTAA | AAAGCTTTAT | TTGTCATCTA | TATTGTCCTA | 5267 |
| ATAGTTTTCA | GTCTGGCTTT | ACGTAACTTT | TACGGAAATT | TCTAACATGT | ACAAATGCCA | 5327 |
| TGTTCCTCCT | TTCTTTCCTA | CATGGCTGAA | TTAGAAAACA | AATTACTTCC | ATTTTAAGTT | 5387 |
| TGGCTAAATT | AGAAAACAAA | TTACTACCAT | TTAAGTTTG | GTGGCTAAAT | AACGTGCTAA | 5447 |
| GGGAACATCT | TAAAAGTGA | ATTTTGATCA | AATATTTCTT | AAGCATATGT | GATAGACTTT | 5507 |
| GAAACCAAAA | AAAAAAAAAA | AAAAAAAAAA | AAAAAAAAAA | AAAAAAA | | 5555 |

( 2 ) INFORMATION FOR SEQ ID NO:4:

( i ) SEQUENCE CHARACTERISTICS:
        ( A ) LENGTH: 1058 amino acids
        ( B ) TYPE: amino acid (D) TOPOLOGY: linear (ii) MOLECULE TYPE: protein (xi) SEQUENCE DESCRIPTION: SEQ ID NO:4:

| Met | Lys | Pro | Ala | Thr | Gly | Leu | Trp | Val | Trp | Val | Ser | Leu | Leu | Val | Ala |
|---|---|---|---|---|---|---|---|---|---|---|---|---|---|---|---|
| 1 | | | | 5 | | | | | 10 | | | | | 15 | |
| Ala | Gly | Thr | Val | Gln | Pro | Ser | Asp | Ser | Gln | Ser | Val | Cys | Ala | Gly | Thr |
| | | | 20 | | | | | 25 | | | | | 30 | | |
| Glu | Asn | Lys | Leu | Ser | Ser | Leu | Ser | Asp | Leu | Glu | Gln | Gln | Tyr | Arg | Ala |
| | | | 35 | | | | | 40 | | | | | 45 | | |
| Leu | Arg | Lys | Tyr | Tyr | Glu | Asn | Cys | Glu | Val | Val | Met | Gly | Asn | Leu | Glu |
| | | 50 | | | | | 55 | | | | | 60 | | | |
| Ile | Thr | Ser | Ile | Glu | His | Asn | Arg | Asp | Leu | Ser | Phe | Leu | Arg | Ser | Val |
| 65 | | | | | 70 | | | | | 75 | | | | | 80 |
| Arg | Glu | Val | Thr | Gly | Tyr | Val | Leu | Val | Ala | Leu | Asn | Gln | Phe | Arg | Tyr |
| | | | | 85 | | | | | 90 | | | | | 95 | |
| Leu | Pro | Leu | Glu | Asn | Leu | Arg | Ile | Ile | Arg | Gly | Thr | Lys | Leu | Tyr | Glu |
| | | | | 100 | | | | | 105 | | | | | 110 | |
| Asp | Arg | Tyr | Ala | Leu | Ala | Ile | Phe | Leu | Asn | Tyr | Arg | Lys | Asp | Gly | Asn |
| | | | 115 | | | | | 120 | | | | | 125 | | |
| Phe | Gly | Leu | Gln | Glu | Leu | Gly | Leu | Lys | Asn | Leu | Thr | Glu | Ile | Leu | Asn |
| | | | 130 | | | | | 135 | | | | | 140 | | |
| Gly | Gly | Val | Tyr | Val | Asp | Gln | Asn | Lys | Phe | Leu | Cys | Tyr | Ala | Asp | Thr |
| 145 | | | | | 150 | | | | | 155 | | | | | 160 |
| Ile | His | Trp | Gln | Asp | Ile | Val | Arg | Asn | Pro | Trp | Pro | Ser | Asn | Leu | Thr |
| | | | | 165 | | | | | 170 | | | | | 175 | |
| Leu | Val | Ser | Thr | Asn | Gly | Ser | Ser | Gly | Cys | Gly | Arg | Cys | His | Lys | Ser |
| | | | | 180 | | | | | 185 | | | | | 190 | |
| Cys | Thr | Gly | Arg | Cys | Trp | Gly | Pro | Thr | Glu | Asn | His | Cys | Gln | Thr | Leu |
| | | | 195 | | | | | 200 | | | | | 205 | | |
| Thr | Arg | Thr | Val | Cys | Ala | Glu | Gln | Cys | Asp | Gly | Arg | Cys | Tyr | Gly | Pro |
| | | 210 | | | | | 215 | | | | | 220 | | | |
| Tyr | Val | Ser | Asp | Cys | Cys | His | Arg | Glu | Cys | Ala | Gly | Gly | Cys | Ser | Gly |
| 225 | | | | | 230 | | | | | 235 | | | | | 240 |
| Pro | Lys | Asp | Thr | Asp | Cys | Phe | Ala | Cys | Met | Asn | Phe | Asn | Asp | Ser | Gly |
| | | | | 245 | | | | | 250 | | | | | 255 | |
| Ala | Cys | Val | Thr | Gln | Cys | Pro | Gln | Thr | Phe | Val | Tyr | Asn | Pro | Thr | Thr |
| | | | 260 | | | | | 265 | | | | | 270 | | |
| Phe | Gln | Leu | Glu | His | Asn | Phe | Asn | Ala | Lys | Tyr | Thr | Tyr | Gly | Ala | Phe |
| | | | 275 | | | | | 280 | | | | | 285 | | |
| Cys | Val | Lys | Lys | Cys | Pro | His | Asn | Phe | Val | Val | Asp | Ser | Ser | Ser | Cys |
| | | 290 | | | | | 295 | | | | | 300 | | | |
| Val | Arg | Ala | Cys | Pro | Ser | Ser | Lys | Met | Glu | Val | Glu | Glu | Asn | Gly | Ile |
| 305 | | | | | 310 | | | | | 315 | | | | | 320 |
| Lys | Met | Cys | Lys | Pro | Cys | Thr | Asp | Ile | Cys | Pro | Lys | Ala | Cys | Asp | Gly |
| | | | | 325 | | | | | 330 | | | | | 335 | |
| Ile | Gly | Thr | Gly | Ser | Leu | Met | Ser | Ala | Gln | Thr | Val | Asp | Ser | Ser | Asn |
| | | | 340 | | | | | 345 | | | | | 350 | | |
| Ile | Asp | Lys | Phe | Ile | Asn | Cys | Thr | Lys | Ile | Asn | Gly | Asn | Leu | Ile | Phe |
| | | | 355 | | | | | 360 | | | | | 365 | | |
| Leu | Val | Thr | Gly | Ile | His | Gly | Asp | Pro | Tyr | Asn | Ala | Ile | Glu | Ala | Ile |
| | | 370 | | | | | 375 | | | | | 380 | | | |
| Asp | Pro | Glu | Lys | Leu | Asn | Val | Phe | Arg | Thr | Val | Arg | Glu | Ile | Thr | Gly |
| 385 | | | | | 390 | | | | | 395 | | | | | 400 |

-continued

| | | | | | | | | | | | | | | |
|---|---|---|---|---|---|---|---|---|---|---|---|---|---|---|
| Phe | Leu | Asn | Ile | Gln | Ser | Trp | Pro | Pro | Asn | Met | Thr | Asp | Phe | Ser | Val |
| | | | | 405 | | | | | 410 | | | | | 415 |
| Phe | Ser | Asn | Leu | Val | Thr | Ile | Gly | Gly | Arg | Val | Leu | Tyr | Ser | Gly | Leu |
| | | | 420 | | | | | 425 | | | | | 430 | | |
| Ser | Leu | Leu | Ile | Leu | Lys | Gln | Gln | Gly | Ile | Thr | Ser | Leu | Gln | Phe | Gln |
| | | | 435 | | | | 440 | | | | | 445 | | | |
| Ser | Leu | Lys | Glu | Ile | Ser | Ala | Gly | Asn | Ile | Tyr | Ile | Thr | Asp | Asn | Ser |
| | 450 | | | | | 455 | | | | | 460 | | | | |
| Asn | Leu | Cys | Tyr | Tyr | His | Thr | Ile | Asn | Trp | Thr | Thr | Leu | Phe | Ser | Thr |
| 465 | | | | | 470 | | | | 475 | | | | | | 480 |
| Ile | Asn | Gln | Arg | Ile | Val | Ile | Arg | Asp | Asn | Arg | Lys | Ala | Glu | Asn | Cys |
| | | | | 485 | | | | | 490 | | | | | 495 | |
| Thr | Ala | Glu | Gly | Met | Val | Cys | Asn | His | Leu | Cys | Ser | Ser | Asp | Gly | Cys |
| | | | 500 | | | | | 505 | | | | 510 | | | |
| Trp | Gly | Pro | Gly | Pro | Asp | Gln | Cys | Leu | Ser | Cys | Arg | Arg | Phe | Ser | Arg |
| | | | 515 | | | | 520 | | | | | 525 | | | |
| Gly | Arg | Ile | Cys | Ile | Glu | Ser | Cys | Asn | Leu | Tyr | Asp | Gly | Glu | Phe | Arg |
| | | 530 | | | | 535 | | | | | 540 | | | | |
| Glu | Phe | Glu | Asn | Gly | Ser | Ile | Cys | Val | Glu | Cys | Asp | Pro | Gln | Cys | Glu |
| 545 | | | | | 550 | | | | | 555 | | | | | 560 |
| Lys | Met | Glu | Asp | Gly | Leu | Leu | Thr | Cys | His | Gly | Pro | Gly | Pro | Asp | Asn |
| | | | | 565 | | | | | 570 | | | | | 575 | |
| Cys | Thr | Lys | Cys | Ser | His | Phe | Lys | Asp | Gly | Pro | Asn | Cys | Val | Glu | Lys |
| | | | 580 | | | | | 585 | | | | | 590 | | |
| Cys | Pro | Asp | Gly | Leu | Gln | Gly | Ala | Asn | Ser | Phe | Ile | Phe | Lys | Tyr | Ala |
| | | 595 | | | | | 600 | | | | | 605 | | | |
| Asp | Pro | Asp | Arg | Glu | Cys | His | Pro | Cys | His | Pro | Asn | Cys | Thr | Gln | Gly |
| | 610 | | | | | 615 | | | | | 620 | | | | |
| Cys | Asn | Gly | Pro | Thr | Ser | His | Asp | Cys | Ile | Tyr | Tyr | Pro | Trp | Thr | Gly |
| 625 | | | | | 630 | | | | | 635 | | | | | 640 |
| His | Ser | Thr | Leu | Pro | Gln | His | Ala | Arg | Thr | Pro | Leu | Ile | Ala | Ala | Gly |
| | | | | 645 | | | | | 650 | | | | | 655 | |
| Val | Ile | Gly | Gly | Leu | Phe | Ile | Leu | Val | Ile | Val | Gly | Leu | Thr | Phe | Ala |
| | | | 660 | | | | | 665 | | | | | 670 | | |
| Val | Tyr | Val | Arg | Arg | Lys | Ser | Ile | Lys | Lys | Lys | Arg | Ala | Leu | Arg | Arg |
| | | 675 | | | | | 680 | | | | | 685 | | | |
| Phe | Leu | Glu | Thr | Glu | Leu | Val | Glu | Pro | Leu | Thr | Pro | Ser | Gly | Thr | Ala |
| | 690 | | | | | 695 | | | | | 700 | | | | |
| Pro | Asn | Gln | Ala | Gln | Leu | Arg | Ile | Leu | Lys | Glu | Thr | Glu | Leu | Lys | Arg |
| 705 | | | | | 710 | | | | | 715 | | | | | 720 |
| Val | Lys | Val | Leu | Gly | Ser | Gly | Ala | Phe | Gly | Thr | Val | Tyr | Lys | Gly | Ile |
| | | | | 725 | | | | | 730 | | | | | 735 | |
| Trp | Val | Pro | Glu | Gly | Glu | Thr | Val | Lys | Ile | Pro | Val | Ala | Ile | Lys | Ile |
| | | | 740 | | | | | 745 | | | | | 750 | | |
| Leu | Asn | Glu | Thr | Thr | Gly | Pro | Lys | Ala | Asn | Val | Glu | Phe | Met | Asp | Glu |
| | | | 755 | | | | | 760 | | | | | 765 | | |
| Ala | Leu | Ile | Met | Ala | Ser | Met | Asp | His | Pro | His | Leu | Val | Arg | Leu | Leu |
| | | 770 | | | | 775 | | | | | 780 | | | | |
| Gly | Val | Cys | Leu | Ser | Pro | Thr | Ile | Gln | Leu | Val | Thr | Gln | Leu | Met | Pro |
| 785 | | | | | 790 | | | | | 795 | | | | | 800 |
| His | Gly | Cys | Leu | Leu | Glu | Tyr | Val | His | Glu | His | Lys | Asp | Asn | Ile | Gly |
| | | | | 805 | | | | | 810 | | | | | 815 | |
| Ser | Gln | Leu | Leu | Leu | Asn | Trp | Cys | Val | Gln | Ile | Ala | Lys | Gly | Met | Met |

|  | 820 |  | 825 |  | 830 |  |
|---|---|---|---|---|---|---|

Tyr Leu Glu Glu Arg Arg Leu Val His Arg Asp Leu Ala Ala Arg Asn
          835                    840                 845

Val Leu Val Lys Ser Pro Asn His Val Lys Ile Thr Asp Phe Gly Leu
850                      855                 860

Ala Arg Leu Leu Glu Gly Asp Glu Lys Glu Tyr Asn Ala Asp Gly Gly
865                 870                 875                 880

Lys Met Pro Ile Lys Trp Met Ala Leu Glu Cys Ile His Tyr Arg Lys
              885                 890                 895

Phe Thr His Gln Ser Asp Val Trp Ser Tyr Gly Val Thr Ile Trp Glu
            900                 905                 910

Leu Met Thr Phe Gly Gly Lys Pro Tyr Asp Gly Ile Pro Thr Arg Glu
        915                 920                 925

Ile Pro Asp Leu Leu Glu Lys Gly Glu Arg Leu Pro Gln Pro Pro Ile
    930                 935                 940

Cys Thr Ile Asp Val Tyr Met Val Met Val Lys Cys Trp Met Ile Asp
945                 950                 955                 960

Ala Asp Ser Arg Pro Lys Phe Lys Glu Leu Ala Ala Glu Phe Ser Arg
              965                 970                 975

Met Ala Arg Asp Pro Gln Arg Tyr Leu Val Ile Gln Gly Asp Asp Arg
            980                 985                 990

Met Lys Leu Pro Ser Pro Asn Asp Ser Lys Phe Phe Gln Asn Leu Leu
        995                 1000                1005

Asp Glu Glu Asp Leu Glu Asp Met Met Asp Ala Glu Glu Tyr Leu Val
    1010                1015                1020

Pro Gln Ala Phe Asn Ile Pro Pro Pro Ile Tyr Thr Ser Arg Ala Arg
1025                1030                1035                1040

Ile Asp Ser Asn Arg Ser Val Arg Asn Asn Tyr Ile His Ile Ser Tyr
              1045                1050                1055

Ser Phe ( 2 ) INFORMATION FOR SEQ ID NO:5:

( i ) SEQUENCE CHARACTERISTICS:
        ( A ) LENGTH: 3321 base pairs
        ( B ) TYPE: nucleic acid
        ( C ) STRANDEDNESS: single
        ( D ) TOPOLOGY: unknown ( i i ) MOLECULE TYPE: DNA (genomic)

( i x ) FEATURE:
        ( A ) NAME/KEY: CDS
        ( B ) LOCATION: 156..1782

( x i ) SEQUENCE DESCRIPTION: SEQ ID NO:5:

CATTAGCTGC AATTGATCAA GTGACTGAGA GAAGGGCAAC ATTCCATGCA ACAGTATAGT    60

GGTATGGAAA GCCCTGGATG TTGAAATCTA GCTTCAAAAA GCCTGTCTGG AAATGTAGTT   120

AATTGGATGA AGTGAGAAGA GATAAAACCA GAGAG GAA GCT CTG ATC ATG GCA   173
                                                      Glu Ala Leu Ile Met Ala
                                                       1               5

AGT ATG GAT CAT CCA CAC CTA GTC CGG TTG CTG GGT GTG TGT CTG AGC   221
Ser Met Asp His Pro His Leu Val Arg Leu Leu Gly Val Cys Leu Ser
          10                           15                       20

CCA ACC ATC CAG CTG GTT ACT CAA CTT ATG CCC CAT GGC TGC CTG TTG   269
Pro Thr Ile Gln Leu Val Thr Gln Leu Met Pro His Gly Cys Leu Leu
          25                           30                       35

GAG TAT GTC CAC GAG CAC AAG GAT AAC ATT GGA TCA CAA CTG CTG CTT   317

```
            Glu  Tyr  Val  His  Glu  His  Lys  Asp  Asn  Ile  Gly  Ser  Gln  Leu  Leu  Leu
                  40                 45                      50

AAC  TGG  TGT  GTC  CAG  ATA  GCT  AAG  GGA  ATG  ATG  TAC  CTG  GAA  GAA  AGA         365
Asn  Trp  Cys  Val  Gln  Ile  Ala  Lys  Gly  Met  Met  Tyr  Leu  Glu  Glu  Arg
 55                 60                      65                           70

CGA  CTC  GTT  CAT  CGG  GAT  TTG  GCA  GCC  CGT  AAT  GTC  TTA  GTG  AAA  TCT         413
Arg  Leu  Val  His  Arg  Asp  Leu  Ala  Ala  Arg  Asn  Val  Leu  Val  Lys  Ser
                     75                      80                      85

CCA  AAC  CAT  GTG  AAA  ATC  ACA  GAT  TTT  GGG  CTA  GCC  AGA  CTC  TTG  GAA         461
Pro  Asn  His  Val  Lys  Ile  Thr  Asp  Phe  Gly  Leu  Ala  Arg  Leu  Leu  Glu
                90                      95                     100

GGA  GAT  GAA  AAA  GAG  TAC  AAT  GCT  GAT  GGA  GGA  AAG  ATG  CCA  ATT  AAA         509
Gly  Asp  Glu  Lys  Glu  Tyr  Asn  Ala  Asp  Gly  Gly  Lys  Met  Pro  Ile  Lys
               105                     110                     115

TGG  ATG  GCT  CTG  GAG  TGT  ATA  CAT  TAC  AGG  AAA  TTC  ACC  CAT  CAG  AGT         557
Trp  Met  Ala  Leu  Glu  Cys  Ile  His  Tyr  Arg  Lys  Phe  Thr  His  Gln  Ser
     120                     125                     130

GAC  GTT  TGG  AGC  TAT  GGA  GTT  ACT  ATA  TGG  GAA  CTG  ATG  ACC  TTT  GGA         605
Asp  Val  Trp  Ser  Tyr  Gly  Val  Thr  Ile  Trp  Glu  Leu  Met  Thr  Phe  Gly
135                      140                     145                          150

GGA  AAA  CCC  TAT  GAT  GGA  ATT  CCA  ACG  CGA  GAA  ATC  CCT  GAT  TTA  TTA         653
Gly  Lys  Pro  Tyr  Asp  Gly  Ile  Pro  Thr  Arg  Glu  Ile  Pro  Asp  Leu  Leu
                    155                     160                          165

GAG  AAA  GGA  GAA  CGT  TTG  CCT  CAG  CCT  CCC  ATC  TGC  ACT  ATT  GAC  GTT         701
Glu  Lys  Gly  Glu  Arg  Leu  Pro  Gln  Pro  Pro  Ile  Cys  Thr  Ile  Asp  Val
               170                     175                     180

TAC  ATG  GTC  ATG  GTC  AAA  TGT  TGG  ATG  ATT  GAT  GCT  GAC  AGT  AGA  CCT         749
Tyr  Met  Val  Met  Val  Lys  Cys  Trp  Met  Ile  Asp  Ala  Asp  Ser  Arg  Pro
          185                     190                     195

AAA  TTT  AAG  GAA  CTG  GCT  GCT  GAG  TTT  TCA  AGG  ATG  GCT  CGA  GAC  CCT         797
Lys  Phe  Lys  Glu  Leu  Ala  Ala  Glu  Phe  Ser  Arg  Met  Ala  Arg  Asp  Pro
     200                     205                     210

CAA  AGA  TAC  CTA  GTT  ATT  CAG  GGT  GAT  GAT  CGT  ATG  AAG  CTT  CCC  AGT         845
Gln  Arg  Tyr  Leu  Val  Ile  Gln  Gly  Asp  Asp  Arg  Met  Lys  Leu  Pro  Ser
215                      220                     225                          230

CCA  AAT  GAC  AGC  AAG  TTC  TTT  CAG  AAT  CTC  TTG  GAT  GAA  GAG  GAT  TTG         893
Pro  Asn  Asp  Ser  Lys  Phe  Phe  Gln  Asn  Leu  Leu  Asp  Glu  Glu  Asp  Leu
                    235                     240                          245

GAA  GAT  ATG  ATG  GAT  GCT  GAG  GAG  TAC  TTG  GTC  CCT  CAG  GCT  TTC  AAC         941
Glu  Asp  Met  Met  Asp  Ala  Glu  Glu  Tyr  Leu  Val  Pro  Gln  Ala  Phe  Asn
               250                     255                     260

ATC  CCA  CCT  CCC  ATC  TAT  ACT  TCC  AGA  GCA  AGA  ATT  GAC  TCG  AAT  AGG         989
Ile  Pro  Pro  Pro  Ile  Tyr  Thr  Ser  Arg  Ala  Arg  Ile  Asp  Ser  Asn  Arg
               265                     270                     275

AGT  GAA  ATT  GGA  CAC  AGC  CCT  CCT  CCT  GCC  TAC  ACC  CCC  ATG  TCA  GGA        1037
Ser  Glu  Ile  Gly  His  Ser  Pro  Pro  Pro  Ala  Tyr  Thr  Pro  Met  Ser  Gly
     280                     285                     290

AAC  CAG  TTT  GTA  TAC  CGA  GAT  GGA  GGT  TTT  GCT  GCT  GAA  CAA  GGA  GTG        1085
Asn  Gln  Phe  Val  Tyr  Arg  Asp  Gly  Gly  Phe  Ala  Ala  Glu  Gln  Gly  Val
295                      300                     305                          310

TCT  GTG  CCC  TAC  AGA  GCC  CCA  ACT  AGC  ACA  ATT  CCA  GAA  GCT  CCT  GTG        1133
Ser  Val  Pro  Tyr  Arg  Ala  Pro  Thr  Ser  Thr  Ile  Pro  Glu  Ala  Pro  Val
                    315                     320                          325

GCA  CAG  GGT  GCT  ACT  GCT  GAG  ATT  TTT  GAT  GAC  TCC  TGC  TGT  AAT  GGC        1181
Ala  Gln  Gly  Ala  Thr  Ala  Glu  Ile  Phe  Asp  Asp  Ser  Cys  Cys  Asn  Gly
               330                     335                     340

ACC  CTA  CGC  AAG  CCA  GTG  GCA  CCC  CAT  GTC  CAA  GAG  GAC  AGT  AGC  ACC        1229
Thr  Leu  Arg  Lys  Pro  Val  Ala  Pro  His  Val  Gln  Glu  Asp  Ser  Ser  Thr
          345                     350                     355

CAG  AGG  TAC  AGT  GCT  GAC  CCC  ACC  GTG  TTT  GCC  CCA  GAA  CGG  AGC  CCA        1277
```

-continued

```
Gln Arg Tyr Ser Ala Asp Pro Thr Val Phe Ala Pro Glu Arg Ser Pro
    360             365                 370

CGA GGA GAG CTG GAT GAG GAA GGT TAC ATG ACT CCT ATG CGA GAC AAA       1325
Arg Gly Glu Leu Asp Glu Glu Gly Tyr Met Thr Pro Met Arg Asp Lys
375             380                 385                 390

CCC AAA CAA GAA TAC CTG AAT CCA GTG GAG GAG AAC CCT TTT GTT TCT       1373
Pro Lys Gln Glu Tyr Leu Asn Pro Val Glu Glu Asn Pro Phe Val Ser
                395                 400                 405

CGG AGA AAA AAT GGA GAC CTT CAA GCA TTG GAT AAT CCC GAA TAT CAC       1421
Arg Arg Lys Asn Gly Asp Leu Gln Ala Leu Asp Asn Pro Glu Tyr His
            410                 415                 420

AAT GCA TCC AAT GGT CCA CCC AAG GCC GAG GAT GAG TAT GTG AAT GAG       1469
Asn Ala Ser Asn Gly Pro Pro Lys Ala Glu Asp Glu Tyr Val Asn Glu
        425                 430                 435

CCA CTG TAC CTC AAC ACC TTT GCC AAC ACC TTG GGA AAA GCT GAG TAC       1517
Pro Leu Tyr Leu Asn Thr Phe Ala Asn Thr Leu Gly Lys Ala Glu Tyr
    440             445                 450

CTG AAG AAC AAC ATA CTG TCA ATG CCA GAG AAG GCC AAG AAA GCG TTT       1565
Leu Lys Asn Asn Ile Leu Ser Met Pro Glu Lys Ala Lys Lys Ala Phe
455             460                 465                 470

GAC AAC CCT GAC TAC TGG AAC CAC AGC CTG CCA CCT CGG AGC ACC CTT       1613
Asp Asn Pro Asp Tyr Trp Asn His Ser Leu Pro Pro Arg Ser Thr Leu
                475                 480                 485

CAG CAC CCA GAC TAC CTG CAG GAG TAC AGC ACA AAA TAT TTT TAT AAA       1661
Gln His Pro Asp Tyr Leu Gln Glu Tyr Ser Thr Lys Tyr Phe Tyr Lys
            490                 495                 500

CAG AAT GGG CGG ATC CGG CCT ATT GTG GCA GAG AAT CCT GAA TAC CTC       1709
Gln Asn Gly Arg Ile Arg Pro Ile Val Ala Glu Asn Pro Glu Tyr Leu
        505                 510                 515

TCT GAG TTC TCC CTG AAG CCA GGC ACT GTG CTG CCG CCT CCA CCT TAC       1757
Ser Glu Phe Ser Leu Lys Pro Gly Thr Val Leu Pro Pro Pro Pro Tyr
    520             525                 530

AGA CAC CGG AAT ACT GTG GTG TAAGCTCAGT TGTGGTTTTT TAGGTGGAGA          1808
Arg His Arg Asn Thr Val Val
535             540

GACACACCTG CTCCAATTTC CCCACCCCCC TCTCTTTCTC TGGTGGTCTT CCTTCTACCC     1868

CAAGGCCAGT AGTTTTGACA CTTCCCAGTG GAAGATACAG AGATGCAATG ATAGTTATGT     1928

GCTTACCTAA CTTGAACATT AGAGGGAAAG ACTGAAAGAG AAAGATAGGA GGAACCACAA     1988

TGTTTCTTCA TTTCTCTGCA TGGGTTGGTC AGGAGAATGA ACAGCTAGA GAAGGACCAG      2048

AAAATGTAAG GCAATGCTGC CTACTATCAA ACTAGCTGTC ACTTTTTTC TTTTTCTTTT      2108

TCTTTCTTTG TTTCTTTCTT CCTCTTCTTT TTTTTTTTT TTTAAAGCA GATGGTTGAA       2168

ACACCCATGC TATCTGTTCC TATCTGCAGG AACTGATGTG TGCATATTTA GCATCCCTGG     2228

AAATCATAAT AAAGTTTCCA TTAGAACAAA GAATAACAT TTTCTATAAC ATATGATAGT      2288

GTCTGAAATT GAGAATCCAG TTTCTTTCCC CAGCAGTTTC TGTCCTAGCA AGTAAGAATG     2348

GCCAACTCAA CTTTCATAAT TTAAAAATCT CCATTAAAGT TATAACTAGT AATTATGTTT     2408

TCAACACTTT TTGGTTTTTT TCATTTGTT TTGCTCTGAC CGATTCCTTT ATATTTGCTC      2468

CCCTATTTTT GGCTTTAATT TCTAATTGCA AAGATGTTTA CATCAAAGCT TCTTCACAGA     2528

ATTTAAGCAA GAAATATTTT AATATAGTGA ATGGCCACT ACTTTAAGTA TACAATCTTT      2588

AAAATAAGAA AGGGAGGCTA ATATTTTTCA TGCTATCAAA TTATCTTCAC CCTCATCCTT     2648

TACATTTTTC AACATTTTTT TTTCTCCATA AATGACACTA CTTGATAGGC CGTTGGTTGT     2708

CTGAAGAGTA GAAGGGAAAC TAAGAGACAG TTCTCTGTGG TTCAGGAAAA CTACTGATAC     2768

TTTCAGGGGT GGCCCAATGA GGGAATCCAT TGAACTGGAA GAAACACACT GGATTGGGTA     2828
```

```
TGTCTACCTG GCAGATACTC AGAAATGTAG TTTGCACTTA AGCTGTAATT TTATTTGTTC        2888

TTTTTCTGAA CTCCATTTTG GATTTGAAT  CAAGCAATAT GGAAGCAACC AGCAAATTAA        2948

CTAATTTAAG TACATTTTTA AAAAAGAGC  TAAGATAAAG ACTGTGGAAA TGCCAAACCA        3008

AGCAAATTAG GAACCTTGCA ACGGTATCCA GGGACTATGA TGAGAGGCCA GCACATTATC        3068

TTCATATGTC ACCTTTGCTA CGCAAGGAAA TTTGTTCAGT TCGTATACTT CGTAAGAAGG        3128

AATGCGAGTA AGGATTGGCT TGAATTCCAT GGAATTTCTA GTATGAGACT ATTTATATGA        3188

AGTAGAAGGT AACTCTTTGC ACATAAATTG GTATAATAAA AAGAAAAACA CAAACATTCA        3248

AAGCTTAGGG ATAGGTCCTT GGGTCAAAAG TTGTAAATAA ATGTGAAACA TCTTCTCAAA        3308

AAAAAAAAAA AAA                                                            3321
```

( 2 ) INFORMATION FOR SEQ ID NO:6:

( i ) SEQUENCE CHARACTERISTICS:
        ( A ) LENGTH: 541 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Glu Ala Leu Ile Met Ala Ser Met Asp His Pro His Leu Val Arg Leu
 1               5                  10                  15

Leu Gly Val Cys Leu Ser Pro Thr Ile Gln Leu Val Thr Gln Leu Met
            20                  25                  30

Pro His Gly Cys Leu Leu Glu Tyr Val His Glu His Lys Asp Asn Ile
            35                  40                  45

Gly Ser Gln Leu Leu Leu Asn Trp Cys Val Gln Ile Ala Lys Gly Met
     50                  55                  60

Met Tyr Leu Glu Glu Arg Arg Leu Val His Arg Asp Leu Ala Ala Arg
 65                 70                  75                  80

Asn Val Leu Val Lys Ser Pro Asn His Val Lys Ile Thr Asp Phe Gly
                85                  90                  95

Leu Ala Arg Leu Leu Glu Gly Asp Glu Lys Glu Tyr Asn Ala Asp Gly
            100                 105                 110

Gly Lys Met Pro Ile Lys Trp Met Ala Leu Glu Cys Ile His Tyr Arg
            115                 120                 125

Lys Phe Thr His Gln Ser Asp Val Trp Ser Tyr Gly Val Thr Ile Trp
     130                 135                 140

Glu Leu Met Thr Phe Gly Gly Lys Pro Tyr Asp Gly Ile Pro Thr Arg
145                 150                 155                 160

Glu Ile Pro Asp Leu Leu Glu Lys Gly Glu Arg Leu Pro Gln Pro Pro
                165                 170                 175

Ile Cys Thr Ile Asp Val Tyr Met Val Met Val Lys Cys Trp Met Ile
            180                 185                 190

Asp Ala Asp Ser Arg Pro Lys Phe Lys Glu Leu Ala Ala Glu Phe Ser
            195                 200                 205

Arg Met Ala Arg Asp Pro Gln Arg Tyr Leu Val Ile Gln Gly Asp Asp
     210                 215                 220

Arg Met Lys Leu Pro Ser Pro Asn Asp Ser Lys Phe Phe Gln Asn Leu
225                 230                 235                 240

Leu Asp Glu Glu Asp Leu Glu Asp Met Met Asp Ala Glu Glu Tyr Leu
                245                 250                 255

Val Pro Gln Ala Phe Asn Ile Pro Pro Pro Ile Tyr Thr Ser Arg Ala
```

```
                        260                         265                         270
Arg  Ile  Asp  Ser  Asn  Arg  Ser  Glu  Ile  Gly  His  Ser  Pro  Pro  Ala
               275                      280                      285
Tyr  Thr  Pro  Met  Ser  Gly  Asn  Gln  Phe  Val  Tyr  Arg  Asp  Gly  Gly  Phe
290                           295                      300
Ala  Ala  Glu  Gln  Gly  Val  Ser  Val  Pro  Tyr  Arg  Ala  Pro  Thr  Ser  Thr
305                           310                      315                      320
Ile  Pro  Glu  Ala  Pro  Val  Ala  Gln  Gly  Ala  Thr  Ala  Glu  Ile  Phe  Asp
                         325                      330                      335
Asp  Ser  Cys  Cys  Asn  Gly  Thr  Leu  Arg  Lys  Pro  Val  Ala  Pro  His  Val
               340                      345                      350
Gln  Glu  Asp  Ser  Ser  Thr  Gln  Arg  Tyr  Ser  Ala  Asp  Pro  Thr  Val  Phe
               355                      360                      365
Ala  Pro  Glu  Arg  Ser  Pro  Arg  Gly  Glu  Leu  Asp  Glu  Gly  Tyr  Met
370                           375                      380
Thr  Pro  Met  Arg  Asp  Lys  Pro  Lys  Gln  Glu  Tyr  Leu  Asn  Pro  Val  Glu
385                           390                      395                      400
Glu  Asn  Pro  Phe  Val  Ser  Arg  Arg  Lys  Asn  Gly  Asp  Leu  Gln  Ala  Leu
                         405                      410                      415
Asp  Asn  Pro  Glu  Tyr  His  Asn  Ala  Ser  Asn  Gly  Pro  Pro  Lys  Ala  Glu
               420                      425                      430
Asp  Glu  Tyr  Val  Asn  Glu  Pro  Leu  Tyr  Leu  Asn  Thr  Phe  Ala  Asn  Thr
               435                      440                      445
Leu  Gly  Lys  Ala  Glu  Tyr  Leu  Lys  Asn  Asn  Ile  Leu  Ser  Met  Pro  Glu
     450                      455                      460
Lys  Ala  Lys  Lys  Ala  Phe  Asp  Asn  Pro  Asp  Tyr  Trp  Asn  His  Ser  Leu
465                      470                      475                      480
Pro  Pro  Arg  Ser  Thr  Leu  Gln  His  Pro  Asp  Tyr  Leu  Gln  Glu  Tyr  Ser
                    485                      490                      495
Thr  Lys  Tyr  Phe  Tyr  Lys  Gln  Asn  Gly  Arg  Ile  Arg  Pro  Ile  Val  Ala
                    500                      505                      510
Glu  Asn  Pro  Glu  Tyr  Leu  Ser  Glu  Phe  Ser  Leu  Lys  Pro  Gly  Thr  Val
               515                      520                      525
Leu  Pro  Pro  Pro  Pro  Tyr  Arg  His  Arg  Asn  Thr  Val  Val
530                           535                      540
```

( 2 ) INFORMATION FOR SEQ ID NO:7:

( i ) SEQUENCE CHARACTERISTICS:
        ( A ) LENGTH: 1210 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:7:

```
Met  Arg  Pro  Ser  Gly  Thr  Ala  Gly  Ala  Ala  Leu  Leu  Ala  Leu  Leu  Ala
1                   5                        10                       15
Ala  Leu  Cys  Pro  Ala  Ser  Arg  Ala  Leu  Glu  Glu  Lys  Lys  Val  Cys  Gln
               20                       25                       30
Gly  Thr  Ser  Asn  Lys  Leu  Thr  Gln  Leu  Gly  Thr  Phe  Glu  Asp  His  Phe
          35                       40                       45
Leu  Ser  Leu  Gln  Arg  Met  Phe  Asn  Asn  Cys  Glu  Val  Val  Leu  Gly  Asn
     50                       55                       60
Leu  Glu  Ile  Thr  Tyr  Val  Gln  Arg  Asn  Tyr  Asp  Leu  Ser  Phe  Leu  Lys
65                       70                       75                       80
```

-continued

```
Thr  Ile  Gln  Glu  Val  Ala  Gly  Tyr  Val  Leu  Ile  Ala  Leu  Asn  Thr  Val
                    85                       90                       95

Glu  Arg  Ile  Pro  Leu  Glu  Asn  Leu  Gln  Ile  Ile  Arg  Gly  Asn  Met  Tyr
               100                      105                      110

Tyr  Glu  Asn  Ser  Tyr  Ala  Leu  Ala  Val  Leu  Ser  Asn  Tyr  Asp  Ala  Asn
          115                      120                      125

Lys  Thr  Gly  Leu  Lys  Glu  Leu  Pro  Met  Arg  Asn  Leu  Gln  Glu  Ile  Leu
     130                      135                      140

His  Gly  Ala  Val  Arg  Phe  Ser  Asn  Asn  Pro  Ala  Leu  Cys  Asn  Val  Glu
145                      150                      155                      160

Ser  Ile  Gln  Trp  Arg  Asp  Ile  Val  Ser  Ser  Asp  Phe  Leu  Ser  Asn  Met
                    165                      170                      175

Ser  Met  Asp  Phe  Gln  Asn  His  Leu  Gly  Ser  Cys  Gln  Lys  Cys  Asp  Pro
               180                      185                      190

Ser  Cys  Pro  Asn  Gly  Ser  Cys  Trp  Gly  Ala  Gly  Glu  Glu  Asn  Cys  Gln
          195                      200                      205

Lys  Leu  Thr  Lys  Ile  Ile  Cys  Ala  Gln  Gln  Cys  Ser  Gly  Arg  Cys  Arg
     210                      215                      220

Gly  Lys  Ser  Pro  Ser  Asp  Cys  Cys  His  Asn  Gln  Cys  Ala  Ala  Gly  Cys
225                      230                      235                      240

Thr  Gly  Pro  Arg  Glu  Ser  Asp  Cys  Leu  Val  Cys  Arg  Lys  Phe  Arg  Asp
                    245                      250                      255

Glu  Ala  Thr  Cys  Lys  Asp  Thr  Cys  Pro  Pro  Leu  Met  Leu  Tyr  Asn  Pro
               260                      265                      270

Thr  Thr  Tyr  Gln  Met  Asp  Val  Asn  Pro  Glu  Gly  Lys  Tyr  Ser  Phe  Gly
          275                      280                      285

Ala  Thr  Cys  Val  Lys  Lys  Cys  Pro  Arg  Asn  Tyr  Val  Val  Thr  Asp  His
     290                      295                      300

Gly  Ser  Cys  Val  Arg  Ala  Cys  Gly  Ala  Asp  Ser  Tyr  Glu  Met  Glu  Glu
305                      310                      315                      320

Asp  Gly  Val  Arg  Lys  Cys  Lys  Lys  Cys  Glu  Gly  Pro  Cys  Arg  Lys  Val
                    325                      330                      335

Cys  Asn  Gly  Ile  Gly  Ile  Gly  Glu  Phe  Lys  Asp  Ser  Leu  Ser  Ile  Asn
               340                      345                      350

Ala  Thr  Asn  Ile  Lys  His  Phe  Lys  Asn  Cys  Thr  Ser  Ile  Ser  Gly  Asp
          355                      360                      365

Leu  His  Ile  Leu  Pro  Val  Ala  Phe  Arg  Gly  Asp  Ser  Phe  Thr  His  Thr
     370                      375                      380

Pro  Pro  Leu  Asp  Pro  Gln  Glu  Leu  Asp  Ile  Leu  Lys  Thr  Val  Lys  Glu
385                      390                      395                      400

Ile  Thr  Gly  Phe  Leu  Leu  Ile  Gln  Ala  Trp  Pro  Glu  Asn  Arg  Thr  Asp
                    405                      410                      415

Leu  His  Ala  Phe  Glu  Asn  Leu  Glu  Ile  Ile  Arg  Gly  Arg  Thr  Lys  Gln
               420                      425                      430

His  Gly  Gln  Phe  Ser  Leu  Ala  Val  Val  Ser  Leu  Asn  Ile  Thr  Ser  Leu
          435                      440                      445

Gly  Leu  Arg  Ser  Leu  Lys  Glu  Ile  Ser  Asp  Gly  Asp  Val  Ile  Ile  Ser
     450                      455                      460

Gly  Asn  Lys  Asn  Leu  Cys  Tyr  Ala  Asn  Thr  Ile  Asn  Trp  Lys  Lys  Leu
465                      470                      475                      480

Phe  Gly  Thr  Ser  Gly  Gln  Lys  Thr  Lys  Ile  Ile  Ser  Asn  Arg  Gly  Glu
                    485                      490                      495

Asn  Ser  Cys  Lys  Ala  Thr  Gly  Gln  Val  Cys  His  Ala  Leu  Cys  Ser  Pro
```

|     |     |     |     |     |     |     |     |     |     |     |     |     |     |     |
|-----|-----|-----|-----|-----|-----|-----|-----|-----|-----|-----|-----|-----|-----|-----|
|     |     |     |     |     | 500 |     |     |     |     | 505 |     |     |     | 510 |
| Glu | Gly | Cys | Trp | Gly | Pro | Glu | Pro | Arg | Asp | Cys | Val | Ser | Cys | Arg | Asn |
|     |     | 515 |     |     |     |     | 520 |     |     |     |     | 525 |     |     |     |
| Val | Ser | Arg | Gly | Arg | Glu | Cys | Val | Asp | Lys | Cys | Lys | Leu | Leu | Glu | Gly |
|     | 530 |     |     |     |     | 535 |     |     |     |     | 540 |     |     |     |     |
| Glu | Pro | Arg | Glu | Phe | Val | Glu | Asn | Ser | Glu | Cys | Ile | Gln | Cys | His | Pro |
| 545 |     |     |     |     | 550 |     |     |     |     | 555 |     |     |     |     | 560 |
| Glu | Cys | Leu | Pro | Gln | Ala | Met | Asn | Ile | Thr | Cys | Thr | Gly | Arg | Gly | Pro |
|     |     |     |     | 565 |     |     |     |     | 570 |     |     |     |     |     | 575 |
| Asp | Asn | Cys | Ile | Gln | Cys | Ala | His | Tyr | Ile | Asp | Gly | Pro | His | Cys | Val |
|     |     |     | 580 |     |     |     |     | 585 |     |     |     |     | 590 |     |     |
| Lys | Thr | Cys | Pro | Ala | Gly | Val | Met | Gly | Glu | Asn | Asn | Thr | Leu | Val | Trp |
|     |     | 595 |     |     |     |     | 600 |     |     |     |     | 605 |     |     |     |
| Lys | Tyr | Ala | Asp | Ala | Gly | His | Val | Cys | His | Leu | Cys | His | Pro | Asn | Cys |
|     | 610 |     |     |     |     | 615 |     |     |     |     | 620 |     |     |     |     |
| Thr | Tyr | Gly | Cys | Thr | Gly | Pro | Gly | Leu | Glu | Gly | Cys | Pro | Thr | Asn | Gly |
| 625 |     |     |     |     | 630 |     |     |     |     | 635 |     |     |     |     | 640 |
| Pro | Lys | Ile | Pro | Ser | Ile | Ala | Thr | Gly | Met | Val | Gly | Ala | Leu | Leu | Leu |
|     |     |     |     | 645 |     |     |     |     | 650 |     |     |     |     | 655 |     |
| Leu | Leu | Val | Val | Ala | Leu | Gly | Ile | Gly | Leu | Phe | Met | Arg | Arg | Arg | His |
|     |     |     | 660 |     |     |     |     | 665 |     |     |     |     | 670 |     |     |
| Ile | Val | Arg | Lys | Arg | Thr | Leu | Arg | Arg | Leu | Leu | Gln | Glu | Arg | Glu | Leu |
|     |     | 675 |     |     |     |     | 680 |     |     |     |     | 685 |     |     |     |
| Val | Glu | Pro | Leu | Thr | Pro | Ser | Gly | Glu | Ala | Pro | Asn | Gln | Ala | Leu | Leu |
|     |     | 690 |     |     |     |     | 695 |     |     |     |     | 700 |     |     |     |
| Arg | Ile | Leu | Lys | Glu | Thr | Glu | Phe | Lys | Lys | Ile | Lys | Val | Leu | Gly | Ser |
| 705 |     |     |     |     | 710 |     |     |     |     | 715 |     |     |     |     | 720 |
| Gly | Ala | Phe | Gly | Thr | Val | Tyr | Lys | Gly | Leu | Trp | Ile | Pro | Glu | Gly | Glu |
|     |     |     |     | 725 |     |     |     |     | 730 |     |     |     |     |     | 735 |
| Lys | Val | Lys | Ile | Pro | Val | Ala | Ile | Lys | Glu | Leu | Arg | Glu | Ala | Thr | Ser |
|     |     |     | 740 |     |     |     |     | 745 |     |     |     |     | 750 |     |     |
| Pro | Lys | Ala | Asn | Lys | Glu | Ile | Leu | Asp | Glu | Ala | Tyr | Val | Met | Ala | Ser |
|     |     | 755 |     |     |     |     | 760 |     |     |     |     | 765 |     |     |     |
| Val | Asp | Asn | Pro | His | Val | Cys | Arg | Leu | Leu | Gly | Ile | Cys | Leu | Thr | Ser |
|     | 770 |     |     |     |     | 775 |     |     |     |     | 780 |     |     |     |     |
| Thr | Val | Gln | Leu | Ile | Thr | Gln | Leu | Met | Pro | Phe | Gly | Cys | Leu | Leu | Asp |
| 785 |     |     |     |     | 790 |     |     |     |     | 795 |     |     |     |     | 800 |
| Tyr | Val | Arg | Glu | His | Lys | Asp | Asn | Ile | Gly | Ser | Gln | Tyr | Leu | Leu | Asn |
|     |     |     |     | 805 |     |     |     |     | 810 |     |     |     |     | 815 |     |
| Trp | Cys | Val | Gln | Ile | Ala | Lys | Gly | Met | Met | Tyr | Leu | Glu | Asp | Arg | Arg |
|     |     |     | 820 |     |     |     |     | 825 |     |     |     |     | 830 |     |     |
| Leu | Val | His | Arg | Asp | Leu | Ala | Ala | Arg | Asn | Val | Leu | Val | Lys | Thr | Pro |
|     |     | 835 |     |     |     |     | 840 |     |     |     |     | 845 |     |     |     |
| Gln | His | Val | Lys | Ile | Thr | Asp | Phe | Gly | Leu | Ala | Lys | Leu | Leu | Gly | Ala |
|     | 850 |     |     |     |     | 855 |     |     |     |     | 860 |     |     |     |     |
| Glu | Glu | Lys | Glu | Tyr | His | Ala | Glu | Gly | Gly | Lys | Val | Pro | Ile | Lys | Trp |
| 865 |     |     |     |     | 870 |     |     |     |     | 875 |     |     |     |     | 880 |
| Met | Ala | Leu | Glu | Ser | Ile | Leu | His | Arg | Ile | Tyr | Thr | His | Gln | Ser | Asp |
|     |     |     |     | 885 |     |     |     |     | 890 |     |     |     |     | 895 |     |
| Val | Trp | Ser | Tyr | Gly | Val | Thr | Val | Trp | Glu | Leu | Met | Thr | Phe | Gly | Ser |
|     |     |     | 900 |     |     |     |     | 905 |     |     |     |     | 910 |     |     |
| Lys | Pro | Tyr | Asp | Gly | Ile | Pro | Ala | Ser | Glu | Ile | Ser | Ser | Ile | Leu | Glu |
|     |     | 915 |     |     |     |     | 920 |     |     |     |     | 925 |     |     |     |

-continued

| | | | | | | | | | | | | | | |
|---|---|---|---|---|---|---|---|---|---|---|---|---|---|---|
| Lys | Gly | Glu | Arg | Leu | Pro | Gln | Pro | Pro | Ile | Cys | Thr | Ile | Asp | Val | Tyr |
| | 930 | | | | 935 | | | | | 940 | | | | | |
| Met | Ile | Met | Val | Lys | Cys | Trp | Met | Ile | Asp | Ala | Asp | Ser | Arg | Pro | Lys |
| 945 | | | | | 950 | | | | | 955 | | | | | 960 |
| Phe | Arg | Glu | Leu | Ile | Ile | Glu | Phe | Ser | Lys | Met | Ala | Arg | Asp | Pro | Gln |
| | | | | 965 | | | | | 970 | | | | | 975 | |
| Arg | Tyr | Leu | Val | Ile | Gln | Gly | Asp | Glu | Arg | Met | His | Leu | Pro | Ser | Pro |
| | | | 980 | | | | | 985 | | | | | 990 | | |
| Thr | Asp | Ser | Asn | Phe | Tyr | Arg | Ala | Leu | Met | Asp | Glu | Glu | Asp | Met | Asp |
| | | 995 | | | | | 1000 | | | | | 1005 | | | |
| Asp | Val | Val | Asp | Ala | Asp | Glu | Tyr | Leu | Ile | Pro | Gln | Gln | Gly | Phe | Phe |
| | 1010 | | | | | 1015 | | | | | 1020 | | | | |
| Ser | Ser | Pro | Ser | Thr | Ser | Arg | Thr | Pro | Leu | Leu | Ser | Ser | Leu | Ser | Ala |
| 1025 | | | | | 1030 | | | | | 1035 | | | | | 1040 |
| Thr | Ser | Asn | Asn | Ser | Thr | Val | Ala | Cys | Ile | Asp | Arg | Asn | Gly | Leu | Gln |
| | | | | 1045 | | | | | 1050 | | | | | 1055 | |
| Ser | Cys | Pro | Ile | Lys | Glu | Asp | Ser | Phe | Leu | Gln | Arg | Tyr | Ser | Ser | Asp |
| | | | 1060 | | | | | 1065 | | | | | 1070 | | |
| Pro | Thr | Gly | Ala | Leu | Thr | Glu | Asp | Ser | Ile | Asp | Asp | Thr | Phe | Leu | Pro |
| | | 1075 | | | | | 1080 | | | | | 1085 | | | |
| Val | Pro | Glu | Tyr | Ile | Asn | Gln | Ser | Val | Pro | Lys | Arg | Pro | Ala | Gly | Ser |
| | 1090 | | | | | 1095 | | | | | 1100 | | | | |
| Val | Gln | Asn | Pro | Val | Tyr | His | Asn | Gln | Pro | Leu | Asn | Pro | Ala | Pro | Ser |
| 1105 | | | | | 1110 | | | | | 1115 | | | | | 1120 |
| Arg | Asp | Pro | His | Tyr | Gln | Asp | Pro | His | Ser | Thr | Ala | Val | Gly | Asn | Pro |
| | | | | 1125 | | | | | 1130 | | | | | 1135 | |
| Glu | Tyr | Leu | Asn | Thr | Val | Gln | Pro | Thr | Cys | Val | Asn | Ser | Thr | Phe | Asp |
| | | | 1140 | | | | | 1145 | | | | | 1150 | | |
| Ser | Pro | Ala | His | Trp | Ala | Gln | Lys | Gly | Ser | His | Gln | Ile | Ser | Leu | Asp |
| | | 1155 | | | | | 1160 | | | | | 1165 | | | |
| Asn | Pro | Asp | Tyr | Gln | Gln | Asp | Phe | Phe | Pro | Lys | Glu | Ala | Lys | Pro | Asn |
| | 1170 | | | | | 1175 | | | | | 1180 | | | | |
| Gly | Ile | Phe | Lys | Gly | Ser | Thr | Ala | Glu | Asn | Ala | Glu | Tyr | Leu | Arg | Val |
| 1185 | | | | | 1190 | | | | | 1195 | | | | | 1200 |
| Ala | Pro | Gln | Ser | Ser | Glu | Phe | Ile | Gly | Ala | | | | | | |
| | | | | 1205 | | | | | 1210 | | | | | | |

( 2 ) INFORMATION FOR SEQ ID NO:8:

( i ) SEQUENCE CHARACTERISTICS:
        ( A ) LENGTH: 1255 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|---|
| Met | Glu | Leu | Ala | Ala | Leu | Cys | Arg | Trp | Gly | Leu | Leu | Leu | Ala | Leu | Leu |
| 1 | | | | 5 | | | | | 10 | | | | | 15 | |
| Pro | Pro | Gly | Ala | Ala | Ser | Thr | Gln | Val | Cys | Thr | Gly | Thr | Asp | Met | Lys |
| | | | 20 | | | | | 25 | | | | | 30 | | |
| Leu | Arg | Leu | Pro | Ala | Ser | Pro | Glu | Thr | His | Leu | Asp | Met | Leu | Arg | His |
| | | 35 | | | | | 40 | | | | | 45 | | | |
| Leu | Tyr | Gln | Gly | Cys | Gln | Val | Val | Gln | Gly | Asn | Leu | Glu | Leu | Thr | Tyr |
| | 50 | | | | | 55 | | | | | 60 | | | | |
| Leu | Pro | Thr | Asn | Ala | Ser | Leu | Ser | Phe | Leu | Gln | Asp | Ile | Gln | Glu | Val |

-continued

```
          65                      70                      75                       80
Gln  Gly  Tyr  Val  Leu  Ile  Ala  His  Asn  Gln  Val  Arg  Gln  Val  Pro  Leu
                    85                      90                      95

Gln  Arg  Leu  Arg  Ile  Val  Arg  Gly  Thr  Gln  Leu  Phe  Glu  Asp  Asn  Tyr
                   100                     105                     110

Ala  Leu  Ala  Val  Leu  Asp  Asn  Gly  Asp  Pro  Leu  Asn  Asn  Thr  Thr  Pro
                   115                     120                     125

Val  Thr  Gly  Ala  Ser  Pro  Gly  Leu  Arg  Glu  Leu  Gln  Leu  Arg  Ser
     130                     135                     140

Leu  Thr  Glu  Ile  Leu  Lys  Gly  Gly  Val  Leu  Ile  Gln  Arg  Asn  Pro  Gln
145                     150                     155                     160

Leu  Cys  Tyr  Gln  Asp  Thr  Ile  Leu  Trp  Lys  Asp  Ile  Phe  His  Lys  Asn
                   165                     170                     175

Asn  Gln  Leu  Ala  Leu  Thr  Leu  Ile  Asp  Thr  Asn  Arg  Ser  Arg  Ala  Cys
                   180                     185                     190

His  Pro  Cys  Ser  Pro  Met  Cys  Lys  Gly  Ser  Arg  Cys  Trp  Gly  Glu  Ser
                   195                     200                     205

Ser  Glu  Asp  Cys  Gln  Ser  Leu  Thr  Arg  Thr  Val  Cys  Ala  Gly  Gly  Cys
     210                     215                     220

Ala  Arg  Cys  Lys  Gly  Pro  Leu  Pro  Thr  Asp  Cys  Cys  His  Glu  Gln  Cys
225                     230                     235                     240

Ala  Ala  Gly  Cys  Thr  Gly  Pro  Lys  His  Ser  Asp  Cys  Leu  Ala  Cys  Leu
                    245                     250                     255

His  Phe  Asn  His  Ser  Gly  Ile  Cys  Glu  Leu  His  Cys  Pro  Ala  Leu  Val
                   260                     265                     270

Thr  Tyr  Asn  Thr  Asp  Thr  Phe  Glu  Ser  Met  Pro  Asn  Pro  Glu  Gly  Arg
                   275                     280                     285

Tyr  Thr  Phe  Gly  Ala  Ser  Cys  Val  Thr  Ala  Cys  Pro  Tyr  Asn  Tyr  Leu
     290                     295                     300

Ser  Thr  Asp  Val  Gly  Ser  Cys  Thr  Leu  Val  Cys  Pro  Leu  His  Asn  Gln
305                     310                     315                     320

Glu  Val  Thr  Ala  Glu  Asp  Gly  Thr  Gln  Arg  Cys  Glu  Lys  Cys  Ser  Lys
                    325                     330                     335

Pro  Cys  Ala  Arg  Val  Cys  Tyr  Gly  Leu  Gly  Met  Glu  His  Leu  Arg  Glu
                    340                     345                     350

Val  Arg  Ala  Val  Thr  Ser  Ala  Asn  Ile  Gln  Glu  Phe  Ala  Gly  Cys  Lys
                    355                     360                     365

Lys  Ile  Phe  Gly  Ser  Leu  Ala  Phe  Leu  Pro  Glu  Ser  Phe  Asp  Gly  Asp
     370                     375                     380

Pro  Ala  Ser  Asn  Thr  Ala  Pro  Leu  Gln  Pro  Glu  Gln  Leu  Gln  Val  Phe
385                     390                     395                     400

Glu  Thr  Leu  Glu  Glu  Ile  Thr  Gly  Tyr  Leu  Tyr  Ile  Ser  Ala  Trp  Pro
                    405                     410                     415

Asp  Ser  Leu  Pro  Asp  Leu  Ser  Val  Phe  Gln  Asn  Leu  Gln  Val  Ile  Arg
               420                     425                     430

Gly  Arg  Ile  Leu  His  Asn  Gly  Ala  Tyr  Ser  Leu  Thr  Leu  Gln  Gly  Leu
          435                     440                     445

Gly  Ile  Ser  Trp  Leu  Gly  Leu  Arg  Ser  Leu  Arg  Glu  Leu  Gly  Ser  Gly
     450                     455                     460

Leu  Ala  Leu  Ile  His  His  Asn  Thr  His  Leu  Cys  Phe  Val  His  Thr  Val
465                     470                     475                     480

Pro  Trp  Asp  Gln  Leu  Phe  Arg  Asn  Pro  His  Gln  Ala  Leu  Leu  His  Thr
               485                     490                     495
```

```
Ala Asn Arg Pro Glu Asp Glu Cys Val Gly Glu Gly Leu Ala Cys His
            500                 505                 510
Gln Leu Cys Ala Arg Arg Ala Leu Leu Gly Ser Gly Pro Thr Gln Cys
        515                 520                 525
Val Asn Cys Ser Gln Phe Arg Gly Gln Glu Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
            565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
            595                 600                 605
Ser Tyr Met Pro Ile Trp Lys Phe Pro Asp Glu Glu Gly Ala Cys Gln
            610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Val Ser
            645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
            675                 680                 685
Arg Leu Leu Gln Glu Thr Glu Leu Val Glu Pro Leu Thr Pro Ser Gly
            690                 695                 700
Ala Met Pro Asn Gln Ala Gln Met Arg Ile Leu Lys Glu Thr Glu Leu
705                 710                 715                 720
Arg Lys Val Lys Val Leu Gly Ser Gly Ala Phe Gly Thr Val Tyr Lys
                725                 730                 735
Gly Ile Trp Ile Pro Asp Gly Glu Asn Val Lys Ile Pro Val Ala Ile
            740                 745                 750
Lys Val Leu Arg Glu Asn Thr Ser Pro Lys Ala Asn Lys Glu Ile Leu
            755                 760                 765
Asp Glu Ala Tyr Val Met Ala Gly Val Gly Ser Pro Tyr Val Ser Arg
770                 775                 780
Leu Leu Gly Ile Cys Leu Thr Ser Thr Val Gln Leu Val Thr Gln Leu
785                 790                 795                 800
Met Pro Tyr Gly Cys Leu Leu Asp His Val Arg Glu Asn Arg Gly Arg
            805                 810                 815
Leu Gly Ser Gln Asp Leu Leu Asn Trp Cys Met Gln Ile Ala Lys Gly
            820                 825                 830
Met Ser Tyr Leu Glu Asp Val Arg Leu Val His Arg Asp Leu Ala Ala
            835                 840                 845
Arg Asn Val Leu Val Lys Ser Pro Asn His Val Lys Ile Thr Asp Phe
850                 855                 860
Gly Leu Ala Arg Leu Leu Asp Ile Asp Glu Thr Glu Tyr His Ala Asp
865                 870                 875                 880
Gly Gly Lys Val Pro Ile Lys Trp Met Ala Leu Glu Ser Ile Leu Arg
            885                 890                 895
Arg Arg Phe Thr His Gln Ser Asp Val Trp Ser Tyr Gly Val Thr Val
            900                 905                 910
Trp Glu Leu Met Thr Phe Gly Ala Lys Pro Tyr Asp Gly Ile Pro Ala
            915                 920                 925
```

```
Arg  Glu  Ile  Pro  Asp  Leu  Leu  Glu  Lys  Gly  Glu  Arg  Leu  Pro  Gln  Pro
     930                 935                      940

Pro  Ile  Cys  Thr  Ile  Asp  Val  Tyr  Met  Ile  Met  Val  Lys  Cys  Trp  Met
945                      950                      955                      960

Ile  Asp  Ser  Glu  Cys  Arg  Pro  Arg  Phe  Arg  Glu  Leu  Val  Ser  Glu  Phe
                    965                      970                      975

Ser  Arg  Met  Ala  Arg  Asp  Pro  Gln  Arg  Phe  Val  Val  Ile  Gln  Asn  Glu
               980                      985                      990

Asp  Leu  Gly  Pro  Ala  Ser  Pro  Leu  Asp  Ser  Thr  Phe  Tyr  Arg  Ser  Leu
          995                      1000                     1005

Leu  Glu  Asp  Asp  Met  Gly  Asp  Leu  Val  Asp  Ala  Glu  Glu  Tyr  Leu
     1010                1015                     1020

Val  Pro  Gln  Gln  Gly  Phe  Phe  Cys  Pro  Asp  Pro  Ala  Pro  Gly  Ala  Gly
1025                     1030                1035                          1040

Gly  Met  Val  His  His  Arg  His  Arg  Ser  Ser  Ser  Thr  Arg  Ser  Gly  Gly
                    1045                     1050                     1055

Gly  Asp  Leu  Thr  Leu  Gly  Leu  Glu  Pro  Ser  Glu  Glu  Glu  Ala  Pro  Arg
               1060                     1065                     1070

Ser  Pro  Leu  Ala  Pro  Ser  Glu  Gly  Ala  Gly  Ser  Asp  Val  Phe  Asp  Gly
          1075                     1080                     1085

Asp  Leu  Gly  Met  Gly  Ala  Ala  Lys  Gly  Leu  Gln  Ser  Leu  Pro  Thr  His
     1090                     1095                     1100

Asp  Pro  Ser  Pro  Leu  Gln  Arg  Tyr  Ser  Glu  Asp  Pro  Thr  Val  Pro  Leu
1105                     1110                     1115                     1120

Pro  Ser  Glu  Thr  Asp  Gly  Tyr  Val  Ala  Pro  Leu  Thr  Cys  Ser  Pro  Gln
               1125                     1130                     1135

Pro  Glu  Tyr  Val  Asn  Gln  Pro  Asp  Val  Arg  Pro  Gln  Pro  Pro  Ser  Pro
               1140                     1145                     1150

Arg  Glu  Gly  Pro  Leu  Pro  Ala  Ala  Arg  Pro  Ala  Gly  Ala  Thr  Leu  Glu
               1155                     1160                     1165

Arg  Ala  Lys  Thr  Leu  Ser  Pro  Gly  Lys  Asn  Gly  Val  Val  Lys  Asp  Val
     1170                     1175                     1180

Phe  Ala  Phe  Gly  Gly  Ala  Val  Glu  Asn  Pro  Glu  Tyr  Leu  Thr  Pro  Gln
1185                     1190                     1195                     1200

Gly  Gly  Ala  Ala  Pro  Gln  Pro  His  Pro  Pro  Ala  Phe  Ser  Pro  Ala
                    1205                1210                     1215

Phe  Asp  Asn  Leu  Tyr  Tyr  Trp  Asp  Gln  Asp  Pro  Pro  Glu  Arg  Gly  Ala
                    1220                     1225                1230

Pro  Pro  Ser  Thr  Phe  Lys  Gly  Thr  Pro  Thr  Val  Ala  Glu  Asn  Pro  Glu
               1235                     1240                     1245

Tyr  Gly  Leu  Asp  Val  Pro  Val
     1250                1255
```

( 2 ) INFORMATION FOR SEQ ID NO:9:

( i ) SEQUENCE CHARACTERISTICS:
        ( A ) LENGTH: 1342 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:9:

```
Met  Arg  Ala  Asn  Asp  Ala  Leu  Gln  Val  Leu  Gly  Leu  Leu  Phe  Ser  Leu
1                   5                        10                       15
```

```
Ala  Arg  Gly  Ser  Glu  Val  Gly  Asn  Ser  Gln  Ala  Val  Cys  Pro  Gly  Thr
          20                       25                       30

Leu  Asn  Gly  Leu  Ser  Val  Thr  Gly  Asp  Ala  Glu  Asn  Gln  Tyr  Gln  Thr
          35                       40                       45

Leu  Tyr  Lys  Leu  Tyr  Glu  Arg  Cys  Glu  Val  Val  Met  Gly  Asn  Leu  Glu
     50                       55                       60

Ile  Val  Leu  Thr  Gly  His  Asn  Ala  Asp  Leu  Ser  Phe  Leu  Gln  Trp  Ile
65                       70                       75                       80

Arg  Glu  Val  Thr  Gly  Tyr  Val  Leu  Val  Ala  Met  Asn  Glu  Phe  Ser  Thr
               85                       90                       95

Leu  Pro  Leu  Pro  Asn  Leu  Arg  Val  Val  Arg  Gly  Thr  Gln  Val  Tyr  Asp
               100                      105                      110

Gly  Lys  Phe  Ala  Ile  Phe  Val  Met  Leu  Asn  Tyr  Asn  Thr  Asn  Ser  Ser
          115                      120                      125

His  Ala  Leu  Arg  Gln  Leu  Arg  Leu  Thr  Gln  Leu  Thr  Glu  Ile  Leu  Ser
          130                      135                      140

Gly  Gly  Val  Tyr  Ile  Glu  Lys  Asn  Asp  Lys  Leu  Cys  His  Met  Asp  Thr
145                      150                      155                      160

Ile  Asp  Trp  Arg  Asp  Ile  Val  Arg  Asp  Arg  Asp  Ala  Glu  Ile  Val  Val
               165                      170                      175

Lys  Asp  Asn  Gly  Arg  Ser  Cys  Pro  Pro  Cys  His  Glu  Val  Cys  Lys  Gly
               180                      185                      190

Arg  Cys  Trp  Gly  Pro  Gly  Ser  Glu  Asp  Cys  Gln  Thr  Leu  Thr  Lys  Thr
          195                      200                      205

Ile  Cys  Ala  Pro  Gln  Cys  Asn  Gly  His  Cys  Phe  Gly  Pro  Asn  Pro  Asn
          210                      215                      220

Gln  Cys  Cys  His  Asp  Glu  Cys  Ala  Gly  Gly  Cys  Ser  Gly  Pro  Gln  Asp
225                      230                      235                      240

Thr  Asp  Cys  Phe  Ala  Cys  Arg  His  Phe  Asn  Asp  Ser  Gly  Ala  Cys  Val
               245                      250                      255

Pro  Arg  Cys  Pro  Gln  Pro  Leu  Val  Tyr  Asn  Lys  Leu  Thr  Phe  Gln  Leu
               260                      265                      270

Glu  Pro  Asn  Pro  His  Thr  Lys  Tyr  Gln  Tyr  Gly  Gly  Val  Cys  Val  Ala
          275                      280                      285

Ser  Cys  Pro  His  Asn  Phe  Val  Val  Asp  Gln  Thr  Ser  Cys  Val  Arg  Ala
     290                      295                      300

Cys  Pro  Pro  Asp  Lys  Met  Glu  Val  Asp  Lys  Asn  Gly  Leu  Lys  Met  Cys
305                      310                      315                      320

Glu  Pro  Cys  Gly  Gly  Leu  Cys  Pro  Lys  Ala  Cys  Glu  Gly  Thr  Gly  Ser
               325                      330                      335

Gly  Ser  Arg  Phe  Gln  Thr  Val  Asp  Ser  Ser  Asn  Ile  Asp  Gly  Phe  Val
          340                      345                      350

Asn  Cys  Thr  Lys  Ile  Leu  Gly  Asn  Leu  Asp  Phe  Leu  Ile  Thr  Gly  Leu
          355                      360                      365

Asn  Gly  Asp  Pro  Trp  His  Lys  Ile  Pro  Ala  Leu  Asp  Pro  Glu  Lys  Leu
     370                      375                      380

Asn  Val  Phe  Arg  Thr  Val  Arg  Glu  Ile  Thr  Gly  Tyr  Leu  Asn  Ile  Gln
385                      390                      395                      400

Ser  Trp  Pro  Pro  His  Met  His  Asn  Phe  Ser  Val  Phe  Ser  Asn  Leu  Thr
                    405                      410                      415

Thr  Ile  Gly  Gly  Arg  Ser  Leu  Tyr  Asn  Arg  Gly  Phe  Ser  Leu  Leu  Ile
               420                      425                      430

Met  Lys  Asn  Leu  Asn  Val  Thr  Ser  Leu  Gly  Phe  Arg  Ser  Leu  Lys  Glu
          435                      440                      445
```

```
Ile  Ser  Ala  Gly  Arg  Ile  Tyr  Ile  Ser  Ala  Asn  Arg  Gln  Leu  Cys  Tyr
     450                      455                 460

His  His  Ser  Leu  Asn  Trp  Thr  Lys  Val  Leu  Arg  Gly  Pro  Thr  Glu  Glu
465                      470                 475                           480

Arg  Leu  Asp  Ile  Lys  His  Asn  Arg  Pro  Arg  Asp  Cys  Val  Ala  Glu
                    485                 490                           495

Gly  Lys  Val  Cys  Asp  Pro  Leu  Cys  Ser  Ser  Gly  Gly  Cys  Trp  Gly  Pro
               500                      505                 510

Gly  Pro  Gly  Gln  Cys  Leu  Ser  Cys  Arg  Asn  Tyr  Ser  Arg  Gly  Gly  Val
               515                 520                 525

Cys  Val  Thr  His  Cys  Asn  Phe  Leu  Asn  Gly  Glu  Pro  Arg  Glu  Phe  Ala
     530                      535                 540

His  Glu  Ala  Glu  Cys  Phe  Ser  Cys  His  Pro  Glu  Cys  Gln  Pro  Met  Gly
545                      550                 555                           560

Gly  Thr  Ala  Thr  Cys  Asn  Gly  Ser  Gly  Ser  Asp  Thr  Cys  Ala  Gln  Cys
               565                 570                           575

Ala  His  Phe  Arg  Asp  Gly  Pro  His  Cys  Val  Ser  Ser  Cys  Pro  His  Gly
               580                 585                           590

Val  Leu  Gly  Ala  Lys  Gly  Pro  Ile  Tyr  Lys  Tyr  Pro  Asp  Val  Gln  Asn
     595                      600                 605

Glu  Cys  Arg  Pro  Cys  His  Glu  Asn  Cys  Thr  Gln  Gly  Cys  Lys  Gly  Pro
     610                      615                 620

Glu  Leu  Gln  Asp  Cys  Leu  Gly  Gln  Thr  Leu  Val  Leu  Ile  Gly  Lys  Thr
625                      630                 635                           640

His  Leu  Thr  Met  Ala  Leu  Thr  Val  Ile  Ala  Gly  Leu  Val  Val  Ile  Phe
                    645                 650                           655

Met  Met  Leu  Gly  Gly  Thr  Phe  Leu  Tyr  Trp  Arg  Gly  Arg  Arg  Ile  Gln
               660                 665                 670

Asn  Lys  Arg  Ala  Met  Arg  Arg  Tyr  Leu  Glu  Arg  Gly  Glu  Ser  Ile  Glu
          675                 680                 685

Pro  Leu  Asp  Pro  Ser  Glu  Lys  Ala  Asn  Lys  Val  Leu  Ala  Arg  Ile  Phe
     690                 695                      700

Lys  Glu  Thr  Glu  Leu  Arg  Lys  Leu  Lys  Val  Leu  Gly  Ser  Gly  Val  Phe
705                      710                 715                           720

Gly  Thr  Val  His  Lys  Gly  Val  Trp  Ile  Pro  Glu  Gly  Glu  Ser  Ile  Lys
               725                 730                 735

Ile  Pro  Val  Cys  Ile  Lys  Val  Ile  Glu  Asp  Lys  Ser  Gly  Arg  Gln  Ser
               740                 745                 750

Phe  Gln  Ala  Val  Thr  Asp  His  Met  Leu  Ala  Ile  Gly  Ser  Leu  Asp  His
          755                 760                 765

Ala  His  Ile  Val  Arg  Leu  Leu  Gly  Leu  Cys  Pro  Gly  Ser  Ser  Leu  Gln
     770                 775                      780

Leu  Val  Thr  Gln  Tyr  Leu  Pro  Leu  Gly  Ser  Leu  Asp  His  Val  Arg
785                      790                 795                           800

Gln  His  Arg  Gly  Ala  Leu  Gly  Pro  Gln  Leu  Leu  Leu  Asn  Trp  Gly  Val
                    805                 810                           815

Gln  Ile  Ala  Lys  Gly  Met  Tyr  Tyr  Leu  Glu  Glu  His  Gly  Met  Val  His
               820                 825                 830

Arg  Asn  Leu  Ala  Ala  Arg  Asn  Val  Leu  Leu  Lys  Ser  Pro  Ser  Gln  Val
               835                 840                 845

Gln  Val  Ala  Asp  Phe  Gly  Val  Ala  Asp  Leu  Leu  Pro  Pro  Asp  Asp  Lys
     850                      855                 860

Gln  Leu  Leu  Tyr  Ser  Glu  Ala  Lys  Thr  Pro  Ile  Lys  Trp  Met  Ala  Leu
```

-continued

```
              865                     870                     875                     880

Glu  Ser  Ile  His  Phe  Gly  Lys  Tyr  Thr  His  Gln  Ser  Asp  Val  Trp  Ser
                    885                     890                          895

Tyr  Gly  Val  Thr  Val  Trp  Glu  Leu  Met  Thr  Phe  Gly  Ala  Glu  Pro  Tyr
               900                     905                     910

Ala  Gly  Leu  Arg  Leu  Ala  Glu  Val  Pro  Asp  Leu  Leu  Glu  Lys  Gly  Glu
               915                     920                     925

Arg  Leu  Ala  Gln  Pro  Gln  Ile  Cys  Thr  Ile  Asp  Val  Tyr  Met  Val  Met
     930                     935                     940

Val  Lys  Cys  Trp  Met  Ile  Asp  Glu  Asn  Ile  Arg  Pro  Thr  Phe  Lys  Glu
945                      950                     955                          960

Leu  Ala  Asn  Glu  Phe  Thr  Arg  Met  Ala  Arg  Asp  Pro  Pro  Arg  Tyr  Leu
                    965                     970                          975

Val  Ile  Lys  Arg  Glu  Ser  Gly  Pro  Gly  Ile  Ala  Pro  Gly  Pro  Glu  Pro
               980                     985                     990

His  Gly  Leu  Thr  Asn  Lys  Lys  Leu  Glu  Glu  Val  Glu  Leu  Glu  Pro  Glu
               995                     1000                    1005

Leu  Asp  Leu  Asp  Leu  Asp  Leu  Glu  Ala  Glu  Glu  Asp  Asn  Leu  Ala  Thr
          1010                    1015                    1020

Thr  Thr  Leu  Gly  Ser  Ala  Leu  Ser  Leu  Pro  Val  Gly  Thr  Leu  Asn  Arg
1025                     1030                    1035                         1040

Pro  Arg  Gly  Ser  Gln  Ser  Leu  Leu  Ser  Pro  Ser  Ser  Gly  Tyr  Met  Pro
                    1045                    1050                    1055

Met  Asn  Gln  Gly  Asn  Leu  Gly  Gly  Ser  Cys  Gln  Glu  Ser  Ala  Val  Ser
                    1060                    1065                    1070

Gly  Ser  Ser  Glu  Arg  Cys  Pro  Arg  Pro  Val  Ser  Leu  His  Pro  Met  Pro
                    1075                    1080                    1085

Arg  Gly  Cys  Leu  Ala  Ser  Glu  Ser  Ser  Glu  Gly  His  Val  Thr  Gly  Ser
     1090                    1095                    1100

Glu  Ala  Glu  Leu  Gln  Glu  Lys  Val  Ser  Met  Cys  Arg  Ser  Arg  Ser  Arg
1105                     1110                    1115                         1120

Ser  Arg  Ser  Pro  Arg  Pro  Arg  Gly  Asp  Ser  Ala  Tyr  His  Ser  Gln  Arg
                    1125                    1130                    1135

His  Ser  Leu  Leu  Thr  Pro  Val  Thr  Pro  Leu  Ser  Pro  Pro  Gly  Leu  Glu
                    1140                    1145                    1150

Glu  Glu  Asp  Val  Asn  Gly  Tyr  Val  Met  Pro  Asp  Thr  His  Leu  Lys  Gly
                    1155                    1160                    1165

Thr  Pro  Ser  Ser  Arg  Glu  Gly  Thr  Leu  Ser  Ser  Val  Gly  Leu  Ser  Ser
          1170                    1175                    1180

Val  Leu  Gly  Thr  Glu  Glu  Glu  Asp  Glu  Asp  Glu  Glu  Tyr  Glu  Tyr  Met
1185                     1190                    1195                         1200

Asn  Arg  Arg  Arg  Arg  His  Ser  Pro  Pro  His  Pro  Pro  Arg  Pro  Ser  Ser
                    1205                    1210                         1215

Leu  Glu  Glu  Leu  Gly  Tyr  Glu  Tyr  Met  Asp  Val  Gly  Ser  Asp  Leu  Ser
                    1220                    1225                    1230

Ala  Ser  Leu  Gly  Ser  Thr  Gln  Ser  Cys  Pro  Leu  His  Pro  Val  Pro  Ile
          1235                    1240                    1245

Met  Pro  Thr  Ala  Gly  Thr  Thr  Pro  Asp  Glu  Asp  Tyr  Glu  Tyr  Met  Asn
     1250                    1255                    1260

Arg  Gln  Arg  Asp  Gly  Gly  Gly  Pro  Gly  Gly  Asp  Tyr  Ala  Ala  Met  Gly
1265                     1270                    1275                         1280

Ala  Cys  Pro  Ala  Ser  Glu  Gln  Gly  Tyr  Glu  Glu  Met  Arg  Ala  Phe  Gln
                    1285                    1290                    1295
```

```
Gly  Pro  Gly  His  Gln  Ala  Pro  His  Val  His  Tyr  Ala  Arg  Leu  Lys  Thr
              1300                1305                     1310

Leu  Arg  Ser  Leu  Glu  Ala  Thr  Asp  Ser  Ala  Phe  Asp  Asn  Pro  Asp  Tyr
              1315                1320                     1325

Trp  His  Ser  Arg  Leu  Phe  Pro  Lys  Ala  Asn  Ala  Gln  Arg  Thr
              1330                1335                     1340
```

( 2 ) INFORMATION FOR SEQ ID NO:10:

( i ) SEQUENCE CHARACTERISTICS:
        ( A ) LENGTH: 911 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:10:

```
Met  Lys  Pro  Ala  Thr  Gly  Leu  Trp  Val  Trp  Val  Ser  Leu  Leu  Val  Ala
1                   5                    10                       15

Ala  Gly  Thr  Val  Gln  Pro  Ser  Asp  Ser  Gln  Ser  Val  Cys  Ala  Gly  Thr
              20                   25                        30

Glu  Asn  Lys  Leu  Ser  Ser  Leu  Ser  Asp  Leu  Glu  Gln  Gln  Tyr  Arg  Ala
              35                   40                        45

Leu  Arg  Lys  Tyr  Tyr  Glu  Asn  Cys  Glu  Val  Val  Met  Gly  Asn  Leu  Glu
     50                        55                      60

Ile  Thr  Ser  Ile  Glu  His  Asn  Arg  Asp  Leu  Ser  Phe  Leu  Arg  Ser  Val
65                            70                      75                      80

Arg  Glu  Val  Thr  Gly  Tyr  Val  Leu  Val  Ala  Leu  Asn  Gln  Phe  Arg  Tyr
                    85                        90                       95

Leu  Pro  Leu  Glu  Asn  Leu  Arg  Ile  Ile  Arg  Gly  Thr  Lys  Leu  Tyr  Glu
                    100                       105                      110

Asp  Arg  Tyr  Ala  Leu  Ala  Ile  Phe  Leu  Asn  Tyr  Arg  Lys  Asp  Gly  Asn
               115                       120                      125

Phe  Gly  Leu  Gln  Glu  Leu  Gly  Leu  Lys  Asn  Leu  Thr  Glu  Ile  Leu  Asn
     130                       135                      140

Gly  Gly  Val  Tyr  Val  Asp  Gln  Asn  Lys  Phe  Leu  Cys  Tyr  Ala  Asp  Thr
145                            150                     155                     160

Ile  His  Trp  Gln  Asp  Ile  Val  Arg  Asn  Pro  Trp  Pro  Ser  Asn  Leu  Thr
                    165                       170                      175

Leu  Val  Ser  Thr  Asn  Gly  Ser  Ser  Gly  Cys  Gly  Arg  Cys  His  Lys  Ser
                    180                       185                      190

Cys  Thr  Gly  Arg  Cys  Trp  Gly  Pro  Thr  Glu  Asn  His  Cys  Gln  Thr  Leu
               195                       200                      205

Thr  Arg  Thr  Val  Cys  Ala  Glu  Gln  Cys  Asp  Gly  Arg  Cys  Tyr  Gly  Pro
     210                       215                      220

Tyr  Val  Ser  Asp  Cys  Cys  His  Arg  Glu  Cys  Ala  Gly  Gly  Cys  Ser  Gly
225                            230                     235                     240

Pro  Lys  Asp  Thr  Asp  Cys  Phe  Ala  Cys  Met  Asn  Phe  Asn  Asp  Ser  Gly
                    245                       250                      255

Ala  Cys  Val  Thr  Gln  Cys  Pro  Gln  Thr  Phe  Val  Tyr  Asn  Pro  Thr  Thr
               260                       265                      270

Phe  Gln  Leu  Glu  His  Asn  Phe  Asn  Ala  Lys  Tyr  Thr  Tyr  Gly  Ala  Phe
          275                       280                       285

Cys  Val  Lys  Lys  Cys  Pro  His  Asn  Phe  Val  Val  Asp  Ser  Ser  Ser  Cys
          290                       295                       300

Val  Arg  Ala  Cys  Pro  Ser  Ser  Lys  Met  Glu  Val  Glu  Glu  Asn  Gly  Ile
```

-continued

|   |     |     |     |     |     |     |     |     |     |     |     |     |     |     |     |
|---|-----|-----|-----|-----|-----|-----|-----|-----|-----|-----|-----|-----|-----|-----|-----|
| 305 | | | | 310 | | | | 315 | | | | 320 | | | |
| Lys | Met | Cys | Lys | Pro | Cys | Thr | Asp | Ile | Cys | Pro | Lys | Ala | Cys | Asp | Gly |
| | | | | 325 | | | | 330 | | | | | | 335 | |
| Ile | Gly | Thr | Gly | Ser | Leu | Met | Ser | Ala | Gln | Thr | Val | Asp | Ser | Ser | Asn |
| | | | 340 | | | | 345 | | | | | 350 | | | |
| Ile | Asp | Lys | Phe | Ile | Asn | Cys | Thr | Lys | Ile | Asn | Gly | Asn | Leu | Ile | Phe |
| | | 355 | | | | 360 | | | | | 365 | | | | |
| Leu | Val | Thr | Gly | Ile | His | Gly | Asp | Pro | Tyr | Asn | Ala | Ile | Glu | Ala | Ile |
| | 370 | | | | 375 | | | | | 380 | | | | | |
| Asp | Pro | Glu | Lys | Leu | Asn | Val | Phe | Arg | Thr | Val | Arg | Glu | Ile | Thr | Gly |
| 385 | | | | | 390 | | | | 395 | | | | | | 400 |
| Phe | Leu | Asn | Ile | Gln | Ser | Trp | Pro | Pro | Asn | Met | Thr | Asp | Phe | Ser | Val |
| | | | | 405 | | | | 410 | | | | | 415 | | |
| Phe | Ser | Asn | Leu | Val | Thr | Ile | Gly | Gly | Arg | Val | Leu | Tyr | Ser | Gly | Leu |
| | | | 420 | | | | | 425 | | | | 430 | | | |
| Ser | Leu | Leu | Ile | Leu | Lys | Gln | Gln | Gly | Ile | Thr | Ser | Leu | Gln | Phe | Gln |
| | | | 435 | | | | | 440 | | | | 445 | | | |
| Ser | Leu | Lys | Glu | Ile | Ser | Ala | Gly | Asn | Ile | Tyr | Ile | Thr | Asp | Asn | Ser |
| | | 450 | | | | 455 | | | | | 460 | | | | |
| Asn | Leu | Cys | Tyr | Tyr | His | Thr | Ile | Asn | Trp | Thr | Thr | Leu | Phe | Ser | Thr |
| 465 | | | | | 470 | | | | 475 | | | | | | 480 |
| Ile | Asn | Gln | Arg | Ile | Val | Ile | Arg | Asp | Asn | Arg | Lys | Ala | Glu | Asn | Cys |
| | | | | 485 | | | | 490 | | | | | 495 | | |
| Thr | Ala | Glu | Gly | Met | Val | Cys | Asn | His | Leu | Cys | Ser | Ser | Asp | Gly | Cys |
| | | | 500 | | | | 505 | | | | | 510 | | | |
| Trp | Gly | Pro | Gly | Pro | Asp | Gln | Cys | Leu | Ser | Cys | Arg | Arg | Phe | Ser | Arg |
| | | 515 | | | | 520 | | | | | 525 | | | | |
| Gly | Arg | Ile | Cys | Ile | Glu | Ser | Cys | Asn | Leu | Tyr | Asp | Gly | Glu | Phe | Arg |
| | 530 | | | | 535 | | | | | 540 | | | | | |
| Glu | Phe | Glu | Asn | Gly | Ser | Ile | Cys | Val | Glu | Cys | Asp | Pro | Gln | Cys | Glu |
| 545 | | | | | 550 | | | | 555 | | | | | | 560 |
| Lys | Met | Glu | Asp | Gly | Leu | Leu | Thr | Cys | His | Gly | Pro | Gly | Pro | Asp | Asn |
| | | | | 565 | | | | 570 | | | | | 575 | | |
| Cys | Thr | Lys | Cys | Ser | His | Phe | Lys | Asp | Gly | Pro | Asn | Cys | Val | Glu | Lys |
| | | | 580 | | | | 585 | | | | | 590 | | | |
| Cys | Pro | Asp | Gly | Leu | Gln | Gly | Ala | Asn | Ser | Phe | Ile | Phe | Lys | Tyr | Ala |
| | | 595 | | | | 600 | | | | | 605 | | | | |
| Asp | Pro | Asp | Arg | Glu | Cys | His | Pro | Cys | His | Pro | Asn | Cys | Thr | Gln | Gly |
| | 610 | | | | 615 | | | | | 620 | | | | | |
| Cys | Asn | Gly | Pro | Thr | Ser | His | Asp | Cys | Ile | Tyr | Tyr | Pro | Trp | Thr | Gly |
| 625 | | | | | 630 | | | | 635 | | | | | | 640 |
| His | Ser | Thr | Leu | Pro | Gln | Asp | Pro | Val | Lys | Val | Lys | Ala | Leu | Glu | Gly |
| | | | | 645 | | | | 650 | | | | | 655 | | |
| Phe | Pro | Arg | Leu | Val | Gly | Pro | Asp | Phe | Gly | Cys | Ala | Glu | Pro | Ala | |
| | | | 660 | | | | 665 | | | | 670 | | | | |
| Asn | Thr | Phe | Leu | Asp | Pro | Glu | Glu | Pro | Lys | Ser | Cys | Asp | Lys | Thr | His |
| | | 675 | | | | 680 | | | | | 685 | | | | |
| Thr | Cys | Pro | Pro | Cys | Pro | Ala | Pro | Glu | Leu | Leu | Gly | Gly | Pro | Ser | Val |
| | 690 | | | | 695 | | | | | 700 | | | | | |
| Phe | Leu | Phe | Pro | Pro | Lys | Pro | Lys | Asp | Thr | Leu | Met | Ile | Ser | Arg | Thr |
| 705 | | | | | 710 | | | | 715 | | | | | | 720 |
| Pro | Glu | Val | Thr | Cys | Val | Val | Val | Asp | Val | Ser | His | Glu | Asp | Pro | Glu |
| | | | | 725 | | | | 730 | | | | | 735 | | |

```
Val Lys Phe Asn Trp Tyr Val Asp Gly Val Glu Val His Val Ala Lys
        740             745             750

Thr Lys Pro Arg Glu Glu Gln Tyr Asn Ser Thr Tyr Arg Val Val Ser
    755             760             765

Val Leu Thr Val Leu His Gln Asp Trp Leu Asn Gly Lys Glu Tyr Lys
    770             775             780

Cys Lys Val Ser Asn Lys Ala Leu Pro Ala Pro Ile Glu Lys Thr Ile
785             790             795                         800

Ser Lys Ala Lys Gly Gln Pro Arg Glu Pro Gln Val Tyr Thr Leu Pro
            805             810                     815

Pro Ser Arg Asp Glu Leu Thr Lys Asn Gln Val Ser Leu Thr Cys Leu
            820             825             830

Val Lys Gly Phe Tyr Pro Ser Asp Ile Ala Val Glu Trp Glu Ser Asn
        835             840             845

Gly Gln Pro Glu Asn Asn Tyr Lys Thr Thr Pro Pro Val Leu Asp Ser
    850             855             860

Asp Gly Ser Phe Phe Leu Tyr Ser Lys Leu Thr Val Asp Lys Ser Arg
865             870             875                         880

Trp Gln Gln Gly Asn Val Phe Ser Cys Ser Val Met His Glu Ala Leu
            885             890                     895

His Asn His Tyr Thr Gln Lys Ser Leu Ser Leu Ser Pro Gly Lys
            900             905             910
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:11:

```
Gly Xaa Gly Xaa Xaa Gly
1               5
```

( 2 ) INFORMATION FOR SEQ ID NO:12:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:12:

```
Asp Leu Ala Ala Arg Asn
1               5
```

( 2 ) INFORMATION FOR SEQ ID NO:13:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: peptide ( x i ) SEQUENCE DESCRIPTION: SEQ ID NO:13:

```
Pro Ile Lys Trp Met Ala
1               5
```

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:14:

ACNGTNTGGG ARYTNAYHAC     20

( 2 ) INFORMATION FOR SEQ ID NO:15:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:15:

CAYGTNAARA THACNGAYTT YGG     23

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:16:

GACGAATTCC NATHAARTGG ATGGC     25

( 2 ) INFORMATION FOR SEQ ID NO:17:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:17:

ACAYTTNARD ATDATCATRT ANAC     24

( 2 ) INFORMATION FOR SEQ ID NO:18:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:18:

AANGTCATNA RYTCCCA     17

( 2 ) INFORMATION FOR SEQ ID NO:19:

( i ) SEQUENCE CHARACTERISTICS:

(A) LENGTH: 23 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:19:

TCCAGNGCGA TCCAYTTDAT NGG       23

(2) INFORMATION FOR SEQ ID NO:20:

(i) SEQUENCE CHARACTERISTICS:
(A) LENGTH: 18 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:20:

GGRTCDATCA TCCARCCT       18

(2) INFORMATION FOR SEQ ID NO:21:

(i) SEQUENCE CHARACTERISTICS:
(A) LENGTH: 20 base pairs
(B) TYPE: nucleic acid
(C) STRANDEDNESS: single
(D) TOPOLOGY: unknown (ii) MOLECULE TYPE: DNA (genomic)

(xi) SEQUENCE DESCRIPTION: SEQ ID NO:21:

CTGCTGTCAG CATCGATCAT       20

(2) INFORMATION FOR SEQ ID NO:22:

(i) SEQUENCE CHARACTERISTICS:
(A) LENGTH: 7 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:22:

Thr Val Trp Glu Leu Met Thr
1               5

(2) INFORMATION FOR SEQ ID NO:23:

(i) SEQUENCE CHARACTERISTICS:
(A) LENGTH: 8 amino acids
(B) TYPE: amino acid
(C) STRANDEDNESS: unknown
(D) TOPOLOGY: unknown (ii) MOLECULE TYPE: peptide (xi) SEQUENCE DESCRIPTION: SEQ ID NO:23:

His Val Lys Ile Thr Asp Phe Gly
1               5

(2) INFORMATION FOR SEQ ID NO:24:

(i) SEQUENCE CHARACTERISTICS:
(A) LENGTH: 7 amino acids
(B) TYPE: amino acid
(C) STRANDEDNESS: unknown (D) TOPOLOGY: unknown (ii) MOLECULE TYPE: peptide (xi) SEQUENCE DESCRIPTION: SEQ ID NO:24:

Val Tyr Met Ile Ile Leu Lys
1               5

(2) INFORMATION FOR SEQ ID NO:25:

(i) SEQUENCE CHARACTERISTICS:
  (A) LENGTH: 6 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:25:

Trp Glu Leu Met Thr Phe
1               5

(2) INFORMATION FOR SEQ ID NO:26:

(i) SEQUENCE CHARACTERISTICS:
  (A) LENGTH: 8 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:26:

Pro Ile Lys Trp Met Ala Leu Glu
1               5

(2) INFORMATION FOR SEQ ID NO:27:

(i) SEQUENCE CHARACTERISTICS:
  (A) LENGTH: 6 amino acids
  (B) TYPE: amino acid
  (C) STRANDEDNESS: unknown
  (D) TOPOLOGY: unknown (ii) MOLECULE TYPE: peptide (xi) SEQUENCE DESCRIPTION: SEQ ID NO:27:

Cys Trp Met Ile Asp Pro
1               5

(2) INFORMATION FOR SEQ ID NO:28:

(i) SEQUENCE CHARACTERISTICS:
  (A) LENGTH: 35 base pairs
  (B) TYPE: nucleic acid
  (C) STRANDEDNESS: single
  (D) TOPOLOGY: unknown (ii) MOLECULE TYPE: DNA (genomic)

(xi) SEQUENCE DESCRIPTION: SEQ ID NO:28:

GACTCGAGTC GACATCGATT TTTTTTTTTT TTTTT                35

(2) INFORMATION FOR SEQ ID NO:29:

(i) SEQUENCE CHARACTERISTICS:
  (A) LENGTH: 24 base pairs
  (B) TYPE: nucleic acid
  (C) STRANDEDNESS: single
  (D) TOPOLOGY: unknown ( i i ) MOLECULE TYPE: DNA (genomic)

( x i ) SEQUENCE DESCRIPTION: SEQ ID NO:29:

GAAGAAAGAC GACTCGTTCA TCGG  24

( 2 ) INFORMATION FOR SEQ ID NO:30:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: unknown ( i i ) MOLECULE TYPE: DNA (genomic)

( x i ) SEQUENCE DESCRIPTION: SEQ ID NO:30:

GACCATGACC ATGTAAACGT CAATA  25

( 2 ) INFORMATION FOR SEQ ID NO:31:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:31:

Leu Ala Arg Leu Leu Glu Gly Asp Glu Lys Glu Tyr Asn Ala Asp Gly
1               5                   10                  15
Gly ( 2 ) INFORMATION FOR SEQ ID NO:32:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: unknown ( i i ) MOLECULE TYPE: peptide ( x i ) SEQUENCE DESCRIPTION: SEQ ID NO:32:

Glu Glu Asp Leu Glu Asp Met Met Asp Ala Glu Glu Tyr
1               5                   10

( 2 ) INFORMATION FOR SEQ ID NO:33:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: unknown ( i i ) MOLECULE TYPE: peptide ( i x ) FEATURE:
        ( A ) NAME/KEY: Xaa
        ( B ) LOCATION: 3
        ( D ) OTHER INFORMATION: "Xaa =Any amino acid"

( i x ) FEATURE:
        ( A ) NAME/KEY: Xaa
        ( B ) LOCATION: 6
        ( D ) OTHER INFORMATION: "Xaa =Any amino acid"

( i x ) FEATURE:
        ( A ) NAME/KEY: Xaa
        ( B ) LOCATION: 7

( D ) OTHER INFORMATION: "Xaa =Any amino acid"

( x i ) SEQUENCE DESCRIPTION: SEQ ID NO:33:

Ser Gly Xaa Lys Pro Xaa Xaa Ala Ala
 1               5

( 2 ) INFORMATION FOR SEQ ID NO:34:

( i ) SEQUENCE CHARACTERISTICS:
        ( A ) LENGTH: 25 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:34:

CGGAAGCTTC TAGAGATCCC TCGAC  25

( 2 ) INFORMATION FOR SEQ ID NO:35:

( i ) SEQUENCE CHARACTERISTICS:
        ( A ) LENGTH: 50 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:35:

GTTTTTACCT TTTTTATCTT CTTTGTGTTC GGTTGTGTAT TTCACACGCC  50

( 2 ) INFORMATION FOR SEQ ID NO:36:

( i ) SEQUENCE CHARACTERISTICS:
        ( A ) LENGTH: 50 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:36:

CAAAAATGGA AAAAATAGAA GAAACAGAAG CCATCTCATAA AGTGTGCGG  50

( 2 ) INFORMATION FOR SEQ ID NO:37:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:37:

GTTCTTTTTC GCCTCCTTGA GATGATTAGA TCTCTG  36

( 2 ) INFORMATION FOR SEQ ID NO:38:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:38:

GTCAGAGTTC ATATGGTAGT TAAGCCCCCC CAAAAC                                        36

(2) INFORMATION FOR SEQ ID NO:39:

(i) SEQUENCE CHARACTERISTICS:
        (A) LENGTH: 114 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:39:

CAAAGATCCT CTAAGCTTGT AGAGTTCCTC CGATTTGTAA AAAGATGCCA TAACATAGTT             60

CTGGCAACGG TCGCCAGTAA ATTCGTTCGG GCACTTGCAC AAGTATCTTG ACGG                 114

(2) INFORMATION FOR SEQ ID NO:40:

(i) SEQUENCE CHARACTERISTICS:
        (A) LENGTH: 95 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:40:

```
Met Val Val Lys Pro Pro Gln Asn Lys Thr Glu Ser Glu Asn Thr Ser
 1           5                  10                  15

Asp Lys Pro Lys Arg Lys Lys Lys Gly Gly Lys Asn Gly Lys Asn Arg
                20                  25                  30

Arg Asn Arg Ser His Leu Ile Lys Cys Ala Glu Lys Glu Lys Thr Phe
            35                  40                  45

Cys Val Asn Gly Gly Glu Cys Phe Thr Val Lys Asp Leu Ser Asn Pro
                50                  55                  60

Ser Arg Tyr Leu Cys Lys Cys Pro Asn Glu Phe Thr Gly Asp Arg Cys
         65                  70                  75                  80

Gln Asn Tyr Val Met Ala Ser Phe Tyr Lys Ala Glu Glu Leu Tyr
             85                  90                  95
```

(2) INFORMATION FOR SEQ ID NO:41:

(i) SEQUENCE CHARACTERISTICS:
        (A) LENGTH: 1389 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: CDS
        (B) LOCATION: 1..1386

(xi) SEQUENCE DESCRIPTION: SEQ ID NO:41:

```
ATG GTA GTT AAG CCC CCC CAA AAC AAG ACG GAA AGT GAA AAT ACT TCA              48
Met Val Val Lys Pro Pro Gln Asn Lys Thr Glu Ser Glu Asn Thr Ser
 1           5                  10                  15

GAT AAA CCC AAA AGA AAG AAA AAG GGA GGC AAA AAT GGA AAA AAT AGA              96
Asp Lys Pro Lys Arg Lys Lys Lys Gly Gly Lys Asn Gly Lys Asn Arg
                20                  25                  30

AGA AAC AGA AGC CAT CTC ATA AAG TGT GCG GAG AAG GAG AAA ACT TTC             144
Arg Asn Arg Ser His Leu Ile Lys Cys Ala Glu Lys Glu Lys Thr Phe
            35                  40                  45

TGT GTG AAT GGG GGC GAG TGC TTC ACG GTG AAG GAC CTG TCA AAC CCG             192
```

-continued

| | | | | | | | | | | | | | | | | |
|---|---|---|---|---|---|---|---|---|---|---|---|---|---|---|---|---|
| | Cys | Val | Asn | Gly | Gly | Glu | Cys | Phe | Thr | Val | Lys | Asp | Leu | Ser | Asn | Pro |
| | | 50 | | | | 55 | | | | | 60 | | | | | |

| | | | | | | | | | | | | | | | | |
|---|---|---|---|---|---|---|---|---|---|---|---|---|---|---|---|---|
| TCA | AGA | TAC | TTG | TGC | AAG | TGC | CCG | AAC | GAA | TTT | ACT | GGC | GAC | CGT | TGC | 240 |
| Ser | Arg | Tyr | Leu | Cys | Lys | Cys | Pro | Asn | Glu | Phe | Thr | Gly | Asp | Arg | Cys | |
| 65 | | | | 70 | | | | | 75 | | | | | 80 | | |

| CAG | AAC | TAT | GTT | ATG | GCA | TCT | TTT | TAC | AAA | GCG | GAG | GAA | CTC | TAC | AAG | 288 |
|---|---|---|---|---|---|---|---|---|---|---|---|---|---|---|---|---|
| Gln | Asn | Tyr | Val | Met | Ala | Ser | Phe | Tyr | Lys | Ala | Glu | Glu | Leu | Tyr | Lys | |
| | | | | 85 | | | | | 90 | | | | | 95 | | |

| CTT | ATG | GCC | GAG | GAA | GGC | GGC | AGC | CTG | GCC | GCG | CTG | ACC | GCG | CAC | CAG | 336 |
|---|---|---|---|---|---|---|---|---|---|---|---|---|---|---|---|---|
| Leu | Met | Ala | Glu | Glu | Gly | Gly | Ser | Leu | Ala | Ala | Leu | Thr | Ala | His | Gln | |
| | | | 100 | | | | | 105 | | | | | 110 | | | |

| GCT | TGC | CAC | CTG | CCG | CTG | GAG | ACT | TTC | ACC | CGT | CAT | CGC | CAG | CCG | CGC | 384 |
|---|---|---|---|---|---|---|---|---|---|---|---|---|---|---|---|---|
| Ala | Cys | His | Leu | Pro | Leu | Glu | Thr | Phe | Thr | Arg | His | Arg | Gln | Pro | Arg | |
| | | 115 | | | | | 120 | | | | | 125 | | | | |

| GGC | TGG | GAA | CAA | CTG | GAG | CAG | TGC | GGC | TAT | CCG | GTG | CAG | CGG | CTG | GTC | 432 |
|---|---|---|---|---|---|---|---|---|---|---|---|---|---|---|---|---|
| Gly | Trp | Glu | Gln | Leu | Glu | Gln | Cys | Gly | Tyr | Pro | Val | Gln | Arg | Leu | Val | |
| | 130 | | | | | 135 | | | | | 140 | | | | | |

| GCC | CTC | TAC | CTG | GCG | GCG | CGG | CTG | TCG | TGG | AAC | CAG | GTC | GAC | CAG | GTG | 480 |
|---|---|---|---|---|---|---|---|---|---|---|---|---|---|---|---|---|
| Ala | Leu | Tyr | Leu | Ala | Ala | Arg | Leu | Ser | Trp | Asn | Gln | Val | Asp | Gln | Val | |
| 145 | | | | 150 | | | | | 155 | | | | | 160 | | |

| ATC | CGC | AAC | GCC | CTG | GCC | AGC | CCC | GGC | AGC | GGC | GAC | CTG | GGC | GAA | | 528 |
|---|---|---|---|---|---|---|---|---|---|---|---|---|---|---|---|---|
| Ile | Arg | Asn | Ala | Leu | Ala | Ser | Pro | Gly | Ser | Gly | Asp | Leu | Gly | Glu | | |
| | | | | 165 | | | | | 170 | | | | | 175 | | |

| GCG | ATC | CGC | GAG | CAG | CCG | GAG | CAG | GCC | CGT | CTG | GCC | CTG | ACC | CTG | GCC | 576 |
|---|---|---|---|---|---|---|---|---|---|---|---|---|---|---|---|---|
| Ala | Ile | Arg | Glu | Gln | Pro | Glu | Gln | Ala | Arg | Leu | Ala | Leu | Thr | Leu | Ala | |
| | | | 180 | | | | | 185 | | | | | 190 | | | |

| GCC | GCC | GAG | AGC | GAG | CGC | TTC | GTC | CGG | CAG | GGC | ACC | GGC | AAC | GAC | GAG | 624 |
|---|---|---|---|---|---|---|---|---|---|---|---|---|---|---|---|---|
| Ala | Ala | Glu | Ser | Glu | Arg | Phe | Val | Arg | Gln | Gly | Thr | Gly | Asn | Asp | Glu | |
| | | | 195 | | | | | 200 | | | | | 205 | | | |

| GCC | GGC | GCG | GCC | AAC | GCC | GAC | GTG | GTG | AGC | CTG | ACC | TGC | CCG | GTC | GCC | 672 |
|---|---|---|---|---|---|---|---|---|---|---|---|---|---|---|---|---|
| Ala | Gly | Ala | Ala | Asn | Ala | Asp | Val | Val | Ser | Leu | Thr | Cys | Pro | Val | Ala | |
| | 210 | | | | | 215 | | | | | 220 | | | | | |

| GCC | GGT | GAA | TGC | GCG | GGC | CCG | GCG | GAC | AGC | GGC | GAC | GCC | CTG | CTG | GAG | 720 |
|---|---|---|---|---|---|---|---|---|---|---|---|---|---|---|---|---|
| Ala | Gly | Glu | Cys | Ala | Gly | Pro | Ala | Asp | Ser | Gly | Asp | Ala | Leu | Leu | Glu | |
| 225 | | | | 230 | | | | | 235 | | | | | | 240 | |

| CGC | AAC | TAT | CCC | ACT | GGC | GCG | GAG | TTC | CTC | GGC | GAC | GGC | GGC | GAC | GTC | 768 |
|---|---|---|---|---|---|---|---|---|---|---|---|---|---|---|---|---|
| Arg | Asn | Tyr | Pro | Thr | Gly | Ala | Glu | Phe | Leu | Gly | Asp | Gly | Gly | Asp | Val | |
| | | | | 245 | | | | | 250 | | | | | 255 | | |

| AGC | TTC | AGC | ACC | CGC | GGC | ACG | CAG | AAC | TGG | ACG | GTG | GAG | CGG | CTG | CTC | 816 |
|---|---|---|---|---|---|---|---|---|---|---|---|---|---|---|---|---|
| Ser | Phe | Ser | Thr | Arg | Gly | Thr | Gln | Asn | Trp | Thr | Val | Glu | Arg | Leu | Leu | |
| | | | | 260 | | | | | 265 | | | | | 270 | | |

| CAG | GCG | CAC | CGC | CAA | CTG | GAG | GAG | CGC | GGC | TAT | GTG | TTC | GTC | GGC | TAC | 864 |
|---|---|---|---|---|---|---|---|---|---|---|---|---|---|---|---|---|
| Gln | Ala | His | Arg | Gln | Leu | Glu | Glu | Arg | Gly | Tyr | Val | Phe | Val | Gly | Tyr | |
| | | 275 | | | | | 280 | | | | | 285 | | | | |

| CAC | GGC | ACC | TTC | CTC | GAA | GCG | GCG | CAA | AGC | ATC | GTC | TTC | GGC | GGG | GTG | 912 |
|---|---|---|---|---|---|---|---|---|---|---|---|---|---|---|---|---|
| His | Gly | Thr | Phe | Leu | Glu | Ala | Ala | Gln | Ser | Ile | Val | Phe | Gly | Gly | Val | |
| | | 290 | | | | | 295 | | | | | 300 | | | | |

| CGC | GCG | CGC | AGC | CAG | GAC | CTC | GAC | GCG | ATC | TGG | CGC | GGT | TTC | TAT | ATC | 960 |
|---|---|---|---|---|---|---|---|---|---|---|---|---|---|---|---|---|
| Arg | Ala | Arg | Ser | Gln | Asp | Leu | Asp | Ala | Ile | Trp | Arg | Gly | Phe | Tyr | Ile | |
| 305 | | | | 310 | | | | | 315 | | | | | | 320 | |

| GCC | GGC | GAT | CCG | GCG | CTG | GCC | TAC | GGC | TAC | GCC | CAG | GAC | CAG | GAA | CCC | 1008 |
|---|---|---|---|---|---|---|---|---|---|---|---|---|---|---|---|---|
| Ala | Gly | Asp | Pro | Ala | Leu | Ala | Tyr | Gly | Tyr | Ala | Gln | Asp | Gln | Glu | Pro | |
| | | | | 325 | | | | | 330 | | | | | 335 | | |

| GAC | GCA | CGC | GGC | CGG | ATC | CGC | AAC | GGT | GCC | CTG | CTG | CGG | GTC | TAT | GTG | 1056 |
|---|---|---|---|---|---|---|---|---|---|---|---|---|---|---|---|---|
| Asp | Ala | Arg | Gly | Arg | Ile | Arg | Asn | Gly | Ala | Leu | Leu | Arg | Val | Tyr | Val | |
| | | | 340 | | | | | 345 | | | | | 350 | | | |

| CCG | CGC | TCG | AGC | CTG | CCG | GGC | TTC | TAC | CGC | ACC | AGC | CTG | ACC | CTG | GCC | 1104 |
|---|---|---|---|---|---|---|---|---|---|---|---|---|---|---|---|---|
| Pro | Arg | Ser | Ser | Leu | Pro | Gly | Phe | Tyr | Arg | Thr | Ser | Leu | Thr | Leu | Ala | |
| | | 355 | | | | | 360 | | | | | 365 | | | | |

| GGC | GGC | GAG | GCG | GCG | GGC | GAG | GTC | GAA | CGG | CTG | ATC | GGC | CAT | CCG | CTG | 1152 |

```
Gly Gly Glu Ala Ala Gly Glu Val Glu Arg Leu Ile Gly His Pro Leu
    370                 375                 380

CCG CTG CGC CTG GAC GCC ATC ACC GGC CCC GAG GAG GAA GGC GGG CGC              1200
Pro Leu Arg Leu Asp Ala Ile Thr Gly Pro Glu Glu Glu Gly Gly Arg
385                 390                 395                 400

CTG GAG ACC ATT CTC GGC TGG CCG CTG GCC GAG CGC ACC GTG GTG ATT              1248
Leu Glu Thr Ile Leu Gly Trp Pro Leu Ala Glu Arg Thr Val Val Ile
                405                 410                 415

CCC TCG GCG ATC CCC ACC GAC CCG CGC AAC GTC GGC GGC GAC CTC GAC              1296
Pro Ser Ala Ile Pro Thr Asp Pro Arg Asn Val Gly Gly Asp Leu Asp
            420                 425                 430

CCG TCC AGC ATC CCC GAC AAG GAA CAG GCG ATC AGC GCC CTG CCG GAC              1344
Pro Ser Ser Ile Pro Asp Lys Glu Gln Ala Ile Ser Ala Leu Pro Asp
        435                 440                 445

TAC GCC AGC CAG CCC GGC AAA CCG CCG CGC GAG GAC CTG AAG TAA                  1389
Tyr Ala Ser Gln Pro Gly Lys Pro Pro Arg Glu Asp Leu Lys
    450                 455                 460
```

( 2 ) INFORMATION FOR SEQ ID NO:42:

( i ) SEQUENCE CHARACTERISTICS:
        ( A ) LENGTH: 462 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

```
Met Val Val Lys Pro Pro Gln Asn Lys Thr Glu Ser Glu Asn Thr Ser
1               5                   10                  15

Asp Lys Pro Lys Arg Lys Lys Lys Gly Gly Lys Asn Gly Lys Asn Arg
                20                  25                  30

Arg Asn Arg Ser His Leu Ile Lys Cys Ala Glu Lys Glu Lys Thr Phe
            35                  40                  45

Cys Val Asn Gly Gly Glu Cys Phe Thr Val Lys Asp Leu Ser Asn Pro
        50                  55                  60

Ser Arg Tyr Leu Cys Lys Cys Pro Asn Glu Phe Thr Gly Asp Arg Cys
65                  70                  75                  80

Gln Asn Tyr Val Met Ala Ser Phe Tyr Lys Ala Glu Glu Leu Tyr Lys
                85                  90                  95

Leu Met Ala Glu Gly Gly Ser Leu Ala Ala Leu Thr Ala His Gln
                100                 105                 110

Ala Cys His Leu Pro Leu Glu Thr Phe Thr Arg His Arg Gln Pro Arg
            115                 120                 125

Gly Trp Glu Gln Leu Glu Gln Cys Gly Tyr Pro Val Gln Arg Leu Val
        130                 135                 140

Ala Leu Tyr Leu Ala Ala Arg Leu Ser Trp Asn Gln Val Asp Gln Val
145                 150                 155                 160

Ile Arg Asn Ala Leu Ala Ser Pro Gly Ser Gly Gly Asp Leu Gly Glu
                165                 170                 175

Ala Ile Arg Glu Gln Pro Glu Gln Ala Arg Leu Ala Leu Thr Leu Ala
            180                 185                 190

Ala Ala Glu Ser Glu Arg Phe Val Arg Gln Gly Thr Gly Asn Asp Glu
        195                 200                 205

Ala Gly Ala Ala Asn Ala Asp Val Val Ser Leu Thr Cys Pro Val Ala
210                 215                 220

Ala Gly Glu Cys Ala Gly Pro Ala Asp Ser Gly Asp Ala Leu Leu Glu
225                 230                 235                 240
```

-continued

| | | | | | | | | | | | | | | |
|---|---|---|---|---|---|---|---|---|---|---|---|---|---|---|
| Arg | Asn | Tyr | Pro | Thr 245 | Gly | Ala | Glu | Phe | Leu 250 | Gly | Asp | Gly | Gly | Asp 255 | Val |
| Ser | Phe | Ser | Thr 260 | Arg | Gly | Thr | Gln | Asn 265 | Trp | Thr | Val | Glu | Arg 270 | Leu | Leu |
| Gln | Ala | His 275 | Arg | Gln | Leu | Glu | Glu 280 | Arg | Gly | Tyr | Val | Phe 285 | Val | Gly | Tyr |
| His | Gly 290 | Thr | Phe | Leu | Glu | Ala 295 | Ala | Gln | Ser | Ile | Val 300 | Phe | Gly | Gly | Val |
| Arg 305 | Ala | Arg | Ser | Gln | Asp 310 | Leu | Asp | Ala | Ile | Trp 315 | Arg | Gly | Phe | Tyr | Ile 320 |
| Ala | Gly | Asp | Pro | Ala 325 | Leu | Ala | Tyr | Gly | Tyr 330 | Ala | Gln | Asp | Gln | Glu 335 | Pro |
| Asp | Ala | Arg | Gly 340 | Arg | Ile | Arg | Asn | Gly 345 | Ala | Leu | Leu | Arg | Val 350 | Tyr | Val |
| Pro | Arg | Ser 355 | Ser | Leu | Pro | Gly | Phe 360 | Tyr | Arg | Thr | Ser | Leu 365 | Thr | Leu | Ala |
| Gly | Gly 370 | Glu | Ala | Ala | Gly | Glu 375 | Val | Glu | Arg | Leu | Ile 380 | Gly | His | Pro | Leu |
| Pro 385 | Leu | Arg | Leu | Asp | Ala 390 | Ile | Thr | Gly | Pro | Glu 395 | Glu | Glu | Gly | Gly | Arg 400 |
| Leu | Glu | Thr | Ile | Leu 405 | Gly | Trp | Pro | Leu | Ala 410 | Glu | Arg | Thr | Val | Val 415 | Ile |
| Pro | Ser | Ala | Ile 420 | Pro | Thr | Asp | Pro | Arg 425 | Asn | Val | Gly | Gly | Asp 430 | Leu | Asp |
| Pro | Ser | Ser 435 | Ile | Pro | Asp | Lys | Glu 440 | Gln | Ala | Ile | Ser | Ala 445 | Leu | Pro | Asp |
| Tyr | Ala 450 | Ser | Gln | Pro | Gly | Lys 455 | Pro | Pro | Arg | Glu | Asp 460 | Leu | Lys | | |

ANTIBODIES TO HER4, HUMAN RECEPTOR TYROSINE KINASE

This application is a divisional of application Ser. No. 08/323,442 filed Oct. 14, 1994, which is a CIP of U.S. Ser. No. 08/150,704 abandoned, filed Nov. 10, 1993, which is a CIP of U.S. Ser. No. 07/981,165 filed Nov. 24, 1992, abandoned, each of which applications are incorporated herein in their entireties.

1. INTRODUCTION

The present invention is generally directed to a novel receptor tyrosine kinase related to the epidermal growth factor receptor, termed HER4/p180$^{erbB4}$ ("HER4"), and to novel diagnostic and therapeutic compositions comprising HER4-derived or HER4-related biological components. The invention is based in part upon applicants discovery of human HER4, its complete nucleotide coding sequence, and functional properties of the HER4 receptor protein. More specifically, the invention is directed to HER4 biologics comprising, for example, polynucleotide molecules encoding HER4, HER4 polypeptides, anti-HER4 antibodies which recognize epitopes of HER4 polypeptides, ligands which interact with HER4, and diagnostic and therapeutic compositions and methods based fundamentally upon such molecules. In view of the expression of HER4 in several human cancers and in certain tissues of neuronal and muscular origin, the present invention provides a framework upon which effective biological therapies may be designed. The invention is hereinafter described in detail, in part by way of experimental examples specifically illustrating various aspects of the invention and particular embodiments thereof.

2. BACKGROUND OF THE INVENTION

Cells of virtually all tissue types express transmembrane receptor molecules with intrinsic tyrosine kinase activity through which various growth and differentiation factors mediate a range of biological effects (reviewed in Aaronson, 1991, *Science* 254:1146–52). Included in this group of receptor tyrosine kinases (RTKs) are the receptors for polypeptide growth factors such as epidermal growth factor (EGF), insulin, platelet-derived growth factor (PDGF), neurotrophins (i.e., NGF), and fibroblast growth factor (FGF). Recently, the ligands for several previously-characterized receptors have been identified, including ligands for c-kit (steel factor), met (hepatocyte growth factor), trk (nerve growth factor) (see, respectively, Zsebo et al., 1990, *Cell* 63:195–201; Bottardo et al., 1991, *Science* 251:802–04; Kaplan et al., 1991, *Nature* 350:158–160). In addition, the soluble factor NDF, or heregulin-alpha (HRG-α), has been identified as the ligand for HER2, a receptor which is highly related to HER4 (Wen et al., 1992, *Cell* 69:559–72; Holmes et al., 1992, *Science* 256:1205–10).

The heregulins are a family of molecules that were first isolated as specific ligands for HER2 (Wen, et al., 1992, *Cell,* 69:559–572; Holmes et al., 1992, *Science* 256:1205–1210; Falls et al., 1993, *Cell* 72:801–815; and Marchionni et al., 1993, *Nature* 362:312–318). A rat homologue was termed Neu differentiation factor (NDF) based on its ability to induce differentiation of breast cancer cells through its interaction with HER2/Neu (Wen et al., supra). Heregulin also appears to play an important role in development and maintenance of the nervous system based on its abundant expression in cells of neuronal origin and on the recognition that alternatively spliced forms of the heregulin gene encode for two recently characterized neurotrophic activities. One neural-derived factor is termed acetylcholine receptor inducing activity (ARIA)(Falls et al., supra). This heregulin isoform is responsible for stimulation of neurotransmitter receptor synthesis during formation of the neuromuscular junction. A second factor is called glial growth factor (GGF) reflecting the proliferative affect this molecule has on glial cells in the central and peripheral nervous system (Marchionni et al., supra). Additional, less well characterized molecules that appear to be isoforms of heregulin, include p45, gp30, and p75 (Lupu et al., 1990, *Science* 249:1552–1555; and Lupu et al., 1992, *Proc. Natl. Acad. Sci. U.S.A.* 89:2287–2291).

Several HER2-neutralizing antibodies fail to block heregulin activation of human breast cancer cells. Heregulin only activates tyrosine phosphorylation of HER2 in cells of breast, colon, and neuronal origin, and not in fibroblasts or ovarian cell lines that overexpress recombinant HER2 (Peles et al., 1993, *EMBO J.* 12:961–971).

Biological relationships between various human malignancies and genetic aberrations in growth factor-receptor tyrosine kinase signal pathways are known to exist. Among the most notable such relationships involve the EGF receptor (EGFR) family of receptor tyrosine kinases (see Aaronson, supra). Three human EGFR-family members have been identified and are known to those skilled in the art: EGFR, HER2/p185$^{erbB2}$ and HER3/p160$^{erbB3}$ (see, respectively, Ullrich et al., 1984, *Nature* 309:418–25; Coussens et al., 1985, *Science* 230:1132–39; Plowman et al., 1990, *Proc. Natl. Acad. Sci. U.S.A.* 87:4905–09). EGFR-related molecules from other species have also been identified.

The complete nucleotide coding sequence of other EGFR-family members has also been determined from other organisms including: the drosophila EGFR ("DER": Livneh et al., 1985, *Cell* 40:599–607), nematode EGFR ("let-23": Aroian et al., 1990, *Nature* 348:693–698), chicken EGFR ("CER": Lax et al., 1988, *Mol. Cell. Biol.* 8:1970–1978), rat EGFR (Petch et al., 1990, *Mol. Cell. Biol.* 10:2973–2982), rat HER2/Neu (Bargmann et al., 1986, *Nature,* 319:226–230) and a novel member isolated from the fish and termed Xiphophorus melanoma related kinase ("Xmrk": Wittbrodt et al., 1989, *Nature* 342:415–421). In addition, PCR technology has led to the isolation of other short DNA fragments that may encode novel receptors or may represent species-specific homologs of known receptors. One recent example is the isolation tyro-2 (Lai, C. and Lemke, G., 1991, *Neuron* 6:691–704) a fragment encoding 54 amino acids that is most related to the EGFR family.

Overexpression of EGFR-family receptors is frequently observed in a variety of aggressive human epithelial carcinomas. In particular, increased expression of EGFR is associated with more aggressive carcinomas of the breast, bladder, lung and stomach (see, for example, Neal et al., 1985, *Lancet* 1:366–68; Sainsbury et al., 1987, *Lancet* 1:1398–1402; Yasui et al., 1988, *Int. J. Cancer* 41:211–17; Veale et al., 1987, *Cancer* 55:513–16). In addition, amplification and overexpression of HER2 has been associated with a wide variety of human malignancies, particularly breast and ovarian carcinomas, for which a strong correlation between HER2 overexpression and poor clinical prognosis and/or increased relapse probability have been established (see, for example, Slamon et al., 1987, *Science* 235:177–82, and 1989, *Science* 244:707–12). Overexpression of HER2 has also been correlated with other human carcinomas, including carcinoma of the stomach, endometrium, salivary gland, bladder, and lung (Yokota et al., 1986, *Lancet* 1:765–67; Fukushigi et al., 1986, *Mol.*

Cell. Biol. 6:955–58; Yonemura et al., 1991, Cancer Res. 51:1034; Weiner et al., 1990, Cancer Res. 50:421–25; Geurin et al., 1988, Oncogene Res. 3:21–31; Semba et al., 1985, Proc. Natl. Acad. Sci. U.S.A. 82:6497–6501; Zhau et al., 1990, Mol. Carcinog. 3:354–57; McCann et al., 1990, Cancer 65:88–92). Most recently, a potential link between HER2 overexpression and gastric carcinoma has been reported (Jaehne et al., 1992, J. Cancer Res. Clin. Oncol. 118:474–79). Finally, amplified expression of the recently described HER3 receptor has been observed in a wide variety of human adenocarcinomas (Poller et al., 1992, J. Path 168:275–280; Krause et al., 1989, Proc. Natl. Acad. Sci. U.S.A. 86:9193–97; European Patent Application No. 91301737, published 9.4.91, EP 444 961).

Several structurally related soluble polypeptides capable of specifically binding to EGFR have been identified and characterized, including EGF, transforming growth factor-alpha (TGF-α), amphiregulin (AR), heparin-binding EGF (HB-EGF), and vaccinia virus growth factor (VGF) (see, respectively, Savage et al., 1972, J. Biol. Chem. 247:7612–21; Marquardt et al., 1984, Science 223:1079–82; Shoyab et al., 1989, Science 243:1074–76; Higashiyama et al., 1991, Science 251:936–39; Twardzik et al., 1985, Proc. Natl. Acad. Sci. U.S.A. 82:5300–04). Despite the close structural relationships among receptors of the EGFR-family, none of these ligands has been conclusively shown to interact with HER2 or HER3.

Recently, several groups have reported the identification of specific ligands for HER2. Some of these ligands, such as gp30 (Lupu et al., 1990, Science 249:1552–55; Bacus et al., 1992, Cell Growth and Differentiation 3:401–11) interact with both EGFR and HER2, while others are reported to bind specifically to HER2 (Wen et al., 1992, Cell 69:559–72; Peles et al., 1992, Cell 69:205–16; Holmes et al., 1992, Science 256:1205–10; Lupu et al., 1992, Proc. Natl. Acad. Sci. U.S.A. 89:2287–91; Huang et al., 1992, J. Biol. Chem. 276:11508–121). The best characterized of these ligands are neu differentiation factor (NDF) purified and cloned from ras-transformed Rat1-EJ cells (Wen et al., Peles et al., supra), and the heregulins (HRG-α, -β1, -β2, -β3), purified and cloned from human MDA-MB-231 cells (Holmes et al., supra). NDF and HRG-α share 93% sequence identity and appear to be the rat and human homologs of the same protein. Both of these proteins are similar size (44–45 kDa), increase tyrosine phosphorylation of HER2 in MDA-MB-453 cells and not the EGF-receptor, and have been reported to bind to HER2 in cross-linking studies on human breast cancer cells. In addition, NDF has been shown to induce differentiation of human mammary tumor cells to milk-producing, growth-arrested cells, whereas the heregulin family have been reported to stimulate proliferation of cultured human breast cancers cell monolayers.

Interestingly, although members of the heregulin family are capable of stimulating tyrosine phosphorylation of HER2 in many mammary carcinoma cell lines, they are not able to act on this receptor in the ovarian carcinoma cell line SKOV3 or in HER2 transfected fibroblasts (Peles et al., 1993, EMBO J. 12:961–971). These observations indicated the existence of other receptors for heregulin responsible for the activation of HER2. Such cross-activation between members of the receptor tyrosine kinase family has been already reported and is believed to arise from a ligand induced receptor heterodimerization event (Wada et al., 1990, Cell 61:1339–1347). Recently, it has been reported that HER3 binds heregulin (Carraway et al., 1994, J. Biol. Chem. 269:14303–14306), and in fact, this receptor seems to be involved in the heregulin-mediated tyrosine kinase activation of HER2 (Carraway et al., supra; Sliwkowski et al., 1994, J. Biol. Chem. 269:14661–14665).

The means by which receptor polypeptides transduce regulatory signals in response to ligand binding is not fully understood, and continues to be the subject of intensive investigation. However, important components of the process have been uncovered, including the understanding that phosphorylation of and by cell surface receptors hold fundamental roles in signal transduction. In addition to the involvement of phosphorylation in the signal process, the intracellular phenomena of receptor dimerization and receptor crosstalk function as primary components of the circuit through which ligand binding triggers a resulting cellular response. Ligand binding to transmembrane receptor tyrosine kinases induces receptor dimerization, leading to activation of kinase function through the interaction of adjacent cytoplasmic domains. Receptor crosstalk refers to intracellular communication between two or more proximate receptor molecules mediated by, for example, activation of one receptor through a mechanism involving the kinase activity of the other. One particularly relevant example of such a phenomenon is the binding of EGF to the EGFR, resulting in activation of the EGFR kinase domain and cross-phosphorylation of HER2 (Kokai et al., 1989, Cell 58:287–92; Stern et al., 1988, EMBO J. 7:995–1001; King et al., 1989, Oncogene 4:13–18).

3. SUMMARY OF THE INVENTION

HER4 is the fourth member of the EGFR-family of receptor tyrosine kinases and is likely to be involved not only in regulating normal cellular function but also in the loss of normal growth control associated with certain human cancers. In this connection, HER4 appears to be closely connected with certain carcinomas of epithelial origin, such as adenocarcinoma of the breast. As such, its discovery, and the elucidation of the HER4 coding sequence, open a number of novel approaches to the diagnosis and treatment of human cancers in which the aberrant expression and/or function of this cell surface receptor is involved.

The complete nucleotide sequence encoding the prototype HER4 polypeptide of the invention is disclosed herein, and provides the basis for several general aspects of the invention hereinafter described. Thus, the invention includes embodiments directly involving the production and use of HER4 polynucleotide molecules. In addition, the invention provides HER4 polypeptides, such as the prototype HER4 polypeptide disclosed and characterized in the sections which follow. Polypeptides sharing nearly equivalent structural characteristics with the prototype HER4 molecule are also included within the scope of this invention. Furthermore, the invention includes polypeptides which interact with HER4 expressed on the surface of certain cells thereby affecting their growth and/or differentiation. The invention is also directed to anti-HER4 antibodies, which have a variety of uses including but not limited to their use as components of novel biological approaches to human cancer diagnosis and therapy provided by the invention.

The invention also relates to the identification of HER4 ligands and methods for their purification.

The invention also relates to the discovery of an apparent functional relationship between HER4 and HER2, and the therapeutic aspects of the invention include those which are based on applicants' preliminary understanding of this relationship. Applicants' data strongly suggests that HER4 interacts with HER2 either by heterodimer formation or receptor crosstalk, and that such interaction appears to be one mechanism by which the HER4 receptor mediates effects on cell behavior. The reciprocal consequence is that HER2 activation is in some circumstances mediated through HER4.

In this connection, it appears that although heregulin induces phosphorylation of HER2 in cells expressing HER2 and HER4. Heregulin does not directly stimulate HER2 but acts by stimulating tyrosine phosphorylation of HER4.

Recognition of HER4 as a primary component of the heregulin signal transduction pathway opens a number of novel approaches to the diagnosis and treatment of human cancers in which the aberrant expression and/or function of heregulin and/or HER4 are involved. The therapeutic aspects of this invention thus include mediating a ligand's affect on HER4 and HER2 through antagonists, agonists or antibodies to HER4 ligands or HER4 receptor itself.

The invention also relates to chimeric proteins that specifically target and kill HER4 expressing tumor cells, polynucleotides encoding such chimeric proteins, and methods of using both in the therapeutic treatment of cancer and other human malignancies. Applicants' data demonstrate that such recombinant chimeric proteins specifically bind to the HER4 receptor and are cytotoxic against tumor cells that express HER4 on their surface. The bifunctional retention of both the specificity of the cell-binding portion of the molecule and the cytotoxic potential of the toxin portion makes for a very potent and targeted reagent.

The invention further relates to a method allowing determination of the cytotoxic activity of HER4 directed cytotoxic substances on cancer cells, thereby providing a powerful diagnostic tool; this will be of particular interest for prognosis of the effectiveness of these substances on an individual malignancy prior their therapeutic use.

4. BRIEF DESCRIPTION OF THE FIGURES

FIGS. 1A, 1B, 1C, and 1D. Nucleotide sequence [SEQ ID No:1] and deduced amino acid sequence of HER4 of the coding sequence from position 34 to 3961 (1308 amino acid residues) [SEQ ID No:2]. Nucleotides are numbered on the left, and amino acids are numbered above the sequence.

FIGS. 2A, 2B, 2C, and 2D. Nucleotide sequence [SEQ ID No:3] and deduced amino acid sequence ([SEQ ID No:4] of cDNAs encoding HER4 with alternate 3' end and without autophosphorylation domain. This sequence is identical with that of HER4 shown in FIGS. 1A and 1B up to nucleotide 3168, where the sequence diverges and the open reading frame stops after 13 amino acids, followed by an extended, unique 3'-untranslated region.

FIG. 3. Nucleotide sequence [SEQ ID No:5] and deduced amino acid sequence [SEQ ID No:6] of cDNA encoding HER4 with a N-terminal truncation. This sequence contains the 3'-portion of the HER4 sequence where nucleotide position 156 of the truncated sequence aligns with position 2335 of the complete HER4 sequence shown in FIGS. 1A and 1B (just downstream from the region encoding the ATP-binding site of the HER4 kinase). The first 155 nucleotides of the truncated sequence are unique from HER4 and may represent the 5'-untranslated region of a transcript derived from a cryptic promoter within an intron of the HER4 gene. (Section 6.2.2., infra).

FIGS. 4 and 5. The deduced amino acid sequence of two variant forms of human HER4 aligned with the full length HER4 receptor as represented in FIGS. 1A and 1B. Sequences are displayed using the single-letter code and are numbered on the right with the complete HER4 sequence on top and the variant sequences below. Identical residues are indicated by a colon between the aligned residues.

FIG. 4. HER4 with alternate 3'-end, lacking an autophosphorylation domain [SEQ ID No. 4]. This sequence is identical with that of HER4, shown in FIGS. 1A and 1B, up to amino acid 1045, where the sequence diverges and continues for 13 amino acids before reaching a stop codon.

FIG. 5. HER4 with N-terminal truncation [SEQ ID No. 6]. This sequence is identical to the 3'-portion of the HER4 shown in FIGS. 1A and 1B beginning at amino acid 768. (Section 6.2.2., infra).

Figure 6B:
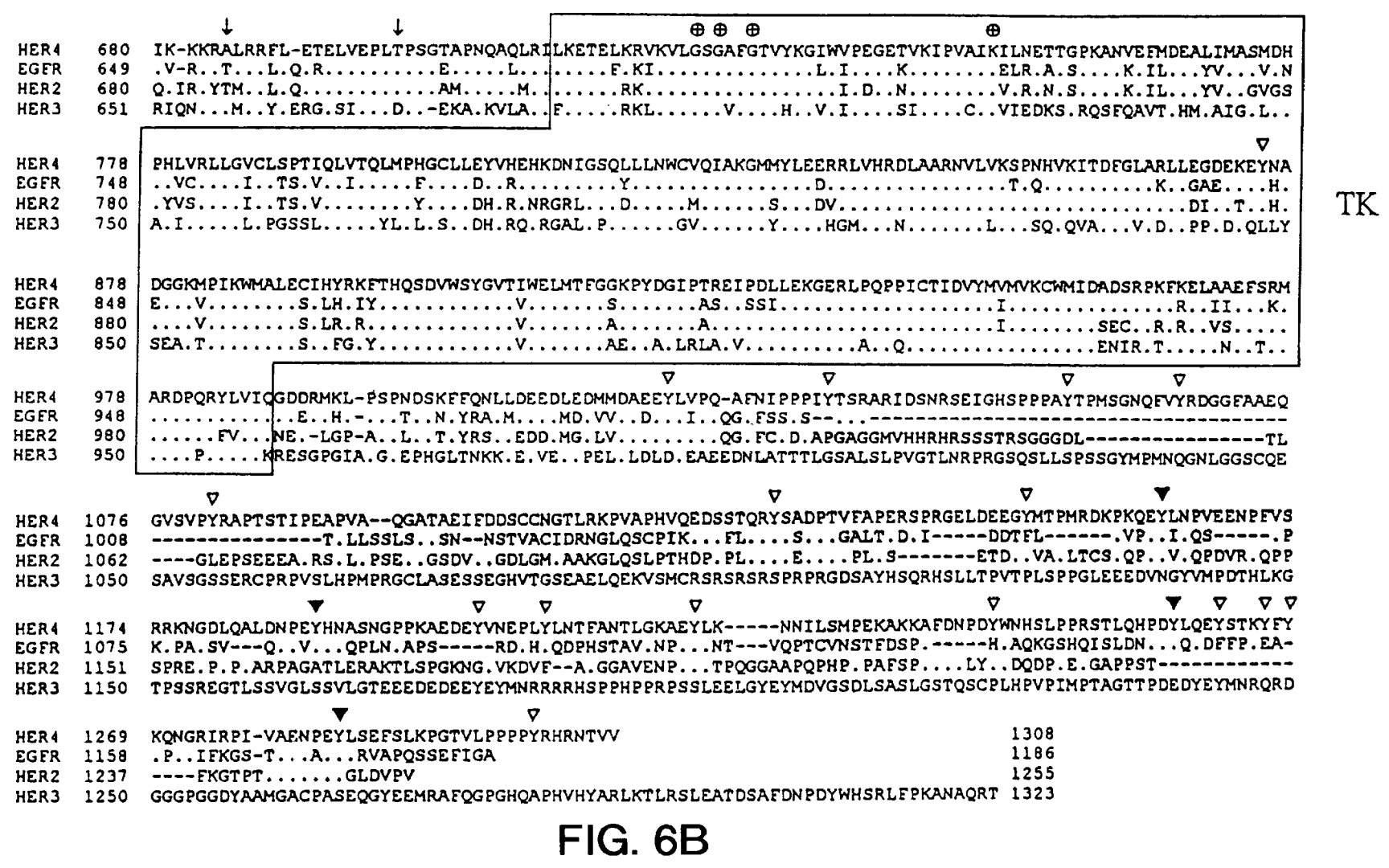

FIGS. 6A and 6B. Deduced amino acid sequence of human HER4 and alignment with other human EGFR-family members (EGFR [SEQ ID No:7]; HER2 [SEQ ID No:8]; HER3 [SEQ ID No:9]). Sequences are displayed using the single-letter code and are numbered on the left. Identical residues are denoted with dots, gaps are introduced for optimal alignment, cysteine residues are marked with an asterisk, and N-linked glycosylation sites are denoted with a plus (+). Potential protein kinase C phosphorylation sites are indicated by arrows (HER4 amino acid positions 679, 685, and 699). The predicted ATP-binding site is shown with 4 circled crosses, C-terminal tyrosines are denoted with open triangles, and tyrosines in HER4 that are conserved with the major autophosphorylation sites in the EGFR are indicated with black triangles. The predicted extracellular domain extends from the boundary of the signal sequence marked by an arrow at position 25, to the hydrophobic transmembrane domain which is overlined from amino acid positions 650 through 675. Various subdomains are labeled on the right: I, II, III, and IV=extracellular subdomains (domains II and IV are cysteine-rich); TM=transmembrane domain; TK=tyrosine kinase domain. Domains I, III, TK are boxed.

FIG. 7. Hydropathy profile of HER4, aligned with a comparison of protein domains for HER4 (1308 amino acids), EGFR (1210 amino acids), HER2 (1255 amino acids), and HER3 (1342 amino acids). The signal peptide is represented by a stippled box, the cysteine-rich extracellular subdomains are hatched, the transmembrane domain is filled, and the cytoplasmic tyrosine kinase domain is stippled. The percent amino acid sequence identities between HER4 and other EGFR-family members are indicated. Sig, signal peptide; I, II, III, and IV, extracellular domains; TM, transmembrane domain; JM, juxtamembrane domain; CaIn, calcium influx and internalization domain; 3'UTR, 3' untranslated region.

FIG. 8. Northern blot analysis from human tissues hybridized to HER4 probes. RNA size markers (in kilobases) are shown on the left. Lanes 1 through 8 represent 2 $\mu$g of poly(A)+ mRNA from pancreas, kidney, skeletal muscle, liver, lung, placenta, brain, and heart, respectively. FIG. 8 (Panel 1), Northern blot analysis of mRNA from human tissues hybridized to HER4 probes from the 3'-autophosphorylation domain; FIG. 8 (Panel 2), Northern blot analysis from human tissues hybridized to HER4 probes from the 5'-extracellular domain (see Section 6.2.3., infra).

FIG. 9. Immunoblot analysis of recombinant HER4 stably expressed in CHO-KI cells, according to procedure outlined in Section 7.1.3, infra. Membrane preparations from CHO-KI cells expressing recombinant HER4 were separated on 7% SDS-polyacrylamide gels and transferred to nitrocellulose. In FIG. 9 (Panel 1), blots were hybridized with a monoclonal antibody to the C-terminus of HER2 (Ab3, Oncogene Science, Uniondale, N.Y.) that cross-reacts with HER4. In FIG. 9 (Panel 2), blots were hybridized with a sheep antipeptide polyclonal antibody to a common epitope of HER2 and HER4. Lane 1, parental CHO-KI cells; lanes 2–4, CHO-KI/HER4 cell clones 6, 21, and 3, respectively.

Note the 180 kDa HER4 protein and the 130 kDa cross-reactive species. The size in kilodaltons of prestained high molecular weight markers (BioRad, Richmond, Calif.) is shown on the left.

Figure 10:
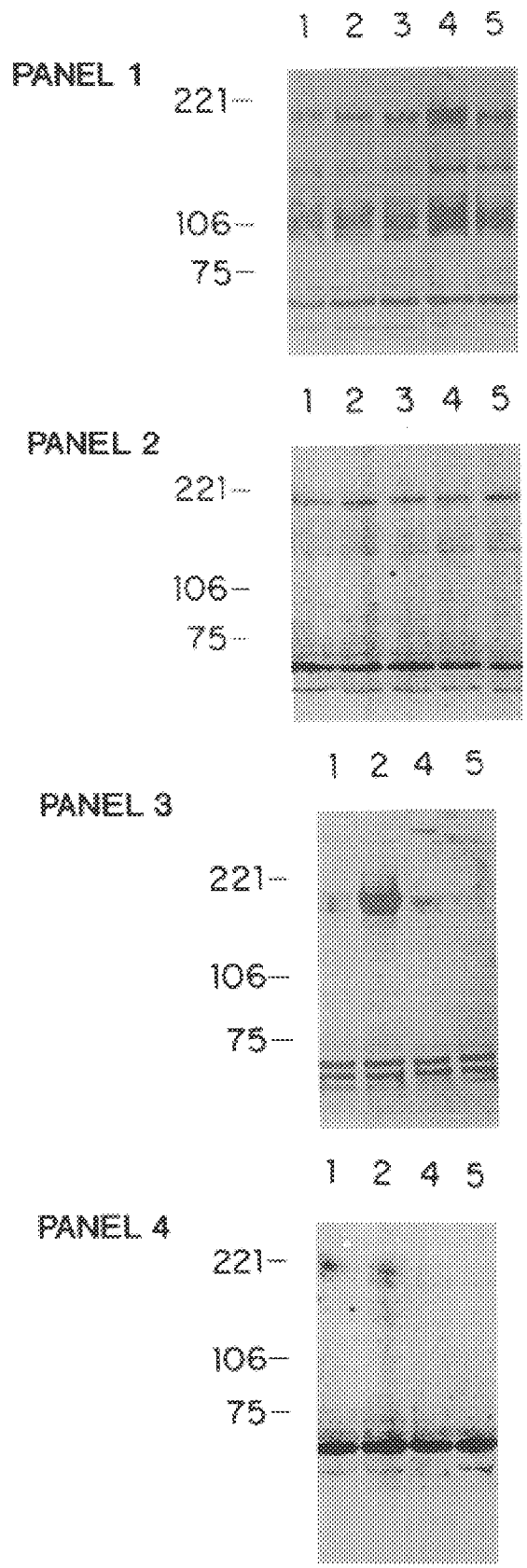

FIG. 10. Specific activation of HER4 tyrosine kinase by a breast cancer differentiation factor (see Section 8., infra). Four recombinant cell lines, each of which was engineered to overexpress a single member of EGFR-family of tyrosine kinase receptors (EGFR, HER2, HER3, and HER4), were prepared according to the methods described in Sections 7.1.2 and 8.1., infra. Cells from each of the four recombinant cell lines were stimulated with various ligand preparations and assayed for receptor tyrosine phosphorylation using the assay described in Section 8.2., infra. FIG. 10 (Panel 1), CHO/HER4 #3 cells; FIG. 10 (Panel 2), CHO/HER2 cells; FIG. 10 (Panel 3), NRHER5 cells; and FIG. 10 (Panel 4), 293/HER3 cells. Cells stimulated with: lane 1, buffer control; lane 2, 100 ng/ml EGF; lane 3, 200 ng/ml amphiregulin; lane 4, 10 μl phenyl, column fraction 17 (Section 9, infra); lane 5, 10 μl phenyl column fraction 14 (Section 9., infra, and see description of FIG. 9 below). The size (in kilodaltons) of the prestained molecular weight markers are labeled on the left of each panel. The phosphorylated receptor in each series migrates just below the 221 kDa marker. Bands at the bottom of the gels are extraneous and are due to the reaction of secondary antibodies with the antibodies used in the immunoprecipitation.

Figures 11A, 11B, 11C:
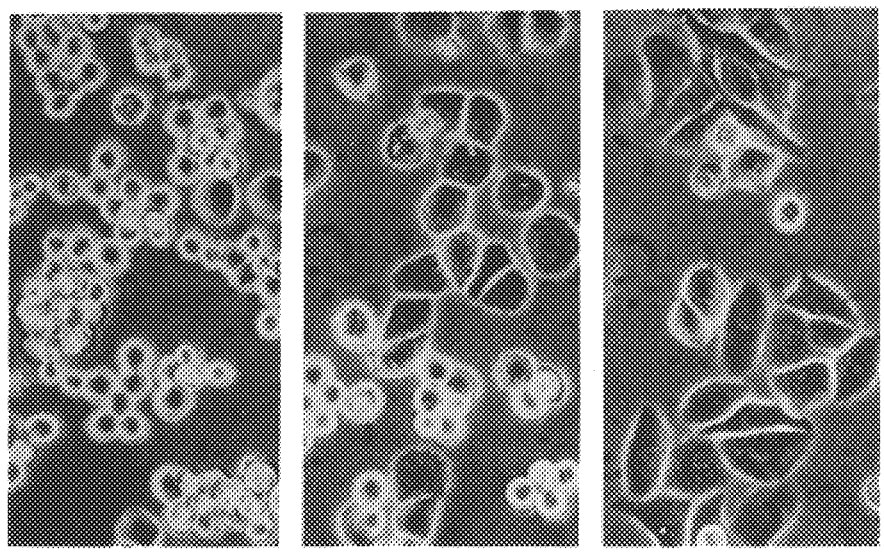
Figure 11D:
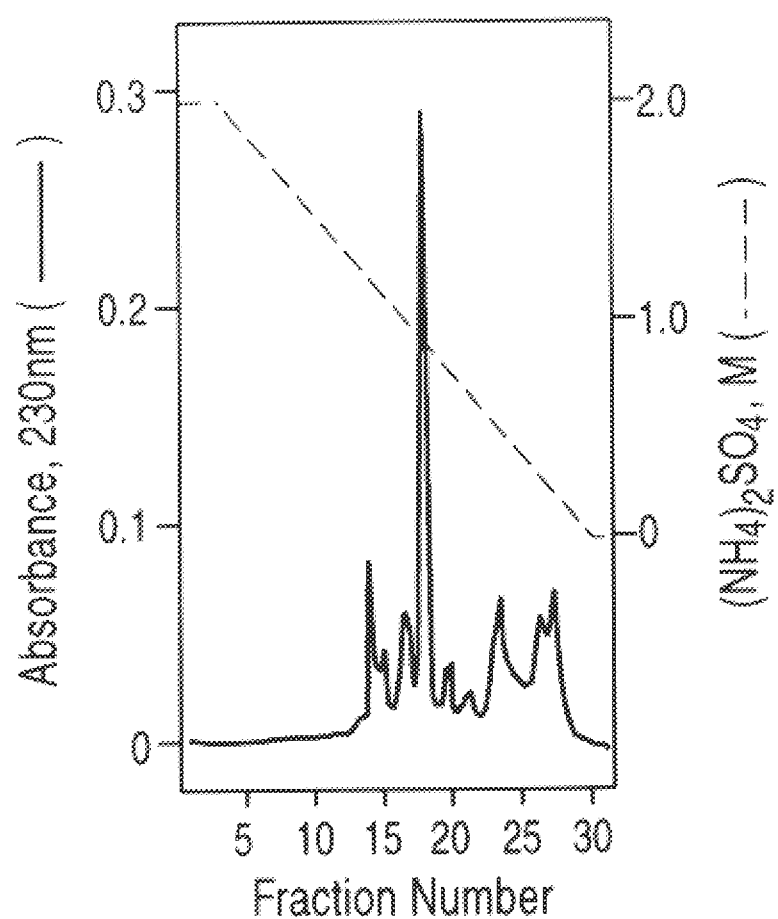
Figure 11E:
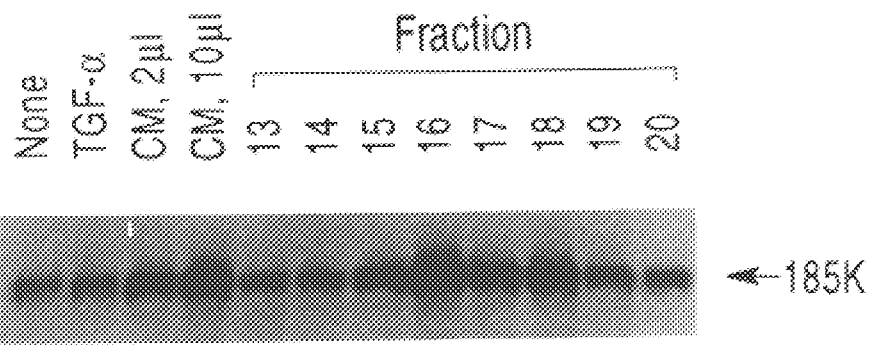
Figure 11F:
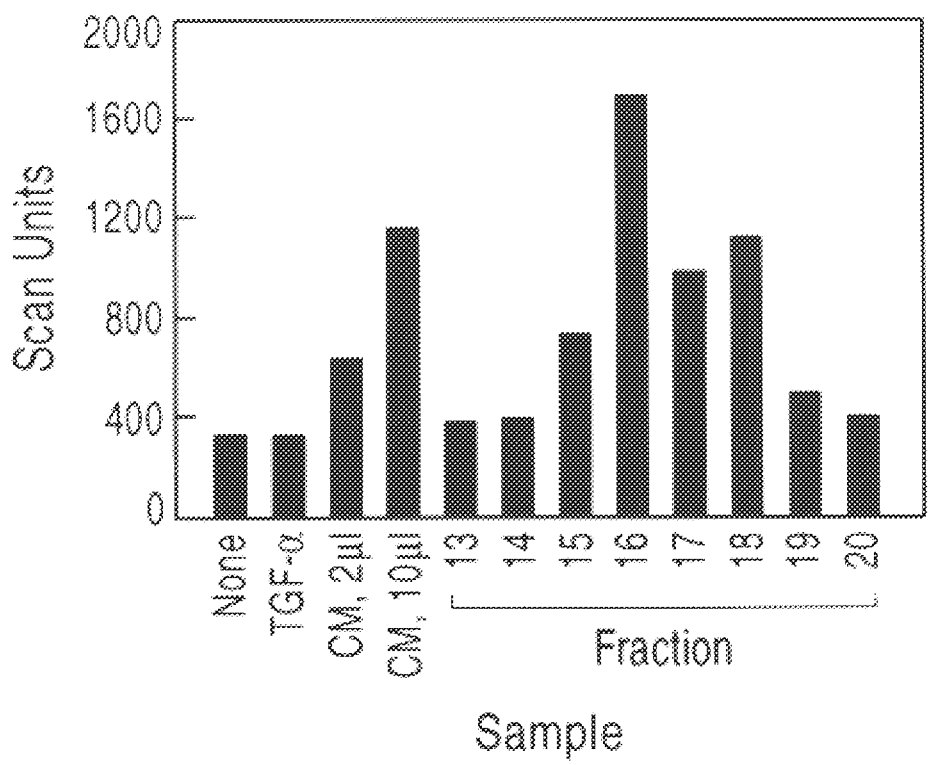

FIGS. 11A–11F. Biological and biochemical properties of the MDA-MB-453-cell differentiation activity purified from the conditioned media of HepG2 cells (Section 9., infra). FIGS. 11A and B show induction of morphologic differentiation. Conditioned media from HepG2 cells was subjected to ammonium sulfate fractionation, followed by dialysis against PBS. Dilutions of this material were added to MDA-MB-453 monolayer at the indicated protein concentrations. FIG. 11A, control; FIG. 11B, 80 ng per well; FIG. 11C, 2.0 μg per well; FIG. 11D, Phenyl-5PW column elution profile monitored at 230 nm absorbance; FIG. 11E, Stimulation of MDA-MB-453 tyrosine autophosphorylation with the following ligand preparations: None (control with no factor added); TGF-α (50 ng/ml); CM (16-fold concentrated HepG2 conditioned medium tested at 2 μl and 10 μl per well); fraction (phenyl column fractions 13 to 20, 10 μl per well). FIG. 11F, Densitometry analysis of the phosphorylation signals shown in FIG. 11E.

Figure 12A:
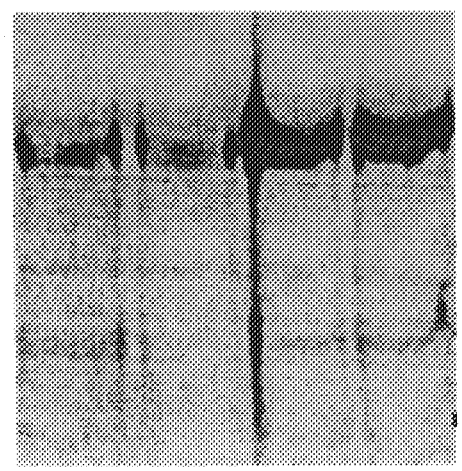
Figure 12B:
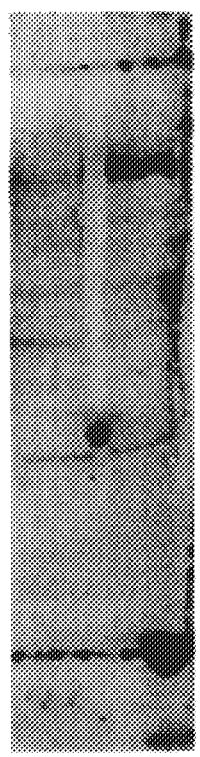

FIG. 12. NDF-induced tyrosine phosphorylation. FIG. 12 (Panel 1), MDA-MB-453 cells (lane 1, mock transfected COS cell supernatant; lane 2, NDF transfected COS cell supernatant); FIG. 12 (Panel 2), CHO/HER4 21-2 cells (lanes 1 and 2, mock transfected COS cell supernatant; lanes 3 and 4, NDF transfected COS cell supernatant). See Section 10., infra. Tyrosine phosphorylation was determined by the tyrosine kinase stimulation assay described in Section 8.2., infra.

Figure 13A:
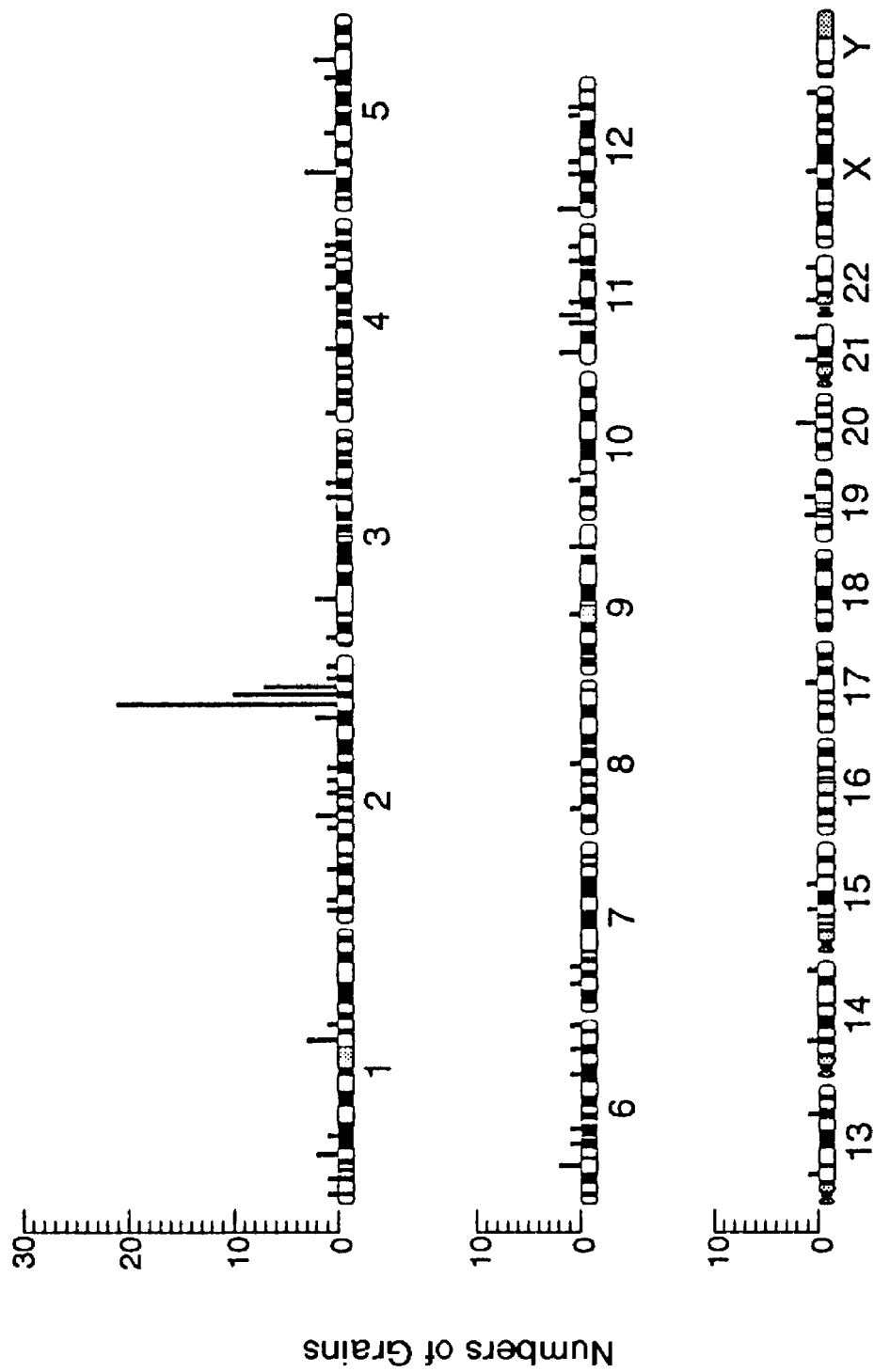
Figure 13B:
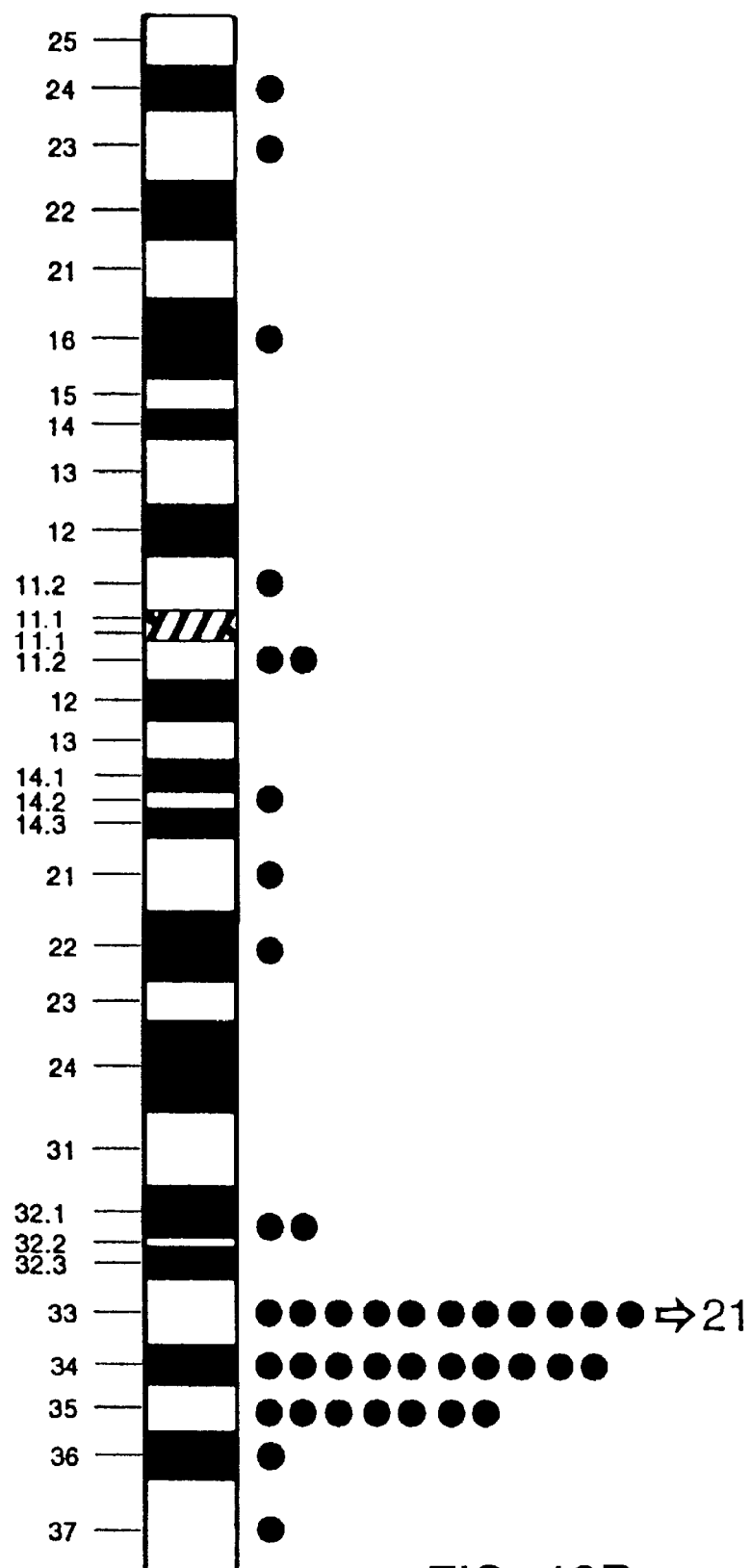

FIG. 13. Regional location of the HER4 gene to human chromosome 2 band q33. FIG. 13 (Panel 1), Distribution of 124 sites of hybridization on human chromosomes; FIG. 13 (Panel 2), Distribution of autoradiographic grains on diagram of chromosome 2.

FIG. 14. Amino acid sequence of HER4-Ig fusion protein [SEQ ID No:10] (Section 5.4., infra).

Figure 15:
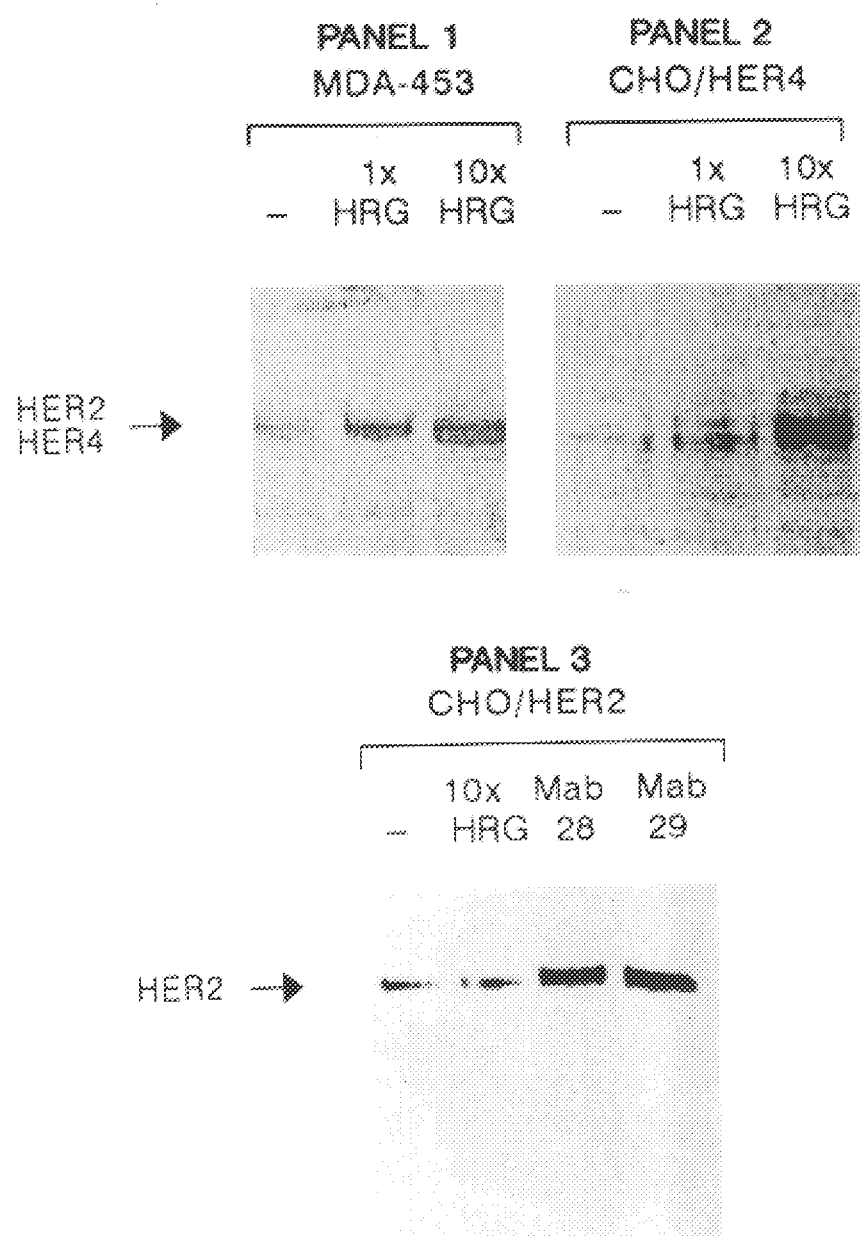

FIG. 15. Recombinant heregulin induces tyrosine phosphorylation of HER4. Tyrosine phosphorylated receptors were detected by Western blotting with an anti-phosphotyrosine Mab. Arrows indicate the HER2 and HER4 proteins. FIG. 15 (Panel 1), Monolayers of MDA-MB453 or FIG. 15 (Panel 2), CHO/HER4 cells were incubated with media from COS-1 cells transfected with a rat heregulin expression plasmid (HRG), or with a CDM8 vector control (−). The media was either applied directly (1×) or after concentrating 20-fold (20×, and vector control). Solubilized cells were immunoprecipitated with anti-phosphotyrosine Mab. FIG. 15 (Panel 3), Monolayers of CHO/HER2 cells were incubated as above with transfected Cos-1 cell supernatants or with two stimulatory Mabs to HER2 (Mab 28 and 29). Solubilized cells were immunoprecipitated with anti-HER2 Mab.

Figure 16:
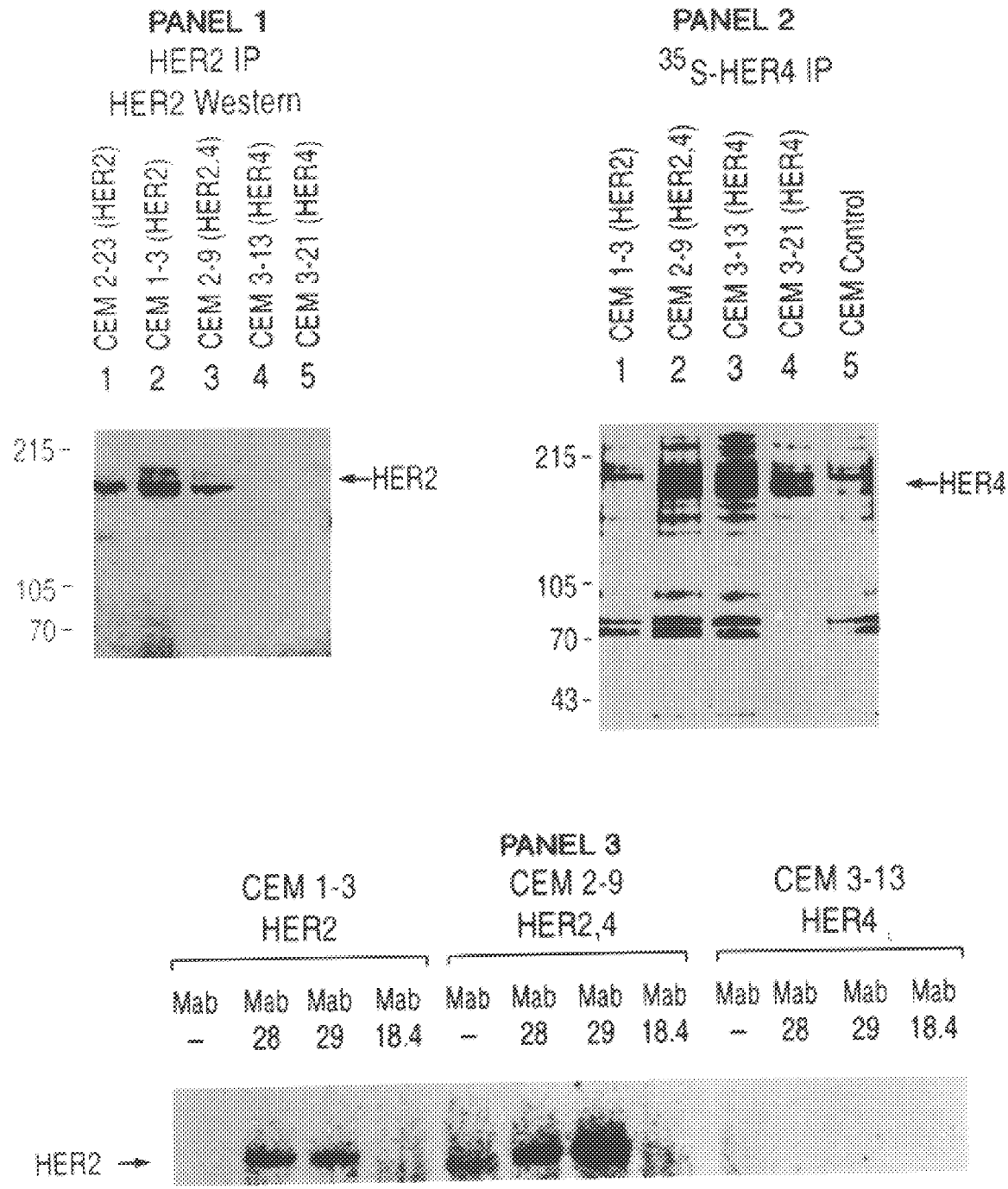

FIG. 16. Expression of recombinant HER2 and HER4 in human CEM cells. Transfected CEM cells were selected that stably express either HER2, HER4, or both recombinant receptors. In FIG. 16 (Panel 1), recombinant HER2 was detected by immunmoprecipitation of cell lysates with anti-HER2 Mab (Ab-2) and Western blotting with another anti-HER2 Mab (Ab-3). In FIG. 16 (Panel 2), Recombinant HER4 was detected by immunoprecipitation of $^{35}$S-labeled cell lysates with HER4-specific rabbit anti-peptide antisera. In FIG. 16 (Panel 3), Three CEM cell lines were selected that express one or both recombinant receptors and aliquots of each were incubated with media control (−), with two HER2-stimulatory Mabs (Mab 28 and 29), or with an isotype matched control Mab (18.4). Solubilized cells were immunoprecipitated with anti-HER2 Mab (Ab-2) and tyrosine phosphorylated HER2 was detected by Western blotting with an anti-phosphotyrosine Mab. The size in kilodaltons of prestained high molecular weight markers (Bio-Rad) is shown on the left and arrows indicate the HER2 and HER4 proteins.

Figure 17:
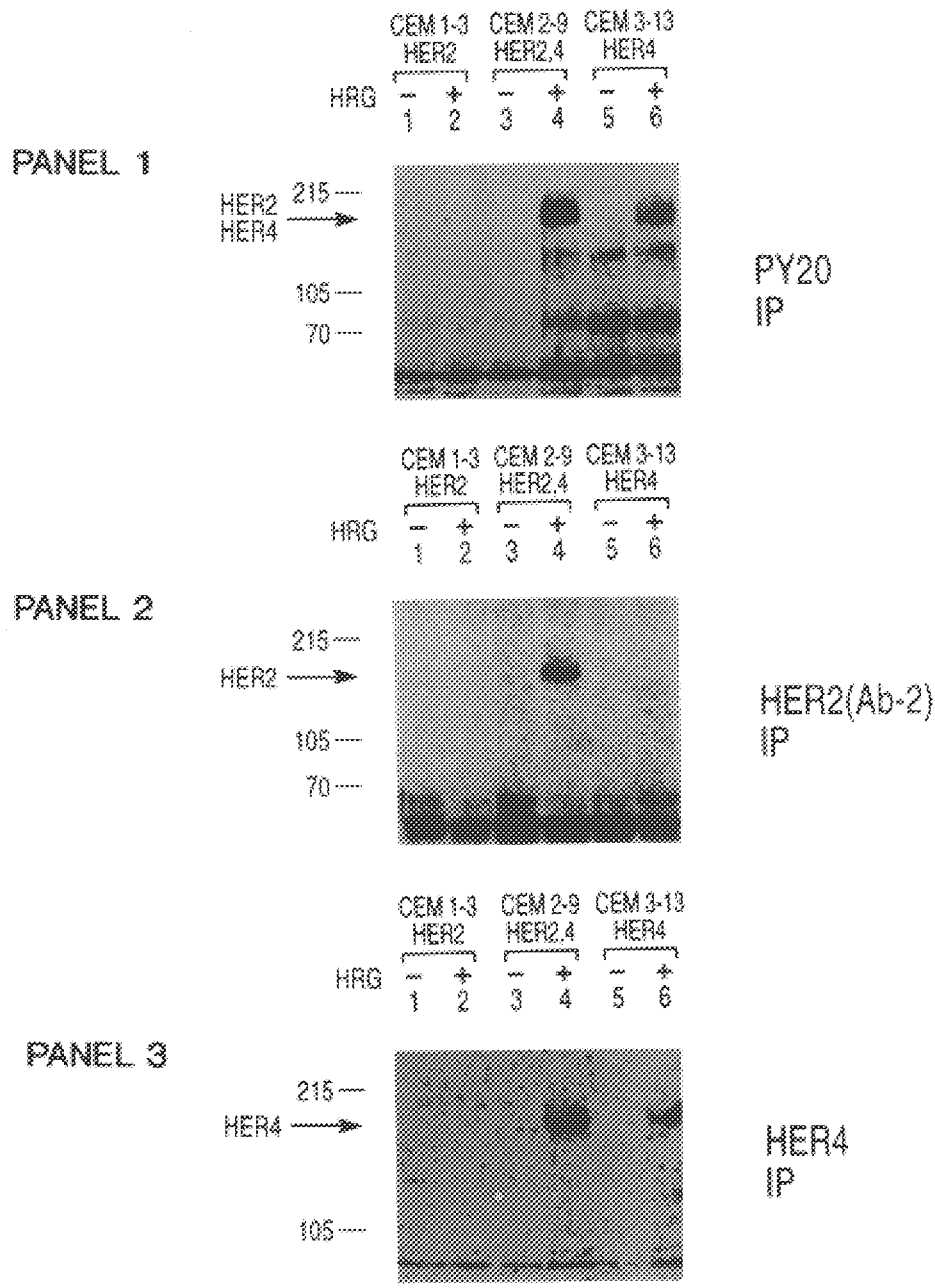

FIG. 17. Heregulin induces tyrosine phosphorylation in CEM cells expressing HER4. Three CEM cell lines that express either HER2 or HER4 alone (CEM 1–3 and CEM 3–13) or together (CEM 2–9) were incubated with 7× concentrated supernatants from mock-(−) or heregulin-transfected (+) COS-1 cells. Solubilized cells were immunoprecipitated (IP) with anti-phosphotyrosine Mab (PY20); in FIG. 17 (Panel 1), HER2-specific anti-HER2 Mab (Ab-2); in FIG. 17 (Panel 2), HER4-specific Mab (6-4); in FIG. 17 (Panel 3), in each case tyrosine phosphorylated receptors were detected by Western blotting with anti-phosphotyrosine Mab. The size in kilodaltons of prestained molecular weight markers (BioRad) is shown on the left and arrows indicate the HER2 and HER4 proteins. HRG, recombinant rat heregulin.

Figure 18:
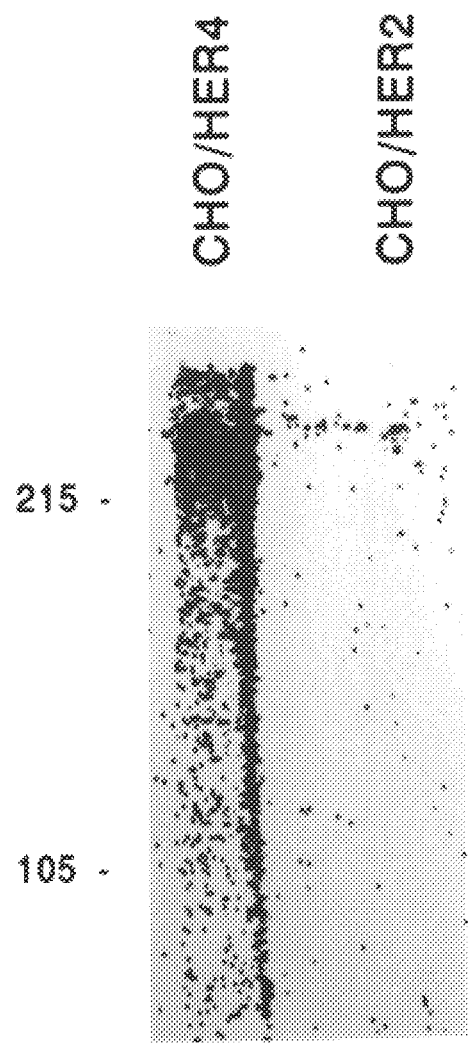

FIG. 18. Covalent cross-linking of iodinated heregulin to HER4. $^{125}$I-heregulin was added to CHO/HER4 or CHO/HER2 cells for 2 h at 4° C. Washed cells were cross-linked with BS$^3$, lysed, and the proteins separated using 7% PAGE. Labeled bands were detected on the phosphorimager. Molecular weight markers are shown on the left.

Figure 19A:
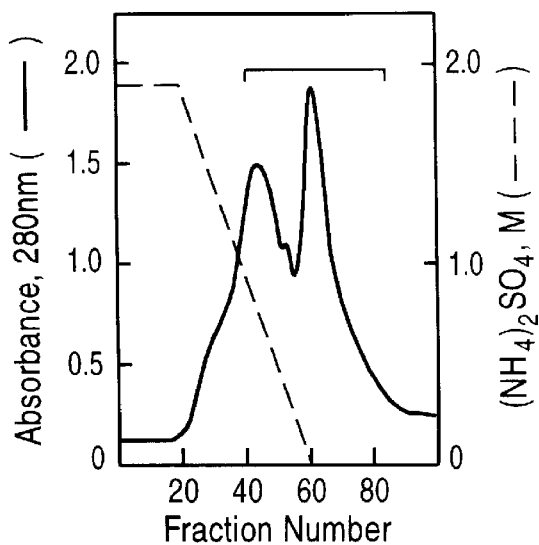
Figure 19C:
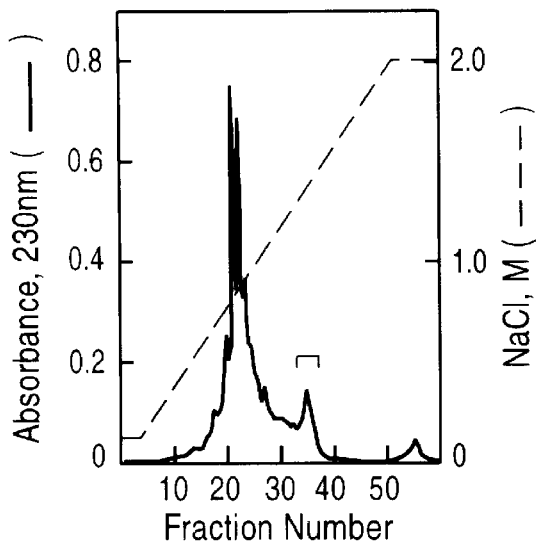
Figure 19B:
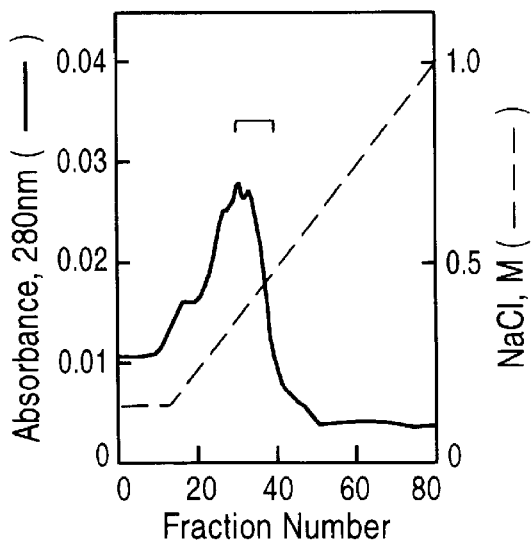
Figure 19D:
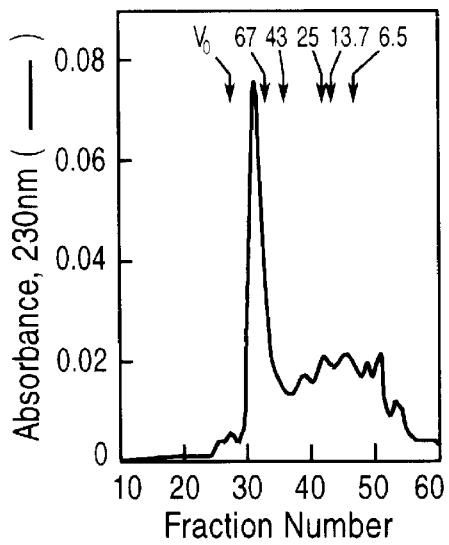

FIGS. 19A–D. Purification of p45 from HepG2 conditioned media. Column fractions were tested for their potential to induce differentiation of MDA-MB-453 cells. Active fractions were pooled as indicated by an horizontal bar. FIG. 19A, Concentrated HepG2 conditioned medium was subjected to 50% ammonium sulfate precipitation. Supernatant resulting from this step was subjected to hydrophobic interaction chromatography using phenyl-Sepharose. Pooled fractions were then loaded on a DEAE-Sepharose column. FIG. 19B, the DEAE-Sepharose column flow-through was subjected to CM-Sepharose chromatography. FIG. 19C, Affinity Chromatography of the MDA-MB-453 differentiation factor using heparin-5PW column. Fractions 35–38 eluting around 1.3M NaCl were pooled. FIG. 19D, Size Exclusion chromatography of the differentiation factor. The molecular masses of calibration standards are indicated in kilodaltons.

Figure 20:
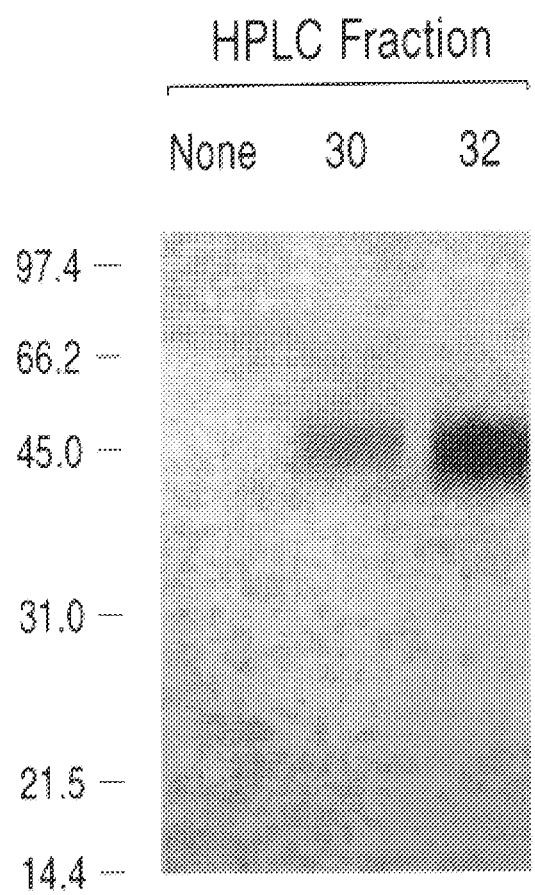

FIG. 20. Aliquots (25 microliter) of the active size exclusion column fractions (30 and 32) were electrophoresed under reducing conditions on a 12.5% polyacrylamide gel. The gel was silver-stained. Molecular masses of Bio-Rad silver stain standards are indicated in kilodaltons.

Figure 21A:
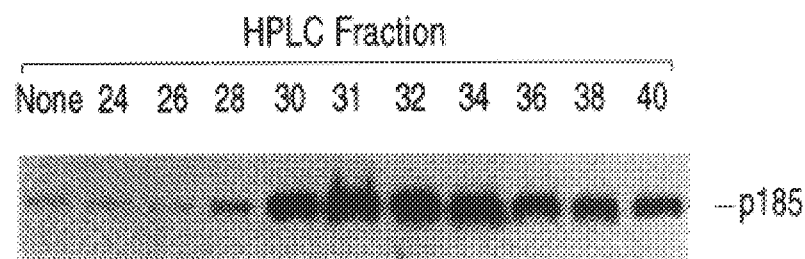
Figures 21B, 21C:
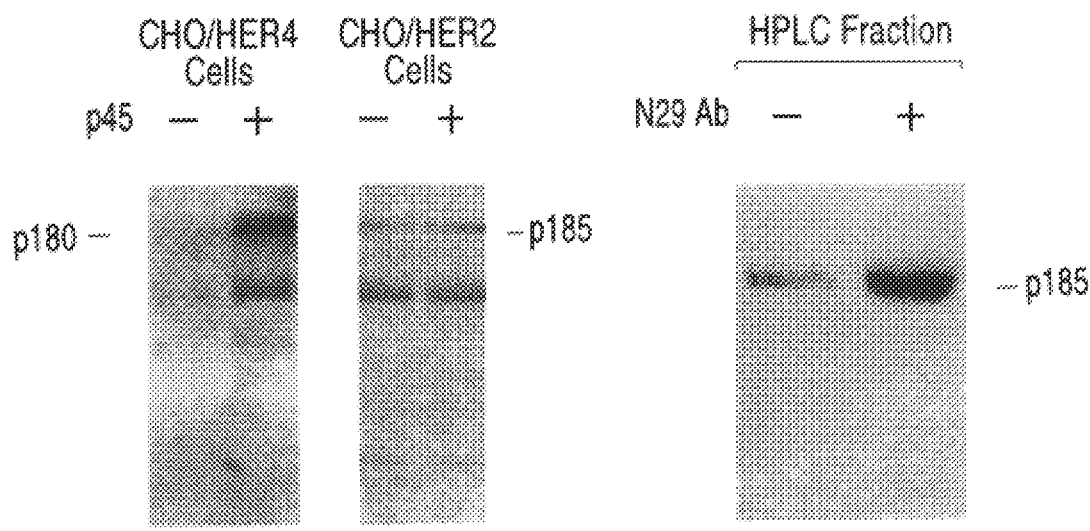

FIGS. 21A–C. Stimulation of tyrosine phosphorylation by p45. FIG. 21A, Size exclusion column fractions were tested on MDA-MB-453 cells for the induction of tyrosine phosphorylation. Cell lysates were then electrophoresed on a 4–15% polyacrylamide gel. After transfer to nitrocellulose, proteins were probed with a phosphotyrosine antibody and phosphoproteins detected by chemiluminescence. The molecular mass of the predominantly phosphorylated protein is indicated. FIG. 21B, the experiments were performed on cells that had been transfected with expression plasmids for either HER4 (CHO/HER4) or HER2 (CHO/HER2). Cell monolayers were incubated in the absence or the presence of p45 (size exclusion column fraction 32, 100 ng/ml). Samples were then processed as indicated in FIG. 21A except that a 7.5% polyacrylamide gel was used to separate the CHO/HER2 cell lysates. FIG. 21C, CHO/HER2 cells were incubated in the presence or the absence of N29 monoclonal antibody to the extracellular domain of $p185^{erbB2}$. Cell lysates were immunoprecipitated with the Ab-3 monoclonal antibody to $p185^{erbB2}$. Precipitated proteins were subjected to SDS-PAGE, and phosphoproteins were detected as indicated under Section 13.4., supra.

Figure 22A:
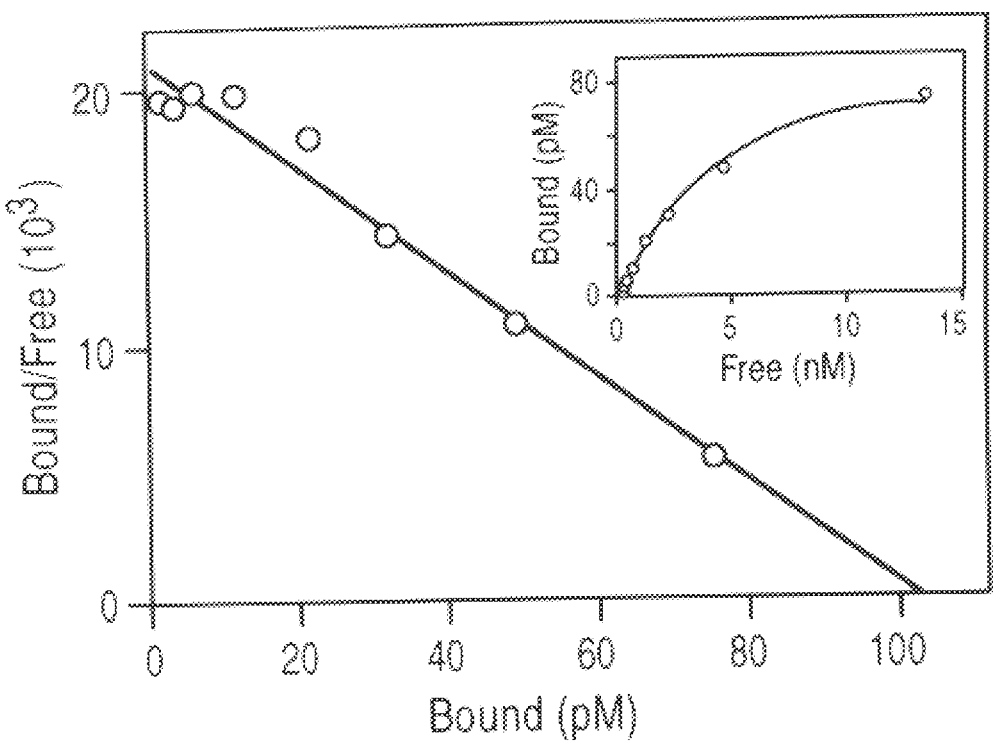
Figure 22B:
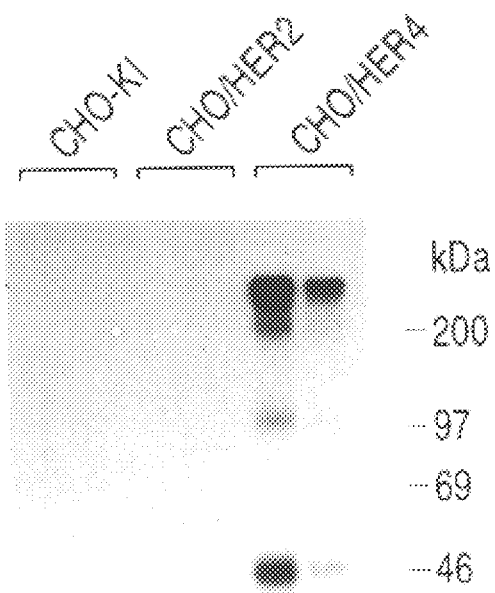

FIG. 22A–B. Binding and cross-linking of $^{125}$I-p45 to CHO-KI, CHO-HER2 and CHO/HER4 cells. FIG. 22A, Scatchard analysis of the binding of $^{125}$I-p45 to CHO/HER4 cells. Increasing concentrations of $^{125}$I-p45 were incubated with cell monolayers for 2 h at 4° C. Nonspecific binding was subtracted from all cell-associated radioactivity data values. A Scatchard plot as well as a saturation curve of the binding data are shown. FIG. 22B, Covalent cross-linking. $^{125}$I-p45 was added to the cells in the presence or absence of an excess of unlabeled p45 for 2 h at 4° C. After washing of the cells to remove unbound iodinated material, the cross-linking reagent bis-(sulfosuccinimidyl)-suberate was added to the cells for 45 min. at 4° C. Cells were lysed and proteins separated by electrophoresis on a 7.5% polyacrylamide gel. Molecular masses of protein standards are indicated in kilodaltons. A Molecular Dynamics Phosphorimager was used to visualize the radioactive species.

Figure 23:
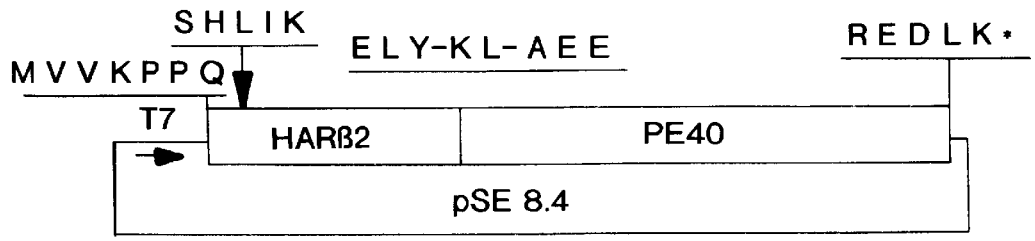

FIG. 23. Construction of the HAR-TX β2 expression plasmid, encoding the hydrophilic leader sequence of amphiregulin (AR), heregulin β2, and PE40, under control of the IPTG inducible T7 promoter; FIG. 23 (Panel 1), schematic diagram of the expression plasmid pSE 8.4, encoding HAR-TX β2; FIG. 23 (Panel 2), amino acid sequence of HAR β2, the ligand portion of HAR-TX β2, composed of the AR leader sequence and rat heregulin β2 [SEQ ID No:40].

FIGS. 24A and 24B. cDNA sequence [SEQ ID No:41] and deduced amino acid sequence [SEQ ID No:42] of the chimera HAR-TX β2, comprising the amphiregulin (AR) leader sequence and the coding sequences of rat heregulin Pseudomonas exotoxin PE40. The linker sequence between the two portions is indicated by a bar above the sequence, the ligand portion is located at the 5' (N-terminal), the PE40 exotoxin portion is located at the 3' (C-terminal) part of the sequence. Nucleotides are numbered on the right side, and amino acids are numbered below the sequence.

Figure 25:
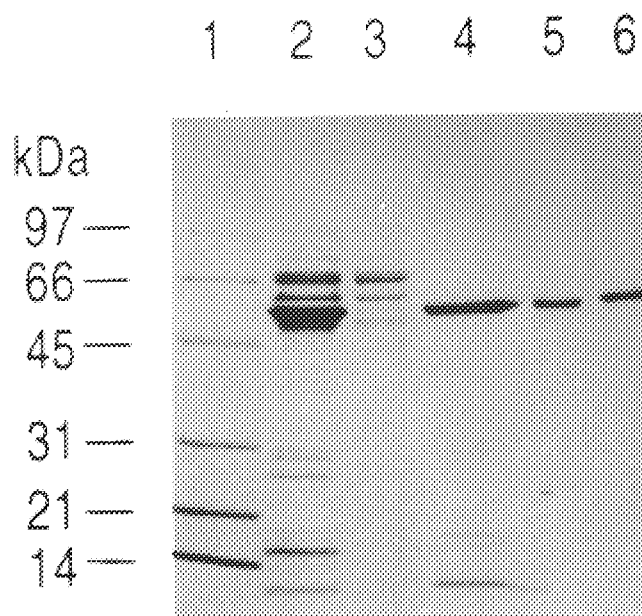

FIG. 25. Purification of the chimeric HAR-TX β2 protein: shown is a Coomassie brilliant blue stained SDS-PAGE (4–20%) of the different purification steps. Lanes 1–5 have been loaded under reducing conditions. Lane 1, MW standards; lane 2, refolded HAR-TX β2, 20× concentrated; lane 3, POROS HS flow-through, 20× concentrated; lane 4, POROS HS eluate; lane 5, Source 15S eluate (pure HAR-TX β2, 2 μg); lane 6, 2 μg HAR-TX β2, loaded under non-reducing conditions.

Figure 26:
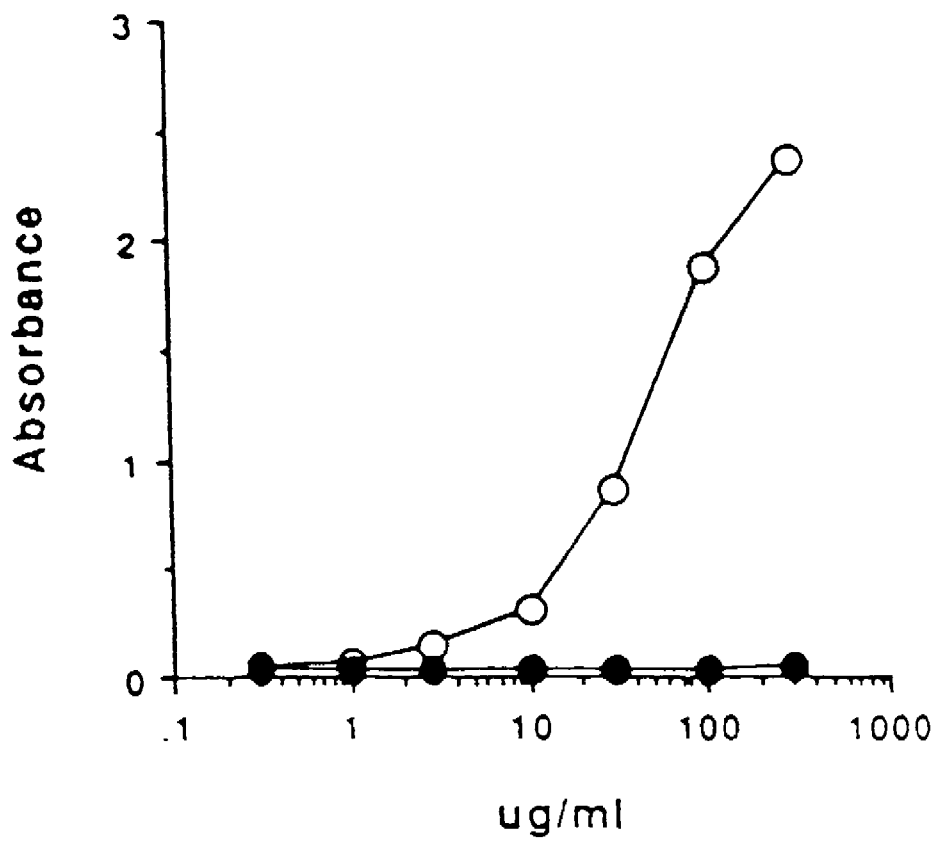

FIG. 26. Membrane-based ELISA binding analysis, performed to determine the binding activity of the purified HAR-TX β2 protein. Binding of HAR-TX β2 (○) and PE40 (●) to membranes prepared from the HER4 expressing human breast carcinoma cell line.

Figure 27:
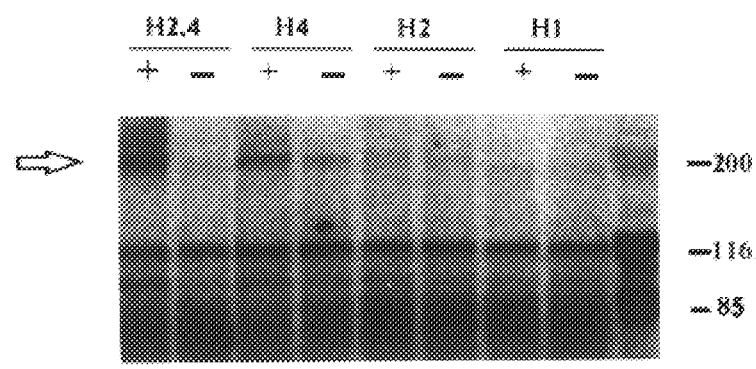

FIG. 27. HAR-TX β2 induced tyrosine phosphorylation in transfected CEM cells. CEM cells co-expressing HER4 and HER2 (H2,4), or expressing HER4 (H4), HER2 (H2), HER1 (H1) alone, respectively, were incubated in the presence (+) or absence (−) of HAR-TX β2, then solubilized, and immunoblotted with the monoclonal anti-phosphotyrosine antibody PY20. The arrow indicates the phosphorylated receptor band, the molecular weight is indicated in kDA.

FIG. 28. Cytotoxic effect of HAR-TX β2 on tumor cell lines. FIG. 28 (Panel 1), following 48 hours incubation with HAR-TX β2, the cell killing effect of HAR-TX β2 on the tumor cell lines LNCaP (■), AU565 (○), SKBR3 (●), and SKOV3 (□) by quantification of fluorescent calcein cleaved from calcein-AM. FIG. 28 (Panel 2), Competitive cytotoxicity of HAR-TX β2 with heregulin β2-Ig. LNCaP cells were co-incubated with 50 ng/ml HAR-TX β2 and increasing concentrations (2–5000 ng/ml) of either heregulin β2-Ig (□) or L6-Ig (■). The data represent the mean of triplicate assays.

Figure 29:
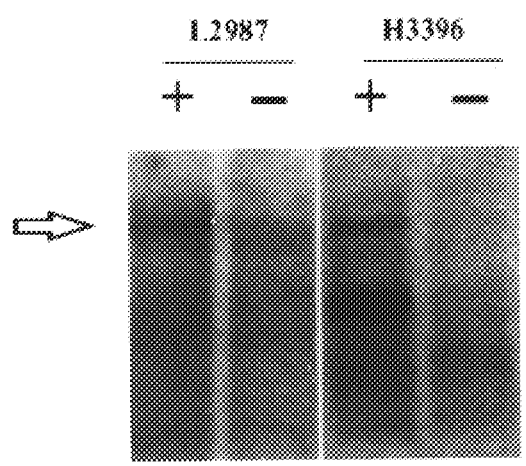

FIG. 29. HAR-TX β2 induced tyrosine phosphorylation in tumor cells expressing HER3 (L2987) or co-expressing HER2 and HER3 (H3396). Cells were incubated in the presence (+) or in the absence (−) of HAR-TX β2, solubilized, and immunoblotted with the monoclonal anti-phosphotyrosine antibody PY20. Phosphorylated receptors are indicated by an arrow, the molecular weight is indicated in kDa.

5. DETAILED DESCRIPTION OF THE INVENTION

The present invention is directed to HER4/$p180^{erbB4}$ ("HER4"), a closely related yet distinct member of the Human EGF Receptor (HER)/neu subfamily of receptor tyrosine kinases, as well as HER4-encoding polynucleotides (e.g., cDNAs, genomic DNAs, RNAs, anti-sense RNAs, etc.), the production of mature and precursor forms of HER4 from a HER4 polynucleotide coding sequence, recombinant HER4 expression vectors, HER4 analogues and derivatives, anti-HER4 antibodies, HER4 ligands, and diagnostic and therapeutic uses of HER4 polynucleotides, polypeptides, ligands, and antibodies in the field of human oncology and neurobiology.

As discussed in Section 2, supra, HER2 has been reported to be associated with a wide variety of human malignancies, thus the understanding of its activation mechanisms as well as the identification of molecules involved are of particular clinical interest. This invention uncovers an apparent functional relationship between the HER4 and HER2 receptors involving HER4-mediated phosphorylation of HER2, potentially via intracellular receptor crosstalk or receptor dimerization. In this connection, the invention also provides HER4 ligands capable of inducing cellular differentiation in breast carcinoma cells that appears to involve HER4-mediated phosphorylation of HER2. Furthermore, applicants' data provide evidence that heregulin mediates biological effects on such cells not directly through HER2, as has been reported (Peles et al., 1992, Cell 69:205–216), but instead by means of a direct interaction with HER4, and/or through an interaction with a HER2/ HER4 complex. In cell lines expressing both HER2 and HER4, binding of heregulin to HER4 may stimulate HER2 either by heterodimer formation of these two related receptors or by intracellular receptor crosstalk.

Recently, also HER3 has been reported to bind heregulin (see Section 2, supra). However, various observations indicate that the heregulin-mediated activation of HER3 varies considerably, depending on the context of expression, suggesting that other cellular components may be involved in the modulation of HER3 activity (reviewed in: Carraway and Cantley, 1994, Cell 78:5–8).

Unless otherwise indicated, the practice of the present invention utilizes standard techniques of molecular biology and molecular cloning, microbiology, immunology, and recombinant DNA known in the art. Such techniques are described and explained throughout the literature, and can be found in a number of more comprehensive publications such as, for example, Sambrook et al., Molecular Cloning; A Laboratory Manual (Second Edition, 1989).

5.1. HER4 Polynucleotides

One aspect of the present invention is directed to HER4 polynucleotides, including recombinant polynucleotides encoding the prototype HER4 polypeptide shown in FIGS. 1A and 1B, polynucleotides which are related or are complementary thereto, and recombinant vectors and cell lines incorporating such recombinant polynucleotides. The term "recombinant polynucleotide" as used herein refers to a polynucleotide of genomic, cDNA, synthetic or semisynthetic origin which, by virtue of its origin or manipulation, is not associated with any portion of the polynucleotide with which it is associated in nature, and may be linked to a polynucleotide other than that to which it is linked in nature, and includes single or double stranded polymers of ribonucleotides, deoxyribonucleotides, nucleotide analogs, or combinations thereof. The term also includes various modifications known in the art, including but not limited to radioactive and chemical labels, methylation, caps, internucleotide modifications such as those with charged linkages (e.g., phosphorothothioates, phosphorodithothioates, etc.) and uncharged linkages (e.g., methyl phosphonates, phosphotriesters, phosphoamidites, carbamites, etc.), as well as those containing pendant moeties, intercalcators, chelators, alkylators, etc. Related polynucleotides are those having a contiguous stretch of about 200 or more nucleotides and sharing at least about 80% homology to a corresponding sequence of nucleotides within the nucleotide sequence disclosed in FIGS. 1A and 1B. Several particular embodiments of such HER4 polynucleotides and vectors are provided in example Sections 6 and 7, infra.

HER4 polynucleotides may be obtained using a variety of general techniques known in the art, including molecular cloning and chemical synthetic methods. One method by which the molecular cloning of cDNAs encoding the prototype HER4 polypeptide of the invention (FIGS. 1A and 1B), as well as several HER4 polypeptide variants, is described by way of example in Section 6., infra. Conserved regions of the sequences of EGFR, HER2, HER3, and Xmrk are used for selection of the degenerate oligonucleotide primers which are then used to isolate HER4. Since many of these sequences have extended regions of amino acid identity, it is difficult to determine if a short PCR fragment represents a unique molecule or merely the species-specific counterpart of EGFR, HER2, or HER3. Often the species differences for one protein are as great as the differences within species for two distinct proteins. For example, fish Xmrk has regions of 47/55 (85%) amino acid identity to human EGFR, suggesting it might be the fish EGFR, however isolation of another clone that has an amino acid sequence identical to Xmrk in this region (57/57) shows a much higher homology to human EGFR in its flanking sequence (92% amino acid homology) thereby suggesting that it, and not Xmrk, is the fish EGFR (Wittbrodt et al., 1989, Nature 342:415–421). As described in Section 6., infra, it was necessary to confirm that a murine HER4/erbB4 PCR fragment was indeed a unique gene, and not the murine homolog of EGFR, HER2, or HER3, by isolating genomic fragments corresponding to murine EGFR, erbB2 and erbB3. Sequence analysis of these clones confirmed that this fragment was a novel member of the EGFR family. Notably a region of the murine clone had a stretch of 60/64 amino acid identity to human HER2, but comparison with the amino acid and DNA sequences of the other EGFR homologs from the same species (mouse) firmly established it encoded a novel transcript.

HER4 polynucleotides may be obtained from a variety of cell sources which produce HER4-like activities and/or which express HER4-encoding mRNA. In this connection, applicants have identified a number of suitable human cell sources for HER4 polynucleotides, including but not limited to brain, cerebellum, pituitary, heart, skeletal muscle, and a variety of breast carcinoma cell lines (see Section 6., infra).

For example, polynucleotides encoding HER4 polypeptides may be obtained by cDNA cloning from RNA isolated and purified from such cell sources or by genomic cloning. Either cDNA or genomic libraries of clones may be prepared using techniques well known in the art and may be screened for particular HER4-encoding DNAs with nucleotide probes which are substantially complementary to any portion of the HER4 gene. Various PCR cloning techniques may also be used to obtain the HER4 polynucleotides of the invention. A number of PCR cloning protocols suitable for the isolation of HER4 polynucleotides have been reported in the literature (see, for example, PCR protocols: A Guide to Methods and Applications, Eds. Inis et al., Academic Press, 1990).

For the construction of expression vectors, polynucleotides containing the entire coding region of the desired HER4 may be isolated as full length clones or prepared by splicing two or more polynucleotides together. Alternatively, HER4-encoding DNAs may be synthesized in whole or in part by chemical synthesis using techniques standard in the art. Due to the inherent degeneracy of nucleotide coding sequences, any polynucleotide encoding the desired HER4 polypeptide may be used for recombinant expression. Thus, for example, the nucleotide sequence encoding the prototype HER4 of the invention provided in FIGS. 1A and 1B may be altered by substituting nucleotides such that the same HER4 product is obtained.

The invention also provides a number of useful applications of the HER4 polynucleotides of the invention, including but not limited to their use in the preparation of HER4 expression vectors, primers and probes to detect and/or clone HER4, and diagnostic reagents. Diagnostics based upon HER4 polynucleotides include various hybridization and PCR assays known in the art, utilizing HER4 polynucleotides as primers or probes, as appropriate. One particular aspect of the invention relates to a PCR kit comprising a pair of primers capable of priming cDNA synthesis in a PCR reaction, wherein each of the primers is a HER4 polynucleotide of the invention. Such a kit may be useful in the diagnosis of certain human cancers which are characterized by aberrant HER4 expression. For example, certain human carcinomas may overexpress HER4 relative to their normal cell counterparts, such as human carcinomas of the breast. Thus, detection of HER4 overexpression mRNA in breast tissue may be an indication of neoplasia. In another, related embodiment, human carcinomas characterized by overexpression of HER2 and expression or overexpression of HER4 may be diagnosed by a polynucleotide-based assay kit capable of detecting both HER2 and HER4 mRNAs, such a kit comprising, for example, a set of PCR primer pairs derived from divergent sequences in the HER2 and HER4 genes, respectively.

5.2. HER4 Polypeptides

Another aspect of the invention is directed to HER4 polypeptides, including the prototype HER4 polypeptide provided herein, as well as polypeptides derived from or having substantial homology to the amino acid sequence of the prototype HER4 molecule. The term "polypeptide" in this context refers to a polypeptide prepared by synthetic or recombinant means, or which is isolated from natural sources. The term "substantially homologous" in this context refers to polypeptides of about 80 or more amino acids sharing greater than about 90% amino acid homology to a corresponding contiguous amino acid sequence in the prototype HER4 primary structure (FIGS. 1A and 1B). The term "prototype HER4" refers to a polypeptide having the amino acid sequence of precursor or mature HER4 as provided in FIGS. 1A and 1B, which is encoded by the consensus cDNA nucleotide sequence also provided therein, or by any polynucleotide sequence which encodes the same amino acid sequence.

HER4 polypeptides of the invention may contain deletions, additions or substitutions of amino acid residues relative to the sequence of the prototype HER4 depicted in FIGS. 1A and 1B which result in silent changes thus producing a bioactive product. Such amino acid substitutions may be made on the basis of similarity in polarity, charge, solubility, hydrophobicity, hydrophilicity and/or the amphipathic nature of the resides involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

The HER4 polypeptide depicted in FIGS. 1A and 1B has all of the fundamental structural features characterizing the EGFR-family of receptor tyrosine kinases (Hanks et al., 1988, *Science* 241:42–52). The precursor contains a single hydrophobic stretch of 26 amino acids characteristic of a transmembrane region that bisects the protein into a 625 amino acid extracellular ligand binding domain, and a 633 amino acid C-terminal cytoplasmic domain. The ligand binding domain can be further divided into 4 subdomains (I–IV), including two cysteine-rich regions (II, residues 186–334; and IV, residues 496–633), and two flanking domains (I, residues 29–185; and III, residues 335–495) that may define specificity for ligand binding (Lax et al., 1988, *Mol. Cell. Biol.* 8:1970–78). The extracellular domain of HER4 is most similar to HER3, where domains II–IV of HER4 share 56–67% identity to the respective domains of HER3. In contrast, the same regions of EGFR and HER2 exhibit 43–51% and 34–46% homology to HER4, respectively (FIGS. 6A and 6B). The 4 extracellular subdomains of EGFR and HER2 share 39–50% identity. HER4 also conserves all 50 cysteines present in the extracellular portion of EGFR, HER2, and HER3, except that the HER2 protein lacks the fourth cysteine in domain IV. There are 11 potential N-linked glycosylation sites in HER4, conserving 4 of 12 potential sites in EGFR, 3 of 8 sites in HER2, and 4 of 10 sites in HER3.

Following the transmembrane domain of HER4 is a cytoplasmic juxtamembrane region of 37 amino acids. This region shares the highest degree of homology with EGFR (73% amino acid identity) and contains two consensus protein kinase C phosphorylation sites at amino acid residue numbers 679 (Serine) and 699 (Threonine) in the FIGS. 1A and 1B sequence, the latter of which is present in EGFR and HER2. Notably, HER4 lacks a site analogous to Thr654 of EGFR. Phosphorylation of this residue in the EGFR appears to block ligand-induced internalization and plays an important role in its transmembrane signaling (Livneh et al., 1988, *Mol. Cell. Biol.* 8:2302–08). HER4 also contains Thr692 analogous to Thr694 of HER2. This threonine is absent in EGFR and HER3 and has been proposed to impart cell-type specificity to the mitogenic and transforming activity of the HER2 kinase (DiFiore et al. 1992, *EMBO J.* 11:3927–33). The juxtamembrane region of HER4 also contains a MAP kinase consensus phosphorylation site at amino acid number 699 (Threonine), in a position homologous to Thr699 of EGFR which is phosphorylated by MAP kinase in response to EGF stimulation (Takishima et al., 1991, *Proc. Natl. Acad. Sci. U.S.A.* 88:2520–25).

The remaining cytoplasmic portion of HER4 consists of a 276 amino acid tyrosine kinase domain, an acidic helical structure of 38 amino acids that is homologous to a domain required for ligand-induced internalization of the EGFR (Chen et al., 1989, *Cell* 59:33–43), and a 282 amino acid region containing 18 tyrosine residues characteristic of the autophosphorylation domains of other EGFR-related proteins (FIGS. 6A and 6B). The 276 amino acid tyrosine kinase domain conserves all the diagnostic structural motifs of a tyrosine kinase, and is most related to the catalytic domains of EGFR (79% identity) and HER2 (77% identity), and to a lesser degree, HER3 (63% identity). In this same region, EGFR and HER2 share 83% identity. Examples of the various conserved structural motifs include the following: the ATP-binding motif (GXGXXG) [SEQ ID No:11] with a distal lysine residue that is predicted to be involved in the phosphotransfer reaction (Hanks et al., 198, *Science* 241:42–52; Hunter and Cooper, in The Enzymes Vol. 17 (eds. Boyer and Krebs) pp. 191–246 (Academic Press 1986)); tyrosine-kinase specific signature sequences (DLAARN [SEQ ID No:12] and PIKWMA [SEQ ID No:13]) and Tyr875 (FIGS. 6A and 6B), a residue that frequently serves as an autophosphorylation site in many tyrosine kinases (Hunter and Cooper, supra); and approximately 15 residues that are either highly or completely conserved among all known protein kinases (Plowman et al., 1990, *Proc. Natl. Acad. Sci. U.S.A.* 87:4905–09; Hanks et al., supra). The C-terminal 282 amino acids of HER4 has limited homology with HER2 (27%) and EGFR (19%). However, the C- terminal domain of each EGFR-family receptor is proline-rich and conserves stretches of 2–7 amino acids that are generally centered around a tyrosine residue. These residues include the major tyrosine autophosphorylation sites of EGFR at Tyr1068, Tyr1086, Tyr1148, and Tyr1173 (FIGS. 6A and 6B, filled triangles; Margolis et al., 1989, *J. Biol. Chem.* 264:10667–71).

5.3. Recombinant Synthesis of KER4 Polypeptides

The HER4 polypeptides of the invention may be produced by the cloning and expression of DNA encoding the desired HER4 polypeptide. Such DNA may be ligated into a number of expression vectors well known in the art and suitable for use in a number of acceptable host organisms, in fused or mature form, and may contain a signal sequence to permit secretion. Both prokaryotic and eukaryotic host expression systems may be employed in the production of recombinant HER4 polypeptides. For example, the prototype HER4 precursor coding sequence or its functional equivalent may be used in a host cell capable of processing the precursor correctly. Alternatively, the coding sequence for mature HER4 may be used to directly express the mature HER4 molecule. Functional equivalents of the HER4 precursor coding sequence include any DNA sequence which, when expressed inside the appropriate host cell, is capable of directing the synthesis, processing and/or export of HER4.

Production of a HER4 polypeptide using recombinant DNA technology may be divided into a four-step process for the purposes of description: (1) isolation or generation of DNA encoding the desired HER4 polypeptide; (2) construction of an expression vector capable of directing the synthesis of the desired HER4 polypeptide; (3) transfection or transformation of appropriate host cells capable of replicating and expressing the HER4 coding sequence and/or processing the initial product to produce the desired HER4 polypeptide; and (4) identification and purification of the desired HER4 product.

5.3.1. Isolation or Generation of HER4 Encoding DNA

HER4-encoding DNA, or functional equivalents thereof, may be used to construct recombinant expression vectors which will direct the expression of the desired HER4 polypeptide product. In a specific embodiment, DNA encoding the prototype HER4 polypeptide (FIGS. 1A and 1B), or fragments or functional equivalents thereof, may be used to generate the recombinant molecules which will direct the expression of the recombinant HER4 product in appropriate host cells. HER4-encoding nucleotide sequences may be obtained from a variety of cell sources which produce HER4-like activities and/or which express HER4-encoding mRNA. For example, HER4-encoding cDNAs may be obtained from the breast adenocarcinoma cell line MDA-MB-453 (ATCC HTB131) as described in Section 6., infra. In addition, a number of human cell sources are suitable for obtaining HER4 cDNAs, including but not limited to various epidermoid and breast carcinoma cells, and normal heart, kidney, and brain cells (see Section 6.2.3., infra).

The HER4 coding sequence may be obtained by molecular cloning from RNA isolated and purified from such cell sources or by genomic cloning. Either cDNA or genomic libraries of clones may be prepared using techniques well known in the art and may be screened for particular HER4-encoding DNAs with nucleotide probes which are substantially complementary to any portion of the HER4 gene. Alternatively, cDNA or genomic DNA may be used as templates for PCR cloning with suitable oligonucleotide primers. Full length clones, i.e., those containing the entire coding region of the desired HER4 may be selected for constructing expression vectors, or overlapping cDNAs can be ligated together to form a complete coding sequence. Alternatively, HER4-encoding DNAs may be synthesized in whole or in part by chemical synthesis using techniques standard in the art.

5.3.2. Construction of HER4 Expression Vectors

Various expression vector/host systems may be utilized equally well by those skilled in the art for the recombinant expression of HER4 polypeptides. Such systems include but are not limited to microorganisms such as bacteria transformed with recombinant bacteriophage DNA, plasmid DNA or cosmid DNA expression vectors containing the desired HER4 coding sequence; yeast transformed with recombinant yeast expression vectors containing the desired HER4 coding sequence; insect cell systems infected with recombinant virus expression vectors (e.g., baculovirus) containing the desired HER4 coding sequence; plant cell systems infected with recombinant virus expression vectors (e.g., cauliflower mosaic virus CaMV; tobacco mosaic virus, TMV) or transformed with recombinant plasmid expression vectors (e.g., Ti plasmid) containing the desired HER4 coding sequence; or animal cell systems infected with recombinant virus expression vectors (e.g., adenovirus, vaccinia virus) including cell lines engineered to contain multiple copies of the HER4 DNA either stably amplified (e.g., CHO/dhfr, CHO/glutamine synthetase) or unstably amplified in double-minute chromosomes (e.g., murine cell lines).

The expression elements of these vectors vary in their strength and specificities. Depending on the host/vector system utilized, any one of a number of suitable transcription and translation elements may be used. For instance, when cloning in mammalian cell systems, promoters isolated from the genome of mammalian cells, (e.g., mouse metallothionein promoter) or from viruses that grow in these cells, (e.g., vaccinia virus 7.5K promoter or Moloney murine sarcoma virus long terminal repeat) may be used. Promoters produced by recombinant DNA or synthetic techniques may also be used to provide for transcription of the inserted sequences.

Specific initiation signals are also required for sufficient translation of inserted protein coding sequences. These signals include the ATG initiation codon and adjacent sequences. In cases where the entire HER4 gene including its own initiation codon and adjacent sequences are inserted into the appropriate expression vectors, no additional translational control signals may be needed. However, in cases where only a portion of the coding sequence is inserted, exogenous translational control signals, including the ATG initiation codon must be provided.

Furthermore, the initiation codon must be in phase with the reading frame of the HER4 coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

For example, in cases where an adenovirus is used as a vector for driving expression in infected cells, the desired HER4 coding sequence may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E3 or E4) will result in a recombinant virus that is viable and capable of expressing HER4 in infected hosts. Similarly, the vaccinia 7.5K promoter may be used. An alternative expression system which could be used to express HER4 is an insect system. In one such system, *Autographa californica* nuclear polyhidrosis virus (AcNPV) is used as a vector to express foreign genes. The virus grows in *Spodoptera frugiperda* cells. The HER4 coding sequence may be cloned into non-essential regions (for example the polyhedrin gene) of the virus and placed under control of an AcNPV promoter (for example the polyhedrin promoter). Successful insertion of the HER4 coding sequence will result in inactivation of the polyhedrin gene and production of non-occluded recombinant virus (i.e., virus lacking the proteinaceous coat encoded by the polyhedrin gene). These recombinant viruses are then used to infect *Spodoptera frugiperda* cells in which the inserted gene is expressed. Yet another approach uses retroviral vectors prepared in amphotropic packaging cell lines, which permit high efficiency expression in numerous cells types. This method allows one to assess cell-type specific processing, regulation or function of the inserted protein coding sequence.

In addition, a host cell strain may be chosen which modulates the expression of the inserted sequences, or modifies and processes the gene product in the specific fashion desired. Expression from certain promoters can be elevated in the presence of certain inducers (e.g., zinc and cadmium ions for metallothionein promoters). Therefore, expression of the recombinant HER4 polypeptide may be controlled. This is important if the protein product of the cloned foreign gene is lethal to host cells. Furthermore, modifications (e.g., phosphorylation) and processing (e.g., cleavage) of protein products are important for the function of the protein. Different host cells have characteristic and specific mechanisms for the post-translational processing and modification of protein. Appropriate cell lines or host systems can be chosen to ensure the correct modification and processing of the foreign protein expressed.

5.3.3. Transformants Expressing HER4 Gene Products

The host cells which contain the recombinant coding sequence and which express the desired HER4 polypeptide product may be identified by at least four general approaches (a) DNA-DNA, DNA-RNA or RNA-antisense RNA hybridization; (b) the presence or absence of "marker" gene functions; (c) assessing the level of transcription as measured by the expression of HER4 mRNA transcripts in the host cell; and (d) detection of the HER4 product as measured by immunoassay and, ultimately, by its biological activities.

In the first approach, for example, the presence of HER4 coding sequences inserted into expression vectors can be detected by DNA-DNA hybridization using hybridization probes and/or primers for PCR reactions comprising polynucleotides that are homologous to the HER4 coding sequence.

In the second approach, the recombinant expression vector/host system can be identified and selected based upon the presence or absence of certain "marker" gene functions (e.g., thymidine kinase activity, resistance to antibiotics, resistance to methotrexate (MTX), resistance to methionine sulfoximine (MSX), transformation phenotype, occlusion body formation in baculovirus, etc.). For example, if the HER4 coding sequence is inserted within a marker gene sequence of the vector, recombinants containing that coding sequence can be identified by the absence of the marker gene function. Alternatively, a marker gene can be placed in tandem with the HER4 sequence under the control of the same or different promoter used to control the expression of the HER4 coding sequence. Expression of the marker in response to induction or selection indicates expression of the HER4 coding sequence. In a particular embodiment described by way of example herein, a HER4 expression vector incorporating glutamine synthetase as a selectable marker is constructed, used to transfect CHO cells, and amplified expression of HER4 in CHO cells is obtained by selection with increasing concentration of MSX.

In the third approach, transcriptional activity for the HER4 coding region can be assessed by hybridization assays. For example, polyadenylated RNA can be isolated and analyzed by Northern blot using a probe homologous to the HER4 coding sequence or particular portions thereof. Alternatively, total nucleic acids of the host cell may be extracted and assayed for hybridization to such probes.

In the fourth approach, the expression of HER4 can be assessed immunologically, for example by Western blots, immunoassays such as radioimmunoprecipitation, enzyme-linked immunoassays and the like. Alternatively, expression of HER4 may be assessed by detecting a biologically active product. Where the host cell secretes the gene product the cell free media obtained from the cultured transfectant host cell may be assayed for HER4 activity. Where the gene product is not secreted, cell lysates may be assayed for such activity. In either case, assays which measure ligand binding to HER4, HER4 phosphorylation, or other bioactivities of HER4 may be used.

5.4. Anti-HER4 Antibodies

The invention is also directed to polyclonal and monoclonal antibodies which recognize immunospecifically binds, epitopes of HER4 polypeptides. Anti-HER4 antibodies are expected to have a variety of useful applications in the field of oncology, several of which are described generally below. More detailed and specific descriptions of various uses for anti-HER4 antibodies are provided in the sections and subsections which follow. Briefly, anti-HER4 antibodies may be used for the detection and quantification of HER4 polypeptide expression in cultured cells, tissue samples, and in vivo. Such immunological detection of HER4 may be used, for example, to identify, monitor, and assist in the prognosis of neoplasms characterized by aberrant or attenuated HER4 expression and/or function. Additionally, monoclonal antibodies recognizing epitopes from different parts of the HER4 structure may be used to detect and/or distinguish between native HER4 and various subcomponent and/or mutant forms of the molecule. Anti-HER4 antibody preparations are also envisioned as useful biomodulatory agents capable of effectively treating particular human cancers. In addition to the various diagnostic and therapeutic utilities of anti-HER4 antibodies, a number of industrial and research applications will be obvious to those skilled in the art, including, for example, the use of anti-HER4 antibodies as affinity reagents for the purification of HER4 polypeptides, and as immunological probes for elucidating the biosynthesis, metabolism and biological functions of HER4.

Anti-HER4 antibodies may be useful for influencing cell functions and behaviors which are directly or indirectly mediated by HER4. As an example, modulation of HER4 biological activity with anti-HER4 antibodies may influence HER2 activation and, as a consequence, modulate intracellular signals generated by HER2. In this regard, anti-HER4 antibodies may be useful to effectively block ligand-induced, HER4-mediated activation of HER2, thereby affecting HER2 biological activity. Conversely, anti-HER4 antibodies capable of acting as HER4 ligands may be used to trigger HER4 biological activity and/or initiate a ligand-induced, HER4-mediated effect on HER2 biological activity, resulting in a cellular response such as differentiation, growth inhibition, etc.

Additionally, anti-HER4 antibodies conjugated to cytotoxic compounds may be used to selectively target such compounds to tumor cells expressing HER4, resulting in tumor cell death and reduction or eradication of the tumor. In a particular embodiment, toxin-conjugated antibodies having the capacity to bind to HER4 and internalize into such cells are administered systemically for targeted cytotoxic effect. The preparation and use of radionuclide and toxin conjugated anti-HER4 antibodies are further described in Section 5.5., infra.

Overexpression of HER2 is associated with several human cancers. Applicants' data indicate that HER4 is expressed in certain human carcinomas in which HER2 overexpression is present. Therefore, anti-HER4 antibodies may have growth and differentiation regulatory effects on cells which overexpress HER2 in combination with HER4 expression, including but not limited to breast adenocarcinoma cells. Accordingly, this invention includes antibodies capable of binding to the HER4 receptor and modulating HER2 or HER2-HER4 functionality, thereby affecting a response in the target cell. For the treatment of cancers involving HER4-mediated regulation of HER2 biological activity, agents capable of selectively and specifically affecting the intracellular molecular interaction between these two receptors may be conjugated to internalizing anti-HER4 antibodies. The specificity of such agents may result in biological effects only in cells which co-express HER2 and HER4, such as breast cancer cells.

Various procedures known in the art may be used for the production of polyclonal antibodies to epitopes of HER4. For the production of polyclonal antibodies, a number of host animals are acceptable for the generation of anti-HER4 antibodies by immunization with one or more injections of a HER4 polypeptide preparation, including but not limited to rabbits, mice, rats, etc. Various adjuvants may be used to increase the immunological response in the host animal, depending on the host species, including but not limited to Freund's (complete and incomplete), mineral gels such as aluminum hydroxide, surface active substances such as lysolecithin, pluronic polyols, polyanions, oil emulsions, keyhole lympet hemocyanins, dinitrophenol, and potentially useful human adjuvants such as BCG (bacille Calmette-Guerin) and *Corynebacterium parvum*.

A monoclonal antibody to an epitope of HER4 may be prepared by using any technique which provides for the production of antibody molecules by continuous cell lines in culture. These include but are not limited to the hybridoma technique originally described by Kohler and Milstein (1975, Nature 256, 495–497), and the more recent human B-cell hybridoma technique (Kosbor et al., 1983, *Immunology Today* 4:72) and EBV-hybridoma technique (Cole et al., 1985, Monoclonal Antibodies and Cancer Therapy, Alan R. Liss, Inc., pp. 77–96). In addition, techniques developed for the production of "chimeric antibodies" by splicing the genes from a mouse antibody molecule of appropriate antigen specificity together with genes from a human antibody molecule of appropriate biological activity may be used (Morrison et al., 1984, *Proc. Natl. Acad. Sci.,* 81:6851–6855; Neuberger et al., 1984, *Nature,* 312:604–608; Takeda et al., 1985, *Nature,* 314:452–454). Alternatively, techniques described for the production of single chain antibodies (U.S. Pat. No. 4,946,778) can be adapted to produce HER4-specific single chain antibodies. Recombinant human or humanized versions of anti-HER4 monoclonal antibodies are a preferred embodiment for human therapeutic applications. Humanized antibodies may be prepared according to procedures in the literature (e.g., Jones et al., 1986, *Nature* 321:522–25;Reichman et al., 1988, *Nature* 332:323–27; Verhoeyen et al., 1988, *Science* 239:1534–36). The recently described "gene conversion mutagenesis" strategy for the production of humanized anti-HER2 monoclonal antibody may also be employed in the production of humanized anti-HER4 antibodies (Carter et al., 1992, *Proc. Natl. Acad. Sci. U.S.A.* 89:4285–89). Alternatively, techniques for generating a recombinant phage library of random combinations of heavy and light regions may be used to prepare recombinant anti-HER4 antibodies (e.g., Huse et al., 1989, *Science* 246:1275–81).

As an example, anti-HER4 monoclonal antibodies may be generated by immunization of mice with cells selectively overexpressing HER4 (e.g., CHO/HER4 21-2 cells as deposited with the ATCC) or with partially purified recombinant HER4 polypeptides. In one embodiment, the full length HER4 polypeptide (FIGS. 1A and 1B) may be expressed in Baculovirus systems, and membrane fractions of the recombinant cells used to immunize mice. Hybridomas are then screened on CHO/HER4 cells (e.g., CHO HER4 21-2 cells as deposited with the ATCC) to identify monoclonal antibodies reactive with the extracellular domain of HER4. Such monoclonal antibodies may be evaluated for their ability to block NDF, or HepG2-differentiating factor, binding to HER4; for their ability to bind and stay resident on the cell surface, or to internalize into cells expressing HER4; and for their ability to directly upregulate or downregulate HER4 tyrosine autophosphorylation and/or to directly induce a HER4-mediated signal resulting in modulation of cell growth or differentiation. In this connection, monoclonal antibodies N28 and N29, directed to HER2, specifically bind HER2 with high affinity. However, monoclonal N29 binding results in receptor internalization and downregulation, morphologic differentiation, and inhibition of HER2 expressing tumor cells in athymic mice. In contrast, monoclonal N28 binding to HER2 expressing cells results in stimulation of autophosphorylation, and an acceleration of tumor cell growth both in vitro and in vivo (Bacus et al., 1992, *Cancer Res.* 52:2580–89; Stancovski et al., 1991, *Proc. Natl. Acad. Sci. U.S.A.* 88:8691–95). In yet another embodiment, a soluble recombinant HER4-Immunoglobulin (HER4-Ig) fusion protein is expressed and purified on a Protein A affinity column. The amino acid sequence of one such HER4-Ig fusion protein is provided in FIG. 14. The soluble HER4-Ig fusion protein may then be used to screen phage libraries designed so that all available combinations of a variable domain of the antibody binding site are presented on the surfaces of the phages in the library. Recombinant anti-HER4 antibodies may be propagated from phage which specifically recognize the HER4-Ig fusion protein.

Antibody fragments which contain the idiotype of the molecule may be generated by known techniques. For example, such fragments include but are not limited to: the $F(ab)^{2'}$ fragment which can be produced by pepsin digestion of the intact antibody molecule; the Fab' fragments which can be generated by reducing the disulfide bridges of the F(ab')2 fragment, and the two Fab fragments which can be generated by treating the antibody molecule with papain and a reducing agent. Alternatively, Fab expression libraries may be constructed (Huse et al., 1989, *Science,* 246:1275–1281) to allow rapid and easy identification of monoclonal Fab fragments with the desired specificity to HER4 protein.

Further, monoclonal antibodies which competitively inhibit the inmuunospecific binding of a monoclonal antibody to human HER4 to its epitope can be obtained by methods known to one of skill in the art.

5.5. HER4 Ligands

One aspect of the present invention is directed to HER4 ligands. As defined herein, HER4 ligands are capable of binding to the 180K transmembrane protein, HER4/p180$^{erbB4}$ or functional analogues thereof, and activating tyrosine kinase activity. Functional analogues of HER4/p180$^{erbB4}$-ligands are capable of activating HER4 tyrosine kinase activity. Activation of the tyrosine kinase activity may stimulate autophosphorylation and may affect a biological activity mediated by HER4. It has been observed in systems described in Section 12 and 13 that binding of HER4 ligands to HER4 triggers tyrosine phosphorylation and affects differentiation of breast cancer cells.

The HER4 ligands of the present invention include NDF, a 44 kDa glycoprotein isolated from ras-transformed rat fibroblasts (Wen et al., 1992, Cell 69:559–572); heregulin, its human homologue, which exists as multiple isoforms (Peles et al., 1992, Cell 69:205–218 and Holmes et al., 1992, Science 256:1205–1210) including p45, a 45K heparin-binding glycoprotein that shares several features with the heregulin-family of proteins including molecular weight, ability to induce differentiation of breast cancer cells, activation of tyrosine phosphorylation in MDA-MB453 cells, and N-terminal amino acid sequence (Section 13, infra), gp30, and p75 (Lupu et al., 1990, Science 249:1552–1555 and Lupu et al., 1992, Proc. Natl. Acad. Sci. USA 89:2287–2291).

HER4 ligands of the present invention can be prepared by synthetic or recombinant means, or can be isolated from natural sources. The HER4 ligand of the present invention may contain deletions, additions or substitutions of amino acid residues relative to the sequence of NDF, p45 or other heregulins or any HER4 ligand known in the art as long as the ligand maintains HER4 receptor binding and tyrosine kinase activation capacity. Such amino acid substitutions may be made on the basis of similarity in polarity, charge, solubility, hydrophobicity, hydrophilicity and/or the amphipathic nature of the resides involved. For example, negatively charged amino acids include aspartic acid and glutamic acid; positively charged amino acids include lysine and arginine; amino acids with uncharged polar head groups or nonpolar head groups having similar hydrophilicity values include the following: leucine, isoleucine, valine; glycine, alanine; asparagine, glutamine; serine, threonine; phenylalanine, tyrosine.

5.5.1. Recombinant Expression of HER4 Ligands

The HER4 ligands of the present invention may be produced by the cloning and expression of DNA encoding the desired HER4 ligand. Such DNA may be ligated into a number of expression vectors well known in the art and suitable for use in a number of acceptable host organisms, in fused or mature form, and may contain a signal sequence to permit secretion. Both prokaryotic and eukaryotic host expression systems may be employed in the production of recombinant HER4 ligands. For example, a HER4 ligand precursor coding sequence or its functional equivalent may be used in a host cell capable of processing the precursor correctly. Alternatively, the coding sequence for a mature HER4 ligand may be used to directly express the mature HER4 ligand molecule. Functional equivalents of the HER4 ligand precursor coding sequence include any DNA sequence which, when expressed inside the appropriate host cell, is capable of directing the synthesis, processing and/or export of the HER4 ligand.

Production of a HER4 ligand using recombinant DNA technology may be divided into a four-step process for the purposes of description: (1) isolation or generation of DNA encoding the desired HER4 ligand; (2) construction of an expression vector capable of directing the synthesis of the desired HER4 ligand; (3) transfection or transformation of appropriate host cells capable of replicating and expressing the HER4 ligand coding sequence and/or processing the initial product to produce the desired HER4 ligand; and (4) identification and purification of the desired HER4 ligand product.

5.5.2. Isolation of HER4 Encoding DNA

HER4 ligand-encoding nucleic acid sequences may be obtained from human hepatocellular carcinoma cell lines, specifically the HepG2 cells available from the ATCC, accession number HB 8065. In addition, a number of human cell sources are suitable for obtaining HER4 ligand nucleic acids, including MDA-MB-231 cells available from the ATCC, accession number HTB 26, brain tissue (Falls et al., 1993, Cell 72:801–815 and Marchionni et al., 1993 Nature 362:312–318), and any cell source capable of producing an activity capable of binding to the 180K transmembrane protein, HER4/p180$^{erbB4}$, encoded by the HER4/ERBB4 gene and activating tyrosine kinase activity.

Methods useful in assaying for the identification of HER4 ligands is disclosed in Section 5.8., infra.

The techniques disclosed in Sections 5.3.2. and 5.3.3., infra apply to the construction of HER4 ligand expression vectors and identification of recombinant transformants expressing HER4 ligand gene products.

5.5.3. Anti-HER4 Ligand Antibodies

The present invention is also directed to polyclonal and monoclonal antibodies which recognize eptitopes of HER4 ligand polypeptides. Anti-HER4 ligand antibodies are expected to have a variety of useful applications in the field of oncology. Briefly, anti-HER4 ligand antibodies may be used for the detection and quantification of HER4 ligand polypeptide expression in cultured cells, tissue samples, and in vivo. For example, monoclonal antibodies recognizing epitopes from different parts of the HER4 ligand structure may be used to detect and/or distinguish binding from non-binding regions of the ligand. Anti-HER4 ligand antibody preparations are also envisioned as useful biomodulatory agents capable of effectively treating particular human cancers. An anti-HER4 ligand antibody could be used to block signal transduction mediated through HER4, thereby inhibiting undesirable biological responses. In addition to the various diagnostic and therapeutic utilities of anti-HER4 ligand antibodies, a number of industrial and research applications will be obvious to those skilled in the art, including, for example, the use of anti-HER4 ligand antibodies as affinity reagents for the purification of HER4 ligand polypeptides, and as immunological probes for elucidating the biosynthesis, metabolism and biological functions of HER4 ligands.

Anti-HER4 ligand antibodies may be useful for influencing cell functions and behaviors which are directly or indirectly mediated by HER4. As an example, modulation of HER4 biological activity with anti-HER4 ligand antibodies may influence HER2 activation and, as a consequence, modulate intracellular signals generated by HER2. In this regard, anti-HER4 ligand antibodies may be useful to effectively block ligand-induced, HER4-mediated activation of HER2, thereby affecting HER2 biological activity. Conversely, anti-HER4 ligand antibodies capable of acting as HER4 ligands may be used to trigger HER4 biological activity and/or initiate a ligand-induced, HER4-mediated effect on HER2 biological activity, resulting in a cellular response such as differentiation, growth inhibition, etc.

Additionally, anti-HER4 ligand antibodies conjugated to cytotoxic compounds may be used to selectively target such compounds to tumor cells expressing HER4, resulting in tumor cell death and reduction or eradication of the tumor.

Various procedures known in the art may be used for the production of antibodies to epitopes of HER4 ligand (see Section 5.4, supra).

5.6. Diagnostic methods

The invention also relates to the detection of human neoplastic conditions, particularly carcinomas of epithelial origin, and more particularly human breast carcinomas. In one embodiment, oligomers corresponding to portions of the consensus HER4 cDNA sequence provided in FIGS. 1A and 1B are used for the quantitative detection of HER4 mRNA levels in a human biological sample, such as blood, serum, or tissue biopsy samples, using a suitable hybridization or PCR format assay, in order to detect cells or tissues expressing abnormally high levels of HER4 as an indication of neoplasia. In a related embodiment, detection of HER4 mRNA may be combined with the detection HER2 mRNA overexpression, using appropriate HER2 sequences, to identify neoplasias in which a functional relationship between HER2 and HER4 may exist.

In another embodiment, labeled anti-HER4 antibodies or antibody derivatives are used to detect the presence of HER4 in biological samples, using a variety of immunoassay formats well known in the art, and may be used for in situ diagnostic radioimmunoimaging. Current diagnostic and staging techniques do not routinely provide a comprehensive scan of the body for metastatic tumors. Accordingly, anti-HER4 antibodies labeled with, for example, fluorescent, chemiluminescent, and radioactive molecules may overcome this limitation. In a preferred embodiment, a gamma-emitting diagnostic radionuclide is attached to a monoclonal antibody which is specific for an epitope of HER4, but not significantly cross-reactive with other EGFR-family members. The labeled antibody is then injected into a patient systemically, and total body imaging for the distribution and density of HER4 molecules is performed using gamma cameras, followed by localized imaging using computerized tomography or magnetic resonance imaging to confirm and/or evaluate the condition, if necessary. Preferred diagnostic radionuclides include but are not limited to technetium-99m, indium-111, iodine-123, and iodine-131.

Recombinant antibody-metallothionein chimeras (Ab-MTs) may be generated as recently described (Das et al., 1992, *Proc. Natl. Acad. Sci. U.S.A.* 89:9749–53). Such Ab-MTs can be loaded with technitium-99m by virtue of the metallothionein chelating function, and may offer advantages over chemically conjugated chelators. In particular, the highly conserved metallothionein structure may result in minimal immunogenicity.

5.7. Assays for the Identification of HER4 Ligands

Cell lines overexpressing a single member of the EGFR-family can be generated by transfection of a variety of parental cell types with an appropriate expression vector as described in Section 7., infra. Candidate ligands, or partially purified preparations, may be applied to such cells and assayed for receptor binding and/or activation. For example, a CHO-KI cell line transfected with a HER4 expression plasmid and lacking detectable EGFR, HER2, or HER3 may be used to screen for HER4-specific ligands. A particular embodiment of such a cell line is described in Section 7., infra, and has been deposited with the ATCC (CHO/HER4 21-2). Ligands may be identified by detection of HER4 autophosphorylation, stimulation of DNA synthesis, induction of morphologic differentiation, relief from serum or growth factor requirements in the culture media, and direct binding of labeled purified growth factor. The invention also relates to a bioassay for testing potential analogs of HER4 ligands based on a capacity to affect a biological activity mediated by the HER4 receptor.

5.8. Use Of The Invention in Cancer Therapy

5.8.1. Targeted Cancer Therapy

The invention is also directed to methods for the treatment of human cancers involving abnormal expression and/or function of HER4 and cancers in which HER2 overexpression is combined with the proximate expression of HER4, including but not limited to human breast carcinomas and other neoplasms overexpressing HER4 or overexpressing HER2 in combination with expression of HER4. The cancer therapy methods of the invention are generally based on treatments with unconjugated, toxin- or radionuclide- conjugated HER4 antibodies, ligands, and derivatives or fragments thereof. In one specific embodiment, such HER4 antibodies or ligands may be used for systemic and targeted therapy of certain cancers overexpressing HER2 and/or HER4, such as metastatic breast cancer, with minimal toxicity to normal tissues and organs. Importantly, in this connection, an anti-HER2 monoclonal antibody has been shown to inhibit the growth of human tumor cells overexpressing HER2 (Bacus et al., 1992, *Cancer Res.* 52:2580–89). In addition to conjugated antibody therapy, modulation of heregulin signaling through HER4 provides a means to affect the growth and differentiation of cells overexpressing HER2, such as certain breast cancer cells, using HER4-neutralizing monoclonal antibodies, NDF/HER4 antagonists, monoclonal antibodies or ligands which act as super-agonists for HER4 activation, or agents which block the interaction between HER2 and HER4, either by disrupting heterodimer formation or by blocking HER-mediated phosphorylation of the HER2 substrate.

For targeted immunotoxin-mediated cancer therapy, various drugs or toxins may be conjugated to anti-HER4 antibodies and fragments thereof, such as plant and bacterial toxins. For example, ricin, a cytotoxin from the *Ricinis communis* plant may be conjugated to an anti-HER4 antibody using methods known in the art (e.g., Blakey et al., 1988, *Prog. Allergy* 45:50–90; Marsh and Neville, 1988, *J. Immunol.* 140:3674–78). Once ricin is inside the cell cytoplasm, its A chain inhibits protein synthesis by inactivating the 60S ribosomal subunit (May et al., 1989, *EMBO J.* 8:301–08). Immunotoxins of ricin are therefore extremely cytotoxic. However, ricin immunotoxins are not ideally specific because the B chain can bind to virtually all cell surface receptors, and immunotoxins made with ricin A chain alone have increased specificity. Recombinant or deglycosylated forms of the ricin A chain may result in improved survival (i.e., slower clearance from circulation) of the immunotoxins. Methods for conjugating ricin A chain to antibodies are known (e.g., Vitella and Thorpe, in: Seminars in *Cell Biology*, pp 47–58; Saunders, Philadelphia 1991). Additional toxins which may be used in the formulation of immunotoxins include but are not limited to daunorubicin, methotrexate, ribosome inhibitors (e.g., trichosanthin, trichokirin, gelonin, saporin, mormordin, and pokeweed antiviral protein) and various bacterial toxins (e.g., *Pseudomonas exotoxin*). Immunotoxins for targeted cancer therapy may be administered by any route which will result in antibody interaction with the target cancer cells, including systemic administration and injection directly to the site of tumor. Another therapeutic strategy may be the administration of immunotoxins by sustained-release systems, such as semipermeable matrices of solid hydrophobic polymers containing the therapeutic agent. Various of sustained-release materials have been established and are well known by those skilled in the art. Sustained-release capsules may, depending on their chemical nature, release immunotoxic molecules for a few weeks up to over 100 days. Depending on the chemical nature and the biological stability of the therapeutic reagent, additional strategies for protein stabilization may be employed.

For targeted radiotherapy using anti-HER4 antibodies, preferred radionuclides for labeling include alpha, beta, and Auger electron emitters. Examples of alpha emitters include astatine 211 and bismuth 212; beta emitters include iodine 131, rhenium 188, copper 67 and yttrium 90; and iodine 125 is an example of an Auger electron emitter.

Similarly as suggested for the use of toxin-conjugated antibodies as therapeutic agents for targeted cancer therapy, purified ligand molecules may be chemically conjugated to cytotoxic substances. In addition, recombinant chimeric polypeptides comprising a HER4 binding (=ligand) portion fused to all or part of a cytotoxin may be engineered by constructing vectors comprising DNA encoding the ligand in reading frame with DNA encoding the toxin or part thereof. Such recombinant ligand-toxins may be used to specifically target HER4 expressing cancer cells. A particular embodiment of such a ligand-toxin is disclosed herein and described in more detail in Sections 5.8.2., infra, and Section 15, infra.

5.8.2. The Generation Of A Heregulin-toxin Specifically Targeting HER4 Expressing Tumor Cells Another aspect of the invention relates to the development of a strategy to selectively target and kill HER4 expressing tumor cells. More particularly, HER4 expressing tumor cells may be specifically targeted and killed by contacting such tumor cells with a fusion protein comprising a cytotoxic polypeptide covalently linked to a polypeptide which is capable of activating HER4 expressed on such cells.

In a specific embodiment described by way of example in Section 15, infra, a fusion protein comprising a chimeric heregulin β2 ligand and the cytotoxic substance PE40 is generated by expression of the corresponding chimeric coding sequence. PE40 is a derivative of the Pseudomonas exotoxin PE, a potent cell killing agent made by *Pseudomonas aeruginosa* (Fitzgerald et al., 1980, *Cell* 21:867–873). The wildtype protein PE contains three domains whose functions are cell recognition, membrane translocation, and ADP ribosylation of elongation factor 2. It kills cells by binding to a cell surface receptor, entering the cell via an endocytotic vesicle and catalyzing ADP-ribosylation of elongation factor 2. The derivative PE40 lacks the cell binding function of the wildtype protein, but still exhibits strong cytotoxic activity. Generation of PE40 fusion proteins with specific cell targeting molecules have been described (Kondo et al., 1988, *J. Biol. Chem.* 263:9470–9475 (PE40 fusions with different monoclonal antibodies); Friedman et al., 1993, *Cancer Res.* 53:334–339 (BR96/PE40 fusions); U.S. Pat. No. 5,206,353 (CD4/PE40 fusions); U.S. Pat. No. 5,082,927 (IL-4/PE40 fusions) and U.S. Pat. No. 4,892,827 (TGF-α/PE40 and IL-2/PE40 fusions)).

The chimeric heregulin-toxin protein HAR-TX β2 described in Section 15, infra, contains the amphiregulin (AR) leader sequence thereby facilitating the purification of the recombinant protein. As confirmed by applicants' data, the AR leader has no influence on the binding specificity of the recombinant heregulin-toxin. Related embodiments include, for example, PE40 linked to other members of the heregulin family, like heregulin-β1 and heregulin-α, and other molecules capable of activating HER4.

In a cytotoxicity assay with cultured tumor cell lines, the applicants demonstrate specificity of the cytotoxic effect of the chimeric heregulin-PE40 protein to HER4 expressing cancer cells; they include but are not limited to prostate carcinoma, bladder carcinoma, and a considerable number of different breast cancer types, including breast carcinoma cells with amplified HER2 expression. The bifunctional retention of both the specificity of the cell binding portion of the molecule and the cytotoxic potential of PE40 provides a very potent and targeted reagent.

An effective therapeutic amount of heregulin-toxin will depend upon the therapeutic objectives, the route of administration, and the condition of the patient. Accordingly, dosages should be titrated and the route of administration modified as required to obtain the optimal therapeutic effect. A typical daily dosage may be in the range of 0.1 mg/kg–1 mg/kg, preferably between 0.1 and 0.5 mg/kg, with intravenous administration. For regression of solid tumors, it may take 3–5 doses, with schedules such as 3 doses, each four days apart. Also the use of sustained-release preparations (see Section 5.8.1., supra) may be considered for administration of the reagent. The therapeutic efficacy of heregulin-toxin may be between 2 and 10, which means that a tumor regression effect would be expected between 2- and 10-fold below the toxic dose (see Section 15, infra). Desirably, the heregulin-toxin will be administered at a dose and frequency that achieves the desired therapeutic effect, which can be monitored using conventional assays.

Cancer therapy with heregulin-toxins of the invention may be combined with chemotherapy, surgery, and radiation therapy, depending on the type of tumor. One advantage of using a low molecular weight toxin drug is that they are capable of targeting metastatic lesions that cannot be located and removed by surgery. Heregulin-toxins may also be particularly useful on patients that are MDR (Multi Drug Resistance) positive since their mechanism of action is not inhibited by the p-glycoprotein pump of MDR positive cells as are many standard cancer therapeutic drugs.

5.9. Other Therapeutic Use Of HER4 Ligands

Additional therapeutic uses of HER4 ligands may include other diseases caused by deficient HER4 receptor tyrosine kinase activation rather than by hyperactivation. In this regard, type II diabetes mellitus is the consequence of deficient insulin-mediated signal transduction, caused by mutations in the insulin-receptor, including mutations in the ligand-binding domain (Taira et al., 1889, *Science* 245:63–66; Odawara et al., 1989, *Science* 245:66–68; Obermeier-Kusser et al., 1989, *J. Biol. Chem.* 264:9497–9504). Such diseases might be treated by administration of modified ligands or ligand-analogues which re-establish a functional ligand-receptor interaction.

5.10. HER4 Analogues

The production and use of derivatives, analogues and peptides related to HER4 are also envisioned and are within the scope of the invention. Such derivatives, analogues and peptides may be used to compete with native HER4 for binding of HER4 specific ligand, thereby inhibiting HER4 signal transduction and function. The inhibition of HER4 function may be utilized in several applications, including but not limited to the treatment of cancers in which HER4 biological activity is involved.

In a specific embodiment, a series of deletion mutants in the HER4 nucleotide coding sequence depicted in FIGS. 1A and 1B may be constructed and analyzed to determine the minimum amino acid sequence requirements for binding of a HER4 ligand. Deletion mutants of the HER4 coding sequence may be constructed using methods known in the art which include but are not limited to use of nucleases and/or restriction enzymes; site-directed mutagenesis techniques, PCR, etc. The mutated polypeptides expressed may be assayed for their ability to bind HER4 ligand.

The DNA sequence encoding the desired HER4 analogue may then be cloned into an appropriate expression vector for overexpression in either bacteria or eukaryotic cells. Peptides may be purified from cell extracts in a number of ways including but not limited to ion-exchange chromatography or affinity chromatography using HER4 ligand or antibody. Alternatively, polypeptides may be synthesized by solid phase techniques followed by cleavage from resin and purification by high performance liquid chromatography.

6. EXAMPLE: Isolation of cDNAS Encoding HER4

EGFR and the related proteins, HER2, HER3, and Xmrk exhibit extensive amino acid homology in their tyrosine kinase domains (Kaplan et al., 1991, *Nature* 350:158–160; Wen et al., 1992, *Cell* 69:559–72; Holmes et al., 1992, *Science* 256:1205–10; Hirai et al., *Science* 1987 238:1717–20). In addition, there is strict conservation of the exon-intron boundaries within the genomic regions that encode these catalytic domains (Wen et al., supra; Lindberg and Hunter, 1990, *Mol. Cell. Biol.* 10:6316–24; and unpublished observations). Degenerate oligonucleotide primers were designed based on conserved amino acids encoded by a single exon or adjacent exons from the kinase domains of these four proteins. These primers were used in a polymerase chain reaction (PCR) to isolate genomic fragments corresponding to murine EGFR, erbB2 and erbB3. In addition, a highly related DNA fragment (designated MER4) was identified as distinct from these other genes. A similar strategy was used to obtain a cDNA clone corresponding to the human homologue of MER4 from the breast cancer cell line, MDA-MB-453. Using this fragment as a probe, several breast cancer cell lines and human heart were found to be an abundant source of the EGFR-related transcript. cDNA libraries were constructed using RNA from human heart and MDA-MB-453 cells, and overlapping clones were isolated spanning the complete open reading frame of HER4/erbB4.

6.1. Materials and Methods

6.1.1. Molecular Cloning

Several pools of degenerate oligonucleotides were synthesized based on conserved sequences from EGFR-family members (Table I) (5'-ACNGTNTGGGARYTNAYHAC-3' [SEQ ID No:14]; 5'-CAYGTNAARATHACNGAYTTYGG-3' [SEQ ID No:16]; 5'-GACGAATTCCNATHAARTGGATGGC-3' [SEQ ID No:17]; 5'-AANGTCATNARYTCCCA-3' [SEQ ID No:18]; 5'-TCCAGNGCGATCCAYTTDATNGG-3' [SEQ ID No:19]; 5'-GGRTCDATCATCCARCCT-3' [SEQ ID No:20]; 5'-CTGCTGTCAGCATCGATCAT-3' [SEQ ID No:21]; TVWELMT [SEQ ID No:22]; HVKITDFG [SEQ ID No:23]; PIKWMA [SEQ ID No:13]; VYMIILK [SEQ ID No:24]; WELMTF [SEQ ID No:25]; PIKWMALE [SEQ ID No:26]; CWMIDP [SEQ ID No:27]. Total genomic DNA was isolated from subconfluent murine K1735 melanoma cells and used as a template with these oligonucleotide primers in a 40 cycle PCR amplification. PCR products were resolved on agarose gels and hybridized to $^{32}$P-labeled probes from the kinase domain of human EGFR and HER2. Distinct DNA bands were isolated and subcloned for sequence analysis. Using the degenerate oligonucleotides H4VWELM and H4VYMIIL as primers in a PCR amplification (Plowman et al., 1990, *Proc. Natl. Acad. Sci. U.S.A.* 87:4905–09), one clone (MER4–85) was identified that contained a 144 nucleotide insert corresponding to murine erbB4. This $^{32}$P-labeled insert was used to isolate a 17-kilobase fragment from a murine T-cell genomic library (Stratagene, La Jolla, Calif.) that was found to contain two exons of the murine erbB4 gene. A specific oligonucleotide (4M3070) was synthesized based on the DNA sequence of an erbB4 exon, and used in a PCR protocol with a degenerate 5'-oligonucleotide (H4PIKWMA) on a template of single stranded MDA-MB-453 cDNA. This reaction generated a 260 nucleotide fragment (pMDAPIK) corresponding to human HER4. cDNA libraries were constructed in lambda ZAP II (Stratagene) from oligo(dT)- and specific-primed MDA-MB453 and human heart RNA (Plowman et al., supra; Plowman et al., 1990, *Mol. Cell. Biol.* 10:1969–81). HER4-specific clones were isolated by probing the libraries with the $^{32}$P-labeled insert from pMDAPIK. To complete the cloning of the 5'-portion of HER4, we used a PCR strategy to allow for rapid amplification of cDNA ends (Plowman et al., supra; Frohman et al., 1988, *Proc. Natl. Acad. Sci. U.S.A.* 85:8998–9002). All cDNA clones and several PCR generated clones were sequenced on both strands using T7 polymerase with oligonucleotide primers (Tabor and Richardson, 1987, *Proc. Natl. Acad. Sci. U.S.A.* 84:4767–71).

TABLE I

OLIGONUCLEOTIDE PREPARATIONS FOR CLONING HER 4

| Designation | Nucleotide Sequence[1] | Degeneracy | Encoded Sequence | Orientation | Seq. ID. No. |
| --- | --- | --- | --- | --- | --- |
| H4TVWELM | 5'-ACNGTNTGGGARYTNAYHAC-3' | 256-fold | TVWELMT | sense | 14 |

TABLE I-continued

OLIGONUCLEOTIDE PREPARATIONS FOR CLONING HER 4

| Designation | Nucleotide Sequence[1] | Degeneracy | Encoded Sequence | Orientation | Seq. ID. No. |
|---|---|---|---|---|---|
| H4KITDFG | 5'-CAYGTNAARATHACNGAYTTYGG-3' | 768-fold | HVKITDFG | sense | 15 |
| H4PIKWMA | 5'-GACGAATTCCNATHAARTGGATGGC | 48-fold | PIKWMA | sense | 16 |
| H4VYMIIL | 5'-ACAYTTNARDATDATCATRTANAC-3' | 576-fold | VYMIILK | antisense | 17 |
| H4WELMTF | 5'-AANGTCATNARYTCCCA-3' | 32-fold | WELMTF | antisense | 18 |
| H4PIKWMA | 5'-TCCAGNGCGATCCAYTTDATNGG-3' | 96-fold | PIKWMALE | antisense | 19 |
| H4CWMIDP | 5'-GGRTCDATCATCCARCCT-3' | 12-fold | CWMIDP | antisense | 20 |
| 4M3070 | 5'-CTGCTGTCAGCATCGATCAT-3' | zero | erbB4 exon | antisense | 21 |

[1]Degenerate nucleotide residue designations:
D = A, G, or T;
H = A, C, or T;
N = A, C, G, or T;
R = A or G; and
Y = C or T.

6.1.2. Northern Blot Analysis

3'- and 5'-HER4 specific [$\alpha^{32}$P]UTP-labeled antisense RNA probes were synthesized from the linearized plasmids pHt1B1.6 (containing an 800 bp HER4 fragment beginning at nucleotide 3098) and p5'H4E7 (containing a 1 kb fragment from the 5'-end of the HER4 sequence), respectively. For tissue distribution analysis (Section 6.2.3., infra), the Northern blot (Clontech, Palo Alto, Calif.) contained 2 Mg poly(A)+ mRNA per lane from 8 human tissue samples immobilized on a nylon membrane. The filter was prehybridized at 60° C. for several hours in RNA hybridization mixture (50% formamide, 5× SSC, 0.5% SDS, 10× Denhardt's solution, 100 μg/ml denatured herring sperm DNA, 100 μg/ml tRNA, and 10 μg/ml polyadenosine) and hybridized in the same buffer at 60° C., overnight with 1–1.5×10$^6$ cpm/ml of $^{32}$P-labeled antisense RNA probe. The filters were washed in 0.1×SSC/0.1% SDS, 65° C., and exposed overnight on a PhosphoImager (Molecular Dynamics, Sunnyvale, Calif.).

6.1.3. Semi-Quantitative PCR Detection of HER4

RNA was isolated from a variety of human cell lines, fresh frozen tissues, and primary tumors. Single stranded CDNA was synthesized from 10 μg of each RNA by priming with an oligonucleotide containing a T17 track on its 3'-end (XSCT17:5'GACTCGAGTCGACATCGATTTTTTT-TTTTTTTTTT-3') [SEQ ID No:28]. 1% or 5% of each single strand template preparation was then used in a 35 cycle PCR reaction with two HER4-specific oligonucleotides:

4H2674: 5'-GAAGAAAGACGACTCGTTCATCGG-3' [SEQ ID No:29], and

4H2965: 5'-GACCATGACCATGTAAACGTCAATA-3' [SEQ ID No:30].

Reaction products were electrophoresed on 2% agarose gels, stained with ethidium bromide and photographed on a UV light box. The relative intensity of the 291-bp HER4-specific bands were estimated for each sample as shown in Table II.

6.2. Results

6.2.1. Sequence Analysis of CDNA Clones Encoding HER4

CDNA clones encoding parts of the HER4 coding and non-coding nucleotide sequences were isolated by PCR cloning according to the method outlined in Section 6.1.1., supra. The complete HER4 nucleotide sequence assembled from these cDNAs is shown in FIGS. 1A and 1B and contains a single open reading frame encoding a polypeptide of 1308 amino acids. The HER4 coding region is flanked by a 33 nucleotide 5'-untranslated region and a 1517 nucleotide 3'-untranslated region ending with a poly(A) tail. A 25 amino acid hydrophobic signal sequence follows a consensus initiating methionine at position number 1 in the amino acid sequence depicted in FIGS. 1A and 1B. In relation to this signal sequence, the mature HER4 polypeptide would be predicted to begin at amino acid residue number 26 in the sequence depicted in FIGS. 1A and 1B (Gln), followed by the next 1283 amino acids in the sequence. Thus the prototype mature HER4 of the invention is a polypeptide of 1284 amino acids, having a calculated Mr of 144,260 daltons and an amino acid sequence corresponding to residues 26 through 1309 in FIGS. 1A and 1B.

Comparison of the HER4 nucleotide and deduced amino acid sequences (FIGS. 1A and 1B) with the available DNA and protein sequence databases indicated that the HER4 nucleotide sequence is unique, and revealed a 60/64 amino acid identity with HER2 and a 54/54 amino acid identity to a fragment of a rat EGFR homolog, tyro-2.

6.2.2. Sequence Analysis of Related cDNAs

Several cDNAs encoding polypeptides related to the prototype HER4 polypeptide (FIGS. 1A and 1B) were also isolated from the MDA-MB-453 cDNA library and comprised two forms.

The first alternative type of CDNA was identical to the consensus HER4 nucleotide sequence up to nucleotide 3168 (encoding Arg at amino acid position 1045 in the FIGS. 1A and 1B) and then abruptly diverges into an apparently unrelated sequence (FIG. 2A and 2B, FIG. 4). Downstream from this residue the open reading frame continues for another 13 amino acids before reaching a stop codon followed by a 2 kb 3'-untranslated sequence and poly(A) tail. This cDNA would be predicted to result in a HER4 variant having the C-terminal autophosphorylation domain of the prototype HER4 deleted.

A second type of cDNA was isolated as 4 independent clones each with a 3'-sequence identical to the HER4 consensus, but then diverging on the 5'-side of nucleotide 2335 (encoding Glu at amino acid position 768 in the FIGS. 1A and 1B), continuing upstream for only another 114–154 nucleotides (FIG. 3, FIG. 5). Nucleotide 2335 is the precise location of an intron-exon junction in the HER2 gene (Coussens et al., 1985, *Science* 230:1132–39; Semba et al., 1985, *Proc. Natl. Acad. Sci. U.S.A.* 82:6497–6501), suggesting these cDNAs could be derived from mRNAs that have initiated from a cryptic promoter within the flanking intron. These 5'-truncated transcripts contain an open reading frame identical to that of the HER4 CDNA sequence of FIGS. 1A and 1B, beginning with the codon for Met at amino acid position 772 in FIGS. 1A and 1B. These cDNAs would be predicted to encode a cytoplasmic HER4 variant polypeptide that initiates just downstream from the ATP-binding domain of the HER4 kinase.

6.2.3. Human Tissue Distribution of HER4 Expression

Northern blots of poly(A)+ mRNA from human tissue samples were hybridized with antisense RNA probes to the 3'-end of HER4, encoding the autophosphorylation domain, as described in Section 6.1.2., supra. A HER4 mRNA transcript of approximately 6 kb was identified, and was found to be most abundant in the heart and skeletal muscle (FIG. 8, Panel 1). An mRNA of greater than approximately 15 kb was detected in the brain, with lower levels also detected in heart, skeletal muscle, kidney, and pancreas tissue samples.

The same blot was stripped and rehybridized with a probe from the 5'-end of HER4, within the extracellular domain coding region, using identical procedures. This hybridization confirmed the distribution of the 15 kb HER4 mRNA species, and detected a 6.5 kb mRNA species in heart, skeletal muscle, kidney, and pancreas tissue samples (FIG. 8, Panel 2) with weaker signals in lung, liver, and placenta. In addition, minor transcripts of 1.7–2.6 kb were also detected in pancreas, lung, brain, and skeletal muscle tissue samples. The significance of the different sized RNA transcripts is not known.

Various human tissues were also examined for the presence of HER4 mRNA using the semi-quantitative PCR assay described in Section 6.1.3., supra. The results are shown in Table II, together with results of the assay on primary tumor samples and neoplastic cell lines (Section 6.2.4., immediately below). These results correlate well with the Northern and solution hybridization analysis results on the selected RNA samples. The highest levels of HER4 transcript expression were found in heart, kidney, and brain tissue samples. In addition, high levels of HER4 mRNA expression were found in parathyroid, cerebellum, pituitary, spleen, testis, and breast tissue samples. Lower expression levels were found in thymus, lung, salivary gland, and pancreas tissue samples, Finally, low or negative expression was observed in liver, prostate, ovary, adrenal, colon, duodenum, epidermis, and bone marrow samples.

6.2.4. HER4 mRNA Expression in Primary Tumors and Various Cell Lines of Neoplastic Origin HER4 mRNA expression profiles in several primary tumors and a number of cell lines of diverse neoplastic origin were determined with the semi-quantitative PCR assay (Section 6.1.3, supra) using primers from sequences in the HER4 kinase domain. The results are included in Table II. This analysis detected the highest expression of HER4 RNA in 4 human mammary adenocarcinoma cell lines (T-47D, MDA-MB-453, BT-474, and H3396), and in neuroblastoma (SK-N-MC), and pancreatic carcinoma (Hs766T) cell lines. Intermediate expression was detected in 3 additional mammary carcinoma cell lines (MCF-7, MDA-MB-330, MDA-MB-361). Low or undetectable expression was found in other cell lines derived from carcinomas of the breast (MDB-MB-231, MDA-MB-157, MDA-MB-468, SK-BR-3), kidney (Caki-1, Caki-2, G-401), liver (SK-HEP-1, HepG2), pancreas (PANC-1, AsPC-1, Capan-1), colon (HT-29), cervix (CaSki), vulva (A-41), ovary (PA-1, Caov-3), melanoma (SK-MEL-28), or in a variety of leukemic cell lines. Finally, high level expression was observed in Wilms (kidney) and breast carcinoma primary tumor samples.

TABLE II

HER4 EXPRESSION BY PRC ANALYSIS

| VERY STRONG | STRONG | MEDIUM |
|---|---|---|
| T47D (breast) | MDA-MB-453 (breast) | MCF-7 (breast) |
|  | BT-474 (breast) | MDA-MB-330 (breast) |
|  | H3396 (breast) | MDA-MB-157 (breast) |
|  | Hs766T (pancreatic) | JEG-3 (choriocarcinoma) |
| Kidney | Brain | Skeletal Muscle |
| Heart | Cerebellum | Thymus |
| Parathyroid | Pituitary | Pancreas |
|  | Breast | Lung |
|  | Testis | Salivary Gland |
|  | Spleen |  |
|  | WEAK | NEGATIVE |
|  | MDB-MB-231 (breast) | MDA-MB-468 (breast) |
|  | MDA-MB-157 (breast) | G-401 (kidney) |
|  | SK-BR-3 (breast) | HepG2 (liver) |
|  | A0431 (vulva) | PANC-1 (pancreas) |
|  | Caki-1 (kidney) | AsPC-1 (pancreas) |
|  | Caki-2 (kidney) | Capan-1 (pancreas) |
|  | SK-HEP-1 (liver) | HT-29 (colon) |
|  | THP-1 (macrophage) | CaSki (cervix) |
|  |  | PA-1 (ovary) |
|  | Prostate | Caov-3 (ovary) |
|  | Adrenal | SK-MEL-28 (melanoma) |
|  | Ovary | HUF (fibroblast) |
|  | Colon | H2981 (lung) |
|  | Placenta | Ovarian tumor |
|  |  | GEO (colon) |
|  |  | ALL bone marrow |
|  |  | AML bone marrow |
|  |  | Duodenum |
|  |  | Epidermis |
|  |  | Liver |
|  |  | Bone marrow stroma |

7. EXAMPLE: Recombinant Expression of HER4

7.1. Materials and Methods

7.1.1. CHO-KI Cells and Culture Conditions

CHO-KI cells were obtained from the ATCC (Accession Number CCL 61). These cells lack any detectable EGFR, HER2, or HER3 by immunoblot, tyrosine phosphorylation, and $^{35}$S-labeled immunoprecipitation analysis. Transfected cell colonies expressing HER4 were selected in glutamine-free Glasgow modified Eagle's medium (GMEM-S, Gibco) supplemented with 10% dialyzed fetal bovine serum and increasing concentrations of methionine sulfoximine (Bebbington, 1991, in *Methods: A Companion to Methods in Enzymology* 2:136–145 Academic Press).

7.1.2. Expression Vector Construction and Transfections

The complete 4 kilobase coding sequence of prototype HER4 was reconstructed and inserted into a glutamine synthetase expression vector, pEE14, under the control of the cytomegalovirus immediate-early promoter (Bebbington, supra) to generate the HER4 expression vector pEEHER4. This construct (pEEHER4) was linearized with MluI and transfected into CHO-KI cells by calcium phosphate precipitation using standard techniques. Cells were placed on selective media consisting of GMEM-S supplemented with 10% dialyzed fetal bovine serum and methionine sulfoximine at an initial concentration of 25 $\mu$M (L-MSX) as described in Bebbington, supra, for the selection of initial resistant colonies. After 2 weeks, isolated colonies were transferred to 48-well plates and expanded for HER4 expression immunoassays as described immediately below. Subsequent rounds of selection using higher concentrations of MSX were used to isolate cell colonies tolerating the highest concentrations of MSX. A number of CHO/HER4 clones selected at various concentrations of MSX were isolated in this manner.

7.1.3. HER4 Expression Immunoassay

Confluent cell monolayers were scraped into hypotonic lysis buffer (10 mM Tris pH7.4, 1 mM KCl, 2 mM $MgCl_2$) at 4° C., dounce homogenized with 30 strokes, and the cell debris was removed by centrifugation at 3500×g, 5 min. Membrane fractions were collected by centrifugation at 100,000×g, 20 min, and the pellet was resuspended in hot Laemmli sample buffer with 2-mercaptoethanol. Expression of the HER4 polypeptide was detected by immunoblot analysis on solubilized cells or membrane preparations using HER2 immunoreagents generated to either a 19 amino acid region of the HER2 kinase domain, which coincidentally is identical to the HER4 sequence (residues 927–945), or to the C-terminal 14 residues of HER2, which share a stretch of 7 consecutive residues with a region near the C-terminus of HER4. On further amplification, HER4 was detected from solubilized cell extracts by immunoblot analysis with PY20 anti-phosphotyrosine antibody (ICN Biochemicals), presumably reflecting autoactivation and autophosphorylation of HER4 due to receptor aggregation resulting from abberantly high receptor density. More specifically, expression was detected by immunobloting with a primary murine monoclonal antibody to HER2 (Neu-Ab3, Oncogene Science) diluted 1:50 in blotto (2.5% dry milk, 0.2% NP40 in PBS) using $^{125}$I-goat anti-mouse Ig F(ab')2 (Amersham, UK) diluted 1:500 in blotto as a second antibody. Alternatively, a sheep polyclonal antipeptide antibody against HER2 residues 929–947 (Cambridge Research Biochemicals, Valleystream, N.Y.) was used as a primary immunoreagent diluted 1:100 in blotto with $^{125}$I-Protein G (Amersham) diluted 1:200 in blotto as a second antibody. Filters were washed with blotto and exposed overnight on a phosphoImager (Molecular Dynamics).

7.2. Results

CHO-KI cells transfected with a vector encoding the complete human prototype HER4 polypeptide were selected for amplified expression in media containing increasing concentrations of methionine sulfoximine as outlined in Section 7.1., et seq., supra. Expression of HER4 was evaluated using the immunoassay described in Section 7.1.3., supra. Several transfected CHO-KI cell clones stably expressing HER4 were isolated. One particular clone, CHO/HER4 21-2, was selected in media supplemented with 250 $\mu$M MSX, and expresses high levels of HER4. CHO/HER4 21-2 cells have been deposited with the ATCC.

Recombinant HER4 expressed in CHO/HER4 cells migrated with an apparent Mr of 180,000, slightly less than HER2, whereas the parental CHO cells showed no cross-reactive bands (FIG. 9). In addition, a 130 kDa band was also detected in the CHO/HER4 cells, and presumably represents a degradation product of the 180 kDa mature protein. CHO/HER4 cells were used to identify ligand specific binding and autophosphorylation of the HER4 tyrosine kinase (see Section 9., et seq., infra).

8. EXAMPLE: Assay for Detecting EGPR-Family Ligands

8.1. Cell Lines

A panel of four recombinant cell lines, each expressing a single member of the human EGFR-family, were generated for use in the tyrosine kinase stimulatory assay described in Section 8.2., below. The cell line CHO/HER4 3 was generated as described in Section 7.1.2, supra.

CHO/HER2 cells (clone 1–2500) were selected to express high levels of recombinant human p185$^{erbB2}$ by dihydrofolate reductase-induced gene amplification in dhfr-deficient CHO cells. The HER2 expression plasmid, cDNeu, was generated by insertion of a full length HER2 coding sequence into a modified pCDM8 (Invitrogen, San Diego, Calif.) expression vector (Seed and Aruffo, 1987, Proc. Natl. Adad. Sci. U.S.A. 84:3365–69) in which an expression cassette from pSV2DHFR (containing the murine dhfr cDNA driven by the SV40 early promoter) has been inserted at the pCDM8 vector's unique BamHI site. This construct drives HER2 expression from the CMV immediate-early promoter.

NRHER5 cells (Velu et al., 1987, Science 1408–10) were obtained from Dr. Hsing-Jien Kung (Case Western Reserve University, Cleveland, Ohio). This murine cell line was clonally isolated from NR6 cells infected with a retrovirus stock carrying the human EGFR, and was found to have approximately 10$^6$ human EGFRs per cell.

The cell line 293/HER3 was selected for high level expression of p160$^{erbB3}$. The parental cell line, 293 human embryonic kidney cells, constitutively expresses adenovirus E1a and have low levels of EGFR expression. This line was established by cotransfection of linearized cHER3 (Plowman et al., 1990, Proc. Natl. Acad. Sci. U.S.A. 87:4905–09) and pMC1neoPolyA (neomycin selectable marker with an Herpes simplex thymidine kinase promoter, Stratagene), with selection in DMEM/F12 media containing 500 $\mu$g/ml G418.

8.2. Tyrosine Kinase Stimulation Assay

Cells were plated in 6-well tissue culture plates (Falcon), and allowed to attach at 37° C. for 18–24 hr. Prior to the assay, the cells were changed to serum-free media for at least 1 hour. Cell monolayers were then incubated with the amounts of ligand preparations indicated in Section 7.3., below for 5 min at 37° C. Cells were then washed with PBS and solubilized on ice with 0.5 ml PBSTDS containing phosphatase inhibitors (10 mM NaHPO4, 7.25, 150 mM NaCl, 1% Triton X-100, 0.5% deoxycholate, 0.1% SDS, 0.2% sodium azide, 1 mM NaF, 1 mM EGTA, 4 mM sodium orthovanadate, 1% aprotinin, 5 $\mu$g/ml leupeptin). Cell debris was removed by centrifugation (12000×g, 15 min, 4° C.) and the cleared supernatant reacted with 1 $\mu$g murine monoclonal antibody to phosphotyrosine (PY20, ICN Biochemicals, Cleveland, Ohio) for CHO/HER4 and 293/HER3 cells, or 1 $\mu$g murine monoclonal antibody to HER2 (Neu-Ab3, Oncogene Sciences) for CHO/HER2 cells, or 1 mg murine monoclonal antibody EGFR-1 to human EGFR (Amersham) for NRHER5 cells. Following a 1 hr incubation at 4° C., 30 $\mu$l of a 1:1 slurry (in PBSTDS) of anti-mouse IgG-agarose (for PY20 and Neu-Ab3 antibodies) or protein A-sepharose (for EGFR-R1 antibody) was added and the incubation was allowed to continue an additional 30 minutes. The beads were washed 3 times in PBSTDS and the complexes resolved by electrophoresis on reducing 7% SDS-polyacrylamide gels. The gels were transferred to nitrocellulose and blocked in TNET (10 mM Tris pH7.4, 75 mM NaCl, 0.1% Tween-20, 1 mM EDTA). PY20 antiphosphotyrosine antibody diluted 1:1000 in TNET was used as the primary antibody followed by $^{125}$I-goat anti-mouse Ig F(ab')2 diluted 1:500 in TNET. Blots were washed with TNET and exposed on a phosphorimager (Molecular Dynamics).

8.3. Results

Several EGF-family member polypeptide and ligand preparations were tested for their ability to stimulate tyrosine phosphorylation of each of four EGFR-family receptors expressed in recombinant CHO cells using the tyrosine phosphorylation stimulation assay described in Section 8.2., above. The particular preparations tested for each of the four recombinant cell lines and the results obtained in the assay are tabulated below, and autoradiographs of some of these results are shown in FIG. 10.

TABLE III

STIMULATION OF TYR PHOSPHORYLATION
OF EGFR-FAMILY RECFEPTORS

| | RECOMBINANT CELLS | | | |
|---|---|---|---|---|
| PREPARATION | CHO/HER4#3 | CHO/HER2 | NRHER5 | 2293/HER3 |
| EGF | − | − | + | − |
| AMPHIREGULIN | − | − | + | − |
| TGF-α | − | − | + | − |
| HB-EGF | − | − | + | − |
| FRACTION 17* | + | − | − | − |
| FRACTION 14* | − | − | − | − |

*The identification of the HER4 tyrosine kinase stimulatory activity within the conditioned media of HepG2 cells and the isolation of these preparations is described in Section 9, infra.

The results indicate that EGF, AR, TGF-α, and HB-EGF, four related ligands which mediate their growth regulatory signals in part through interaction with EGFR, were able to stimulate tyrosine phosphorylation of EGFR expressed in recombinant NIH3T3 cells (for EGF, see FIG. 10, Panel 3, lane 2 ), but not HER4, HER2, or HER3 expressed in recombinant CHO or 293 cells (FIG. 10, Panel 1, 2, 4, lanes 2 and 3). Additionally, as discussed in more detail below, the assay identified a HepG2-derived preparation (fraction 17) as a HER4 ligand capable of specifically stimulating tyrosine phoshorylation of HER4 expressed in CHO/HER4 cells alone.

9. EXAMPLE: Isolation of a HER4 Ligand

9.1. Materials and Methods

9.1.1. Cell Differentiation Assay

For the identification of ligands specific for HER2, HER3 or HER4, the receptor expression profile of MDA-MB-453 cells offers an excellent indicator for morphologic differentiation inducing activity. This cell line is known to express HER2 and HER3, but contains no detectable EGFR. The results of the semi-quantitative PCR assays (Table III) indicated high level expression of HER4 in MDA-MB-453 cells. In addition, cDNA encoding the prototype HER4 polypeptide of the invention was first isolated from this cell line (Section 6., supra).

MDA-MB-453 cells (7500/well) were grown in 50 ml DMEM supplemented with 5% FBS and 1× essential amino acids. Cells were allowed to adhere to 96-well plates for 24 hr. Samples were diluted in the above medium, added to the cell monolayer in 50 ml final volume, and the incubation continued for an additional 3 days. Cells were then examined by inverted light microscopy for morphologic changes.

9.1.2. Source Cells

Serum free media from a panel of cultures of human cancer cells were screened for growth regulatory activity on MDA-MB-453 cells. A human hepatocarcinoma cell line, HepG2, was identified as a source of a factor which induced dramatic morphologic differentiation of the MDA-MB-453 cells.

9.1.3. Purification of HER4 Ligand

The cell differentiation assay described in Section 10.1.1., supra, was used throughout the purification procedure to monitor the column fractions that induce morphological changes in MDA-MB-453 cells. For large-scale production of conditioned medium, HepG2 cells were cultured in DMEM containing 10% fetal bovine serum using Nunc cell factories. At about 70% confluence, cells were washed then incubated with serum-free DMEM. Conditioned medium (HepG2-CM) was collected 3 days later, and fresh serum-free medium added to the cells. Two additional harvests of HepG2-CM were collected per cell factory. The medium was centrifuged and stored at −20° C. in the presence of 500 mM PMSF.

Ten liters of HepG2-CM were concentrated 16-fold using an Amicon ultrafiltration unit (10,000 molecular weight cutoff membrane), and subjected to sequential precipitation with 20% and 60% ammonium sulfate. After centrifugation at 15,000×g, the supernatant was extensively dialyzed against PBS and passed through a DEAE-sepharose (Pharmacia) column pre-equilibrated with PBS. The flow-through fraction was then applied onto a 4 ml heparin-acrylic (Bio-Rad) column equilibrated with PBS. Differentiation inducing activity eluted from the heparin column between 0.4 and 0.8M NaCl. Active heparin fractions were pooled, brought to 2.0M ammonium sulfate, centrifuged at 12,000×g for 5 min, and the resulting supernatant was loaded onto a phenyl-5PW column (8×75 mm, Waters). Bound proteins were eluted with a decreasing gradient from 2.0M ammonium sulfate in 0.1M Na$_2$HPO$_4$, pH 7.4 to 0.1M Na$_2$HPO$_4$. Dialyzed fractions were assayed for tyrosine phosphorylation of MDA-MB-453 cells, essentially as described (Wen et al., 1992, Cell 69:559–72), except PY20 was used as the primary antibody and horseradish peroxidase-conjugated goat F(ab')2 anti-mouse Ig (Cappell) and chemiluminescence were used for detection. Phosphorylation signals were analyzed using the Molecular Dynamics personal densitometer.

9.2. Results

Semi-purified HepG2-derived factor demonstrated a capacity to induce differentiation in MDA-MB-453 cells (FIG. 11, Panel 1–3). With reference to the micrographs shown in FIG. 11, Panel 1–3, untreated MDA-MB-453 cells are moderately adherent and show a rounded morphology (FIG. 11, Panel 1). In contrast, the addition of semi-purified HepG2-derived factor induces these cells to display a noticeably flattened morphology with larger nuclei and increased cytoplasm (FIG. 11, Panel 2 and 3). This HepG2-derived factor preparation also binds to heparin, a property which was utilized for purifying the activity.

On further purification, the HepG2-derived factor was found to elute from a phenyl hydrophobic interaction column at 1.0M ammonium sulfate (fractions 16 to 18). FIG. 11, Panel 4, shows the phenyl column elution profile. Tyrosine phosphorylation assays of the phenyl column fractions revealed that the same fractions found to induce differentiation of the human breast carcinoma cells are also able to stimulate tyrosine phosphorylation of a 185 kDa protein in MDA-MB-453 cells (FIG. 11, Panel 5). In particular, fraction 16 induced a 4.5-fold increase in the phosphorylation signal compared to the baseline signal observed in unstimulated cells, as determined by densitometry analysis (FIG. 11, Panel 6).

The phenyl fractions were also tested against the panel of cell lines which each overexpress a single member of the EGFR-family (Section 9.1., supra). Fraction 17 induced a significant and specific activation of the HER4 kinase ( FIG. 10, Panel 1, lane 4) without directly affecting the phosphorylation of HER2, EGFR, or HER3 (FIG. 10, Panel 1–4, lane 4). Adjacent fraction 14 was used as a control and had no effect on the phosphorylation of any of the EGFR-family receptors (FIG. 10, Panel 1–4, lane 5). Further purification and analysis of the factor present in fraction 17 indicates that it is a glycoprotein of 40 to 45 kDa, approximately the same size as NDF and HRG. The HepG2-derived factor also has functional properties similar to NDF and HRG, inasmuch as it stimulates tyrosine phosphorylation of HER2/p185 in MDA-MB-453 cells, but not EGFR in NR5 cells, and induces morphologic differentiation of HER2 overexpressing human breast cancer cells.

Recently, several groups have reported the identification of specific ligands for HER2 (see Section 2., supra., including NDF and HRG-α. In contrast to these molecules, the HepG2-derived factor described herein failed to stimulate phosphorylation of HER2 in CHO/HER2 cells, but did stimulate phosphorylation of HER4 in CHO/HER4 cells. These findings are intriguing in view of the ability of the HepG2-derived factor to stimulate phosphorylation of MDA-MD-453 cells, a cell line known to overexpress HER2 and HER3 and the source from which HER4 was cloned. Since EGFR and HER2 have been shown to act synergistically, it is conceivable that HER4 may also interact with other EGFR-family members. In this connection, these results suggest that NDF may bind to HER4 in MDA-MB-453 cells resulting in the activation of HER2. The results described in Section 10., immediately below, provide evidence that NDF interacts directly with HER4, resulting in activation of HER2.

10. EXAMPLE: Recombinant NDF-Induced, HER4 Mediated Phosphorylation of HER2

Recombinant NDF was expressed in COS cells and tested for its activity on HER4 in an assay system essentially devoid of other known members of the EGFR-family, notably EGFR and HER2.

A full length rat NDF cDNA was isolated from normal rat kidney RNA and inserted into a cDM8-based expression vector to generate cNDF1.6. This construct was transiently expressed in COS cells, and conditioned cell supernatants were tested for NDF activity using the tyrosine kinase stimulation assay described in Section 8.2., supra. Supernatants from cNDF1.6 transfected cells upregulated tyrosine phosphorylation in MDA-MB-453 cells relative to mock transfected COS media FIG. 12, Panel 1. Phosphorylation peaked 10–15 minutes after addition on NDF.

The crude NDF supernatants were also tested for the ability to phosphorylate EGFR (NR5 cells), HER2 (CHO/HER2 1–2500 cells), and HER4 (CHO/HER4 21-2 cells). The NDF preparation had no effect on phosphorylation of EGFR, or HER2 containing cells, but induced a 2.4 to 4 fold increase in tyrosine phosphorylation of HER4 after 15 minutes incubation (see FIG. 12, Panel 2). These findings provide preliminary evidence that NDF/HRG-α mediate their effects not through direct binding to HER2, but instead by means of a direct interaction with HER4. In cell lines expressing both HER2 and HER4, such as MDA-MB-453 cells and other breast carcinoma cells, binding of NDF to HER4 may stimulate HER2 either by heterodimer formation of these two related transmembrane receptors, or by intracellular crosstalk. Formal proof of the direct interaction between NDF and HER4 will require crosslinking of $^{125}$I-NDF to CHO/HER4 cells and a detailed analysis of its binding characteristics.

11. EXAMPLE: Chromosomal Mapping of the HER4 Gene

A HER4 cDNA probe corresponding to the 5' portion of the gene (nucleotide positions 34–1303) was used for in situ hybridization mapping of the HER4 gene. In situ hybridization to metaphase chromosomes from lymphocytes of two normal male donors was conducted using the HER4 probe labeled with $^3$H to a specific activity of $2.6 \times 10^7$ cpm/μg as described (Marth et al., 1986, Proc. Natl. Acad. Sci. U.S.A. 83:7400–04). The final probe concentration was 0.05 μg/μl of hybridization mixture. Slides were exposed for one month. Chromosomes were identified by Q banding.

11.1. Results

A total of 58 metaphase cells with autoradiographic grains were examined. Of the 124 hybridization sites scored, 38 (31%) were located on the distal portion of the long arm of chromosome 2 (FIG. 13). The greatest number of grains (21 grains) was located at band q33, with significant numbers of grains on bands q34 (10 grains) and q35 (7 grains). No significant hybridization on other human chromosomes was detected.

12. EXAMPLE: Activation of the HER4 Receptor is Involved in Signal Transduction by Heregulin

12.1. Recombinant Heregulin Induction of Tyrosine Phosphorylation of HER4

12.1.1 Materials and Methods

CHO cells expressing recombinant HER4 or HER2 were generated as previously described in Section 8. Cells ($1 \times 10^5$ of CHO/HER2 and CHO/HER4, and $5 \times 10^5$ of MDA-MB453) were seeded in 24 well plates and cultured 24 h. Cells were starved in serum free media for 1–6 h prior to addition of conditioned media from transfected COS cells, or 25 μg/ml HER2-stimulatory Mab (N28 and N29) (Stancovski et al., 1991, Proc. Natl. Acad. Sci. U.S.A. 88:8691–8695). Following 10 min treatment at room temperature, cells were solubilized (Section 13, infra) and immunoprecipitated with 2 μg anti-phosphotyrosine Mab (PY20, ICN Biochemicals) or anti-HER2 Mab (c-neu Ab-2, Oncogene Sciences) and anti-mouse IgG-agarose (Sigma). Western blots were performed using PY20 as described supra, and bands were detected on a Molecular Dynamics phosphorimager.

Recombinant rat heregulin was produced as follows. A 1.6 kb fragment encoding the entire open reading frame of rat heregulin (and 324 bp of 5'-untranslated sequence) was obtained by PCR using normal rat kidney RNA as a template. This fragment was inserted into a CDM8-based expression vector (Invitrogen) to generate cNDF1.6. The expression plasmid was introduced into COS-1 cells using the DEAE-dextranchloroquine method (Seed et al., *Proc. Natl. Acad. Sci. U.S.A.* 1987, 84:3365–3369). After two days of growth in Dulbecco's Modified Eagle Medium (DMEM) /10% FBS, the medium was replaced with DMEM and the incubation continued for an additional 48 h. Clarified conditioned medium was either used directly or was dialyzed against 0.1M acetic acid for 2 days, dried, and resuspended as a 20-fold concentrate in DMEM.

12.1.2. HER Tyrosine Phosphorylation

As shown in FIG. 15, recombinant heregulin induces tyrosine phosphorylation of HER4. Tyrosine phosphorylated receptors were detected by Western blotting with an anti-phosphotyrosine Mab a, Monolayers of MDA-MB453 or CHO/HER4 cells were incubated with media from COS-1 cells transfected with a rat heregulin expression plasmid (HRG), or with a cDM8 vector control (−). The media was either applied directly (1x) or after concentrating 20-fold (20x, and vector control). Solubilized cells were immunoprecipitated with anti-phosphotyrosine Mab. b, Monolayers of CHO/HER2 cells were incubated as above with transfected Cos-1 cell supernatants or with two stimulatory Mabs to HER2 (Mab 28 and 29). Solubilized cells were immunoprecipitated with anti-HER2 Mab. Arrows indicate the HER2 and HER4 proteins.

12.1.3. Results

In order to determine if HER4 is involved in signaling by heregulin, the ability of recombinant rat heregulin to stimulate tyrosine phosphorylation in a panel of Chinese hamster ovary (CHO) cells that ectopically express human HER2 or HER4 was examined. The activity of recombinant heregulin was first confirmed by its ability to stimulate differentiation of human breast cancer cells (data not shown) and to induce tyrosine phosphorylation of a high molecular weight protein in MDA-MB453 cells (FIG. 15, Panel 1). Heregulin had no effect on CHO cells expressing only HER2 (FIG. 15, Panel 3), yet these cells were shown to have a functional receptor since their tyrosine kinase activity could be stimulated by either of two antibodies specific to the extracellular domain of HER2 (FIG. 15, Panel 3). However, heregulin was able to induce tyrosine phosphorylation of a 180 kDa protein in CHO cells expressing HER4 (FIG. 15, Panel 2).

Species differences in ligand-receptor interactions have been reported for EGF receptor (Lax et al., 1988, *Mol. Cell. Biol.* 8:1970–1978). It is unlikely that such differences are responsible for our failure to detect a direct interaction between rat heregulin and human HER2, since previous studies have shown that rat heregulin does not directly interact with rat HER2/neu (Peles et al., supra). In addition, rat, rabbit, and human heregulin share high sequence homology and have been shown to induce tyrosine phosphorylation in their target cells of human origin (Wen D. et al., supra; Holmes et al., supra; and Falls et al., supra).

12.2. Expression of Recombinant HER2 and HER4 in Human CEM Cells

12.2.1. Materials and Methods cNHER2 and cNHER4 expression plasmids were generated by insertion of the complete coding sequences of human HER2 and HER4 into cNEO, an expression vector that contains an SV2-NEO expression unit inserted at a unique BamHI site of CDM8. These constructs were linearized and transfected into CEM cells by electroporation with a Bio-Rad Gene Pulser apparatus essentially as previously described (Wen et al., supra). Stable clones were selected in RPMI/10% FBS supplemented with 500 μg/ml active Geneticin. HER2 immunoprecipitations were as described in FIG. 15, using 5×10$^6$ cells per reaction, and the HER2 Western blots were performed with a second anti-HER2 Mab (c-neu Ab-3, Oncogence Sciences). For metabolic labeling of HER4, 5×10$^6$ cells were incubated for 4–6 h in methionine and cysteine-free Minimal Essential Medium (MEM) supplemented with 2% FBS and 250 μCi/ml [$^{35}$S]Express protein labeling mix (New England Nuclear). Cells were washed twice in RPMI and solubilized as above. Lysates were then incubated for 6 h, 4° C. with 3 μl each of two rabbit antisera raised against synthetic peptides corresponding to two regions of the cytoplasmic domain of human HER4 ($^{864}$LARLLEGDEKEYNADGG$^{88}$ [SEQ ID No:31] and $^{1010}$EEDLEDMMDAEEY$^{1022}$ [SEQ ID No:32]). Immune complexes were precipitated with 5 μg goat anti-rabbit Ig (Cappel) and Protein G Sepharose (Pharmacia). Proteins were resolved on 7% SDS-polyacrylamide gels and exposed on the phosphorimager. For Mab-stimulation assays, 5×10$^6$ cells were resuspended in 100 μl RPMI and 25 μg/ml Mab was added for 15 min at room temperature. Control Mab 18.4 is a murine IgG$_1$ specific to human amphiregulin (Plowman et al., 1990, *Mol. Cell. Biol.* 10:1969–1981). Following Mab-treatment, cells were washed in PBS, solubilized (Section 13, infra), and immunoprecipitated with anti-HER2 Mab (Ab-2). Tyrosine phosphorylated HER2 was detected by PY20 Western blot as in FIG. 15.

12.2.2. Expression of HER2 and HER4 in Human CEM Cells

Expression of recombinant HER2 and HER4 in human CEM cells is shown in FIG. 16. Transfected CEM cells were selected that stably express either HER2, HER4, or both recombinant receptors. In FIG. 16, Panel 1, recombinant HER2 was detected by immunmoprecipitation of cell lysates with anti-HER2 Mab (Ab-2) and Western blotting with another anti-HER2 Mab (Ab-3). In FIG. 16, Panel 2, recombinant HER4 was detected by immunoprecipitation of $^{35}$S-labeled cell lysates with HER4-specific rabbit anti-peptide antisera. In FIG. 16, Panel 3, three CEM cell lines were selected that express one or both recombinant receptors and aliquots of each were incubated with media control (−), with two HER2-stimulatory Mabs (Mab 28 and 29), or with an isotype matched control Mab (18.4). Solubilized cells were immunoprecipitated with anti-HER2 Mab (Ab-2) and tyrosine phosphorylated HER2 was detected by Western blotting with an anti-phosphotyrosine Mab. The size in kilodaltons of prestained high molecular weight markers (Bio-Rad) is shown on the left and arrows indicate the HER2 and HER4 proteins.

12.2.3. Results

These findings of Example 12 support the earlier observation that HER2 alone is not sufficient to transduce the heregulin signal. To further address this possibility, a panel of human CEM cells that express the recombinant receptors either alone or in combination was established. The desired model system was of human origin, since many of the reagents against erbB family members are specific to the human homologues. CEM cells are a human T lymphoblastoid cell line and were found to lack expression of EGF receptor, HER2, HER3, or HER4, by a variety of immunologic, biologic, and genetic analyses (data not shown). FIG. 16 demonstrates the selection of three CEM cell lines that express only HER2 (CEM 1–3), only HER4 (CEM 3–13), or both HER2 and HER4 (CEM 2–9). The presence of a functionally and structurally intact HER2 in the appropriate cells was confirmed by the induction of HER2 tyrosine phosphorylation by each of the two antibodies specific to the extracellular domain of HER2, but not by an isotype matched control antibody (FIG. 16, Panel 3).

12.3. Heregulin Induction of Tyrosine Phosphorylation in CEM Cells Expressing HER4

12.3.1. Materials and Methods

Recombinant rat heregulin was prepared as in FIG. 15, and diluted to 7× in RPMI. The HER4-specific Mab was prepared by immunization of mice with recombinant HER4 (manuscript in preparation). CEM cells ($5\times10^6$) were treated with the concentrated supernatants for 10 is min, room temperature and precipitated with PY20 or anti-HER2 Mab (Ab-2) as described in FIG. 15. Immunoprecipitation with anti-HER4 Mab was performed by incubation of cells lysates with a 1:5 dilution of hybridoma supernatent for several hours followed by 2 µg rabbit anti-mouse Ig (Cappel) and Protein A Sepharose CL-4B (Pharmacia). PY20 Westerns as described in FIG. 15.

12.3.2. Heregulin Induction of Tyrosine Phosphorylation in CEM Cells Expressing HER4

As shown in FIG. 17, heregulin induces tyrosine phosphorylation in CEM cells expressing HER4. Three CEM cell lines that express either HER2 or HER4 alone (CEM 1–3 and CEM 3–13) or together (CEM 2–9) were incubated with 7× concentrated supernatants from mock-(−) or heregulin-transfected (+) COS-1 cells. Solubilized cells were immunoprecipitated (IP) with anti-phosphotyrosine Mab (PY20) (FIG. 17, Panel 1); HER2-specific anti-HER2 Mab (Ab-2) (FIG. 17, Panel 2); or HER4-specific Mab (6-4) (FIG. 17, Panel 3). In each case, tyrosine phosphorylated receptors were detected by Western blotting with anti-phosphotyrosine Mab. The size in kilodaltons of prestained molecular weight markers (BioRad) is shown on the left and arrows indicate the HER2 and HER4 proteins.

12.3.3 Results

The panel of CEM cells were then analyzed by phosphotyrosine Western blots of cells lysates following treatment with heregulin and immunoprecipitation with three different monoclonal antibodies (Mabs). Precipitation with an anti-phosphotyrosine antibody (PY20) again demonstrates that heregulin is able to stimulate tyrosine phosphorylation in cells expressing HER4, but not in cells expressing only HER2 (FIG. 17, Panel 1). However, precipitation with an antibody specific to the extracellular domain of HER2 demonstrates that HER2 is tyrosine phosphorylated in response to heregulin in cells that co-express HER4 (FIG. 17, Panel 2). Furthermore, precipitation with a HER4-specific Mab confirms that heregulin induces tyrosine phosphorylation of HER4 irrespective of HER2 expression (FIG. 17, Panel 3). Due to co-expression of HER2 and HER4 in many breast carcinomas, these findings suggest that earlier studies of heregulin-HER2 interactions may require reevaluation.

12.4. Covalent Cross-linking of Iodinated Heregulin to HER4

12.4.1. Materials and Methods

To facilitate purification, recombinant heregulin was produced as an epitope-tagged fusion with amphiregulin. The 63 amino acid EGF-structural motif of rat heregulin (Wen et al., supra) from serine 177 to tyrosine 239 was fused to the N-terminal 141 amino acids of the human amphiregulin precursor (Plowman et al., supra). This truncated portion of heregulin has previously been shown to be active when expressed in E. coli (Holmes et al., supra), and the N-terminal residues of amphiregulin provide an epitope for immunologic detection and purification of the recombinant protein. This CDNA fragment was spliced into a CDM8 based expression vector for transient expression in COS-1 cells. Recombinant heregulin was purified by anion exchange and reverse phase chromatography as shown to be active based on the specific stimulation of HER4 tyrosine phosphorylation. Purified heregulin was iodinated with 250 µCi of $^{125}$I-labeled Bolton-Hunter reagent (NEN). CHO/HER4 or CHO/HER2 cells were incubated with $^{125}$I-heregulin ($10^5$-cpm) for 2 h at 4° C. Monolayers were washed in PBS and 3 mM Bis(sulfosuccinimidyl) suberate ($BS^3$, Pierce) was added for 30 min on ice. The cells were washed in tris-buffered saline, dissolved in SDS sample buffer, run on a 7% polyacrylamide gel, and visualized on the phosphorimager.

12.4.2. Results

As shown in FIG. 18, previous binding and covalent cross-linking studies have demonstrated that p45 binds specifically to HER4 and displays a single high-affinity site with a $K_d$ of 5 nM on CHO/HER4 cells (Section 13, infra). Preliminary cross-linking studies have been performed on these cells with recombinant heregulin revealing a high molecular weight species that corresponds to the heregulin-HER4 receptor complex.

12.5 Results

As the data demonstrate heregulin induces tyrosine phosphorylation of HER4 in the absence of HER2. In contrast, heregulin does not directly stimulate HER2. However, in the presence of HER4, heregulin induces phosphorylation of HER2, presumably either by transphosphorylation or through receptor heterodimerization. Together, these experiments suggest that HER4 is the receptor for heregulin.

Most breast cancer cells that overexpress HER2 have been shown to be responsive to heregulin, whereas HER2-positive ovarian and fibroblast lines do not respond to the ligand. This observation could be explained by the fact that HER4 is co-expressed with HER2 in most or all of the breast cancer cell lines studied, but not in the ovarian carcinomas. Furthermore, overexpression of HER2 in heregulin-responsive breast cancer cells leads to increased binding, whereas expression of HER2 in heregulin-unresponsive ovarian or fibroblast cells has no effect (Peles et al., supra).

Northern and in situ hybridization analyses localizes HER4 to the white matter and glial cells of the central and peripheral nervous system, as well as to cardiac, skeletal, and smooth muscle. This distribution is consistent with HER4 being involved in signaling by the neurotropic factors, GGF, and ARIA. Recognition of HER4 as a primary component of the heregulin signal transduction pathway will assist in deciphering the molecular mechanisms that results in its diverse biologic effects.

13. EXAMPLE: Purification of the HER4 Ligand, p45

13.1 Materials and Methods

13.1.1. Cell Culture and Reagents

MDA-MB 453 cells were obtained from the American Type Culture Collection (Rockville, Md.) and cultured in Dulbecco's modified Eagle's medium (DMEM) supplemented with 10% fetal bovine serum and amino acids (Life Technologies, Inc.). HepG2 cells were obtained from Dr. S. Radka and cultured in 10% fetal bovine serum containing DMEM. For large scale production of serum-free conditioned medium, HepG2 cells were propagated in Nunc cell factories. Chinese hamster ovary cells (CHO-KI) expressing high levels of either recombinant human $p185^{erbB2}$ (CHO/HER2) or recombinant human $p180^{erbB4}$ (CHO/HER4) were generated and cultured as described in Section 8. N29 monoclonal antibody to the extracellular portion of the human HER2 receptor was a gift from Dr. Y. Yarden. Ab-3 c-neu monoclonal antibody that reacts with the human $p185^{erbB2}$ was from Oncogene Science Inc.

13.1.2. Human Breast Cancer Cell Differentiation Assay

MDA-MB-453 human breast cancer cells overexpress $p185^{erbB2}$ but do not express the EGFR at their surface (Kraus, 1987, *EMBO J.* 6:605–610). A cell differentiation assay was used to monitor the chromatography fractions for their ability to induce phenotypic differentiation in MDA-MB-453 cells.

13.1.3. Purification of p45

Medium conditioned by HepG2 cells (HepG2-CM, 60 liters) was concentrated 26-fold using an Amicon ultrafiltration unit (10,000 molecular weight cutoff membranes) and then subjected to 50% ammonium sulfate (($NH_4)_2SO_4$) precipitation. After centrifugation at 25,000×g for 1 h, the supernatant was loaded, as five separate runs, on a phenyl-Sepharose column (2.5×24.5 cm, Pharmacia LKB Biotechnology Inc.) equilibrated with 1.9M ($NH_4)_2SO_4$ in 0.1M $Na_2HPO_4$, pH 5 7.4. Bound proteins were eluted with a 240 ml linear decreasing gradient from 1.9M to 0M ($NH_4)_2SO_4$ in 0.1M phosphate buffer, pH 7.4. The flow rate was 70 ml/h, and 5.8-ml fractions were collected. Active fractions were pooled, concentrated, dialyzed against PBS, and then applied (three separate runs) to a DEAE-Sepharose column (2.5×25 cm, Pharmacia) equilibrated with PBS, pH 7.3. The flow rate was 1 ml/min. The column flow-through was then loaded (two separate runs) on a CM-Sepharose Fast Flow column (2.5×13.5 cm, Pharmacia) pre-equilibrated with PBS, pH 7.3. Proteins were eluted at 1 ml/min. with a 330-ml gradient from PBS to 1M NaCl in PBS. Fractions of 5 ml were collected. The active material was loaded on a TSKgel heparin-5PW HPLC column (7.5×75 mm, TosoHaas) equilibrated with PBS. The flow rate was 0.5 ml/min. A 50-ml linear NaCl gradient (PBS to 2M in PBS) followed by an isocratic elution with 2M NaCl was used to elute the bound proteins. Fractions of 1 ml were collected. Active fractions corresponding to the 1.3M NaCl peak of protein were pooled and concentrated. A Protein Pak SW-200 size exclusion chromatography column (8×300 mm, Waters) equilibrated with 100 mM $Na_2HPO_4$, pH7.4, 0.01% Tween 20 was used as a final step of purification. The flow rate was 0.5 ml/min., and 250-$\mu$l fractions were collected. Column fractions were then analyzed by SDS-PAGE (12.5% gel) under reducing conditions and proteins detected by silver staining.

13.1.4. Detection of Tyrosine-Phosphorylated Proteins by Western Blotting

Aliquots of PBS-dialyzed column fractions were diluted to 200 $\mu$l in PBS, then added to individual wells of 48-well plated containing either $5\times10^5$ MDA-MB-453 cells, $2\times10^4$ CHO/HER2 cells or $5\times10^4$ CHO/HER2 cells. Following a 10-min. incubation at 37° C., cells were washed and then lysed in 100 $\mu$l of boiling electrophoresis sample buffer. Lysates were heated at 100° C. for 5 min., cleared by centrifugation, and then subjected to SDS-PAGE. After electrophoresis, proteins were transferred to nitrocellulose. The membrane was blocked for 2 h at room temperature with 6% bovine serum albumin in 10 mM Tris-HCl, pH 8.0, 150 mM NaCl, 0.05% Tween 20. PY20 monoclonal anti-phosphotyrosine antibody (ICN, 2 h at 22° C.) and horseradish peroxidase-conjugated goat anti-mouse IgG F(ab')$_2$ (Cappel, 1 h at 22° C.) were used as primary and secondary probing reagents, respectively. Proteins phosphorylated on tyrosine residues were detected with a chemiluminescence reagent (Amersham Corp.).

13.1.5. CHO/HER2 Stimulation Assay

CHO/HER2 cells were seeded in 24-well plates at $1\times10^5$ cells/well and cultured 24 h. Monoclonal antibody N29 specific to the extracellular domain of $p185^{erbB2}$ (Stancovski et al., 1991, *PNAS* 88:8691–8695) was added at 25 $\mu$g/ml. Following a 20-min. incubation at room temperature, media were removed and cells were solubilized for 10 min. on ice in PBS-TDS (10 mM sodium phosphate, pH 7.25, 150 mM NaCl, 1% Triton, 0.5% sodium deoxycholate, 0.1% SDS, 0.2% $NaN_3$, 1 mM NaF, 1 mM phenylmethylsulfonyl fluoride, 20 $\mu$g/ml aprotinin) with occasional vortexing. Clarified extracts were incubated for 2 h at 4° C. with an antip-$185^{erbB2}$ antibody (Ab-3 c-neu, Oncogene Science Inc.). Rabbit anti-mouse IgG (Cappel) and protein A-Sepharose were then added, and samples were incubated an additional 30 min. Immune complexes were washed 3 times with PBS-TDS, resolved on a 7% polyacrylamide gel, and electrophoretically transferred to nitrocellulose. Phosphorylation of the receptor was assessed by Western blot using a 1:1000 dilution of PY20 phosphotyrosine primary antibody (ICN Biochemicals) and a 1:500 dilution of $^{125}$I-sheep anti-mouse F(ab')$_2$ (Amersham Corp.).

13.1.6. Covalent Cross-linking of Iodinated p45

HPLC-purified p45 (1.5 $\mu$g) was iodinated with 250 $\mu$Ci of $^{125}$I-labeled Bolton-Hunter reagent obtained from Du Pont-New England Nuclear. $^{125}$I-p45 was purified by filtration through a Pharmacia PD-10 column. The specific activity was $10^4$ cpm/ng. 125I-p45 retained its biological activity as confirmed in a differentiation assay as well as a kinase stimulation assay (data not shown). Binding of radiolabeled p45 was performed on $2\times10^5$ CHO/HER4 cells and $4\times10^5$ CHO-KI or CHO/HER2 cells in 12-well plates. Cell monolayers were washed twice with 1 ml of ice-cold binding buffer (DMEM supplemented with 44 mM sodium bicarbonate, 50 mM BES [N-,N-Bis(2-hydroxyethyl)-2-aminoethan-sulfonic acid], pH 7.0, 0.1% bovine serum albumin) and then incubated on ice for 2 h with 50 ng/ml $^{125}$I-p45 in the absence or the presence of 250 ng/ml unlabeled p45. The monolayers were washed twice with PBS and then incubated in the presence of 1 mM bis (sulfosuccinimidyl)suberate (BS$^3$, Pierce) in PBS for 45 min. on ice. Supernatants were discarded, and the reaction was quenched by adding 0.2M glycine in PBS. Cells were washed and then lysed by adding 150 $\mu$l of boiling electrophoresis sample buffer containing 0.1M dithiothreitol. Samples were boiled for 5 min. and 50 $\mu$l of each sample was loaded on 7.5% polyacrylamide gels. Dried gels were analyzed using a Molecular Dynamics PhosphorImager and then exposed to Kodak X-Omat AR films.

13.1.7. Binding Analysis of Iodinated p45

CHO/HER4 cells, CHO-KI cells ($10^5$ cells/well), and CHO/HER2 cells ($2\times10^5$ cells/well) were seeded in 24-well plates. After 48 h, cells were washed with binding buffer and then incubated with increasing concentrations of $^{125}$I-p45. Nonspecific binding was determined in the presence of excess unlabeled p45. After a 2-h incubation at 4° C., the cells were washed three times with binding buffer and then lysed in 500 μl of 0.5M NaOH, 0.1% SDS. Cell-associated radioactivity was determined by using a γ-counter. Scatchard analysis was performed using the computerized LIGAND program (Munson and Rodbard, 1980, *Anal. Biochem* 107:220–239).

13.1.8. N-terminal Amino Acid Sequence

The N-terminal sequence analysis of p45 (25 pmol) was performed as previously described (Shoyab et al., 1990, *Proc. Natl. Acad. Sci.* 87:7912–7916).

13.2. Purification of the HER4 Ligand, p45

Sixty liters of medium conditioned by HEPG2 cells was used as a starting material, and throughout the purification procedure, bioactivity was assessed by a cell differentiation assay described in Section 10.1.1., supra. After concentration (1540 mg of protein) and ammonium sulfate precipitation, the active material (1010 mg of protein) was loaded on a phenyl-Sepharose column (FIG. 19, Panel 1). Column fractions 40–85 (348 mg of protein eluting between 1M ammonium sulfate and 10M ammonium sulfate) were found to induce morphological changes in MDA-MB-453 cells. The biologically active column flow-through (174 mg of protein) was subjected to a cation-exchange chromotography (FIG. 19, Panel 2) with activity eluting between 0.35 and 0.48M NaCl. The active fractions were pooled (1.5 mg of protein) and applied to an analytical heparin column (FIG. 19, Panel 3). The differentiation activity eluted from the heparin column between 0.97 and 1.45M NaCl (fractions 27–38). Size exclusion chromatography of the heparin column fractions 35–38 achieved a homogeneous preparation of the human breast cancer cell differentiation factor. A major protein peak eluted with a molecular weight greater than 70,000 (FIG. 19, Panel 4). Fractions 30 and 32 assayed at 30 ng/ml confirmed the bioactivity of this protein with phenotypic changes being apparent after 24 hours. SDS-PAGE analysis of these column fractions followed by silver staining of the gel showed that the biologically active peak contained a single protein migrating around 45 kDa (FIG. 20). The faint 67 kDa band corresponds to a staining artifact, as evidenced by the left lane of the gel, which contained no sample. The amount of pure protein recovered in fractions 30–33 was estimated to be 6 micrograms. The difference in the molecular weight estimated by size exclusion chromatography and SDS-PAGE indicates that this protein may form dimers or oligomers under non-denaturing conditions.

13.3. N-terminal Amino Acid Sequence of p45

Twenty-five pmol of p45 was subjected to direct amino acid sequencing, identifying the sequence Ser-Gly-X-Lys-Pro-X-X-Ala-Ala [SEQ ID No:33]. An X denotes a sequenator cycle in which a precise amino acid could not be assigned. Comparison of this partial sequence with two protein data bases (GenBank release 73, EMBL release 32) revealed a perfect homology between the identified residues and a region of the amino terminus of heregulin (Holmes et al., supra) The N-terminal serine residue of p45 corresponds to residue 20 of the deduced amino acid sequence of heregulins.

13.4. p45 Stimulates Protein Phosphorylation

FIG. 21, Panel 1 shows the stimulatory effect of sequential fractions from the size exclusion chromatography column on tyrosine phosphorylation in MDA-MB-453 cells. Densitometric analysis of the autoradiogram revealed that fractions 30–34 were essentially equipotent. Homogeneously purified p45 specifically stimulated tyrosine phosphorylation of p180$^{erbB4}$ (FIG. 21, Panel 2). p45 was not able to stimulate phosphorylation in CHO/HER2 cells, and the cell were found to express functional p185$^{erbB2}$ receptor as evidenced by immunoreactivity with 5 monoclonal antibodies specific to different regions of p185$^{erbB2}$. p45 has an N-terminal amino acid sequence similar to the recently isolated p185$^{erbB2}$ ligand.

13.5. Binding and Covalent Cross-linking of p45 to p180$^{erbB4}$

Binding and cross-linking studies were performed in order to confirm that p45 was able to bind to p180$^{erbB4}$. Binding studies revealed that while no specific binding of $^{125}$I-p45 to CHO-KI and CHO/HER2 cells could be measured, CHO/HER4 cells displayed a single high affinity site (Kd about 5 nM) with 7×10$^4$ receptors/cell (FIG. 22, Panel 1). The results of iodinated p45 cross-linking to CHO-KI, CHO/HER2, or CHO/HER4 cells are presented in FIG. 22, Panel 2. Whereas no cross-linked species was observed in either CHO-KI or CHO/HER2 cells, four distinct bands were observed in CHO/HER4 cells, migrating as 45-, 100-, and 210-kDa species, and a very high molecular weight species. In the presence of unlabeled p45, $^{125}$I-p45 binding was greatly reduced. The 45 kDa band represents uncross-linked yet p180$^{erbB4}$ associated $^{25}$I-p45. The 210 kDa band corresponds to the p45-p180$^{erbB4}$ complex (assuming an equimolar stoichiometry of ligand and receptor), whereas the high molecular weight band is presumed to be a dimerized form of the receptor-ligand complex. The 100 kDa band could represent a truncated portion of the extracellular domain of the p180$^{erbB4}$ receptor complexed to $^{125}$I-p45 or a covalently associated p45 dimer. The c-kit ligand provides precedence for cross-linked dimers (Williams et al., 1990, *Cell* 63:167–174).

13.6. Results

The HER4 ligand, p45, purified from medium conditioned by HepG2, induces differentiation of breast cancer cells and activates tyrosine phosphorylation of a 185 kDa protein in MDA-MB-453 cells. p45 is not capable of directly binding to p185$^{erbB2}$ but shows specificity to HER4/p180$^{erbB4}$.

14. EXAMPLE: Targeted Cytotoxicity Mediated By A Chimeric Heregulin-Toxin Protein

14.1. Materials and Methods

14.1.1. Reagents and Cell Lines

Heregulin β2-Ig and the mouse monoclonal antibody directed against the Pseudomonas exotoxin (PE) was supplied by Dr. J. -M. Colusco and by Dr. Tony Siadek, respectively (Bristol-Myers-Squibb, Seattle, Wash.). The cell lines BT474, MDA-MB-453, T47D, SKBR-3, and MCF-7 (all breast carcinoma), LNCaP (prostate carcinoma), CEM (T-cell leukemia) and SKOV3 (ovarian carcinoma) were obtained from ATCC (Rockville, Md.). The H3396 breast carcinoma cell line and the L2987 lung carcinoma cell line were established at Bristol-Myers-Squibb (Seattle, Wash.). The AU565 breast carcinoma cell line was purchased from the Cell Culture laboratory, Naval Biosciences Laboratory (Naval Supply Center, Oakland, Calif.). All cell lines were of human origin. BT474 and T47D cells were cultured in IMDM supplemented with 10% fetal bovine serum (FBS) and 10 μg/ml insulin. MCF-7, H3396, LNCaP and L2987 were cultured in IMDM supplemented with 10% FBS. SKBR3 and SKOV3 cells were grown in McCoys media supplemented with 10% FBS and 0.5% non-essential amino acids. AU565 cells were cultured in RPMI 1640 media supplemented with 15% FBS and CEM transfectants (see section 15.1.5., infra) were cultured in RPMI 1640 supplemented with 10% FBS and 500 µg/ml G418.

14.1.2. Construction of HAR-TX β2 Expression Plasmid

Rat heregulin cDNA (Wen et al., 1994, *Mol. Cell. Biol.* 14:1909–1919) was isolated by RT-PCR using mRNA from rat kidney cells as template. The cDNA was prepared in chimeric form with the AR leader sequence by a two-step PCR insertional cloning protocol using cARP (Plowman et al., 1990, *Mol. Cell. Biol.* 10:1969–1981) as template to amplify the 5' end of the chimeric ligand using the oligonucleotide primers

CARP5:
(5'-CGGAAGCTTCTAGAGATCCCTCGAC-3') [SEQ ID NO:34]

and

ANSHLIK2:
(3'CCGCACACTTTATGTGTTGGCTTGTGTTTCTTCTATTTTTTCCATTTTTG-5'). [SEQ ID NO:35]

The EGF-like domain PCR was amplified from cNDF1.6 (Plowman et al., 1993, *Nature* 366:473–475) using the oligonucleotide primers ANSHLIK1:
(5'-CAAAAATGGAAAAAATAGAAGAAACAGAAGCCATCTCATAAAGTGTGCGG-3') [SEQ ID NO:36]

and

XNDF1053:
(3'-GTCTCTAGATTAGTAGAGTTCCTCCGCTTTTTCTTG-5'). [SEQ ID NO:37]

The products were combined and reamplified using the oligonucleotide primers CARP5 and XNDF1053. The HAR (heregulin-amphiregulin) construct (cNANSHLIK) was PCR amplified in order to insert an Nde I restriction site on the 5' end and a Hind III restriction site on the 3' end with the oligonucleotide primers

NARP1:
(5'-GTCAGAGTTCATATGGTAGTTAAGCCCCCCCAAAAC-3') [SEQ ID NO:38]

and

NARP4:
(3'-GGCAGTTCTATGAACACGTTCACGGGCTTGCTTAAATGACCGCTGGCA
ACGGTCTTGATACAATACCGTAGAAAAATGTTTAGCCTCCTTGAGATGTTCGAATCTCCTAGAAAC-5'). [SEQ ID NO:39]

The resulting 287 bp DNA fragment was digested with Nde I and Hind III, followed by ligation into the compatibly digested expression plasmid pBW 7.0 which contained, in frame at the 5' fusion site, the nucleotide sequence encoding for of PE40 (Friedman et al., 1993, *Cancer Res.* 53:334–339). The resulting expression plasmid pSE 8.4 then contained the gene fusion encoding the chimeric heregulin-toxin protein, under the control of a IPTG-inducible T7 promoter.

14.1.3. Expression and Isolation of Recombinant HAR-TX β2 Protein

The plasmid pSE 8.4 encoding the chimeric protein HAR-TX β2 was transformed into the *E. coli* strain BL21 (λDE3). Cells were grown by fermentation in T broth containing 100 µg/ml ampicillin at 37° C. to a optical density of $A_{650}$=4.8, followed by induction of protein expression with 1 mM isopropyl-1-thio-β-D-galactopyranoside (IPTG). After 90 minutes the cells were harvested by centrifugation. The cell pellet was frozen at −70° C., then thawed and resuspended at 4° C. in solubilization buffer (50 mM Tris-HCl (pH 8.0), 10 mM EDTA, 1 ug/ml leupeptin, 2 ug/ml aprotinin, 1 ug/ml pepstatin-A, 0.5 mM PMSF) containing 1% tergitol by homogenization and sonication. The insoluble material of the suspension, containing inclusion bodies with the HAR-TX β2 protein, was pelleted by centrifugation and washed three times with solubilization buffer containing 0.5% tergitol (first wash), 1M NaCl (second wash), and buffer alone (third wash).

The resulting pellet containing pre-purified inclusion bodies was dissolved in 6.5M guanidine-HCl, 0.1M Tris-HCl (pH 8.0), 5 mM EDTA; sonicated; and refolded by rapid dilution (100-fold) into 0.1M Tris-HCl (pH 8.0), 1.3M urea, 5 mM EDTA, 1 mM glutathione, and 0.1 mM oxidized glutathione at 4° C. The addition of the denaturating agent urea at low concentration was utilized to allow slow refolding and avoid the formation of aggregates. The refolded HAR-TX β2 protein was diluted 2-fold with 50 mM sodium phosphate (pH 7.0) and applied to a cation-exchange resin (POROS 50 HS, PerSeptive Biosystems, Cambridge, Mass.), pre-equilibrated in the same buffer. The HAR-TX β2 protein was eluted with a 450 nM NaCl step gradient in 50 mM sodium phosphate (pH 7.0) and fractions were analyzed using SDS-PAGE and Coomassie blue staining. Final purification of pooled fractions was performed by chromatography using Source 15S cation-exchange media (Pharmacia, Uppsala, Sweden) equilibrated with 50 mM sodium phosphate (pH 6.0). Chimeric HAR-TX β2 protein was eluted with a gradient of 0–1M NaCl in the same buffer and analyzed by SDS-PAGE.

14.1.4. ELISA Test for Determination of Binding Activity

Membranes from $5\times10^7$ MDA-MB-453 cells were prepared and coated to 96 well plates as previously described for H3396 human breast carcinoma cells (Siegall et al., 1994, *J. Immunol.* 152:2377–2384). Subsequently, the membranes were incubated with titrations of either HAR-TX β2 or PE40 ranging from 0.3–300 ug/ml and the mouse monoclonal anti-PE antibody EXA2-1H8 as the secondary reagent (Siegall et al., supra). The isolate of the toxin portion PE40 alone was used to determine unspecific binding activity to the membrane preparations, in comparison with the specific binding activity of HAR-TX β2.

14.1.5. Phosphotyrosine Analysis of transfected CEM cell lines

CEM cells expressing various receptors of the EGF-R family ($1-5\times10^6$ cells) were stimulated with 500 ng/ml HAR-TX β2 for 5 minutes at room temperature. The cells were pelleted and resuspended in 0.1 ml lysis buffer (50 mM Tris-HCl, pH 7.4, 150 mM NaCl, 5 mM $MgCl_2$, 1% NP40, 0.5% deoxycholate, 0.1% sodium dodecylsulfate, 1 mM sodium orthovanadate) at 4° C. Insoluble material was pelleted by centrifugation at 10,000×g for 30 seconds, and samples were analyzed by SDS-PAGE and subsequent Western blot analysis using the anti-phosphotyrosine antibodies 4G10 (ICN, Irvine, Calif.) and PY20 (Upstate Biotechnology, Lake Placid, N.Y.).

14.1.6. Cytotoxicity Assays

For cytotoxicity assays, tumor cells ($10^5$ cells/ml) in growth medium were added to 96-well flat bottom tissue culture plates (0.1 ml/well) and incubated at 37° C. for 16 h. Cells were incubated with HAR-TX β2 for 48 h at 37° C., washed twice with phosphate buffered saline (PBS), followed by addition of 200 $\mu$l/well of 1.5 $\mu$M calcein-AM (Molecular Probes Inc., Eugene, Oreg.). The plates were incubated for 40 minutes at room temperature (RT), and the fluorescence measured using a Fluorescence Concentration Analyzer (Baxter Heathcare Corp., Mundelein, Ill.) at excitation/emission wavelengths of 485/530 nm. Calcein-AM is membrane permeable and virtually non-fluorescent. When it is hydrolyzed by intracellular esterases, an intensely fluorescent product, calcein is formed. The % cytotoxicity was calculated as previously described (Siegall et al., supra). To determine the specificity of the cytotoxic effect of HAR-TX β2 competitive assays were performed on LNCaP and on MDA-MB-453 cells. Treated essentially as described above, plates were incubated with increasing concentrations of HAR-TX β2 in presence heregulin 62 2-Ig (0.002–5.0 $\mu$g/ml) or with HAR-TX β2 (50 ng/ml). Isotype matched L6-Ig (Hellström et al., 1986, *Cancer Res.* 46:3917–3923) was used as negative control for the competition assay.

14.1.7. Generation of Monoclonal Antibodies to HER4

HER4, expressed in baculovirus, was used as the immunogen for subcutaneous injection into 4–6 week old female BALB/c mice. Immunization was performed 4 times (approximately 1 month apart) with 20 $\mu$g of HER4 protein given each time. Spleen cells from immunized mice were removed four days after the final immunization and fused with the mouse myeloma line P2x63-Ag8.653 as previously described (Siegall et al., supra). Positive hybridoma supernatants were selected by ELISA screening on plates coated with HER4 transfected CHO cells (Plowman et al., 1993, *Nature* 366:473–475) and selected against parental CHO cells and human fibroblasts. Secondary screening was performed by ELISA on plates coated with baculovirus/HER4 membranes. Positive hybridomas were rescreened by two additional rounds of ELISA using CHO/HER4 and HER4 negative cells, and identified false positive were removed. Positive hybridomas were cloned in soft agar and tested for reactivity with the HER4 positives MDA-MB-453 human breast carcinoma cell line and CEM cells co-transfected with HER4 and HER2. Anti-HER4 hybridoma line 6-4-11 (IgGl) was cloned in soft agar and screened for reactivity to native and denatured HER4. A second antibody (7-142, IgG2a) was also selected and found to bind to the cytoplasmic domain of HER4.

The characteristics for both antibodies are summarized in Table VI (see section 15.2.8., infra)

14.1.8. Quantitation of HER2, HER3, and HER4 Protein in tumor cell lines

Cell-surface expression of HER2, HER3, and HER4 protein was determined by quantification of specific antibody binding, detected by the CAS Red Chromagen system (Becton Dickson Cellular Imaging System, Elmhurst, Ill.). HER2 staining was performed by using mouse anti-HER2 mAb 24.7 (Stancovski et al., 1991, *Proc. Natl. Acad. Sci. USA* 88:8691–8695) as primary, and biotinylated goat anti-mouse IgG (Jackson Labs, West Grove, Pa.) as secondary antibody as previously described (Bacus et al., 1993, *Cancer Res.* 53:5251–5261). For detection of HER3 and HER4 the primary antibodies used were, respectively, mouse anti-HER3 mAb RTJ2 (Santa Cruz Biotech, Santa Cruz, Calif.) at 2.5 $\mu$g/ml concentration or mouse anti-HER4 mAb 6-4-11 at 15 $\mu$g/ml concentration followed by incubation with biotinylated rabbit anti-mouse IgG (Zymed Labs, South San Francisco, Calif.).

The staining procedure was performed at RT as follows: cells were fixed in 10% neutral buffered formalin for 60 minutes, washed with $H_2O$ and rinsed with Tris buffered saline (TBS; 0.05M Tris, 0.15M NaCl, pH 7.6). Unspecific binding sites were blocked by incubation with 10% goat serum (for HER2) or rabbit serum (for HER3 and HER4) in 0.1% bovine serum albumin/TBS for 15 minutes. Subsequently, cells were incubated with primary and secondary antibodies for 30 and 20 minutes, respectively, followed by incubation with alkaline phosphatase conjugated streptavidin (Jackson Labs) for 15 minutes, with TBS washing between the steps. Detection of antibody binding was achieved using CAS Red Chromagen (Becton Dickinson Cellular Imaging System, supra) for 4 minutes (HER2), 8–10 minutes (HER3), and 10–12 minutes (HER4). Cells were counterstained as described in the CAS DNA stain protocol (Becton Dickinson Cellular Imaging System).

14.1.9. Image Analysis

Image analysis was performed as previously described (Bacus et al., 1993, supra; Bacus et al., 1992, *Cancer Res.* 52:2580–2589; Peles et al., 1992, *Cell* 69:205–216). In the quantitation of HER2, both solid state imaging channels of the CAS 200 Image Analyzer (Becton Dickinson Cellular Imaging System), a microscope-based, two-color system were used. The two imaging channels were specifically matched to the two components of the stains used. One channel was used for quantitating the total DNA of the cells in the field following Feulgen staining as described (Bacus et al., 1990, *Mol. Carcinog.* 3:350–362), and the other for quantitating the level of HER2, HER3, and HER4 proteins following immunostaining. When the total DNA amount per cell was known, the average total HER2, HER3, and HER4 per cell were computed. Sparsely growing AU565 cells were used for calibrating the HER2 protein. Their level of staining was defined as 100% of HER2 protein content (1.0 relative amounts=10,000 sum of optical density); all other measurements of HER2, HER3, and HER4 protein were related to this value.

14.1.10. Determination of the $LD_{50}$ of HAR-TX β2

For toxicity studies, HAR-TX β2 at different concentrations was administered intravenous in 0.2 ml PBS. Per group each two mice and two rats were injected.

14.2. RESULTS

14.2.1. Construction, Expression, and Purification of HAR-TX β2

The HAR-TX β2 expression plasmid, encoding the hydrophilic leader sequence from amphiregulin (AR), heregulin β2, and PE40, under control of the IPTG inducible T7 promoter, was constructed as described in Section 15.1.2., supra, and is diagrammatically shown in FIG. 23, Panel 1. The AR leader sequence was added to the N-terminus of heregulin to facilitate the purification procedure (FIG. 23, Panel 2). FIGS. 24A and 24B show the nucleotide sequence and the deduced amino acid sequence of the cDNA encoding HAR-TX β2

Chimeric HAR-TX β2 protein was expressed in E. coli of inclusion bodies. Recombinant protein was denatured and refolded as described in Section 15.1.2., supra, and applied to cation-exchange chromatography on a POROS HS column. Semi-purified HAR-TX β2 protein was detected by PAGE and Coomassie blue staining as major band migrating at 51 kDa (FIG. 25, lane 2). The column flow-through from POROS HS contained only small amounts of HAR-TX β2 (FIG. 25, lane 3). POROS HS chromatography resulted in >50% purity of HAR-TX β2 (FIG. 25, lane 4). Further purification, to >95% purity, was done by chromatography using Source 15S cation-exchange resin (FIG. 25, lane 5). The monomeric nature of purified HAR-TX β2 was determined by non-reducing SDS-PAGE (FIG. 25, lane 6) which exhibited the same migration pattern as under reducing conditions (FIG. 25, lane 5).

14.2.2. Binding of HAR-TX β2 to MDA-MB-453 Cell Membranes

To determine the specific binding activity of HAR-TX β2, an ELISA assay was performed using membranes of the HER4 positive human breast carcinoma cell line MDA-MB-453 as the target for binding. HAR-TX β2 was found to bind to the immobilized cell membranes in a dose-dependent fashion up to 300 μg/ml (FIG. 26). PE40, the toxin component of HAR-TX β2 used as negative control, was unable to bind to MDA-MB-453 membranes.

14.2.3. Tyrosine Phosphorylation of HER Forms on Transfected CEM Cells

To test the biological activity of HAR-TX β2 a HER4 receptor phosphorylation assay was performed as previously described for heregulin (Carraway et al., 1994, *J. Biol. Chem.* 269:14303–14306). CEM cells expressing different HER family members were exposed to HAR-TX β2 and stimulation of tyrosine phosphorylation was analyzed by phosphotyrosine immunoblot analysis (Section 4, supra; Section 15.1.5., supra). As shown in FIG. 27, HAR-TX β2 induced tyrosine phosphorylation in CEM cells expressing HER4 either alone or together with HER2, but not in cells expressing only HER2 or HER1. This result demonstrates that HER4 is sufficient and necessary for induction of tyrosine phosphorylation in response to HAR-TX β2, which is not true for HER1 and for HER2. The fact that HAR-TX β2 does not induce tyrosine phosphorylation in CEM cells transfected with HER1 confirms that the hydrophilic leader sequence of amphiregulin does not affect the specificity of the heregulin moiety in its selective interaction between receptor family members.

14.2.4. Cytotoxicity of HAR-TX β2 Against Tumor Cells

The cell killing activity of HAR-TX β2 was determined against a variety of human cancer cell lines. AU565 and SKBR3 breast carcinomas and LNCaP prostate carcinoma were sensitive to HAR-TX β2 with $EC_{50}$ values of 25, 20, 4.5 ng/ml, respectively, while SKOV3 ovarian carcinoma cells were insensitive to HAR-TX β2 ($EC_{50}$>2000 ng/ml) (FIG. 28, Panel 1). Addition of heregulin β2-Ig to LNCaP cells reduced the cytotoxic activity of HAR-TX β2 (FIG. 28, Panel 2). In contrast, L6-Ig, a chimeric mouse-human antibody with a non-related specificity but matching human Fc domains (Hellström et al., supra), did not inhibit the HAR-TX β2 cytotoxic activity (FIG. 28, Panel 2). Thus, the cytotoxic effect of HAR-TX β2 was due to specific heregulin-mediated binding. Similar data were obtained using MDA-MB-453 cells (not shown).

14.2.5. HER2, HER3, and HER4 Receptor Density on Human Tumor Cells: Correlation with HAR-TX β2-Mediated Cytotoxicity To understand why cell lines differed in their sensitivity to HAR-TX β2, their levels of HER2, HER3, and HER4 were quantitated by image analysis (see Section 15.1.8. and 15.1.9., supra) using receptor specific monoclonal antibodies (Table IV). The data strongly indicate that HER4 expression is required for heregulin directed cytotoxic activity. All seven of the tumor cell lines which expressed detectable levels of HER4 were found to be sensitive to HAR-TX β2-mediated killing with $EC_{50}$ values ranging from 1–125 ng/ml. Moreover, the sensitivity of the different cell lines correlates directly with the expression level of HER4: MCF-7 cells displaying the lowest detectable levels of HER4 were found to be the least sensitive ($EC_{50}$=125 ng/ml) of the cells which did respond. All four cell lines which were found to be devoid of any detectable HER4 expression on their surface were found to be resistant to HAR-TX β2. Three of them, SKOV3, L2987 and H3396, displayed both HER2 and HER3 in the absence of HER4.

TABLE IV

Comparative HER2, HER3, and HER4 cell surface receptor density and cytotoxicity of HAR-TX β2 on human tumor cell lines

| Cell Line | Type | RELATIVE AMOUNTS HER2 | HER3 | HER4 | $EC_{50}$, (ng/ml) |
|---|---|---|---|---|---|
| BT474 | Breast | 1.6 | 0.32 | 0.3 | 1 |
| MDA-MD-453 | Breast | 1.2 | 1.08 | 0.3 | 2 |
| LNCaP | Prostate | 0.7 | 2.6 | 0.85 | 4.5 |
| T47D | Breast | 0.04 | 0.1 | 0.1 | 9.5 |
| SKBR3 | Breast | 4.6 | 2.5 | 0.56 | 20 |
| AU565 | Breast | 4.6 | 0.73 | 0.18 | 25 |
| MCF-7 | Breast | 0.04 | 1.8 | 0.05 | 125 |
| H3396 | Breast | 0.6 | 2.5 | — | >2000 |
| SK0V3 | Ovarian | 0.64 | 1.3 | — | >2000 |

TABLE IV-continued Comparative HER2, HER3, and HER4 cell surface receptor density and cytotoxicity of HAR-TX β2 on human tumor cell lines
RELATIVE AMOUNTS

| Cell Line | Type | HER2 | HER3 | HER4 | $EC_{50}$, (ng/ml) |
|---|---|---|---|---|---|
| L2987 | Lung | 0.16 | 1.4 | — | >2000 |
| CEM | T leukemia | — | — | — | >2000 |

14.2.6. HAR-TX β2 Induces Tyrosine Phosphorylation in Tumor Cells That Do Not Express HER4

In contrast to reports that heregulin directly binds to both HER3 and HER2/HER3 in a heterodimer configuration (Carraway et al., 1994, *J. Biol. Chem.* 269:14303–14306; Sliwkowski et al., 1994, *J. Biol. Chem.* 269:14661–15665), tumor cells that express HER3 alone (L2987) or co-express HER2 and HER3 (H3396 and SKOV3) were insensitive to HAR-TX β2. Direct interaction of H3396 and L2987 cells with the chimeric protein was determined by phosphotyrosine immunoblots following HAR-TX β2 induction. HAR-TX β2 was found to induce tyrosine phosphorylation in both tumor cell types (FIG. 29) similar to that previously seen in COS-7 cells transfected with HER2 and HER3 (Sliwkowski et al., supra). SKOV3 cells were found to exhibit the same tyrosine phosphorylation pattern in the presence or absence of heregulin and thus direct interaction between receptors and heregulin could not be established (data not shown). However, previous studies indicate that heregulin does not bind to these cells (Peles et al., supra).

14.2.7. Toxicity of HAT-TX β2

For the toxicity studies, HAR-TX β2 was administered as described in section 15.1.10. In mice, 2/2 animals died at 2 mg/kg, 2/2 died at 1 mg/kg, 1/2 died at 0.75 mg/kg, and 0/2 died at 0.5 mg/kg, thus the $LD_{50}$ is about 0.75 mg/kg (Table V). In rats the determined $LD_{50}$ was slightly higher, as 50% of the animals died at 1 mg/kg (Table V).

TABLE V

Toxicity of HAR-TX β2

| Species | dose [mg/ng] | Lethality [%] |
|---|---|---|
| mouse | 0.5 | 0 |
|  | 0.75 | 50 |
|  | 1 | 100 |
|  | 2 | 100 |

TABLE V-continued

Toxicity of HAR-TX β2

| Species | dose [mg/ng] | Lethality [%] |
|---|---|---|
| rat | 1 | 50 |
|  | 2 | 100 |

14.2.8. Characteristics of HER4 Specific Monoclonal Antibodies

The characteristics of the HER4 specific monoclonal antibodies disclosed herein are summarized in Table VI.

TABLE VI

Characteristics of HER4 Antibodies
Abbreviations: Cyto, cytoplasmic domain;
ECD, extracellular domain; FACS, fluorescence-activated cell sorter analysis; fibro, fibroblasts; ICC, immunocytochemistry; RIP, receptor immunoprecipitation;

| Hybridoma | Isotype | RIP | Western | Domain | FACS | HER4 Ig + HER2 Ig | ICC fibro. | ICC CHO/H4 |
|---|---|---|---|---|---|---|---|---|
| 6-4-11 | IgG1 | ++ | – | ECD | + | + | – | ++++ |
| 7-142 | IgG2a | – | ++ | Cyto | – | – | – | – |

15. Microorganism and Cell Deposits

The following microorganisms and cell lines have been deposited with the American Type Culture Collection, 12301 Parklawn Drive, Rockville, Md. 20852-1776, and have been assigned the following accession numbers:

| Microorganism | Plasmid | Accession Number | Date of Deposit |
|---|---|---|---|
| *E. coli* SCS-1 | pBSHER4Y | 69131 | November 23, 1991 |

(containing the complete human HER4 coding sequence)

| Cell Line | Accession Number | Date of Deposit |
|---|---|---|
| CHO/HER4 21-2 | CRL11205 | November 23, 1992 |
| Hybridoma Cell Line 6-4-11 | HB11715 | September 19, 1994 |
| Hybridoma Cell Line 7-142 | HB11716 | September 19, 1994 |

The present invention is not to be limited in scope by the microorganisms and cell lines deposited or the embodiments disclosed herein, which are intended as single illustrations of one aspect of the invention, and any which are functionally equivalent are within the scope of the invention. Indeed, various modifications of the invention, in addition to those shown and described herein, will become apparent to those skilled in the art from the foregoing description. Such modifications are intended to fall within the scope of the appended claims. All base pair and amino acid residue numbers and sizes given for polynucleotides and polypeptides are approximate and used for the purpose of description.

All publications and patent applications mentioned in this specification are indicative of the level of skill of those skilled in the art to which the invention pertains. All publications and patent applications are herein incorporated by reference to the same extent as if each individual publication or patent application was specifically and individually indicated to be incorporated by reference.

---

What is claimed is:

1. An antibody which specifically binds to human HER4, but does not bind to HER2 or HER3.

2. An antibody according to claim 1 which resides on the cell surface after binding to HER4.

3. An antibody according to claim 1 which is internalized into the cell after binding to HER4.

4. An antibody which specifically binds to human HER4 expressed in CHO/HER4 21-2 cells as deposited with the American Type Culture Collection and assigned accession number CRL 11205, wherein the antibody does not bind to HER2 or HER3.

5. An antibody according to claim 1 which is conjugated to a drug or toxin.

6. An antibody according to claim 1 which is radiolabeled.

7. A method for the in vivo delivery of a drug or toxin to cells expressing HER4 comprising conjugating an antibody according to claim 1 or 4, or an active fragment thereof, to the drug or toxin, and delivering the resulting conjugate to an individual by using a formulation, dose, and route of administration such that the conjugate binds to HER4.

8. A monoclonal antibody which specifically binds the epitope recognized by the monoclonal antibody produced by hybridoma cell line 6-4-11 as deposited with the American Type Culture Collection and assigned accession number HB11715.

9. A monoclonal antibody which specifically binds the epitope recognized by the monoclonal antibody produced by hybridoma cell line 7-142 as deposited with the American Type Culture Collection and assigned accession number HB11716.

10. Hybridoma cell line 6-4-11 as deposited with the ATCC and assigned accession number HB11715.

11. Hybridoma cell line 7-142 as deposited with the ATCC and assigned accession number HB11716.

12. The antibody according to claim 1 wherein the antibody is monoclonal.

13. The antibody according to claim 1 wherein the antibody is a chimeric, single chain or humanized antibody.

14. The antibody according to claim 1 which inhibits the interaction of HER4 with its ligand.

15. The antibody according to claim 14 wherein the ligand is heregulin.

16. The antibody according to claim 1 which inhibits a HER4-mediated signal in a cell, which signal results in modulation of growth or differentiation of the cells.

17. The antibody of claim 1 which inhibits the HepG2 fraction 17-stimulated tyrosine phosphorylation of HER4 expressed in CHO/HER4 21-2 cells as deposited with the American Type Culture Collection and assigned accession number CRL 11205.

* * * * *